(12) United States Patent
Sethuraman et al.

(10) Patent No.: US 8,715,963 B2
(45) Date of Patent: May 6, 2014

(54) **METHOD FOR INCREASING N-GLYCOSYLATION SITE OCCUPANCY ON THERAPEUTIC GLYCOPROTEINS PRODUCED IN *PICHIA PASTORIS***

(75) Inventors: Natarajan Sethuraman, Lebanon, NH (US); Byung-Kwon Choi, Lebanon, NH (US); Bianka Prinz, Lebanon, NH (US); Michael Meehl, Lebanon, NH (US); Terrance Stadheim, Lyme, NH (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 13/579,972

(22) PCT Filed: Feb. 23, 2011

(86) PCT No.: PCT/US2011/025878
§ 371 (c)(1),
(2), (4) Date: Aug. 20, 2012

(87) PCT Pub. No.: WO2011/106389
PCT Pub. Date: Sep. 1, 2011

(65) Prior Publication Data
US 2012/0328626 A1   Dec. 27, 2012

Related U.S. Application Data

(60) Provisional application No. 61/307,642, filed on Feb. 24, 2010.

(51) Int. Cl.
| C12P 21/06 | (2006.01) |
| C12P 21/04 | (2006.01) |
| C12P 1/02 | (2006.01) |
| C12N 15/74 | (2006.01) |
| C12N 5/07 | (2010.01) |
| C12N 1/00 | (2006.01) |

(52) U.S. Cl.
USPC ......... 435/69.1; 435/71.1; 435/171; 435/471; 435/326; 435/335; 435/336; 435/254.11; 435/254.23

(58) Field of Classification Search
None
See application file for complete search history.

(56) References Cited

U.S. PATENT DOCUMENTS

| 5,714,377 | A |  | 2/1998 | Tanner et al. |
| 7,029,872 | B2 | * | 4/2006 | Gerngross ............... 435/69.1 |
| 7,198,921 | B2 |  | 4/2007 | Miura et al. |
| 7,259,007 | B2 |  | 8/2007 | Bobrowicz et al. |
| 7,405,198 | B2 | * | 7/2008 | DeFrees et al. ............. 514/1.3 |
| 7,449,308 | B2 |  | 11/2008 | Gerngross et al. |
| 7,598,055 | B2 |  | 10/2009 | Bobrowicz et al. |
| 7,625,756 | B2 |  | 12/2009 | Hamilton |
| 7,713,719 | B2 |  | 5/2010 | Bobrowicz et al. |
| 2004/0018590 | A1 |  | 1/2004 | Gerngross et al. |
| 2004/0171826 | A1 |  | 9/2004 | Hamilton |
| 2004/0230042 | A1 |  | 11/2004 | Hamilton |
| 2005/0170452 | A1 |  | 8/2005 | Wildt et al. |
| 2005/0208617 | A1 |  | 9/2005 | Bobrowicz et al. |
| 2005/0260729 | A1 |  | 11/2005 | Hamilton |
| 2006/0040353 | A1 |  | 2/2006 | Davidson et al. |
| 2006/0252672 | A1 | * | 11/2006 | Betenbaugh et al. ............. 514/8 |
| 2006/0286637 | A1 |  | 12/2006 | Hamilton |
| 2007/0037248 | A1 |  | 2/2007 | Bobrowicz et al. |
| 2009/0124000 | A1 |  | 5/2009 | Nett et al. |

FOREIGN PATENT DOCUMENTS

| WO | WO2006107990 | 10/2006 |
| WO | WO2007061631 | 5/2007 |
| WO | WO2009085135 | 7/2009 |
| WO | WO2009105357 | 8/2009 |
| WO | WO2010019487 | 2/2010 |
| WO | WO2010049177 | 5/2010 |

OTHER PUBLICATIONS

Nasab et al. 2008. Mol Biol Cell. 19:3758-3768.*
Sethuraman et al. 2006. Current Opinion in Biotech. 17:341-346.*
Takeuchi et al. 1988. J. Biol. Chem. 263:3657-3663.*
Li et al. 2006. Nature Biotech. 24:210-215.*
Berriman et al., "The genome of the African trypanosome *Trypanosoma brucei*" Science (2005) 309: 416-422.
Bosch et al., "Characterization of dolichol diphosphate oligosaccharide: protein oligosaccharyltransferase and glycoprotein-processing glucosidases occurring in trypanosomatid protozoa" *J. Biol. Chem.* (1988) 263:17360-17365.

(Continued)

*Primary Examiner* — Shulamith H Shafer
(74) *Attorney, Agent, or Firm* — John David Reilly; Immac J. Thampoe

(57) ABSTRACT

Described is a method for increasing the N-glycosylation site occupancy of a therapeutic glycoprotein produced in recombinant host cells modified as described herein and genetically engineered to express the glycoprotein compared to the N-glycosylation site occupancy of the therapeutic glycoprotein produced in a recombinant host cell not modified as described herein. In particular, the method provides recombinant host cells that overexpress a heterologous single-subunit oligosaccharyltransferase, which in particular embodiments is capable of functionally suppressing the lethal phenotype of a mutation of at least one essential protein of the yeast oligosaccharyltransferase (OTase) complex, for example, the *Leishmania major* STT3D protein, in the presence of expression of the host cell genes encoding the endogenous OTase complex. The method is useful for both producing therapeutic glycoproteins with increased N-glycosylation site occupancy in lower eukaryote cells such as yeast and filamentous fungi and in higher eukaryote cells such as plant and insect cells and mammalian cells.

18 Claims, 45 Drawing Sheets

(56) References Cited

OTHER PUBLICATIONS

Castro et al., "Preferential transfer of the complete glycan is determined by the oligosaccharyltransferase complex and not by the catalytic subunit" *Proc. Natl. Acad. Sci. USA* (2006) 103: 14756-14760.

Cregg et al., "Heterologous protein expression in the methylotrophic yeast *Pichia pastoris*"FEMS Microbiol. Rev. (2000) 24: 45-66.

Gawlitzek et al., "Identification of Cell Culture Conditions to Control N-Glycosylation Site-Occupancy of Recombinant Glycoproteins Expressed in CHO Cells" *Biotechnol. Bioengin.* 103: (2009)1164-1175.

Hese et al. "The yeast oligosaccharyltransferase complex can be replaced by STT3 from *Leishmania major*" *Glycobiology* 19: (2009) 160-171.

Ivens et al., "The Genome of the Kinetoplastid Parasite, Leishmania major" *Science* 309: 436-442 (2005).

Jones et al.,"Controlling N-linked glycan site occupancy" *Biochim. Biophys. Acta.* (2005) 1726:121-137.

Kelleher & Gilmore, "An evolving view of the eukaryotic oligosaccharyltransferase" *Glycobiol.* (2006) 16: 47R-62R.

Kelleher et al., "Identification of cell culture conditions to control N-glycosylation site-occupancy of recombinant glycoproteins expressed in CHO cells" *Mol. Cell.* (2003)12: 101-111.

Knauer & Lehle, "The oligosaccharyltransferase complex from yeast" *Biochim. Biophys. Acta.* (1999) 1426: 259-273.

Kowarik et al."N-Linked Glycosylation of Folded Proteins by the Bacterial Oligosaccharyltransferase" *Science* (2006) 314: 1148-1150.

McConville et al., "Secretory Pathway of Trypanosomatid Parasites" *Microbiol. Mol. Biol. Rev.* (2002) 66: 122-154.

Nasab et al., "All in One: *Leishmania major* STT3 Proteins Substitute for the Whole Oligosaccharyltransferase Complex in *Saccharomyces cerevisiae*" *Molecular Biology of the Cell* (2008) 19: 3758-3768.

Nilsson et al., "Photocross-linking of nascent chains to the STT3 subunit of the oligosaccharyltransferase complex" *J. Cell Biol.* (2003) 161: 715-725.

Parodi, "N-Glycosylation in trypanosomatid protozoa" *Glycobiology* (1993) 3: 193-199.

Samuelson et al.,"The diversity of dolichol-linked precursors to Asn-linked glycans likely results from secondary loss of sets of glycosyltransferases" *Proc. Natl. Acad. Sci. USA* (2005) 102: 1548-1553.

Schultz & Aebi, "Analysis of Glycosylation Site Occupancy Reveals a Role for Ost3p and Ost6p in Site-specific N-Glycosylation Efficiency" *Molec. Cell. Proteomics* (2009) 8: 357-364.

Shams-Eldin et al., "High-level expression of the *Toxoplasma gondii* STT3 gene is required for suppression of the yeast STT3 gene mutation" *Mol. Biochem. Parasitol.* 143: 6-11 (2005).

Shutter et al., "Genome sequence of the recombinant protein production host *Pichia pastoris*" *Nat. Biotechnol.* (2009) 27: 561-566.

Silberstein & Gilmore, "Biochemistry, molecular biology, and genetics of the oligosaccharyltransferase" *FASEB J.* (1996) 10: 849-858.

Wacker et al., "N-Linked Glycosylation in *Campylobacter jejuni* and Its Functional Transfer into *E. coli*" *Science* 298: (2002) 1790-1793.

Weerapana & Imperiali, "Asparagine-linked protein glycosylation: from eukaryotic to prokaryotic systems" *Glycobiol.* (2006) 16: 91R-101R.

Yan & Lennarz, "Studies on the Function of Oligosaccharyl Transferase Subunits: Stt3p Is Directly Involved in the Glycosylation Process" *J. Biol. Chem.* (2002) 277: 47692-47700.

Dempski & Imperiali, "Oligosaccharyl transferase: gatekeeper to the secretory pathway" *Curr. Opin. Chem. Biol.* (2002) 6: 844-850.

* cited by examiner

YGLY4754

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ-URA5-lacZ/ScGAL10/XB33/DmUGT
arg1Δ::HIS1/KD53/TC54]

↓ Counterselect on 5-FOA

YGLY4799

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54]

pGLY3411 ↓

YGLY6903

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ-URA5-lacZ]

↓ Counterselect on 5-FOA

FIG.1C

YGLY7432 & YGLY7433
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ]

pGLY3419 

YGLY7651 & YGLY7656
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ-URA5-lacZ]

 Counterselect on 5-FOA

YGLY7930 & YGLY7940
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ]

pGLY3421 

FIG.1D

YGLY7961 & YGLY7965
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ URA5-lacZ]

pGLY3673 

YGLY8316 & YGLY8323
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ URA5-lacZ
PRO1::ARG1/AOX1p-TrMDS1]

FIG. 1E

YGLY8316

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ URA5-lacZ]
PRO1::ARG1/AOX1p-TrMDS1]

pGLY6833 

YGLY13992

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ-URA5-lacZ
PRO1::ARG1/AOX1p-TrMDS1]
TRP2::Sh ble/AOX1p-anti-Her2-Ab

FIG. 1F

YGLY8323
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ-URA5-lacZ
PRO1::ARG1/AOX1p-TrMDS1]

pGLY6564 

YGLY14401
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1::lacZ bmt3::lacZ URA5-lacZ
PRO1::ARG1/AOX1p-TrMDS1]
TRP2::Sh ble/AOX1p-anti-RSV-Ab

FIG.1G

Glossary:

| | |
|---|---|
| ScSUC2 | S. cerevisiae Invertase |
| OCH1 | Alpha-1,6-mannosyltransferase |
| KlMNN2-2: | K. lactis UDP-GlcNAc transporter |
| BMT1: | Beta-mannose-transfer (beta-mannose elimination) |
| BMT2: | Beta-mannose-transfer (beta-mannose elimination) |
| BMT3: | Beta-mannose-transfer (beta-mannose elimination) |
| BMT4: | Beta-mannose-transfer (beta-mannose elimination) |
| MNN4L1: | MNN4-like 1 (charge elimination) |
| MmSLC35A3 | Mouse homologue of UDP-GlcNAc Transporter |
| PNO1: | Phosphomannosylation of N-glycans (charge elimination) |
| MNN4: | Mannosyltransferase (charge elimination) |
| ScGAL10 | UDP-glucose 4-epimerase |
| XB33 | Truncated HsGalT1 fused to ScKRE2 leader |
| DmUGT | UDP-Galactose transporter |
| KD53 | Truncated DmMNSII fused to ScMNN2 leader |
| TC54 | Truncated RnGNTII fused to ScMNN2 leader |
| NA10 | Truncated HsGNTI fused to PpSEC12 leader |
| FB8: | Truncated MmMNS1A fused to ScSEC12 leader |
| TrMDS1: | Secreted T. reseei MNS1 |
| Sh ble: | Zeocin resistance marker |

FIG.1H

YGLY7961
[ura5Δ::ScSUC2  och1Δ::lacZ  bmt2Δ::lacZ/KlMNN2-2
mnn4L1Δ::lacZ/MmSLC35A3  pno1Δ  mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ  bmt1Δ::lacZ  bmt3Δ::lacZ-URA5-lacZ]

↓ pGLY2456

YGLY8146
[ura5Δ::ScSUC2  och1Δ::lacZ  bmt2Δ::lacZ/KlMNN2-2
mnn4L1Δ::lacZ/MmSLC35A3  pno1Δ  mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ  bmt1Δ::lacZ  bmt3Δ::lacZ-URA5-lacZ
TRP2::ARG1/MmCST/HsGNE/HsCSS/HsSPS/MmST6-33]

↓ Counterselect on 5-FOA

YGLY9296
[ura5Δ::ScSUC2  och1Δ::lacZ  bmt2Δ::lacZ/KlMNN2-2
mnn4L1Δ::lacZ/MmSLC35A3  pno1Δ  mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ  bmt1Δ::lacZ  bmt3Δ::lacZ
TRP2::ARG1/MmCST/HsGNE/HsCSS/HsSPS/MmST6-33]

↓ pGLY5048

FIG.23A

YGLY9469

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1Δ::lacZ bmt3Δ::lacZ
TRP2::ARG1/MmCST/HsGNE/HsCSS/HsSPS/MmST6-33
ste13Δ::lacZ-URA5-lacZ/TrMDS1]

pGLY5019 ↓

YGLY9797

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1Δ::lacZ bmt3Δ::lacZ
TRP2::ARG1/MmCST/HsGNE/HsCSS/HsSPS/MmST6-33
ste13Δ::lacZ-URA5-lacZ/TrMDS1 dap2Δ::Nat$^R$]

pGLY5085 ↓

FIG. 23B

YGLY12900

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1Δ::lacZ bmt3Δ::lacZ
TRP2::ARG1/MmCST/HsGNE/HsCSS/HsSPS/MmST6-33
ste13Δ::lacZ-URA5-lacZ/TrMDS1 dap2Δ::Nat$^R$
TRP5::Hyg$^R$MmCST/HsGNE/HsCSS/HsSPS/MmST6-33]

pGLY7240 ↓

YGLY15660

[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1Δ::lacZ bmt3Δ::lacZ
TRP2::ARG1/MmCST/HsGNE/HsCSS/HsSPS/MmST6-33
ste13Δ::lacZ-URA5-lacZ/TrMDS1 dap2Δ::Nat$^R$
TRP5::Hyg$^R$MmCST/HsGNE/HsCSS/HsSPS/MmST6-33
TRP2::Sh ble/AOX1p/PpCWP1-GMCSF]

pGLY6301 ↓

FIG. 23C

YGLY16349
[ura5Δ::ScSUC2 och1Δ::lacZ bmt2Δ::lacZ/KlMNN2-2
mnn4L1Δ::lacZ/MmSLC35A3 pno1Δ mnn4Δ::lacZ
ADE1::lacZ/NA10/MmSLC35A3/FB8
his1Δ::lacZ/ScGAL10/XB33/DmUGT
arg1Δ::HIS1/KD53/TC54
bmt4Δ::lacZ bmt1Δ::lacZ bmt3Δ::lacZ
TRP2::ARG1/MmCST/HsGNE/HsCSS/HsSPS/MmST6-33
ste13Δ::lacZ-URA5-lacZ/TrMDS1 dap2Δ::Nat$^R$
TRP5::Hyg$^R$MmCST/HsGNE/HsCSS/HsSPS/MmST6-33
TRP2::Sh ble/AOX1p/PpCWP1-GMCSF
URA6::ScARR3/AOX1p/LmSTT3D]

FIG.23D

Glossary:

| | |
|---|---|
| ScSUC2 | S. cerevisiae Invertase |
| OCH1 | Alpha-1,6-mannosyltransferase |
| KlMNN2-2: | K. lactis UDP-GlcNAc transporter |
| BMT1: | Beta-mannose-transfer (beta-mannose elimination) |
| BMT2: | Beta-mannose-transfer (beta-mannose elimination) |
| BMT3: | Beta-mannose-transfer (beta-mannose elimination) |
| BMT4: | Beta-mannose-transfer (beta-mannose elimination) |
| MNN4L1: | MNN4-like 1 (charge elimination) |
| MmSLC35A3 | Mouse homologue of UDP-GlcNAc transporter |
| PNO1: | Phosphomannosylation of N-linked oligosaccharides (charge elimination) |
| MNN4: | Mannosyltransferase (charge elimination) |
| ScGAL10 | UDP-glucose 4-epimerase |
| XB33 | Truncated HsGalT1 fused to ScKRE2 leader |
| DmUGT | UDP-Galactose transporter |
| KD53 | Truncated DmMNSII fused to ScMNN2 leader |
| TC54 | Truncated RnGNTII fused to ScMNN2 leader |
| NA10 | Truncated HsGNTI fused to PpSEC12 leader |
| FB8: | Truncated MmMNS1A fused to ScSEC12 leader |
| MmCST | Mouse CMP-sialic acid transporter |
| HsGNE | Human UDP-GlcNAc 2-epimerase/N-acetylmannosamine kinase |
| HsCSS | Human CMP-sialic acid synthase |
| HsSPS | Human N-acetylneuraminate-9-phosphate synthase |
| MmST6-33 | Truncated Mouse alpha-2,6-sailyl transferase fused to ScKRE2 leader |
| TrMDS1: | Secreted T. reseei MNS1 |
| STE13 | Golgi dipeptidyl aminopeptidase |
| DAP2 | Vacuolar dipeptidyl aminopeptidase |
| NatR | Nourseothricin resistance marker |
| HygR | Hygromycin resistance marker |

FIG.23E

METHOD FOR INCREASING N-GLYCOSYLATION SITE OCCUPANCY ON THERAPEUTIC GLYCOPROTEINS PRODUCED IN *PICHIA PASTORIS*

CROSS REFERENCE TO RELATED APPLICATIONS

This patent application is a National Phase entry of PCT International Application No. PCT/US2011/025878 filed 23 Feb. 2011 and which claims benefit of U.S. Provisional Application No. 61/307,642, filed 24 Feb. 2010.

REFERENCE TO SEQUENCE LISTING SUBMITTED ELECTRONICALLY

The sequence listing of the present application is submitted electronically via EFS-Web as an ASCII formatted sequence listing with a file name "GFIMIS00010USPCT-SEQTXT-13AUG2012.txt", creation date of Aug. 13, 2012, and a size of 151 KB. This sequence listing submitted via EFS-Web is part of the specification and is herein incorporated by reference in its entirety.

BACKGROUND OF THE INVENTION (1) Field of the Invention

The present invention relates to methods for increasing the N-glycosylation site occupancy of a heterologous glycoprotein produced in a recombinant host cell modified according to the present invention and genetically engineered to express the glycoprotein compared to the N-glycosylation site occupancy of the therapeutic glycoprotein produced in a recombinant host cell not modified according to the present invention. In particular, the present invention provides recombinant host cells that overexpress a heterologous single-subunit oligosaccharyltransferase, which in particular embodiments is capable of functionally suppressing the lethal phenotype of a mutation of at least one essential protein of the yeast oligosaccharyltransferase (OTase) complex in the presence of the host cell's endogenous OTase complex and methods to using these host cells to produce heterologous glycoproteins.

(2) Description of Related Art

The ability to produce recombinant human proteins has led to major advances in human health care and remains an active area of drug discovery. Many therapeutic proteins require the posttranslational addition of glycans to specific asparagine residues (N-glycosylation) of the protein to ensure proper structure-function activity and subsequent stability in human serum. For therapeutic use in humans, glycoproteins require human-like N-glycosylation. Mammalian cell lines (e.g., Chinese hamster ovary (CHO) cells, human retinal cells) that can mimic human-like glycoprotein processing have several drawbacks including low protein titers, long fermentation times, heterogeneous products, and continued viral containment. It is therefore desirable to use an expression system that not only produces high protein titers with short fermentation times, but can also produce human-like glycoproteins.

Fungal hosts such as *Saccharomyces cerevisiae* or methylotrophic yeast such as *Pichia pastoris* have distinct advantages for therapeutic protein expression, for example, they do not secrete high amounts of endogenous proteins, strong inducible promoters for producing heterologous proteins are available, they can be grown in defined chemical media and without the use of animal sera, and they can produce high titers of recombinant proteins (Cregg et al., FEMS Microbiol. Rev. 24: 45-66 (2000)). However, glycosylated proteins expressed in yeast generally contain additional mannose sugars resulting in "high mannose" glycans. Because these high mannose N-glycans can result in adverse responses when administered to certain individuals, yeast have not generally been used to produce therapeutic glycoproteins intended for human use. However, methods for genetically engineering yeast to produce human-like N-glycans are described in U.S. Pat. Nos. 7,029,872 and 7,449,308 along with methods described in U.S. Published Application Nos. 20040230042, 20050208617, 20040171826, 20050208617, and 20060286637. These methods have been used to construct recombinant yeast that can produce therapeutic glycoproteins that have predominantly human-like complex or hybrid N-glycans thereon instead of yeast type N-glycans.

It has been found that while the genetically engineered yeast can produce glycoproteins that have mammalian- or human-like N-glycans, the occupancy of N-glycan attachment sites on glycoproteins varies widely and is generally lower than the occupancy of these same sites in glycoproteins produced in mammalian cells. This has been observed for various recombinant antibodies produced in *Pichia pastoris*. However, variability of occupancy of N-glycan attachment sites has also been observed in mammalian cells as well. For example, Gawlitzek et al., Identification of cell culture conditions to control N-glycosylation site-occupancy of recombinant glycoproteins expressed in CHO cells, Biotechnol. Bioengin. 103: 1164-1175 (2009), disclosed that N-glycosylation site occupancy can vary for particular sites for particular glycoproteins produced in CHO cells and that modifications in growth conditions can be made to control occupancy at these sites. International Published Application No. WO 2006107990 discloses a method for improving protein N-glycosylation of eukaryotic cells using the dolichol-linked oligosaccharide synthesis pathway. Control of N-glycosylation site occupancy has been reviewed by Jones et al., Biochim. Biophys. Acta. 1726: 121-137 (2005). However, there still remains a need for methods for increasing N-glycosylation site occupancy of therapeutic proteins produced in recombinant host cells.

BRIEF SUMMARY OF THE INVENTION

The present invention provides a method for producing therapeutic glycoproteins in recombinant host cells modified as disclosed herein wherein the N-glycosylation site occupancy of the glycoproteins produced in the host cells modified as disclosed herein is increased over the N-glycosylation site occupancy of the same glycoproteins produced in host cells not modified as disclosed herein. For example, in yeast host cells modified as disclosed herein, the N-glycosylation site occupancy of glycoproteins produced therein will be the same as or more similar to the N-glycosylation site occupancy of the same glycoproteins produced in recombinant mammalian or human cells.

To increase the N-glycosylation site occupancy on a glycoprotein produced in a recombinant host cell one or more heterologous single-subunit oligosaccharyltransferase (OTase) is/are overexpressed in the recombinant host cell either before or simultaneously with the expression of the glycoprotein in the host cell. In particular aspects, at least one of the heterologous single-subunit oligosaccharyltransferase is capable of functionally complementing a lethal mutation of one or more essential subunits comprising the endogenous host cell hetero-oligomeric oligosaccharyltransferase (OTase) complex. The *Leishmania major* STT3D protein is an example of a heterologous single-subunit oligosaccharyltransferase that has been shown to suppress a lethal mutation in the STT3 locus and at least one locus selected from WBP1, OST1, SWP1, and OST2 in *Saccharomyces cerevisiae* (Naseb et al., Molec. Biol. Cell 19: 3758-3768 (2008)). In general, the one or more heterologous single-subunit oligosaccharyltransferases is/are overexpressed constitutively or inducibly in the presence of the proteins comprising the host cell's endogenous OTase complex, including the host cell's endogenous STT3 protein. Expression cassettes encoding the heterologous single-subunit oligosaccharyltransferase gene can either be integrated into any site within the host cell genome or located in the extrachromosomal space of the host cell, i.e., autonomously replicating genetic elements such as plasmids, viruses, 2 μm plasmid, minichromosomes, and the like.

In particular embodiments, one or more of the single-subunit oligosaccharyltransferases is/are the *Leishmania* sp. STT3A protein, STT3B protein, STT3C protein, STT3D protein, or combinations thereof. In particular embodiments, the one or more single-subunit oligosaccharyltransferases is/are the *Leishmania major* STT3A protein, STT3B protein, STT3C protein, STT3D protein, or combinations thereof. The nucleic acid molecules encoding the single-subunit oligosaccharyltransferases are not overexpressed in lieu of the expression of the endogenous genes encoding the proteins comprising the host cell's OTase complex, including the host cell STT3 protein. Instead the nucleic acid molecules encoding the single-subunit oligosaccharyltransferases are overexpressed constitutively or inducibly in the presence of the expression of the genes encoding the proteins comprising the host cell's endogenous oligosaccharyltransferase (OTase) complex, which includes expression of the endogenous gene encoding the host cell's STT3. Each expression cassette encoding a single-subunit OTase can either be integrated into any site within the host cell genome or located in the extrachromosomal space of the host cell, i.e., autonomously replicating genetic elements such as plasmids, viruses, 2 μm plasmid, minichromosomes, and the like.

The present invention has been exemplified herein using *Pichia pastoris* host cells genetically engineered to produce mammalian- or human-like complex N-glycans; however, the present invention can be applied to other yeast or filamentous fungal host cells, in particular, yeast or filamentous fungi genetically engineered to produce mammalian- or human-like complex or hybrid N-glycans, to improve the overall N-glycosylation site occupancy of glycoproteins produced in the yeast or filamentous fungus host cell. In further aspects, the host cells are yeast or filamentous fungi that produce recombinant heterologous proteins that have wild-type or endogenous host cell N-glycosylation patterns, e.g., hypermannosylated or high mannose N-glycans. In further aspects, the host cells are yeast or filamentous fungi that lack alpha-1,6-mannosyltransferase activity (e.g., och1p activity in the case of various yeast strains such as but not limited to *Saccharomyces cerevisiae* or *Pichia pastoris*) and thus produce recombinant heterologous proteins that have high mannose N-glycans. Furthermore, the present invention can also be applied to plant and mammalian expression system to improve the overall N-glycosylation site occupancy of glycoproteins produced in these plant or mammalian expression systems, particularly glycoproteins that have more than two N-linked glycosylation sites.

Therefore, in one aspect of the above, provided is a method for producing a heterologous glycoprotein in a recombinant host cell, comprising providing a recombinant host cell that includes one or more nucleic acid molecules encoding one or more heterologous single-subunit oligosaccharyltransferases and a nucleic acid molecule encoding the heterologous glycoprotein; and culturing the host cell under conditions for expressing the heterologous glycoprotein to produce the heterologous glycoprotein.

In a further aspect of the above, provided is a method for producing a heterologous glycoprotein with mammalian- or human-like complex or hybrid N-glycans in a host cell, comprising providing a host cell that includes one or more nucleic acid molecules encoding one or more heterologous single-subunit oligosaccharyltransferases and a nucleic acid molecule encoding the heterologous glycoprotein; and culturing the host cell under conditions for expressing the heterologous glycoprotein to produce the heterologous glycoprotein.

In general, in the above aspects, the endogenous host cell genes encoding the proteins comprising the endogenous oligosaccharyltransferase (OTase) complex are expressed.

In further aspects of the above method, the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum*, and *Neurospora crassa*. In other aspects, the host cell is an insect, plant or mammalian host cell.

In a further aspect of the above, provided is a method for producing a heterologous glycoprotein in a lower eukaryote host cell, comprising providing a recombinant lower eukaryote host cell that includes at least one nucleic acid molecule encoding a heterologous single-subunit oligosaccharyltransferase and a nucleic acid molecule encoding the heterologous glycoprotein and wherein the endogenous host cell genes encoding the proteins comprising the endogenous oligosaccharyltransferase (OTase) complex are expressed; and culturing the host cell under conditions for expressing the heterologous glycoprotein to produce the heterologous glycoprotein.

In further aspects of the above method, the lower eukaryote host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum*, and *Neurospora crassa*.

In a further aspect of the above, provided is a method for producing a heterologous glycoprotein in a recombinant yeast host cell, comprising providing a recombinant yeast host cell that includes at least one nucleic acid molecule encoding a heterologous single-subunit oligosaccharyltransferase and a nucleic acid molecule encoding the heterologous glycoprotein and wherein the endogenous host cell genes encoding the proteins comprising the endogenous oligosaccharyltransferase (OTase) complex are expressed; and culturing the host cell under conditions for expressing the heterologous glycoprotein to produce the heterologous glycoprotein.

In the above methods, the recombinant yeast host cell either produces the glycoprotein with a yeast N-glycan pattern or the yeast has been genetically engineered to produce glycoproteins with a yeast pattern but which lack hypermannosylation but which produce high mannose N-glycans. For example, the yeast can be genetically engineered to lack α1,6-mannosyltransferase activity, e.g., Och1p activity. In further aspects, the yeast is genetically engineered to produce glycoproteins that have mammalian or human-like N-glycans.

In particular embodiments, the single-subunit oligosaccharyltransferase is the *Leishmania* sp. STT3A protein, STT3B protein, STT3C protein, STT3D protein, or combinations thereof. In particular embodiments, the single-subunit oligosaccharyltransferase is the *Leishmania major* STT3A protein, STT3B protein, STT3C protein, STT3D protein, or combinations thereof. In further embodiments, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. For example, in further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisae* OTase complex.

In further aspects of the above method, the yeast host cell is selected from the group consisting of *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia minuta* (*Ogataea minuta*, *Pichia lindneri*), *Pichia* sp., *Saccharomyces cerevisiae*, *Saccharomyces* sp., *Hansenula polymorpha*, *Kluyveromyces* sp., *Kluyveromyces lactis*, and *Candida albicans*.

In a further aspect of the above, provided is a method for producing a heterologous glycoprotein in a recombinant yeast host cell, comprising providing a recombinant yeast host cell that includes at least one nucleic acid molecule encoding a heterologous single-subunit oligosaccharyltransferase capable of functionally suppressing the lethal phenotype of a mutation of at least one essential protein of a yeast oligosaccharyltransferase (OTase) complex, and a nucleic acid molecule encoding the heterologous glycoprotein and wherein the endogenous host cell genes encoding the proteins comprising the endogenous oligosaccharyltransferase (OTase) complex are expressed; and culturing the host cell under conditions for expressing the heterologous glycoprotein to produce the heterologous glycoprotein.

In the above methods, the recombinant yeast host cell either produces the glycoprotein with a yeast N-glycan pattern or the yeast has been genetically engineered to produce glycoproteins with a yeast pattern that includes high mannose N-glycans but which lack hypermannosylation. For example, the yeast can be genetically engineered to lack α1,6-mannosyltransferase activity, e.g., Och1p activity. In further aspects, the yeast is genetically engineered to produce glycoproteins that have mammalian or human-like N-glycans.

In particular embodiments, the host cell further includes one or more nucleic acid molecules encoding the *Leishmania* sp. STT3A protein, STT3B protein, STT3C protein, STT3D protein, or combinations thereof. In particular embodiments, the host cell further includes one or more nucleic acids encoding the *Leishmania major* STT3A protein, STT3B protein, STT3C protein, or combinations thereof.

In further aspects of the above method, the yeast host cell is selected from the group consisting of *Pichia pagans*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia minuta* (*Ogataea minuta*, *Pichia lindneri*), *Pichia* sp., *Saccharomyces cerevisiae*, *Saccharomyces* sp., *Hansenula polymorpha*, *Kluyveromyces* sp., *Kluyveromyces lactis*, and *Candida albicans*.

In a further aspect of the above, provided is a method for producing a heterologous glycoprotein in a filamentous fungus host cell, comprising providing a filamentous fungus host cell that includes at least one nucleic acid molecule encoding a single-subunit heterologous oligosaccharyltransferase and a nucleic acid molecule encoding the heterologous glycoprotein and wherein the endogenous host cell genes encoding the proteins comprising the endogenous oligosaccharyltransferase (OTase) complex are expressed; and culturing the host cell under conditions for expressing the heterologous glycoprotein to produce the heterologous glycoprotein. The filamentous fungus host cell produces the glycoprotein in which the N-glycans have a filamentous fungus pattern or it is genetically engineered to produce glycoproteins that have mammalian or human-like N-glycans.

In particular embodiments, the single-subunit oligosaccharyltransferase is the *Leishmania* sp. STT3A protein, STT3B protein, STT3C protein, STT3D protein, or combinations thereof. In particular embodiments, the single-subunit oligosaccharyltransferase is the *Leishmania major* STT3A protein, STT3B protein, STT3C protein, STT3D protein or combinations thereof. In further embodiments, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. For example, in further aspects, the single-subunit oligosaccharyltransferase is the *Leishmania major* STT3D protein, which is capable of functionally suppressing (or rescuing or complementing) the lethal phenotype of at least one essential protein of the *Saccharomyces cerevisiae* OTase complex.

In further aspects of the above, the filamentous fungus host cell is selected from the group consisting of *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, and *Neurospora crassa*.

In further embodiments of any one of the above methods, the host cell is genetically engineered to produce glycoproteins comprising one or more mammalian- or human-like complex N-glycans selected from G0, G1, G2, A1, or A2. In further embodiments, the host cell is genetically engineered to produce glycoproteins comprising one or more mammalian- or human-like complex N-glycans that have bisected N-glycans or have multiantennary N-glycans. In other embodiments, the host cell is genetically engineered to produce glycoproteins comprising one or more mammalian- or human-like hybrid N-glycans selected from GlcNAcMan$_3$GlcNAc$_2$; GalGlcNAcMan$_3$GlcNAc$_2$; NANAGalGlcNAcMan$_3$GlcNAc$_2$; Man$_5$GlcNAc$_2$, GlcNAcMan$_5$GlcNAc$_2$, GalGlcNAcMan$_5$GlcNAc$_2$, and NANAGalGlcNAcMan$_5$GlcNAc$_2$. In further embodiments, the N-glycan structure consists of the G-2 structure Man$_3$GlcNAc$_2$.

In particular embodiments of any one of the above methods, the heterologous glycoprotein can be for example, erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; or IL-2 receptor agonist.

In further embodiments of any one of the above methods, the heterologous protein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

In particular aspects of any one of the above methods, the host cell includes one or more nucleic acid molecules encoding one or more catalytic domains of a glycosidase, mannosidase, or glycosyltransferase activity derived from a member of the group consisting of UDP-GlcNAc transferase (GnT) I, GnT II, GnT III, GnT IV, GnT V, GnT VI, UDP-galactosyltransferase (GalT), fucosyltransferase, and sialyltransferase. In particular embodiments, the mannosidase is selected from the group consisting of C. elegans mannosidase IA, C. elegans mannosidase IB, D. melanogaster mannosidase IA, H. sapiens mannosidase IB, P. citrinum mannosidase I, mouse mannosidase IA, mouse mannosidase IB, A. nidulans mannosidase IA, A. nidulans mannosidase IB, A. nidulans mannosidase IC, mouse mannosidase II, C. elegans mannosidase II, H. sapiens mannosidase II, and mannosidase III.

In certain aspects of any one of the above methods, at least one catalytic domain is localized by forming a fusion protein comprising the catalytic domain and a cellular targeting signal peptide. The fusion protein can be encoded by at least one genetic construct formed by the in-frame ligation of a DNA fragment encoding a cellular targeting signal peptide with a DNA fragment encoding a catalytic domain having enzymatic activity. Examples of targeting signal peptides include, but are not limited to, membrane-bound proteins of the ER or Golgi, retrieval signals, Type II membrane proteins, Type I membrane proteins, membrane spanning nucleotide sugar transporters, mannosidases, sialyltransferases, glucosidases, mannosyltransferases, and phospho-mannosyltransferases.

In particular aspects of any one of the above methods, the host cell further includes one or more nucleic acid molecules encode one or more enzymes selected from the group consisting of UDP-GlcNAc transporter, UDP-galactose transporter, GDP-fucose transporter, CMP-sialic acid transporter, and nucleotide diphosphatases.

In further aspects of any one of the above methods, the host cell includes one or more nucleic acid molecules encoding an α1,2-mannosidase activity, a UDP-GlcNAc transferase (GnT) I activity, a mannosidase II activity, and a GnT II activity.

In further still aspects of any one of the above methods, the host cell includes one or more nucleic acid molecules encoding an α1,2-mannosidase activity, a UDP-GlcNAc transferase (GnT) I activity, a mannosidase II activity, a GnT II activity, and a UDP-galactosyltransferase (GalT) activity.

In further still aspects of any one of the above methods, the host cell is deficient in the activity of one or more enzymes selected from the group consisting of mannosyltransferases and phosphomannosyltransferases. In further still aspects, the host cell does not express an enzyme selected from the group consisting of 1,6mannosyltransferase, 1,3mannosyltransferase, and 1,2mannosyltransferase.

In a particular aspect of any one of the above methods, the host cell is an och1 mutant of Pichia pastoris.

Further provided is a host cell, comprising (a) a first nucleic acid molecule encoding a heterologous single-subunit oligosaccharyltransferase; and (b) a second nucleic acid molecule encoding a heterologous glycoprotein; and the endogenous host cell genes encoding the proteins comprising the endogenous oligosaccharyltransferase (OTase) complex are expressed, which includes expression of the endogenous host cell STT3 gene.

Further provided is a lower eukaryotic host cell, comprising (a) a first nucleic acid molecule encoding a heterologous single-subunit oligosaccharyltransferase; and (b) a second nucleic acid molecule encoding a heterologous glycoprotein; and the endogenous host cell genes encoding the proteins comprising the endogenous oligosaccharyltransferase (OTase) complex are expressed.

Further provided is a yeast host cell, comprising (a) a first nucleic acid molecule encoding a heterologous single-subunit oligosaccharyltransferase; and (b) a second nucleic acid molecule encoding a heterologous glycoprotein; and the endogenous host cell genes encoding the proteins comprising the endogenous oligosaccharyltransferase (OTase) complex are expressed.

Further provided is a yeast host cell, comprising (a) a first nucleic acid molecule encoding a heterologous single-subunit oligosaccharyltransferase capable of functionally suppressing the lethal phenotype of a mutation of at least one essential protein of a yeast oligosaccharyltransferase (OTase) complex; and (b) a second nucleic acid molecule encoding a heterologous glycoprotein; and the endogenous host cell genes encoding the proteins comprising the endogenous oligosaccharyltransferase (OTase) complex are expressed.

Further provided is a filamentous fungus host cell comprising (a) a first nucleic acid molecule encoding a heterologous single-subunit oligosaccharyltransferase; and (b) a second nucleic acid molecule encoding a heterologous glycoprotein; and the endogenous host cell genes encoding the proteins comprising the endogenous oligosaccharyltransferase (OTase) complex are expressed.

Further provided is a filamentous fungus host cell, comprising (a) a first nucleic acid molecule encoding a heterologous single-subunit oligosaccharyltransferase capable of functionally suppressing the lethal phenotype of a mutation of at least one essential protein of a yeast or filamentous fungus oligosaccharyltransferase (OTase) complex; and (b) a second nucleic acid molecule encoding a heterologous glycoprotein; and the endogenous host cell genes encoding the proteins comprising the endogenous oligosaccharyltransferase (OTase) complex are expressed In particular embodiments, the single-subunit oligosaccharyltransferase is the Leishmania sp. STT3A protein, STT3B protein, STT3C protein, STT3D protein, or combinations thereof. In particular embodiments, the single-subunit oligosaccharyltransferase is the *Leishmania major* STT3A protein, STT3B protein, STT3C protein, STT3D protein, or combinations thereof. In further embodiments, the single-subunit oligosaccharyltransferase is capable of functionally suppressing the lethal phenotype of a mutation of at least one essential protein of an OTase complex, for example, a yeast OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. For example, in further aspects, the for example single-subunit oligosaccharyltransferase is the *Leishmania major* STT3D protein, which is capable of functionally suppressing (or rescuing or complementing) the lethal phenotype of at least one essential protein of the *Saccharomyces cerevisiae* OTase complex.

In further aspects, the above host cells further include one or more nucleic acid molecules encoding a *Leishmania* sp. STT3A protein, STT3B protein, STT3C protein, or combinations thereof.

In further embodiments of any one of the above host cells, the host cell is genetically engineered to produce glycoproteins comprising one or more mammalian- or human-like complex N-glycans selected from G0, G1, G2, A1, or A2. In further embodiments, the host cell is genetically engineered to produce glycoproteins comprising one or more human-like complex N-glycans that bisected N-glycans or have multiantennary N-glycans. In other embodiments, the host cell is genetically engineered to produce glycoproteins comprising one or more mammalian- or human-like hybrid N-glycans selected from $GlcNAcMan_3GlcNAc_2$; $GalGlcNAcMan_3GlcNAc_2$; $NANAGalGlcNAcMan_3GlcNAc_2$; $Man_5GlcNAc_2$, $GlcNAcMan_5GlcNAc_2$, $GalGlcNAcMan_5GlcNAc_2$, and $NANAGalGlcNAcMan_5GlcNAc_2$. In further embodiments, the N-glycan structure consists of the G-2 structure $Man_3GlcNAc_2$.

In particular embodiments of any one of the above host cells, the heterologous glycoprotein can be for example, selected from the group consisting of erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; and IL-2 receptor agonist.

In further embodiments of any one of the above host cells, the heterologous protein is an antibody, examples of which, include but are not limited to, an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, or anti-CD20 antibody.

In particular aspects of the above host cells, the host cell includes one or more nucleic acid molecules encoding one or more catalytic domains of a glycosidase, mannosidase, or glycosyltransferase activity derived from a member of the group consisting of UDP-GlcNAc transferase (GnT) I, GnT II, GnT III, GnT IV, GnT V, GnT VI, UDP-galactosyltransferase (GalT), fucosyltransferase, and sialyltransferase. In particular embodiments, the mannosidase is selected from the group consisting of *C. elegans* mannosidase IA, *C. elegans* mannosidase IB, *D. melanogaster* mannosidase IA, *H. sapiens* mannosidase IB, *P. citrinum* mannosidase I, mouse mannosidase IA, mouse mannosidase IB, *A. nidulans* mannosidase IA, *A. nidulans* mannosidase ID, *A. nidulans* mannosidase IC, mouse mannosidase II, *C. elegans* mannosidase II, *H. sapiens* mannosidase II, and mannosidase III.

In certain aspects of any one of the above host cells, at least one catalytic domain is localized by forming a fusion protein comprising the catalytic domain and a cellular targeting signal peptide. The fusion protein can be encoded by at least one genetic construct formed by the in-frame ligation of a DNA fragment encoding a cellular targeting signal peptide with a DNA fragment encoding a catalytic domain having enzymatic activity. Examples of targeting signal peptides include, but are not limited to, those to membrane-bound proteins of the ER or Golgi, retrieval signals such as HDEL or KDEL, Type II membrane proteins, Type I membrane proteins, membrane spanning nucleotide sugar transporters, mannosidases, sialyltransferases, glucosidases, mannosyltransferases, and phospho-mannosyltransferases.

In particular aspects of any one of the above host cells, the host cell further includes one or more nucleic acid molecules encoding one or more enzymes selected from the group consisting of UDP-GlcNAc transporter, UDP-galactose transporter, GDP-fucose transporter, CMP-sialic acid transporter, and nucleotide diphosphatases.

In further aspects of any one of the above host cells, the host cell includes one or more nucleic acid molecules encoding an α-1,2-mannosidase activity, a UDP-GlcNAc transferase (GnT) I activity, a mannosidase II activity, and a GnT II activity.

In further still aspects of any one of the above host cells, the host cell includes one or more nucleic acid molecules encoding an α-1,2-mannosidase activity, a UDP-GlcNAc transferase (GnT) I activity, a mannosidase II activity, a GnT II activity, and a UDP-galactosyltransferase (GalT) activity.

In further aspects of any one of the above host cells, the host cell is selected from the group consisting of *Pichia pastoris*, *Pichia finlandica*, *Pichia trehalophila*, *Pichia koclamae*, *Pichia membranaefaciens*, *Pichia opuntiae*, *Pichia thermotolerans*, *Pichia salictaria*, *Pichia guercuum*, *Pichia pijperi*, *Pichia stiptis*, *Pichia methanolica*, *Pichia* sp., *Saccharomyces cerevisiae*, *Saccharomyces* sp., *Hansenula polymorpha*, *Kluyveromyces* sp., *Kluyveromyces lactic*, *Candida albicans*, *Aspergillus nidulans*, *Aspergillus niger*, *Aspergillus oryzae*, *Trichoderma reesei*, *Chrysosporium lucknowense*, *Fusarium* sp., *Fusarium gramineum*, *Fusarium venenatum*, *Neurospora crassa*, plant cells, insect cells, and mammalian cells.

In further still aspects of any one of the above host cells, the host cell is deficient in the activity of one or more enzymes selected from the group consisting of mannosyltransferases and phosphomannosyltransferases. In further still aspects, the host cell does not express an enzyme selected from the group consisting of 1,6 mannosyltransferase, 1,3 mannosyltransferase, and 1,2 mannosyltransferase.

In a particular aspect of any one of the above host cells, the host cell is *Pichia pastoris*. In a further aspect, the host cell is an och1 mutant of *Pichia pastoris*.

The methods and host cells herein can be used to produce glycoprotein compositions in which at least 70%, 75%, 80%, 85%, 90%, 95%, 98%, or 99% of the N-glycosylation sites of the glycoproteins in the composition are occupied.

Further, the methods and host cells herein can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that lack fucose.

Further, the methods and yeast or filamentous fungus host cells are genetically engineered to produce mammalian-like or human-like N-glycans can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that lack fucose.

In some aspects, the yeast or filamentous host cells genetically engineered to produce fucosylated mammalian- or human-like N-glycans can be used to produce glycoprotein compositions in which at least 70%, 75%, 80%, 85%, 90%, 95%, 98%, or 99% of the N-glycosylation sites of the glycoproteins in the composition are occupied and which in further aspects have mammalian- or human-like N-glycans that have fucose.

The methods and host cells herein can be used to produce antibody compositions in which at least 70%, 75%, 80%, 85%, 90%, 95%, 98%, or 99% antibody molecules in the compositions have both N-glycosylation sites occupied.

Further, the methods and host cells herein can be used to produce antibody compositions in which at least 70%, 75%, 80%, 85%, 90%, 95%, 98%, or 99% antibody molecules in the compositions have both N-glycosylation sites occupied and the N-glycans lack fucose.

Further, the methods and yeast or filamentous fungus host cells herein can be used to produce antibody compositions in which at least 70%, 75%, 80%, 85%, 90%, 95%, 98%, or 99% antibody molecules in the compositions have both N-glycosylation sites occupied and the N-glycans lack fucose.

Further, the methods and yeast or filamentous fungus host cells genetically engineered to produce mammalian-like or human-like N-glycans can be used to produce antibody compositions in which at least 70%, 75%, 80%, 85%, 90%, 95%, 98%, or 99% antibody molecules in the compositions have both N-glycosylation sites occupied and the antibodies have mammalian- or human-like N-glycans that lack fucose. In some aspects, the yeast or filamentous host cells genetically engineered to produce fucosylated mammalian- or human-like N-glycans can be used to produce antibody compositions in which at least 70%, 75%, 80%, 85%, 90%, 95%, 98%, or 99% antibody molecules in the compositions have both N-glycosylation sites occupied and the antibodies have mammalian- or human-like N-glycans with fucose.

Further provided is a glycoprotein composition comprising a plurality of antibodies wherein about 70% to about 99% of the intact antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 3-15 mole % of the N-glycans have a hybrid structure, and a pharmaceutically acceptable carrier.

Further still is provided is a glycoprotein composition comprising a plurality of antibodies wherein about 70% to 99% of the intact antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a $Man_5GlcNAc_2$ core structure, and a pharmaceutically acceptable carrier.

In particular embodiments, the antibodies comprise an antibody selected from the group consisting of anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, and anti-CD20 antibody.

Further provided are compositions comprising one or more glycoproteins produced by the host cells and methods described herein.

In particular embodiments, the glycoprotein compositions provided herein comprise glycoproteins having fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the glycoprotein compositions provided herein comprise glycoproteins having at least one hybrid N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition. In further aspects, the hybrid N-glycan is a particular N-glycan species that comprises about 30%, 40%, 50%, 60%, 70%, 80%, 90%, 95%, 97%, 98%, 99%, or 100% of the hybrid N-glycans in the composition.

In particular embodiments, the glycoprotein compositions provided herein comprise glycoproteins having at least one complex NV glycan selected from the group consisting of $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlCNAc_2$; and $NANA_2Gal_2GlcNAc_2Man_3GlcNAc_2$. In particular aspects, the complex N-glycan is the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition.

In particular embodiments, the N-glycan is fusosylated. In general, the fucose is in an α-1,3-linkage with the GlcNAc at the reducing end of the N-glycan, an α-1,6-linkage with the GlcNAc at the reducing end of the N-glycan, an α-1,2-linkage with the Gal at the non-reducing end of the N-glycan, an α-1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of $GlcNAcMan_5GlcNAc_2(Fuc)$, $GlcNAcMan_3GlcNAc_2(Fuc)$, $GlcNAc_2Man_3GlcNAc_2(Fuc)$, $GalGlcNAc_2Man_3GlcNAc_2(Fuc)$, $Gal_2GlcNAc_2Man_3GlcNAc_2(Fuc)$, $NANAGal_2GlcNAc_2Man_3GlcNAc_2(Fuc)$, and $NANA_2Gal_2GlcNAc_2Man_3GlcNAc_2(Fuc)$; in an α1,3-linkage or α1,4-linkage fucose to produce a glycoform selected from the group consisting of GlcNAc(Fuc)Man$_5$GlcNAc$_2$, GlcNAc(Fuc)Man$_3$GlcNAc$_2$, GlcNAc$_2$(Fuc$_{1-2}$) Man$_3$GlcNAc$_2$, GalGlcNAc$_2$(Fuc$_{1-2}$)Man$_3$GlcNAc$_2$, Gal$_2$GlcNAc$_2$(Fuc$_{1-2}$)Man3GlcNAc2, NANAGal2GlcNAc2 (Fuc$_{1-2}$)Man$_3$GlcNAc$_2$, and NANA$_2$Gal$_2$GlcNAc$_2$(Fuc$_{1-2}$) Man$_3$GlcNAc$_2$; or in an α1,2-linkage fucose to produce a glycoform selected from the group consisting of Gal(Fuc) GlcNAc$_2$Man$_3$GlcNAc$_2$, Gal$_2$(Fuc$_{1-2}$) GlcNAc$_2$Man$_3$GlcNAc$_2$, NANAGal$_2$(Fuc$_{1-2}$) GlcNAc$_2$Man$_3$GlcNAc$_2$, and NANA$_2$Gal$_2$(Fuc$_{1-2}$) GlcNAc$_2$Man$_3$GlcNAc$_2$.

In further aspects of the above, the complex N-glycans further include fucosylated and non-fucosylated bisected and multiantennary species.

In further aspects, the glycoproteins comprise high mannose N-glycans, including but not limited to, Man$_5$GlcNAc$_2$, or N-glycans that consist of the Man$_3$GlcNAc$_2$ N-glycan structure.

DEFINITIONS

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man3") core structure which is also referred to as the "triammnose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3mannose arm and at least one GlcNAc attached to the 1,6mannose arm of a "trimannose" core. Complex N-glycans may also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans may also have intrachain substitutions comprising "bisecting" GlcNAc and core fucose ("Fuc"). Complex N-glycans may also have multiple antennae on the "trimannose core," often referred to as "multiple antennary glycans." A "hybrid" N-glycan has at least one GlcNAc on the terminal of the 1,3mannose arm of the trimannose core and zero or more mannoses on the 1,6mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as Gal$_2$GlcNAc$_2$Man$_3$GlcNAc$_2$; the term "A1" refers to an N-glycan structure that can be characterized as NANAGal$_2$Gal$_2$GlcNAc$_2$Man$_3$GlcNAc$_2$; and, the term "A2" refers to an N-glycan structure that can be characterized as NANA$_2$Gal$_2$GlcNAc$_2$Man$_3$GlcNAc$_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas GlcNAc$_{(2-4)}$Man$_3$GlcNAc$_2$, Gal$_{(1-4)}$GlcNAc$_{(2-4)}$Man$_3$GlcNAc$_2$, or NANA$_{(1-4)}$Gal$_{(1-4)}$ GlcNAc$_{(2-4)}$Man$_3$GlcNAc$_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula GlcNAc$_3$Man$_3$GlcNAc$_2$ wherein each mannose residue is linked at its non-reducing end to a GlcNAc residue. In contrast, when a multiantennary N-glycan is characterized as GlcNAc$_3$Man$_3$GlcNAc$_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

Abbreviations used herein are of common usage in the art, see, e.g., abbreviations of sugars, above. Other common abbreviations include "PNGase", or "glycanase" or "glucosidase" which all refer to peptide N-glycosidase F (EC 3.2.2.18).

As used herein, the term "glycoprotein" refers to any protein having one or more N-glycans attached thereto. Thus, the term refers both to proteins that are generally recognized in the art as a glycoprotein and to proteins which have been genetically engineered to contain one or more N-linked glycosylation sites.

As used herein, a "humanized glycoprotein" or a "human-like glycoprotein" refers alternatively to a protein having attached thereto N-glycans having fewer than four mannose residues, and synthetic glycoprotein intermediates (which are also useful and can be manipulated further in vitro or in vivo) having at least five mannose residues. Preferably, glycoproteins produced according to the invention contain at least 30 mole %, preferably at least 40 mole % and more preferably 50, 60, 70, 80, 90, or even 100 mole % of the $Man_5GlcNAc_2$ intermediate, at least transiently. This may be achieved, e.g., by engineering a host cell of the invention to express a "better", i.e., a more efficient glycosylation enzyme. For example, a mannosidase is selected such that it will have optimal activity under the conditions present at the site in the host cell where proteins are glycosylated and is introduced into the host cell preferably by targeting the enzyme to a host cell organelle where activity is desired.

The term "recombinant host cell" ("expression host cell", "expression host system", "expression system" or simply "host cell"), as used herein, is intended to refer to a cell into which a recombinant vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism. Preferred host cells are yeasts and fungi.

When referring to "mole percent" of a glycan present in a preparation of a glycoprotein, the term means the molar percent of a particular glycan present in the pool of N-linked oligosaccharides released when the protein preparation is treated with PNGase and then quantified by a method that is not affected by glycoform composition, (for instance, labeling a PNGase released glycan pool with a fluorescent tag such as 2-aminobenzamide and then separating by high performance liquid chromatography or capillary electrophoresis and then quantifying glycans by fluorescence intensity). For example, 50 mole percent $GlcNAc_2Man_3GlcNAc_2Gal_2NANA_2$ means that 50 percent of the released glycans are $GlcNAc_2Man_3GlcNAc_2Gal_2NANA_2$ and the remaining 50 percent are comprised of other N-linked oligosaccharides. In embodiments, the mole percent of a particular glycan in a preparation of glycoprotein will be between 20% and 100%, preferably above 25%, 30%, 35%, 40% or 45%, more preferably above 50%, 55%, 60%, 65% or 70% and most preferably above 75%, 80% 85%, 90% or 95%.

The term "operably linked" expression control sequences refers to a linkage in which the expression control sequence is contiguous with the gene of interest to control the gene of interest, as well as expression control sequences that act in trans or at a distance to control the gene of interest.

The term "expression control sequence" or "regulatory sequences" are used interchangeably and as used herein refer to polynucleotide sequences which are necessary to affect the expression of coding sequences to which they are operably linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transfect", transfection", "transfecting" and the like refer to the introduction of a heterologous nucleic acid into eukaryote cells, both higher and lower eukaryote cells. Historically, the term "transformation" has been used to describe the introduction of a nucleic acid into a yeast or fungal cell; however, herein the term "transfection" is used to refer to the introduction of a nucleic acid into any eukaryote cell, including yeast and fungal cells.

The term "eukaryotic" refers to a nucleated cell or organism, and includes insect cells, plant cells, mammalian cells, animal cells and lower eukaryotic cells.

The term "lower eukaryotic cells" includes yeast and filamentous fungi. Yeast and filamentous fungi include, but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Physcomitrella patens* and *Neurospora crassa. Pichia* sp., any *Saccharomyces* sp., *Hansenula polymorpha*, any *Kluyveromyces* sp., *Candida albicans*, any *Aspergillus* sp., *Trichoderma reesei, Chrysosporium lucknowense*, any *Fusarium* sp. and *Neurospora crassa*.

As used herein, the terms "antibody," "immunoglobulin," "immunoglobulins" and "immunoglobulin molecule" are used interchangeably. Each immunoglobulin molecule has a unique structure that allows it to bind its specific antigen, but all immunoglobulins have the same overall structure as described herein. The basic immunoglobulin structural unit is known to comprise a tetramer of subunits. Each tetramer has two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Light chains are classified as either kappa or lambda. Heavy chains are classified as gamma, mu, alpha, delta, or epsilon, and define the antibody's isotype as IgG, IgM, IgA, IgD, and IgE, respectively.

The light and heavy chains are subdivided into variable regions and constant regions (See generally, Fundamental Immunology (Paul, W., ed., 2nd ed. Raven Press, N.Y., 1989), Ch. 7. The variable regions of each light/heavy chain pair form the antibody binding site. Thus, an intact antibody has two binding sites. Except in bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. The terms include naturally occurring forms, as well as fragments and derivatives. Included within the scope of the term are classes of immunoglobulins (Igs), namely, IgG, IgA, IgE, IgM, and IgD. Also included within the scope of the terms are the subtypes of IgGs, namely, IgG1, IgG2, IgG3, and IgG4. The term is used in the broadest sense and includes single monoclonal antibodies (including agonist and antagonist antibodies) as well as antibody compositions which will bind to multiple epitopes or antigens. The terms specifically cover monoclonal antibodies (including full length monoclonal antibodies), polyclonal antibodies, multispecific antibodies (for example, bispecific antibodies), and antibody fragments so long as they contain or are modified to contain at least the portion of the CH2 domain of the heavy chain immunoglobulin constant region which comprises an N-linked glycosylation site of the CH2 domain, or a variant thereof. Included within the terms are molecules comprising only the Fc region, such as immunoadhesions (U.S. Published Patent Application No. 2004/0136986; the disclosure of which is incorporated herein by reference), Fc fusions, and antibody-like molecules.

The term "Fc fragment" refers to the 'fragment crystallized' C-terminal region of the antibody containing the CH2 and CH3 domains. The term "Fab fragment" refers to the 'fragment antigen binding' region of the antibody containing the VH, CH1, VL and CL domains.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each mAb is directed against a single determinant on the antigen. In addition to their specificity, monoclonal antibodies are advantageous in that they can be produced, for example, by hybridoma culture, uncontaminated by other immunoglobulins. The term "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., (1975) Nature, 256:495, or may be made by recombinant DNA methods (See, for example, U.S. Pat. No. 4,816,567; the disclosure of which is incorporated herein by reference).

The term "fragments" within the scope of the terms "antibody" or "immunoglobulin" include those produced by digestion with various proteases, those produced by chemical cleavage and/or chemical dissociation and those produced recombinantly, so long as the fragment remains capable of specific binding to a target molecule. Among such fragments are Fc, Fab, Fab', Fv, F(ab')2, and single chain Fv (scFv) fragments. Hereinafter, the term "immunoglobulin" also includes the term "fragments" as well.

Immunoglobulins further include immunoglobulins or fragments that have been modified in sequence but remain capable of specific binding to a target molecule, including: interspecies chimeric and humanized antibodies; antibody fusions; heteromeric antibody complexes and antibody fusions, such as diabodies (bispecific antibodies), single-chain diabodies, and intrabodies (See, for example, Intracellular Antibodies: Research and Disease Applications, (Marasco, ed., Springer-Verlag New York, Inc., 1998).

The term "catalytic antibody" refers to immunoglobulin molecules that are capable of catalyzing a biochemical reaction. Catalytic antibodies are well known in the art and have been described in U.S. Pat. Nos. 7,205,136; 4,888,281; 5,037,750 to Schochetman et al., U.S. Pat. Nos. 5,733,757; 5,985,626; and 6,368,839 to Barbas, III et al. (the disclosures of which are all incorporated herein by reference).

The interaction of antibodies and antibody-antigen complexes with cells of the immune system and the variety of responses, including antibody-dependent cell-mediated cytotoxicity (ADCC) and complement-dependent cytotoxicity (CDC), clearance of immunocomplexes (phagocytosis), antibody production by B cells and IgG serum half-life are defined respectively in the following: Daeron et al., Annu. Rev. Immunol. 15: 203-234 (1997); Ward and Ghetie, Therapeutic Immunol. 2:77-94 (1995); Cox and Greenberg, Semin. Immunol. 13: 339-345 (2001); Heyman, Immunol. Lett. 88:157-161 (2003); and Ravetch, Curt Opin. Immunol. 9: 121-125 (1997).

As used herein, the term "consisting essentially of" will be understood to imply the inclusion of a stated integer or group of integers; while excluding modifications or other integers which would materially affect or alter the stated integer. With respect to species of N-glycans, the term "consisting essentially of" a stated N-glycan will be understood to include the N-glycan whether or not that N-glycan is fucosylated at the N-acetylglucosamine (GlcNAc) which is directly linked to the asparagine residue of the glycoprotein.

As used herein, the term "predominantly" or variations such as "the predominant" or "which is predominant" will be understood to mean the glycan species that has the highest mole percent (%) of total neutral N-glycans after the glycoprotein has been treated with PNGase and released glycans analyzed by mass spectroscopy, for example, MALDI-TOF MS or HPLC. In other words, the phrase "predominantly" is defined as an individual entity, such as a specific glycoform, is present in greater mole percent than any other individual entity. For example, if a composition consists of species A at 40 mole percent, species B at 35 mole percent and species C at 25 mole percent, the composition comprises predominantly species A, and species B would be the next most predominant species. Some host cells may produce compositions comprising neutral N-glycans and charged N-glycans such as mannosylphosphate. Therefore, a composition of glycoproteins can include a plurality of charged and uncharged or neutral N-glycans. In the present invention, it is within the context of the total plurality of neutral N-glycans in the composition in which the predominant N-glycan determined. Thus, as used herein, "predominant N-glycan" means that of the total plurality of neutral N-glycans in the composition, the predominant N-glycan is of a particular structure.

As used herein, the term "essentially free of" a particular sugar residue, such as fucose, or galactose and the like, is used to indicate that the glycoprotein composition is substantially devoid of N-glycans which contain such residues. Expressed in terms of purity, essentially free means that the amount of N-glycan structures containing such sugar residues does not exceed 10%, and preferably is below 5%, more preferably below 1%, most preferably below 0.5%, wherein the percentages are by weight or by mole percent. Thus, substantially all of the N-glycan structures in a glycoprotein composition according to the present invention are free of, for example, fucose, or galactose, or both.

As used herein, a glycoprotein composition "lacks" or "is lacking" a particular sugar residue, such as fucose or galactose, when no detectable amount of such sugar residue is present on the N-glycan structures at any time. For example, in preferred embodiments of the present invention, the glycoprotein compositions are produced by lower eukaryotic organisms, as defined above, including yeast (for example, *Pichia* sp.; *Saccharomyces* sp.; *Kluyveromyces* sp.; *Aspergillus* sp.), and will "lack fucose," because the cells of these organisms do not have the enzymes needed to produce fucosylated N-glycan structures. Thus, the term "essentially free of fucose" encompasses the term "lacking fucose." However, a composition may be "essentially free of fucose" even if the composition at one time contained fucosylated N-glycan structures or contains limited, but detectable amounts of fucosylated N-glycan structures as described above.

BRIEF DESCRIPTION OF THE DRAWINGS

FIG. 23 A-D shows the genealogy of *P. pastoris* strain YGLY12900 beginning from YGLY7961.

DETAILED DESCRIPTION OF THE INVENTION

Figure 1A:
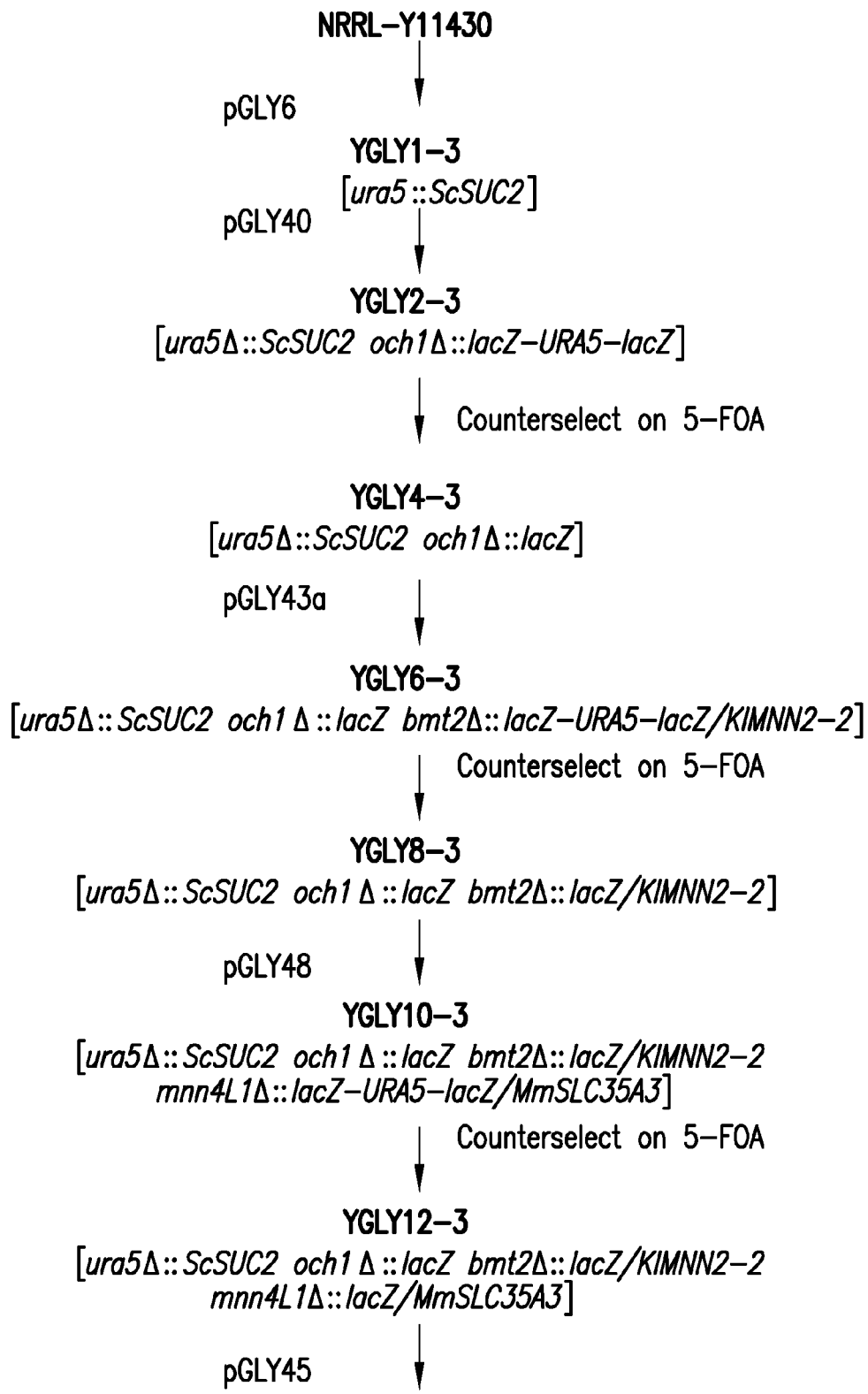
FIGS. 1 A-H shows the genealogy of *P. pastoris* strain YGLY13992 (FIG. 1F) and strain YGLY14401 (FIG. 1G) beginning from wild-type strain NRRL-Y11430 (FIG. 1A).
Figure 1B:
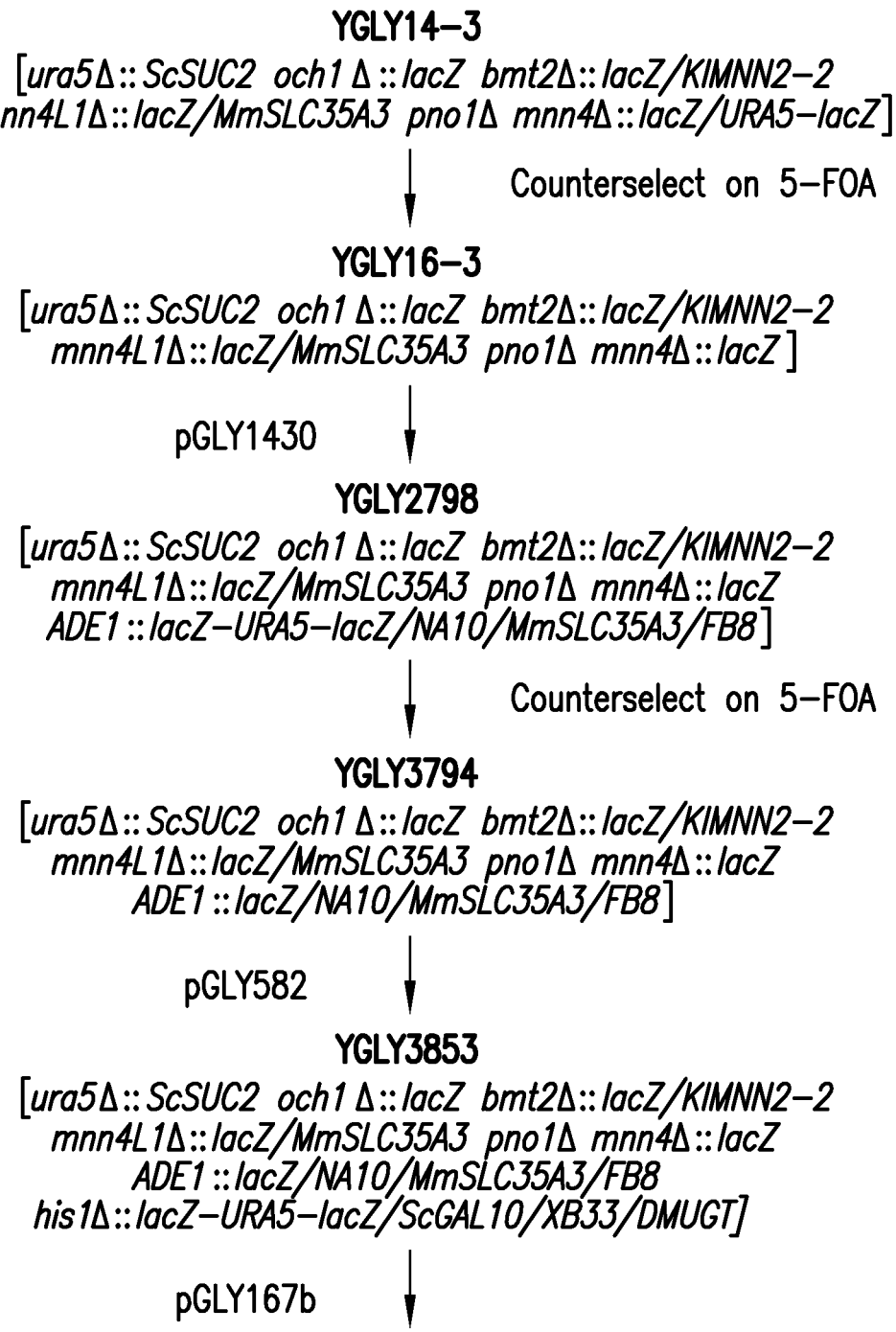

The present invention provides a method for producing a therapeutic glycoprotein in a host cell in which the N-glycosylation site occupancy of the glycoprotein is increased over the N-glycosylation site occupancy of the same glycoprotein produced in a host cell not modified as disclosed herein. When the present invention is practiced in a lower eukaryote host cell, e.g., yeast host cells or filamentous fungal host cells, the N-glycosylation site occupancy of recombinant glycoproteins produced in the host cell is the same as or more similar to the N-glycosylation site occupancy of the same recombinant glycoproteins produced in mammalian or human host cells.

To increase the N-glycosylation site occupancy on a glycoprotein produced in a recombinant host cell, at least one nucleic acid molecule encoding at least one heterologous single-subunit oligosaccharyltransferase, which in particular embodiments at least one is capable of functionally suppressing a lethal mutation of one or more essential subunits comprising the endogenous host cell hetero-oligomeric oligosaccharyltransferase (OTase) complex, is overexpressed in the recombinant host cell either before or simultaneously with the expression of the glycoprotein in the host cell.

The *Leishmania major* STT3A protein, *Leishmania major* STT3B protein, and *Leishmania major* STT3D protein, are single-subunit oligosaccharyltransferases that have been shown to suppress the lethal phenotype of a deletion of the STT3 locus in *Saccharomyces cerevisiae* (Naseb et al., Molec. Biol. Cell 19: 3758-3768 (2008)). Naseb et al. (ibid.) further showed that the *Leishmania major* STT3D protein could suppress the lethal phenotype of a deletion of the WBP1, OST1, SWP1, or OST2 loci. Hese et al. (Glycobiology 19: 160-171 (2009)) teaches that the *Leishmania major* STT3A (STT3-1), STT3B (STT3-2), and STT3D (STT3-4) proteins can functionally complement deletions of the OST2, SWP1, and WBP1 loci. The *Leishmania major* STT3D (LmSTT3D) protein is a heterologous single-subunit oligosaccharyltransferases that is capable of suppressing a lethal phenotype of a Δstt3 mutation and at least one lethal phenotype of a Δwbp1, Δost1, Δswp1, and Δost2 mutation that is shown in the examples herein to be capable of enhancing the N-glycosylation site occupancy of heterologous glycoproteins, for example antibodies, produced by the host cell.

The one or more heterologous single-subunit oligosaccharyltransferases is/are overexpressed constitutively or inducibly in the presence of the proteins comprising the host cell's endogenous OTase complex, including the host cell's STT3 protein. An expression cassette encoding each heterologous single-subunit oligosaccharyltransferase gene can either be integrated into any site within the host cell genome or located in the extrachromosomal space of the host cell, i.e., autonomously replicating genetic elements such as plasmids, viruses, 2 μm plasmid, minichromosomes, and the like. In general, the heterologous single-subunit oligosaccharyltransferases are provided to the host cell in expression cassettes, each comprising a nucleic acid molecule encoding a single-subunit oligosaccharyltransferase open reading frame (ORF) operably linked to a heterologous constitutive or inducible promoter and other heterologous transcriptional or translational regulatory elements suitable for expressing heterologous proteins in a particular host cell. One or more copies of each expression cassette is/are integrated into one or more locations in the host cell's genome either by site-specific targeting of a particular locus for integration or randomly integrating the expression cassette into the genome. The locus for targeted integration can be selected based upon the suitability of the locus for ectopic constitutive or inducible expression of the single-subunit oligosaccharyltransferase in the expression cassette. Methods for integrating heterologous nucleic acid molecules into a host cell genome by techniques such as single- and double-crossover homologous recombination and the like are well known in the art (See for example, U.S. Published Application No. 20090124000 and International Published Application No. WO2009085135, the disclosures of which are incorporated herein by reference). Alternatively, or in addition to integrating one or more copies of the expression cassette into the host cell genome, one or more copies of the expression cassette are located in the extrachromosomal space of the host cell using a 2μ plasmid, viral vector, mini-chromosome, or other genetic vector that replicates autonomously.

While the present invention has been exemplified herein with *Pichia pastoris* host cells genetically engineered to produce mammalian or human-like glycosylation patterns comprising complex N-glycans, the present invention to increase the overall amount of N-glycosylation site occupancy of the glycoproteins produced in the host cell compared to that of glycoproteins produced in the host not modified as disclosed herein to express the single-subunit oligosaccharyltransferase gene can also be applied to *Pichia pastoris* host cells that are not genetically engineered to produce glycoproteins that have mammalian or human glycosylation patterns but instead express glycoproteins that have endogenous or wild-type glycosylation patterns, for example hypermannosylated N-glycosylation or when the host cell lacks alpha-1,6-mannosylatransferase (och1p) activity, high mannose N-glycosylation. The present invention can also be applied to other yeast or filamentous fungi or to plant or algal host cells, which express glycoproteins that have endogenous or wild-type glycosylation patterns, for example hypermannosylated N-glycosylation or when the host cell lacks alpha-1,6-mannosylatransferase (och1p) activity, high mannose N-glycosylation, or which have been genetically engineered to produce mammalian or human-like complex or hybrid N-glycans to increase the overall amount of N-glycosylation site occupancy of the glycoproteins produced in the host cell compared to that of glycoproteins produced in the host not modified as disclosed herein to express the single-subunit oligosaccharyltransferase gene. The present invention can also be applied to mammalian expression systems to increase the overall N-glycosylation site occupancy of glycoproteins that have more than two N-linked sites compared to that of glycoproteins produced in the host cell not modified as disclosed herein to express the single-subunit oligosaccharyltransferase gene.

The OTase complex of animals, plants, and fungi is a hetero-oligomeric protein complex. In the well-studied model organism *Saccharomyces cerevisiae*, the OTase complex currently appears to consist of at least eight different subunits: Ost1p, Ost2p, Wbp1, Stt3p, Swp1p, Ost4p, Ost5p, and Ost3p/Ost6p (Silberstein & Gilmore, FASEB J. 10: 849-858 (1996); Knauer & Lehle, Biochim. Biophys. Acta. 1426: 259-273 (1999); Dempski & Imperiali, Curt Opin. Chem. Biol. 6: 844-850 (2002); Yan & Lennarz, J. Biol. Chem. 277: 47692-47700 (2005); Kelleher & Gilmore, Glycobiol. 16:47R-62R (2006); Weerapana & Imperiali, Glycobiol. 16: 91R-101R (2006)). In *Pichia pastoris*, the OTase complex appears to include at least Ost1p, Ost2p, Ost3p, Ost4p, Ost6p, Wbp1, Swp1p, and Stt3p (See Shutter et al., Nat. Biotechnol. 27: 561-566 (2009)).

It has been hypothesized that the STT3 protein is the catalytic subunit in the OTase complex (Yan & Lennarz, J. Biol. Chem. 277: 47692-47700 (2002); Kelleher et al., Mol. Cell. 12: 101-111 (2003); Nilsson et al., J. Cell Biol. 161: 715-725 (2003)). Support for this hypothesis is from experiments showing that the prokaryotic homologue of yeast Stt3p is an active oligosaccharyltransferase in the absence of any other accessory proteins (Wacker et al., Science, 298: 1790-1793 (2002); Kowarik et al., Science 314: 1148-1150 (2006)). Proteins homologous to yeast Stt3p are encoded in almost all eukaryotic genomes (Kelleher & Gilmore, Glycobiol. 16:47R-62R (2006)). However, comparative genome analysis suggests that the composition of the OTase became increasing complex during the evolutionary divergence of eukaryotes.

Single-subunit oligosaccharyltransferases are present in *Giardia* and kinetoplastids, whereas four subunit oligosaccharyltransferases consisting of the STT3, OST1, OST2, and WBP1 homologues are found in diplomonads, entamoebas, and apicomplexan species. Additionally, multiple forms of the putative STT3 proteins can be encoded in trypanosomatid genomes: three STT3 homologues are found in *Trypanosoma brucei* and four in *Leishmania major* (McConville et al., Microbiol. Mal. Biol. Rev. 66: 122-154 (2002); Berriman et al., Science. 309: 416-422 (2005); Ivens et al., Science. 309: 436-442 (2005); Samuelson et al., Proc. Natl. Acad, Sci. USA 102: 1548-1553 (2005); Kelleher & Gilmore, Glycobiol. 16:47R-62R (2006)).

In trypanosomatid parasites, N-linked glycosylation principally follows the pathway described for fungal or animal cells, but with different oligosaccharide structures transferred to protein (Parodi, Glycobiology 3: 193-199 (1993); McConville et al., Microbiol. Mol. Biol. Rev. 66: 122-154 (2002)). It has been shown that, depending on the species, either $Man_6GlcNAc_2$ or $Man_7GlcNAc_2$ is the largest glycan transferred to protein in the genus *Leishmania* (Parodi, Glycobiology 3: 193-199 (1993). Unlike the yeast and mammalian oligosaccharyltransferase that preferably use $Glc_3Man_9GlcNAc_2$, the trypanosome oligosaccharyltransferase is not selective and transfers different lipid-linked oligosaccharides at the same rate (Bosch et al., J. Biol. Chem. 263:17360-17365 (1988)). Therefore, the simplest eukaryotic oligossaccharyltransferase is a single subunit STT3 protein, similar to the oligosaccharyltransferase found in bacterial N-glycosylation systems. Nasab et al., Molecular Biology of the Cell 19: 3758-3768 (2008) expressed each of the four *Leishmania major* STT3 proteins individually in *Saccharomyces cerevisiae* and found that three of them, LmSTT3A protein, LmSTT3B protein, and LmSTT3D protein, were able to complement a deletion of the yeast STT3 locus. In addition, LmSTT3D expression suppressed the lethal phenotype of single and double deletions in genes encoding various essential OTase subunits. The LmSTT3 proteins did not incorporate into the yeast OTase complex but instead formed a homodimeric enzyme, capable of replacing the endogenous, multimeric enzyme of the yeast cell. The results indicate that while these single-subunit oligosaccharyltransferases may resemble the prokaryotic enzymes, they use substrates typical for eukaryote glycosylation: that is, the N—X—S/T N-glycosylation recognition site and dolicholpyrophosphate-linked high mannose oligosaccharides.

N-glycosylation site occupancy in yeast has also been discussed in reports by, for example, Schultz and Aebi, Molec. Cell. Proteomics 8: 357-364 (2009); Hese et al., op. cit.) and Nasab et al., (op. cit.). Expression of the *Toxoplasma gondii* or *Trypanosoma cruzi* STT3 protein in *Saccharomyces cerevisiae* has been shown to complement the lethal phenotype of an stt3 deletion (Shams-Eldin et al., Mol. Biochem. Parasitol. 143: 6-11 (2005); Castro et al., Proc. Natl. Acad. Sci. USA 103: 14756-14760 (2006) and while the *Trypanosoma cruzi* STT3 protein integrates into the yeast OTase complex the *Leishmania major* STT3 proteins appear to form homodimers instead (Nasab et al., op. cit.). However, in these reports, the LmSTT3D protein had been tested for its functional suppression of a lethal mutation of the endogenous yeast STT3 locus and other essential components of the yeast OTase complex in studies that measured N-glycosylation site occupancy of endogenous proteins. In addition, the yeast strains that were used in the studies produced glycoproteins that had a yeast glycosylation pattern, not a mammalian or human-like glycosylation pattern comprising hybrid or complex N-glycans.

In contrast to the above reports, in the present invention the open reading frame encoding a heterologous single-subunit oligosaccharyltransferase (as exemplified herein with the open reading frame encoding the LmSTT3D) protein is overexpressed constitutively or inducibly in the recombinant host cell in which the host cell further expresses the endogenous genes encoding the proteins comprising the host cell oligosaccharyltransferase (OTase) complex, which includes the expression of the endogenous host cell STT3 gene. Thus, the host cell expresses both the heterologous single-subunit oligosaccharyltransferase and the endogenous host cell OTase complex, including the endogenous host cell SST3 protein. Furthermore, with respect to recombinant yeast, filamentous fungus, algal, or plant host cells, the host cells can further be genetically engineered to produce glycoproteins that comprise a mammalian or human-like glycosylation pattern comprising complex and/or hybrid N-glycans and not glycoproteins that have the host cells' endogenous glycosylation pattern.

The present invention has been exemplified herein using *Pichia pastoris* host cells genetically engineered to produce mammalian- or human-like complex N-glycans; however, the present invention can be applied to other yeast ost cells (including but not limited to *Saccharomyces cerevisiae*, *Schizosaccharomyces pombe*, *Ogataea minuta*, and *Pichia pastoris*) or filamentous fungi (including but not limited to *Tricoderma reesei*) that produce glycoproteins that have yeast or fungal N-glycans (either hypermannosylated N-glycans or high mannose N-glycans) or genetically engineered to produce glycoproteins that have mammalian- or human-like high mannose, complex, or hybrid N-glycans to improve the overall N-glycosylation site occupancy of glycoproteins produced in the host cell. Furthermore, the present invention can also be applied to plant and mammalian expression system to improve the overall N-glycosylation site occupancy of glycoproteins produced in these plant or mammalian expression systems, particularly glycoproteins that have more than two N-linked glycosylation sites.

Therefore, in one aspect of the above, provided is a method for producing a heterologous glycoprotein in a host cell, comprising providing a host cell that includes a nucleic acid molecule encoding at least one heterologous single-subunit oligosaccharyltransferase and a nucleic acid molecule encoding the heterologous glycoprotein and wherein the endogenous host cell genes encoding the proteins comprising the endogenous oligosaccharyltransferase (OTase) complex are expressed; and culturing the host cell under conditions for expressing the heterologous glycoprotein to produce the heterologous glycoprotein.

In a further aspect of the above, provided is a method for producing a heterologous glycoprotein with mammalian- or human-like complex or hybrid N-glycans in a host cell, comprising providing a host cell that is genetically engineered to produce glycoproteins that have human-like N-glycans and includes a nucleic acid molecule encoding at least one heterologous single-subunit oligosaccharyltransferase and a nucleic acid molecule encoding the heterologous glycoprotein and wherein the endogenous host cell genes encoding the proteins comprising the endogenous oligosaccharyltransferase (OTase) complex are expressed; and culturing the host cell under conditions for expressing the heterologous glycoprotein to produce the heterologous glycoprotein.

Expression of the endogenous host cell genes encoding the proteins comprising the oligosaccharyltransferase (OTase) complex includes expression of the endogenous host cell gene encoding the endogenous STT3 protein or homologue. In the case of yeast host cells, the endogenous host cell genes encoding the proteins comprising the OTase complex are expressed, which includes the expression of the endogenous STT3 gene. Currently, the genes encoding proteins comprising the *Saccharomyces cerevisiae* OTase complex are known to include OST1, OST2, OST3, OST4, OST5, OST6, WBP1, SWP1, and STT3 (See for example, Spirig et al., Molec. Gen. Genet. 256: 628-637 (1997) and in *Pichia pastoris*, the OTase complex appears to include at least Ost1p, Ost2p, Ost3p, Ost4p, Ost6p, Wbp1, Swp1p, and Stt3p (See Shutter et al., op. cit.).

In general, the heterologous single-subunit oligosaccharyltransferase is capable of functionally suppressing the lethal phenotype of a mutation of at least one essential protein of an OTase complex, for example, a yeast OTase complex. Thus, the heterologous single-subunit oligosaccharyltransferase is capable of functionally complementing or rescuing a lethal mutation of at least one essential protein of an OTase complex. In further aspects, the essential protein of the OTase complex is encoded by the *Saccharomyces cerevisiae* and/or *Pichia pastoris* STT3 locus, WBP1 locus, OST1 locus, SWP1 locus, or OST2 locus, or homologue thereof. In general, heterologous single-subunit oligosaccharyltransferases that can be used in the methods herein for increasing N-glycosylation site occupancy is a heterologous single-subunit oligosaccharyltransferase that in particular embodiments is capable of functionally suppressing (or rescuing or complementing) the lethal phenotype of at least one essential protein of the *Saccharomyces cerevisiae* and/or *Pichia pastoris* OTase complex. For example, in further aspects, the heterologous single-subunit oligosaccharyltransferase is the *Leishmania major* STT3D protein, which is capable of functionally suppressing (or rescuing or complementing) the lethal phenotype of at least one essential protein of the *Saccharomyces cerevisiae* or *Pichia pastoris* OTase complex. Therefore, for a particular host cell, a particular heterologous single-subunit oligosaccharyltransferase is suitable for expression in the particular host cell provided the single-subunit heterologous oligosaccharyltransferase is capable of suppressing the lethal phenotype of at least one essential protein of the yeast OTase complex. In further aspect, a heterologous single-subunit heterologous oligosaccharyltransferase is selected for expression in a particular host cell provided the single-subunit heterologous oligosaccharyltransferase is capable of suppressing the lethal phenotype of at least one essential protein of the *Saccharomyces cerevisiae* and/or *Pichia pastoris* OTase complex. The essential proteins include OST1, OST2, WBP1, SWP1, and STT3.

As used herein, a lethal mutation includes a deletion or disruption of the gene encoding the essential protein of the OTase complex or a mutation in the coding sequence that renders the essential protein non-functional. The term can further include knock-down mutations wherein production of a functional essential protein is abrogated using snRNA or RNAi.

Further provided is a host cell, comprising a first nucleic acid molecule encoding at least one heterologous single-subunit oligosaccharyltransferase; and a second nucleic acid molecule encoding a heterologous glycoprotein; and the host cell expresses its endogenous genes encoding the proteins comprising the endogenous oligosaccharyltransferase (OTase) complex, which includes expressing the endogenous host cell gene encoding the host cell STT3 protein, which in yeast is the STT3 gene. In further aspects of a yeast host cell, the host cell expresses the endogenous genes encoding the proteins comprising the OTase complex.

In particular aspects of any of the above, the host cell further comprises one or more a nucleic acid molecules encoding additional heterologous oligosaccharyltransferases, which can include single-subunit or multimeric oligosaccharyltransferases. For example, the host cell can comprise one or more nucleic acid molecules encoding one or more single-subunit oligosaccharyltransferases selected from the group consisting of the LmSTT3A protein, LmSTT3B protein, and LmSTT3D protein. In further aspects, the host cell can further include a nucleic acid molecule encoding LmSTT3C protein. In further aspects of any one of the above, the host cell can include one or more nucleic acid molecules encoding one or more oligosaccharyltransferases selected from the group consisting of the *Toxoplasma gondii* STT3 protein, *Trypanosoma cruzi* STT3 protein, *Trypanosoma brucei* STT3 protein, and *C. elegans* STT3 protein. In further still aspects of any one of the above, the host cell can further include a nucleic acid molecule encoding the *Pichia pastoris* STT3 protein.

Lower eukaryotes such as yeast or filamentous fungi are often used for expression of recombinant glycoproteins because they can be economically cultured, give high yields, and when appropriately modified are capable of suitable glycosylation. Yeast in particular offers established genetics allowing for rapid transfections, tested protein localization strategies and facile gene knock-out techniques. Suitable vectors have expression control sequences, such as promoters, including 3-phosphoglycerate kinase or other glycolytic enzymes, and an origin of replication, termination sequences, and the like as desired.

Useful lower eukaryote host cells include but are not limited to *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum* and *Neurospora crassa*. Various yeasts, such as *K. lactis, Pichia pastoris, Pichia methanolica,* and *Hansenula polymorpha* are particularly suitable for cell culture because they are able to grow to high cell densities and secrete large quantities of recombinant protein. Likewise, filamentous fungi, such as *Aspergillus niger, Fusarium* sp, *Neurospora crassa* and others can be used to produce glycoproteins of the invention at an industrial scale. In the case of lower eukaryotes, cells are routinely grown from between about one and a half to three days.

Therefore, provided is a method for producing a heterologous glycoprotein in a lower eukaryote host cell, comprising providing a lower eukaryote host cell that includes a nucleic acid molecule encoding a heterologous single-subunit oligosaccharyltransferase and a nucleic acid molecule encoding the heterologous glycoprotein; and culturing the host cell under conditions for expressing the heterologous glycoprotein to produce the heterologous glycoprotein.

Further provided is a lower eukaryote host cell, comprising a first nucleic acid molecule encoding a heterologous single-subunit oligosaccharyltransferase; and a second nucleic acid molecule encoding a heterologous glycoprotein; and wherein the endogenous host cell genes encoding the proteins comprising the oligosaccharyltransferase (OTase) complex are expressed.

Further provided is a yeast or filamentous fungus host cell, comprising a first nucleic acid molecule encoding a heterologous single-subunit oligosaccharyltransferase; and a second nucleic acid molecule encoding a heterologous glycoprotein; and wherein the endogenous host cell genes encoding the proteins comprising the oligosaccharyltransferase (OTase) complex are expressed. This includes expression of the endogenous STT3 gene, which in yeast is the STT3 gene.

In particular aspects, the above yeast or filamentous fungus host cell can be a host cell that produces glycoproteins that have a yeast-like or filamentous fungus-like glycosylation pattern. The yeast glycosylation pattern can include hypermannosylated N-glycans or the yeast can be genetically engineered to lack α-1,6-mannosyltransferase activity, that is, the yeast host is genetically engineered to lack och1p activity, in which case, the yeast produces glycoproteins that have high mannose N-glycans that are not further hypermannosylated.

In particular embodiments of the above methods and host cells, the heterologous single-subunit oligosaccharyltransferase is capable of functionally suppressing the lethal phenotype of a mutation of at least one essential protein of the OTase complex. In further aspects, the essential protein of the OTase complex is encoded by the STT3 locus, WBP1 locus, OST1 locus, SWP1 locus, or OST2 locus, or homologue thereof. In further aspects, the for example single-subunit oligosaccharyltransferase is the *Leishmania major* STT3D protein.

The methods and host cells herein provide a means for producing heterologous glycoproteins in a host cell wherein the N-glycosylation site occupancy of a composition of the heterologous glycoproteins is greater than the N-glycosylation site occupancy for the heterologous produced in the host cell not modified as described herein to express a heterologous single-subunit oligosaccharyltransferase and the endogenous host cell genes encoding the proteins comprising the oligosaccharyltransferase (OTase) complex. For a lower eukaryote host cell such as yeast, when the N-glycosylation site occupancy of a heterologous glycoprotein is lower than that obtained for the heterologous glycoprotein when produced in mammalian or human cells, the N-glycosylation site occupancy of the glycoprotein produced in the host cell can be made the same as or more similar to the N-glycosylation site occupancy of the glycoprotein in the mammalian or human cell by producing the glycoprotein in a host cell that express a heterologous single-subunit oligosaccharyltransferase and the endogenous host cell genes encoding the proteins comprising the oligosaccharyltransferase (OTase) complex. As shown in the examples, *Pichia pastoris* host cells that express a heterologous single-subunit oligosaccharyltransferase and the endogenous host cell genes encoding the proteins comprising the oligosaccharyltransferase (OTase) complex are capable of producing antibodies wherein the N-glycosylation site occupancy of the antibodies is similar to that of the antibodies produced in Chinese hamster ovary (CHO) cells (See also FIG. 19).

A method for measuring N-glycosylation site occupancy is to separate and measure the amount of glycosylated protein and non-glycosylated protein and determine the N-glycosylation site occupancy using the formula (Moles glycosylated protein)/(moles glycosylated protein+moles non-glycosylated protein)× 100=percent *N*-glycosylation site occupancy When measuring the N-glycosylation site occupancy of antibodies in an antibody composition, the antibodies in the composition are reduced and the moles of glycosylated and non-glycosylated heavy chains determined. Each heavy chain has one N-glycosylation site at Asn-297. The percent N-glycosylation site occupancy is determined based upon total moles of N-glycans released and the total moles of antibody heavy chains. For example, an N-glycosylation site occupancy of 94% would indicate that 94% of the heavy chains in the composition have an N-glycan at Asn-297 and 6% of the heavy chains would lack an N-glycan. Antibodies consist of two heavy chains and two light chains. In the above example, antibodies in the composition can have both heavy chains linked to an N-glycan, one of the two heavy chains with an N-glycan, or neither chain with an N-glycan. Therefore, a 94% N-glycosylation site occupancy of heavy chains would suggest that about 88% of the antibodies in the composition would have both heavy chains N-glycosylated and 11.4% of the antibodies would have only one of the two heavy chains N-glycosylated. To get a qualitative indication that the above is correct, whole antibodies are analyzed by a method such as Q-TOF (hybrid quadrupole time of flight mass spectrometer with MS/MS capability).

A general method for measuring N-glycosylation site occupancy of antibodies can use the following method, which is exemplified in Example 3. The antibodies are reduced to heavy chains (HC) and light chains (LC) and the amount of glycosylated heavy chain (GHC) and non-glycosylated heavy chains (NGHC) are determined by a method such as capillary electrophoresis. The N-glycosylation site occupancy using the formula Moles GHC)/(moles GHC+moles NGHC)×100=percent N-glycosylation site HC occupancy For any N-glycosylation site, the site is either occupied or not. Therefore, N-glycan occupancy of 100% would be equivalent to a ratio of 1:1 (1 mole of N-glycan per 1 mole of N-glycosylation site, e.g., heavy chain from reduced antibody) or 2:1 (2 moles of N-glycan per 1 mole of protein with two N-glycosylation sites, e.g., non-reduced antibody). N-glycan occupancy of 80% would be equivalent to a ratio of 0.8:1 (0.8 mole of N-glycan per 1 mole of N-glycosylation site, e.g., heavy chain from reduced antibody) or 1.6:1 (1.6 moles of N-glycan per mole of protein with two N-glycosylation sites, e.g., non-reduced antibody).

An estimate of the proportion of whole antibodies in which both heavy chains are glycosylated can be approximated by the formula (fraction GHC)$^2$×100=fully occupied antibodies (whole, non-reduced antibodies in which both N-glycosylation sites are occupied). Example 3 shows that the methods herein enable the production of antibody compositions wherein about 70% to about 98% of the non-reduced whole antibody molecules in the composition have both N-glycosylation sites occupied. Since measurement of N-glycosylation site occupancy was determined using reduced antibody molecules, the results herein show that for compositions comprising glycoprotein molecules containing a single glycosylation site, more than 84% to at least 99% of the glycoprotein molecules were N-glycosylated. Therefore, the methods and host cells herein enable production of glycoprotein compositions in which at least 70%, 75%, 80%, 85%, 90%, 95%, 98%, or 99% of the N-glycosylation sites of the glycoproteins in the composition are occupied.

Another method for measuring N-glycosylation site occupancy of glycoproteins in a glycoprotein composition can be accomplished by releasing the N-glycans from the glycoproteins in the composition and measuring the molar amount of the N-glycans released and the molar amount of glycoprotein times the number of glycosylation sites on the glycoprotein. The following formula can be used (Total moles of N-glycans)/(Total moles of glycoprotein×No. of sites)×100=percent N-glycosylation site occupancy.

The above formula will give the percent of total N-glycosylation sites that are occupied.

Lower eukaryotes, particularly yeast, can be genetically modified so that they express glycoproteins in which the glycosylation pattern is mammalian or human-like or humanized. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in U.S. Published Application No. 2004/0018590, the disclosure of which is incorporated herein by reference. If desired, additional genetic engineering of the glycosylation can be performed, such that the glycoprotein can be produced with or without core fucosylation.

Lower eukaryotes such as yeast can be genetically modified so that they express glycoproteins in which the glycosylation pattern is mammalian-like or human-like or humanized. Such can be achieved by eliminating selected endogenous glycosylation enzymes and/or supplying exogenous enzymes as described by Gerngross et al., U.S. Pat. No. 7,449,308, the disclosure of which is incorporated herein by reference. Thus, in particular aspects of the invention, the host cell is yeast, for example, a methylotrophic yeast such as *Pichia pastoris* or *Ogataea minuta* and mutants thereof and genetically engineered variants thereof. In this manner, glycoprotein compositions can be produced in which a specific desired glycoform is predominant in the composition. Such can be achieved by eliminating selected endogenous glycosylation enzymes and/or genetically engineering the host cells and/or supplying exogenous enzymes to mimic all or part of the mammalian glycosylation pathway as described in U.S. Pat. No. 7,449,308, the disclosure of which is incorporated herein by reference. If desired, additional genetic engineering of the glycosylation can be performed, such that the glycoprotein can be produced with or without core fucosylation. Use of lower eukaryotic host cells such as yeast are further advantageous in that these cells are able to produce relatively homogenous compositions of glycoprotein, such that the predominant glycoform of the glycoprotein may be present as greater than thirty mole percent of the glycoprotein in the composition. In particular aspects, the predominant glycoform may be present in greater than forty mole percent, fifty mole percent, sixty mole percent, seventy mole percent and, most preferably, greater than eighty mole percent of the glycoprotein present in the composition. Such can be achieved by eliminating selected endogenous glycosylation enzymes and/or supplying exogenous enzymes as described by Gerngross et al., U.S. Pat. Nos. 7,029,872 and 7,449,308, the disclosures of which are incorporated herein by reference. For example, a host cell can be selected or engineered to be depleted in 1,6-mannosyl transferase activities, which would otherwise add mannose residues onto the N-glycan on a glycoprotein.

In one embodiment, the host cell further includes an α1,2-mannosidase catalytic domain fused to a cellular targeting signal peptide not normally associated with the catalytic domain and selected to target the α1,2-mannosidase activity to the ER or Golgi apparatus of the host cell. Passage of a recombinant glycoprotein through the ER or Golgi apparatus of the host cell produces a recombinant glycoprotein comprising a Man$_5$GlcNAc$_2$ glycoform, for example, a recombinant glycoprotein composition comprising predominantly a Man$_5$GlcNAc$_2$ glycoform. For example, U.S. Pat. Nos. 7,029,872 , 7,449,308, and U.S. Published Patent Application No. 2005/0170452, the disclosures of which are all incorporated herein by reference, disclose lower eukaryote host cells capable of producing a glycoprotein comprising a Man$_5$GlcNAc$_2$ glycoform.

In a further embodiment, the immediately preceding host cell further includes an N-acetylglucosaminyltransferase I (GlcNAc transferase I or GnT I) catalytic domain fused to a cellular targeting signal peptide not normally associated with the catalytic domain and selected to target GlcNAc transferase I activity to the ER or Golgi apparatus of the host cell. Passage of the recombinant glycoprotein through the ER or Golgi apparatus of the host cell produces a recombinant glycoprotein comprising a GlcNAcMan$_5$GlcNAc$_2$ glycoform, for example a recombinant glycoprotein composition comprising predominantly a GlcNAcMan$_5$GlcNAc$_2$ glycoform. U.S. Pat. Nos. 7,029,872, 7,449,308, and U.S. Published Patent Application No. 2005/0170452, the disclosures of which are all incorporated herein by reference, disclose lower eukaryote host cells capable of producing a glycoprotein comprising a GlcNAcMan$_5$GlcNAc$_2$ glycoform. The glycoprotein produced in the above cells can be treated in vitro with a hexaminidase to produce a recombinant glycoprotein comprising a Man$_5$GlcNAc2 glycoform.

In a further embodiment, the immediately preceding host cell further includes a mannosidase II catalytic domain fused to a cellular targeting signal peptide not normally associated with the catalytic domain and selected to target mannosidase II activity to the ER or Golgi apparatus of the host cell. Passage of the recombinant glycoprotein through the ER or Golgi apparatus of the host cell produces a recombinant glycoprotein comprising a GlcNAcMan$_3$GlcNAc$_2$ glycoform, for example a recombinant glycoprotein composition comprising predominantly a GlcNAcMan$_3$GlcNAc$_2$ glycoform. U.S. Pat. Nos. 7,029,872 and 7,625,756, the disclosures of which are all incorporated herein by reference, discloses lower eukaryote host cells that express mannosidase II enzymes and are capable of producing glycoproteins having predominantly a GlcNAc$_2$Man$_3$GlcNAc$_2$ glycoform. The glycoprotein produced in the above cells can be treated in vitro with a hexaminidase to produce a recombinant glycoprotein comprising a Man$_3$GlcNAc$_2$ glycoform.

In a further embodiment, the immediately preceding host cell further includes N-acetylglucosaminyltransferase II (GlcNAc transferase II or GnT II) catalytic domain fused to a cellular targeting signal peptide not normally associated with the catalytic domain and selected to target GlcNAc transferase II activity to the ER or Golgi apparatus of the host cell. Passage of the recombinant glycoprotein through the ER or Golgi apparatus of the host cell produces a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform. U.S. Pat. Nos. 7,029,872 and 7,449,308 and U.S. Published Patent Application No. 2005/0170452, the disclosures of which are all incorporated herein by reference, disclose lower eukaryote host cells capable of producing a glycoprotein comprising a GlcNAc$_2$Man$_3$GlcNAc$_2$ glycoform. The glycoprotein produced in the above cells can be treated in vitro with a hexaminidase to produce a recombinant glycoprotein comprising a Man$_3$GlcNAc$_2$ glycoform.

In a further embodiment, the immediately preceding host cell further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising a GalGlcNAc$_2$Man$_3$GlcNAc$_2$ or Gal$_2$GlcNAc$_2$Man$_3$GlcNAc$_2$ glycoform, or mixture thereof for example a recombinant glycoprotein composition comprising predominantly a GalGlcNAc$_2$Man$_3$GlCNAc$_2$ glycoform or Gal$_2$GlcNAc$_2$Man$_3$GlcNAc$_2$ glycoform or mixture thereof. U.S. Pat. No. 7,029,872 and U.S. Published Patent Application No. 2006/0040353, the disclosures of which are incorporated herein by reference, discloses lower eukaryote host cells capable of producing a glycoprotein comprising a Gal$_2$GlcNAc$_2$Man$_3$GlcNAc$_2$ glycoform. The glycoprotein produced in the above cells can be treated in vitro with a galactosidase to produce a recombinant glycoprotein comprising a GlcNAc$_2$Man$_3$GlcNAc$_2$ glycoform, for example a recombinant glycoprotein composition comprising predominantly a GlcNAc$_2$Man$_3$GlcNAc$_2$ glycoform.

In a further embodiment, the immediately preceding host cell further includes a sialyltransferase catalytic domain fused to a cellular targeting signal peptide not normally associated with the catalytic domain and selected to target sialyltransferase activity to the ER or Golgi apparatus of the host cell. Passage of the recombinant glycoprotein through the ER or Golgi apparatus of the host cell produces a recombinant glycoprotein comprising predominantly a NANA$_2$Gal$_2$GlcNAc$_2$Man$_3$GlcNAc$_2$ glycoform or NANAGal$_2$GlcNAc$_2$Man$_3$GlcNAc$_2$ glycoform or mixture thereof. For lower eukaryote host cells such as yeast and filamentous fungi, it is useful that the host cell further include a means for providing CMP-sialic acid for transfer to the N-glycan. U.S. Published Patent Application No. 2005/0260729, the disclosure of which is incorporated herein by reference, discloses a method for genetically engineering lower eukaryotes to have a CMP-sialic acid synthesis pathway and U.S. Published Patent Application No. 2006/0286637, the disclosure of which is incorporated herein by reference, discloses a method for genetically engineering lower eukaryotes to produce sialylated glycoproteins. The glycoprotein produced in the above cells can be treated in vitro with a neuraminidase to produce a recombinant glycoprotein comprising predominantly a Gal$_2$GlcNAc$_2$Man$_3$GlcNAc$_2$ glycoform or GalGlcNAc$_2$Man$_3$GlcNAc$_2$ glycoform or mixture thereof.

Any one of the preceding host cells can further include one or more GlcNAc transferase selected from the group consisting of GnT III, GnT IV, GnT V, GnT VI, and GnT IX to produce glycoproteins having bisected (GnT III) and/or multiantennary (GnT IV, V, VI, and IX) N-glycan structures such as disclosed in U.S. Pat. No. 7,598,055 and U.S. Published Patent Application No, 2007/0037248, the disclosures of which are all incorporated herein by reference.

In further embodiments, the host cell that produces glycoproteins that have predominantly GlcNAcMan$_5$GlcNAc$_2$ N-glycans further includes a galactosyltransferase catalytic domain fused to a cellular targeting signal peptide not normally associated with the catalytic domain and selected to target galactosyltransferase activity to the ER or Golgi apparatus of the host cell. Passage of the recombinant glycoprotein through the ER or Golgi apparatus of the host cell produces a recombinant glycoprotein comprising predominantly the GalGlcNAcMan$_5$GlcNAc$_2$ glycoform.

In a further embodiment, the immediately preceding host cell that produced glycoproteins that have predominantly the GalGlcNAcMan$_5$GlcNAc$_2$ N-glycans further includes a sialyltransferase catalytic domain fused to a cellular targeting signal peptide not normally associated with the catalytic domain and selected to target sialytransferase activity to the ER or Golgi apparatus of the host cell. Passage of the recombinant glycoprotein through the ER or Golgi apparatus of the host cell produces a recombinant glycoprotein comprising a NANAGalGlcNAcMan$_5$GlcNAc$_2$ glycoform.

In further aspects, any one of the aforementioned host cells, the host cell is further modified to include a fucosyltransferase and a pathway for producing fucose and transporting fucose into the ER or Golgi. Examples of methods for modifying *Pichia pastoris* to render it capable of producing glycoproteins in which one or more of the N-glycans thereon are fucosylated are disclosed in Published International Application No. WO 2008112092, the disclosure of which is incorporated herein by reference. In particular aspects of the invention, the *Pichia pastoris* host cell is further modified to include a fucosylation pathway comprising a GDP-mannose-4,6-dehydratase, GDP-keto-deoxy-mannose-epimerase/GDP-keto-deoxy-galactose-reductase, GDP-fucose transporter, and a fucosyltransferase. In particular aspects, the fucosyltransferase is selected from the group consisting of α1,2-fucosyltransferase, α1,3-fucosyltransferase, α-1,4-fucosyltransferase, and α-1,6-fucosyltransferase.

Various of the preceding host cells further include one or more sugar transporters such as UDP-GlcNAc transporters (for example, *Kluyveromyces lactis* and *Mus musculus* UDP-GlcNAc transporters), UDP-galactose transporters (for example, *Drosophila melanogaster* UDP-galactose transporter), and CMP-sialic acid transporter (for example, human sialic acid transporter). Because lower eukaryote host cells such as yeast and filamentous fungi lack the above transporters, it is preferable that lower eukaryote host cells such as yeast and filamentous fungi be genetically engineered to include the above transporters.

Host cells further include *Pichia pastoris* that are genetically engineered to eliminate glycoproteins having phosphomannose residues by deleting or disrupting one or both of the phosphomannosyltransferase genes PNO1 and MNN4B (See for example, U.S. Pat. Nos. 7,198,921 and 7,259,007; the disclosures of which are all incorporated herein by reference), which in further aspects can also include deleting or disrupting the MNN4A gene. Disruption includes disrupting the open reading frame encoding the particular enzymes or disrupting expression of the open reading frame or abrogating translation of RNAs encoding one or more of the β-mannosyltransferases and/or phosphomannosyltransferases using interfering RNA, antisense RNA, or the like. The host cells can further include any one of the aforementioned host cells modified to produce particular N-glycan structures.

Host cells further include lower eukaryote cells (e.g., yeast such as *Pichia pastoris*) that are genetically modified to control O-glycosylation of the glycoprotein by deleting or disrupting one or more of the protein O-mannosyltransferase (Dol-P-Man:Protein (Ser/Thr) Mannosyl Transferase genes) (PMTs) (See U.S. Pat. No. 5,714,377; the disclosure of which is incorporated herein by reference) or grown in the presence of Pmtp inhibitors and/or an α1,2 mannosidase as disclosed in Published International Application No. WO 2007061631 the disclosure of which is incorporated herein by reference), or both. Disruption includes disrupting the open reading frame encoding the Pmtp or disrupting expression of the open reading frame or abrogating translation of RNAs encoding one or more of the Pmtps using interfering RNA, antisense RNA, or the like. The host cells can further include any one of the aforementioned host cells modified to produce particular N-glycan structures.

Pmtp inhibitors include but are not limited to a benzylidene thiazolidinediones. Examples of benzylidene thiazolidinediones that can be used are 5-[[3,4-bis(phenylmethoxy)phenyl] methylene]-4-oxo-2-thioxo-3-thiazolidineacetic Acid; 5-[[3-(1-Phenylethoxy)-4-(2-phenylethoxy)]phenyl]methylene]-4-oxo-2-thioxo-3-thiazolidineacetic Acid; and 5-[[3-(1-Phenyl-2-hydroxy)ethoxy)-4-(2-phenylethoxy)]phenyl] methylene]-4-oxo-2-thioxo-3-thiazolidineacetic Acid.

In particular embodiments, the function or expression of at least one endogenous PMT gene is reduced, disrupted, or deleted. For example, in particular embodiments the function or expression of at least one endogenous PMT gene selected from the group consisting of the PMT1, PMT2, PMT3, and PMT4 genes is reduced, disrupted, or deleted; or the host cells are cultivated in the presence of one or more PMT inhibitors. In further embodiments, the host cells include one or more PMT gene deletions or disruptions and the host cells are cultivated in the presence of one or more Pmtp inhibitors. In particular aspects of these embodiments, the host cells also express a secreted α-1,2-mannosidase.

PMT deletions or disruptions and/or Pmtp inhibitors control O-glycosylation by reducing O-glycosylation occupancy; that is by reducing the total number of O-glycosylation sites on the glycoprotein that are glycosylated. The further addition of an α-1,2-mannosidase that is secreted by the cell controls O-glycosylation by reducing the mannose chain length of the O-glycans that are on the glycoprotein. Thus, combining PMT deletions or disruptions and/or Pmtp inhibitors with expression of a secreted α-1,2-mannosidase controls O-glycosylation by reducing occupancy and chain length. In particular circumstances, the particular combination of PMT deletions or disruptions, Pmtp inhibitors, and α-1,2-mannosidase is determined empirically as particular heterologous glycoproteins (antibodies, for example) may be expressed and transported through the Golgi apparatus with different degrees of efficiency and thus may require a particular combination of PMT deletions or disruptions, Pmtp inhibitors, and α-1,2-mannosidase. In another aspect, genes encoding one or more endogenous mannosyltransferase enzymes are deleted. The deletion(s) can be in combination with providing the secreted α-1,2-mannosidase and/or PMT inhibitors or can be in lieu of providing the secreted α-1,2-mannosidase and/or PMT inhibitors.

Thus, the control of O-glycosylation can be useful for producing particular glycoproteins in the host cells disclosed herein in better total yield or in yield of properly assembled glycoprotein. The reduction or elimination of O-glycosylation appears to have a beneficial effect on the assembly and transport of glycoproteins such as whole antibodies as they traverse the secretory pathway and are transported to the cell surface. Thus, in cells in which O-glycosylation is controlled, the yield of properly assembled glycoproteins such as antibody fragments is increased over the yield obtained in host cells in which O-glycosylation is not controlled.

To reduce or eliminate the likelihood of N-glycans and O-glycans with β-linked mannose residues, which are resistant to α-mannosidases, the recombinant glycoengineered *Pichia pastoris* host cells are genetically engineered to eliminate glycoproteins having α-mannosidase-resistant N-glycans by deleting or disrupting one or more of the β-mannosyltransferase genes (e.g., BMT1, BMT2, BMT3, and BMT4)(See, U.S. Pat. Nos. 7,465,577 and 7,713,719). The deletion or disruption of BMT2 and one or more of BMT1, BMT3, and BMT4 also reduces or eliminates detectable cross reactivity to antibodies against host cell protein.

Yield of glycoprotein can in some situations be improved by overexpressing nucleic acid molecules encoding mammalian or human chaperone proteins or replacing the genes encoding one or more endogenous chaperone proteins with nucleic acid molecules encoding one or more mammalian or human chaperone proteins. In addition, the expression of mammalian or human chaperone proteins in the host cell also appears to control O-glycosylation in the cell. Thus, further included are the host cells herein wherein the function of at least one endogenous gene encoding a chaperone protein has been reduced or eliminated, and a vector encoding at least one mammalian or human homolog of the chaperone protein is expressed in the host cell. Also included are host cells in which the endogenous host cell chaperones and the mammalian or human chaperone proteins are expressed. In further aspects, the lower eukaryotic host cell is a yeast or filamentous fungi host cell. Examples of the use of chaperones of host cells in which human chaperone proteins are introduced to improve the yield and reduce or control O-glycosylation of recombinant proteins has been disclosed in Published International Application No. WO 2009105357 and WO2010019487 (the disclosures of which are incorporated herein by reference). Like above, further included are lower eukaryotic host cells wherein, in addition to replacing the genes encoding one or more of the endogenous chaperone proteins with nucleic acid molecules encoding one or more mammalian or human chaperone proteins or overexpressing one or more mammalian or human chaperone proteins as described above, the function or expression of at least one endogenous gene encoding a protein O-mannosyltransferase (PMT) protein is reduced, disrupted, or deleted. In particular embodiments, the function of at least one endogenous PMT gene selected from the group consisting of the PMT1, PMT2, PMT3, and PMT4 genes is reduced, disrupted, or deleted.

Therefore, the methods disclose herein can use any host cell that has been genetically modified to produce glycoproteins wherein the predominant N-glycan is selected from the group consisting of complex N-glycans, hybrid N-glycans, and high mannose N-glycans wherein complex N-glycans may be selected from the group consisting of $GlcNAc_{(2-4)}Man_3GlcNAc_2$, $Gal_{(1-4)}GlcNAc_{(2-4)}Man_3GlcNAc_2$, and $NANA_{(1-4)}Gal_{(1-4)}GlcNAc_{(2-4)}Man_3GlcNAc_2$; hybrid N-glycans maybe selected from the group consisting of $GlcNAcMan_3GlcNAc_2$; $GalGlcNAcMan_3GlcNAc_2$; $NANAGalGlcNAcMan_3GlcNAc_2$ $GlcNAcMan_5GlcNAc_2$, $GalGlcNAcMan_5GlcNAc_2$, and $NANAGalGlcNAcMan_5GlcNAc_2$; and high Mannose N-glycans maybe selected from the group consisting of $Man_5GlcNAc_2$, $Man_6GlcNAc_2$, $Man_7GlcNAc_2$, $Man_8GlcNAc_2$, and $Man_9GlcNAc_2$. Further included are glycoproteins having N-glycans consisting of the N-glycan structure $Man_3GlcNAc_2$, for example, as shown in U.S. Published Application No. 20050170452.

Therefore, provided is a method for producing a heterologous glycoprotein with mammalian- or human-like complex or hybrid N-glycans in a lower eukaryote host cell, comprising providing a lower eukaryote host cell that is genetically engineered to produce glycoproteins that have human-like N-glycans and includes a nucleic acid molecule encoding a heterologous single-subunit oligosaccharyltransferase and a nucleic acid molecule encoding the heterologous glycoprotein; and culturing the host cell under conditions for expressing the heterologous glycoprotein to produce the heterologous glycoprotein.

In a further aspect of the above, provided is a method for producing a heterologous glycoprotein with mammalian- or human-like complex or hybrid N-glycans in a yeast or filamentous fungus host cell, comprising providing a yeast or filamentous fungus host cell that is genetically engineered to produce glycoproteins that have human-like N-glycans and includes a nucleic acid molecule encoding a heterologous single-subunit oligosaccharyltransferase and a nucleic acid molecule encoding the heterologous glycoprotein; and culturing the host cell under conditions for expressing the heterologous glycoprotein to produce the heterologous glycoprotein.

Further provided is a yeast or filamentous fungus host cell genetically engineered to produce glycoproteins having mammalian- or human-like N-glycans, comprising a first nucleic acid molecule encoding a heterologous single-subunit oligosaccharyltransferase; and a second nucleic acid molecule encoding a heterologous glycoprotein; and wherein the endogenous host cell genes encoding the proteins comprising the oligosaccharyltransferase (OTase) complex are expressed. This includes expression of the endogenous STT3 gene, which in yeast is the STT3 gene.

In general, in the above methods and host cells, the single-subunit oligosaccharyltransferase is capable of functionally suppressing the lethal phenotype of a mutation of at least one essential protein of the OTase complex. In further aspects, the essential protein of the OTase complex is encoded by the STT3 locus, WBP1 locus, OST1 locus, SWP1 locus, or OST2 locus, or homologue thereof. In further aspects, the for example single-subunit oligosaccharyltransferase is the *Leishmania major* STT3D protein.

Promoters are DNA sequence elements for controlling gene expression. In particular, promoters specify transcription initiation sites and can include a TATA box and upstream promoter elements. The promoters selected are those which would be expected to be operable in the particular host system selected. For example, yeast promoters are used when a yeast such as *Saccharomyces cerevisiae, Kluyveromyces lactis, Ogataea minuta*, or *Pichia pastoris* is the host cell whereas fungal promoters would be used in host cells such as *Aspergillus niger, Neurospora crassa*, or *Tricoderma reesei*. Examples of yeast promoters include but are not limited to the GAPDH, AOX1, SEC4, HH1, PMA1, OCH1, GAL1, PGK, GAP, TPI, CYC1, ADH2, PHO5, CUP1, MFα1, FLD1, PMA1, PDI, TEF, RPL10, and GUT1 promoters. Romanos et al., Yeast 8: 423-488 (1992) provide a review of yeast promoters and expression vectors. Hartner et al., Nucl. Acid Res. 36: e76 (pub on-line 6 Jun. 2008) describes a library of promoters for fine-tuned expression of heterologous proteins in *Pichia pastoris*.

The promoters that are operably linked to the nucleic acid molecules disclosed herein can be constitutive promoters or inducible promoters. An inducible promoter, for example the AOX1 promoter, is a promoter that directs transcription at an increased or decreased rate upon binding of a transcription factor in response to an inducer. Transcription factors as used herein include any factor that can bind to a regulatory or control region of a promoter and thereby affect transcription. The RNA synthesis or the promoter binding ability of a transcription factor within the host cell can be controlled by exposing the host to an inducer or removing an inducer from the host cell medium. Accordingly, to regulate expression of an inducible promoter, an inducer is added or removed from the growth medium of the host cell. Such inducers can include sugars, phosphate, alcohol, metal ions, hormones, heat, cold and the like. For example, commonly used inducers in yeast are glucose, galactose, alcohol, and the like.

Transcription termination sequences that are selected are those that are operable in the particular host cell selected. For example, yeast transcription termination sequences are used in expression vectors when a yeast host cell such as *Saccharomyces cerevisiae, Kluyveromyces lactis*, or *Pichia pastoris* is the host cell whereas fungal transcription termination sequences would be used in host cells such as *Aspergillus niger, Neurospora crassa*, or *Tricoderma reesei*. Transcription termination sequences include but are not limited to the *Saccharomyces cerevisiae* CYC transcription termination sequence (ScCYC TT), the *Pichia pastoris* ALG3 transcription termination sequence (ALG3 TT), the *Pichia pastoris* ALG6 transcription termination sequence (ALG6 TT), the *Pichia pastoris* ALG12 transcription termination sequence (ALG12 TT), the *Pichia pastoris* AOX1 transcription termination sequence (AOX1 TT), the *Pichia pastoris* OCH1 transcription termination sequence (OCH1 TT) and *Pichia pastoris* PMA1 transcription termination sequence (PMA1 TT). Other transcription termination sequences can be found in the examples and in the art.

For genetically engineering yeast, selectable markers can be used to construct the recombinant host cells include drug resistance markers and genetic functions which allow the yeast host cell to synthesize essential cellular nutrients, e.g. amino acids. Drug resistance markers which are commonly used in yeast include chloramphenicol, kanamycin, methotrexate, G418 (geneticin), Zeocin, and the like. Genetic functions which allow the yeast host cell to synthesize essential cellular nutrients are used with available yeast strains having auxotrophic mutations in the corresponding genomic function. Common yeast selectable markers provide genetic functions for synthesizing leucine (LEU2), tryptophan (TRP1 and TRP2), praline (PRO1), uracil (URA3, URA5, URA6), histidine (HIS3), lysine (LYS2), adenine (ADE1 or ADE2), and the like. Other yeast selectable markers include the ARR3 gene from *S. cerevisiae*, which confers arsenite resistance to yeast cells that are grown in the presence of arsenite (Bobrowicz et al., Yeast, 13:819-828 (1997); Wysocki et al., J. Biol. Chem. 272:30061-30066 (1997)). A number of suitable integration sites include those enumerated in U.S. Pat. No. 7,479,389 (the disclosure of which is incorporated herein by reference) and include homologs to loci known for *Saccharomyces cerevisiae* and other yeast or fungi. Methods for integrating vectors into yeast are well known (See for example, U.S. Pat. Nos. 7,479,389, 7,514,253, U.S. Published Application No. 2009012400, and WO2009/085135; the disclosures of which are all incorporated herein by reference). Examples of insertion sites include, but are not limited to, *Pichia* ADE genes; *Pichia* TRP (including TRP1 through TRP2) genes; *Pichia* MCA genes; *Pichia* CYM genes; *Pichia* PEP genes; *Pichia* PRB genes; and *Pichia* LEU genes. The *Pichia* ADE1 and ARG4 genes have been described in Lin Cereghino et al., Gene 263:159-169 (2001) and U.S. Pat. No. 4,818,700 (the disclosure of which is incorporated herein by reference), the HIS3 and TRP1 genes have been described in Cosano et al., Yeast 14:861-867 (1998), HIS4 has been described in GenBank Accession No. X56180.

The methods disclosed herein can be adapted for use in mammalian, plant, and insect cells. Examples of animal cells include, but are not limited to, SC-I cells, LLC-MK cells, CV-I cells, CHO cells, COS cells, murine cells, human cells, HeLa cells, 293 cells, VERO cells, MDBK cells, MDCK cells, MDOK cells, CRFK cells, RAF cells, TCMK cells, LLC-PK cells, PK15 cells, WI-38 cells, MRC-5 cells, T-FLY cells, BHK cells, SP2/0, NSO cells, and derivatives thereof. Insect cells include cells of *Drosophila melanogaster* origin. These cells can be genetically engineered to render the cells capable of making immunoglobulins that have particular or predominantly particular N-glycans. For example, U.S. Pat. No. 6,949,372 discloses methods for making glycoproteins in insect cells that are sialylated. Yamane-Ohnuki et al. Biotechnol. Bioeng. 87: 614-622 (2004), Kanda et al., Biotechnol. Bioeng, 94: 680-688 (2006), Kanda et al., Glycobiol. 17: 104-118 (2006), and U.S. Pub. Application Nos. 2005/0216958 and 2007/0020260 (the disclosures of which are incorporated herein by reference) disclose mammalian cells that are capable of producing immunoglobulins in which the N-glycans thereon lack fucose or have reduced fucose. U.S. Published Patent Application No. 2005/0074843 (the disclosure of which is incorporated herein by reference) discloses making antibodies in mammalian cells that have bisected N-glycans.

The regulatable promoters selected for regulating expression of the expression cassettes in mammalian, insect, or plant cells should be selected for functionality in the cell-type chosen. Examples of suitable regulatable promoters include but are not limited to the tetracycline-regulatable promoters (See for example, Berens & Hillen, Eur. J. Biochem. 270: 3109-3121 (2003)), RU 486-inducible promoters, ecdysone-inducible promoters, and kanamycin-regulatable systems. These promoters can replace the promoters exemplified in the expression cassettes described in the examples. The capture moiety can be fused to a cell surface anchoring protein suitable for use in the cell-type chosen. Cell surface anchoring proteins including GPI proteins are well known for mammalian, insect, and plant cells. GPI-anchored fusion proteins has been described by Kennard et al., Methods Biotechnol. Vo. 8: Animal Cell Biotechnology (Ed. Jenkins. Human Press, Inc., Totowa, N.J.) pp. 187-200 (1999). The genome targeting sequences for integrating the expression cassettes into the host cell genome for making stable recombinants can replace the genome targeting and integration sequences exemplified in the examples. Transfection methods for making stable and transiently transfected mammalian, insect, and plant host cells are well known in the art. Once the transfected host cells have been constructed as disclosed herein, the cells can be screened for expression of the immunoglobulin of interest and selected as disclosed herein.

Therefore, in a further aspect of the above, provided is a method for producing a heterologous glycoprotein in a mammalian or insect host cell, comprising providing a mammalian or insect host cell that includes a nucleic acid molecule encoding a heterologous single-subunit oligosaccharyltransferase (e.g., *Leishmania major* STT3 protein) and a nucleic acid molecule encoding the heterologous glycoprotein; and culturing the host cell under conditions for expressing the heterologous glycoprotein to produce the heterologous glycoprotein. In further aspects, the host cell is genetically engineered to produce glycoproteins with human-like N-glycans or N-glycans not normally endogenous to the host cell.

In a further aspect of the above, provided is a method for producing a heterologous glycoprotein wherein the N-glycosylation site occupancy of the heterologous glycoprotein is greater than 83% in a mammalian or insect host cell, comprising providing a mammalian or insect host cell that includes a nucleic acid molecule encoding a heterologous single-subunit oligosaccharyltransferase (e.g., *Leishmania major* STT3 protein) and a nucleic acid molecule encoding the heterologous glycoprotein; and culturing the host cell under conditions for expressing the heterologous glycoprotein to produce the heterologous glycoprotein wherein the N-glycosylation site occupancy of the heterologous glycoprotein is greater than 83%. In further aspects, the host cell is genetically engineered to produce glycoproteins with human-like N-glycans or N-glycans not normally endogenous to the host cell.

In a further embodiment of the above methods, the endogenous host cell genes encoding the proteins comprising the oligosaccharyltransferase (OTase) complex are expressed.

In particular embodiments of the above methods, the N-glycosylation site occupancy is at least 94%. In further still embodiments, the N-glycosylation site occupancy is at least 99%.

Further provided is a mammalian or insect host cell, comprising a first nucleic acid molecule encoding a heterologous single-subunit oligosaccharyltransferase (e.g., the *Leishmania major* STT3D protein); and a second nucleic acid molecule encoding a heterologous glycoprotein; and wherein the endogenous host cell genes encoding the proteins comprising the endogenous host cell oligosaccharyltransferase (OTase) complex are expressed.

In particular embodiments, the higher eukaryote cell, tissue, or organism can also be from the plant kingdom, for example, wheat, rice, corn, tobacco, and the like. Alternatively, bryophyte cells can be selected, for example from species of the genera *Physcomitrella, Funaria, Sphagnum, Ceratodon, Marchantia,* and *Sphaerocarpos*. Exemplary of plant cells is the bryophyte cell of *Physcomitrella patens*, which has been disclosed in WO 2004/057002 and WO2008/006554 (the disclosures of which are all incorporated herein by reference). Expression systems using plant cells can further be manipulated to have altered glycosylation pathways to enable the cells to produce immunoglobulins that have predominantly particular N-glycans. For example, the cells can be genetically engineered to have a dysfunctional or no core fucosyltransferase and/or a dysfunctional or no xylosyltransferase, and/or a dysfunctional or no β1,4-galactosyltransferase. Alternatively, the galactose, fucose and/or xylose can be removed from the immunoglobulin by treatment with enzymes removing the residues. Any enzyme resulting in the release of galactose, fucose and/or xylose residues from N-glycans which are known in the art can be used, for example α-galactosidase, β-xylosidase, and α-fucosidase. Alternatively, an expression system can be used which synthesizes modified N-glycans which can not be used as substrates by 1,3-fucosyltransferase and/or 1,2-xylosyltransferase, and/or 1,4-galactosyltransferase. Methods for modifying glycosylation pathways in plant cells are disclosed in U.S. Pat. Nos. 7,449,308, 6,998,267 and 7,388,081 (the disclosures of which are incorporated herein by reference) which disclose methods for genetically engineering plants to make recombinant glycoproteins that have human-like N-glycans. WO 2008006554 (the disclosure of which is incorporated herein by reference) discloses methods for making glycoproteins such as antibodies in plants genetically engineered to make glycoproteins without xylose or fucose. WO 2007006570 (the disclosure of which is incorporated herein by reference) discloses methods for genetically engineering bryophytes, ciliates, algae, and yeast to make glycoproteins that have animal or human-like glycosylation patterns.

Therefore, in a further aspect of the above, provided is a method for producing a heterologous glycoprotein with mammalian- or human-like complex or hybrid N-glycans in a plant host cell, comprising providing a plant host cell that is genetically engineered to produce glycoproteins that have mammalian- or human-like N-glycans and includes a nucleic acid molecule encoding a heterologous single-subunit oligosaccharyltransferase (e.g., the *Leishmania major* STT3D protein) and a nucleic acid molecule encoding the heterologous glycoprotein; and culturing the host cell under conditions for expressing the heterologous glycoprotein to produce the heterologous glycoprotein.

In a further aspect of the above, provided is a method for producing a heterologous glycoprotein with mammalian- or human-like complex or hybrid N-glycans wherein the N-glycosylation site occupancy of the heterologous glycoprotein is greater than 83% in a plant host cell, comprising providing a plant host cell that is genetically engineered to produce glycoproteins that have mammalian- or human-like N-glycans and includes a nucleic acid molecule encoding a heterologous single-subunit oligosaccharyltransferase (e.g., the *Leishmania major* STT3D protein) and a nucleic acid molecule encoding the heterologous glycoprotein; and culturing the host cell under conditions for expressing the heterologous glycoprotein to produce the heterologous glycoprotein with mammalian- or human-like N-glycans wherein the N-glycosylation site occupancy of the heterologous glycoprotein is greater than 83%.

In a further embodiment of the above methods, the endogenous host cell genes encoding the proteins comprising the endogenous host cell oligosaccharyltransferase (OTase) complex are expressed.

In particular embodiments of the above methods, the N-glycosylation site occupancy is at least 94%. In further still embodiments, the N-glycosylation site occupancy is at least 99%.

Further provided is a plant host cell, comprising a first nucleic acid molecule encoding a heterologous single-subunit oligosaccharyltransferase (e.g., the *Leishmania major* STT3D protein); and a second nucleic acid molecule encoding a heterologous glycoprotein; and wherein the endogenous host cell genes encoding the proteins comprising the endogenous host cell oligosaccharyltransferase (OTase) complex are expressed.

The host cells and methods herein are useful for producing a wide range of recombinant proteins and glycoproteins. Examples of recombinant proteins and glycoproteins that can be produced in the host cells disclosed herein include but are not limited to erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin,; soluble IgE receptor α-chain; immunoglobulins or antibodies such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; and IL-2 receptor agonist.

The recombinant host cells and methods disclosed herein are particularly useful for producing antibodies, Fc fusion proteins, and the like where it is desirable to provide antibody or Fc fusion protein compositions wherein the percent galactose-containing N-glycans is increased compared to the percent galactose obtainable in the host cells prior to modification as taught herein. Examples of antibodies that can be made in the host cells herein include but are not limited to human antibodies, humanized antibodies, chimeric antibodies, heavy chain antibodies (e.g., camel or llama). Specific antibodies include but are not limited to the following antibodies recited under their generic name (target): Muromonab-CD3 (anti-CD3 receptor antibody), Abciximab (anti-CD41 7E3 antibody), Rituximab (anti-CD20 antibody), Daclizumab (anti-CD25 antibody), Basiliximab (anti-CD25 antibody), Palivizumab (anti-RSV (respiratory syncytial virus) antibody), Infliximab (anti-TNFα antibody), Trastuzumab (anti-Her2 antibody), Gemtuzumab ozogamicin (anti-CD33 antibody), Alemtuzurnab (anti-CD52 antibody), Ibritumomab tiuxeten (anti-CD20 antibody), Adalimumab (anti-TNFα antibody), Omalizumab (anti-IgE antibody), Tositumomab-[131]I (iodinated derivative of an anti-CD20 antibody), Efalizumab (anti-CD11a antibody), Cetuximab (anti-EGF receptor antibody), Golimumab (anti-TNFα antibody), Bevacizumab (anti VEGF-A antibody), and variants thereof. Examples of Fc-fusion proteins that can be made in the host cells disclosed herein include but are not limited to etanercept (TNFR-Fc fusion protein), FGF-21-Fc fusion proteins, GLP-1-Fc fusion proteins, RAGE-Fc fusion proteins, EPO-Fc fusion proteins, ActRIIA-Fc fusion proteins, ActRIIB-Fc fusion proteins, glucagon-Fc fusions, oxyntomodulin-Fc-fusions, and analogs and variants thereof.

Thus, the methods and host cells herein can be used to produce glycoprotein compositions in which at least 70%, 75%, 80%, 85%, 90%, 95%, 98%, or 99% of the N-glycosylation sites of the glycoproteins in the composition are occupied and the glycoproteins have mammalian- or human-like N-glycans.

Further, the methods and host cells herein can be used to produce glycoprotein compositions in which at least 70%, 75%, 80%, 85%, 90%, 95%, 98%, or 99% of the N-glycosylation sites of the glycoproteins in the composition are occupied and the glycoproteins have mammalian- or human-like N-glycans that lack fucose.

Further, the methods and yeast or filamentous fungus host cells genetically engineered to produce mammalian-like or human-like N-glycans can be used to produce glycoprotein compositions in which at least 70%, 75%, 80%, 85%, 90%, 95%, 98%, or 99% of the N-glycosylation sites of the glycoproteins in the composition are occupied and the glycoproteins have mammalian- or human-like N-glycans that lack fucose.

In some aspects, the yeast or filamentous host cells genetically engineered to produce fucosylated mammalian- or human-like N-glycans can be used to produce glycoprotein compositions in which at least 70%, 75%, 80%, 85%, 90%, 95%, 98%, or 99% of the N-glycosylation sites of the glycoproteins in the composition are occupied and the glycoproteins have mammalian- or human-like N-glycans that have fucose.

The recombinant cells disclosed herein can be used to produce antibodies and Fc fragments suitable for chemically conjugating to a heterologous peptide or drug molecule. For example, WO2005047334, WO2005047336, WO2005047337, and WO2006107124 (the disclosures of which are incorporated herein by reference) disclose chemically conjugating peptides or drug molecules to Fc fragments. EP1180121, EP1105409, and U.S. Pat. No. 6,593,295 (the disclosures of which are incorporated herein by reference) disclose chemically conjugating peptides and the like to blood components, which includes whole antibodies.

Thus, the methods and host cells herein can be used to produce antibody compositions in which at least 70%, 75%, 80%, 85%, 90%, 95%, 98%, or 99% of the antibody molecules in the composition have both N-glycosylation sites occupied and the antibodies have mammalian- or human-like N-glycans.

Further, the methods and host cells herein can be used to produce antibody compositions in which at least 70%, 75%, 80%, 85%, 90%, 95%, 98%, or 99% of the antibody molecules in the composition have both N-glycosylation sites occupied and the antibodies have mammalian- or human-like N-glycans that lack fucose.

Further, the methods and yeast or filamentous fungus host cells genetically engineered to produce mammalian-like or human-like N-glycans can be used to produce antibody compositions in which at least 70%, 75%, 80%, 85%, 90%, 95%, 98%, or 99% of the antibody molecules in the composition have both N-glycosylation sites occupied and the antibodies have mammalian- or human-like N-glycans that lack fucose.

In some aspects, the yeast or filamentous host cells genetically engineered to produce fucosylated mammalian- or human-like N-glycans can be used to produce antibody compositions in which at least 70%, 75%, 80%, 85%, 90%, 95%, 98%, or 99% of the antibody molecules in the composition have both N-glycosylation sites occupied and the antibodies have mammalian- or human-like N-glycans that have fucose.

As shown in Example 3, the N-glycosylation composition of antibodies produced in *Pichia pastoris* strains, which have been genetically engineered to make galactose-terminated N-glycans, appear to range from about 50-60 mole % G0, 18-24 mole % G1, 3-8% mole % G2, 12-17 mole % Man5, and 3-6 mole % hybrids.

Therefore, provided is a glycoprotein composition comprising a plurality of antibodies wherein at least 70% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 70% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a $Man_5GlcNAc_2$ core structure, and a pharmaceutically acceptable carrier. In further aspects of the above, the N-glycans further include fucose.

Therefore, provided is a glycoprotein composition comprising a plurality of antibodies wherein at least 75% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 75% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a $Man_5GlcNAc_2$ core structure, and a pharmaceutically acceptable carrier. In further aspects of the above, the N-glycans further include fucose.

Further still, provided is a glycoprotein composition comprising a plurality of antibodies wherein at least 80% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 80% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a $Man_5GlcNAc_2$ core structure, and a pharmaceutically acceptable carrier. In further aspects of the above, the N-glycans further include fucose.

Therefore, provided is a glycoprotein composition comprising a plurality of antibodies wherein at least 85% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 85% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a Man₅GlcNAc₂ core structure, and a pharmaceutically acceptable carrier. In further aspects of the above, the N-glycans further include fucose.

Further still, provided is a glycoprotein composition comprising a plurality of antibodies wherein at least 90% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 90% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a Man₅GlcNAc₂ core structure, and a pharmaceutically acceptable carrier. In further aspects of the above, the N-glycans further include fucose.

Therefore, provided is a glycoprotein composition comprising a plurality of antibodies wherein at least 95% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 95% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a Man₅GlcNAc₂ core structure, and a pharmaceutically acceptable carrier. In further aspects of the above, the N-glycans further include fucose.

Further still, provided is a glycoprotein composition comprising a plurality of antibodies wherein at least 98% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 98% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a Man₅GlcNAc₂ core structure, and a pharmaceutically acceptable carrier. In further aspects of the above, the N-glycans further include fucose.

Therefore, provided is a glycoprotein composition comprising a plurality of antibodies wherein at least 99% of the antibody molecules in the composition have both N-glycosylation sites occupied and about 50-70 mole % of the N-glycans have a G0 structure, 15-25 mole % of the N-glycans have a G1 structure, 4-12 mole % of the N-glycans have a G2 structure, 5-17 mole % of the N-glycans have a Man5 structure, and 5-15 mole % of the N-glycans have a hybrid structure, and a pharmaceutically acceptable carrier. Further still is provided is a glycoprotein composition comprising a plurality of antibodies wherein at least 99% of the antibody molecules in the composition have both N-glycosylation sites occupied and about 53 to 58 mole % of the N-glycans have a G0 structure, 20-22 mole % of the N-glycans have a G1 structure, and about 16 to 18 mole % of the N-glycans comprise a Man₅GlcNAc₂ core structure, and a pharmaceutically acceptable carrier. In further aspects of the above, the N-glycans further include fucose.

In particular embodiments, the antibodies comprise an antibody selected from the group consisting of anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11a antibody, anti-EGF receptor antibody, and anti-CD20 antibody.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety.

The following examples are intended to promote a further understanding of the present invention.

EXAMPLE 1

Plasmids comprising expression cassettes encoding the *Leishmania major* STT3D (LmSTT3D) open reading frame (ORF) operably linked to an inducible or constitutive promoter were constructed as follows.

The open reading frame encoding the LmSTT3D (SEQ ID NO:12) was codon-optimized for optimal expression in *P. pastoris* and synthesized by GeneArt AG, Brandenburg, Germany. The codon-optimized nucleic acid molecule encoding the LmSTT3D was designated pGLY6287 and has the nucleotide sequence shown in SEQ ID NO:11.

Figure 2:
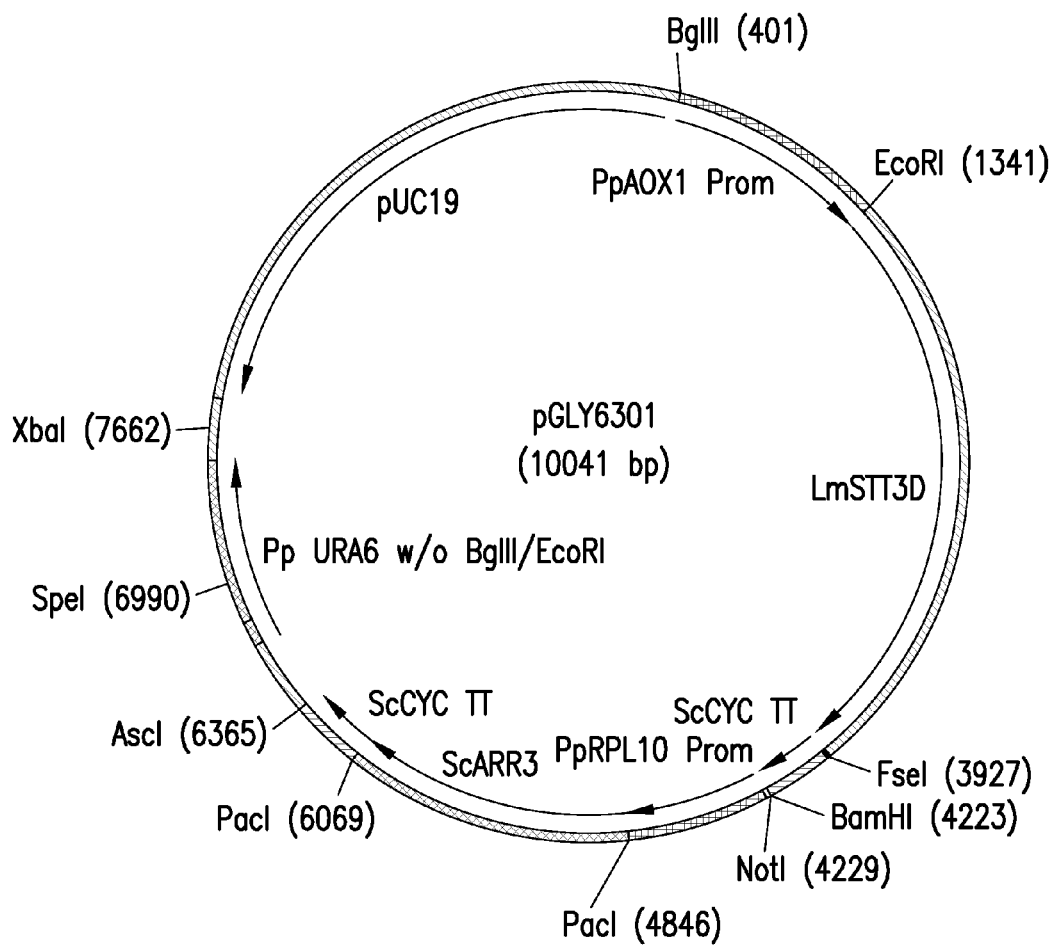
FIG. 2 shows a map of plasmid pGLY6301 encoding the LmSTT3D ORF under the control of the *Pichia pastoris* alcohol oxidase I (AOX1) promoter and *S. cerevisiae* CYC transcription termination sequence. The plasmid is a roll-in vector that targets the URA6 locus. The selection of transformants uses arsenic resistance encoded by the *S. cerevisiae* ARR3 ORF under the control of the *P. pastoris* RPL10 promoter and *S. cerevisiae* CYC transcription termination sequence.

Plasmid pGLY6301 (FIG. 2) is a roll-in integration plasmid that targets the URA6 locus in *P. pastoris*. The expression cassette encoding the LmSTT3D comprises a nucleic acid molecule encoding the LmSTT3D ORF codon-optimized for effective expression in *P. pastoris* operably linked at the 5' end to a nucleic acid molecule that has the inducible *P. pastoris* AOX1 promoter sequence (SEQ ID NO:23) and at the 3' end to a nucleic acid molecule that has the *S. cerevisiae* CYC transcription termination sequence (SEQ ID NO:24). For selecting transformants, the plasmid comprises an expression cassette encoding the *S. cerevisiae* ARR3 ORF in which the nucleic acid molecule encoding the ORF (SEQ ID NO:32) is operably linked at the 5' end to a nucleic acid molecule having the *P. pastoris* RPL10 promoter sequence (SEQ ID NO:25) and at the 3' end to a nucleic acid molecule having the *S. cerevisiae* CYC transcription termination sequence (SEQ ID NO:24). The plasmid further includes a nucleic acid molecule for targeting the URA6 locus (SEQ ID NO:33). Plasmid pGLY6301 was constructed by cloning the DNA fragment encoding the codon-optimized LmSTT3D ORF (pGLY6287) flanked by an EcoRI site at the 5' end and an FseI site at the 3' end into plasmid pGFI30t, which had been digested with EreoRI and FseI.

Figure 3:
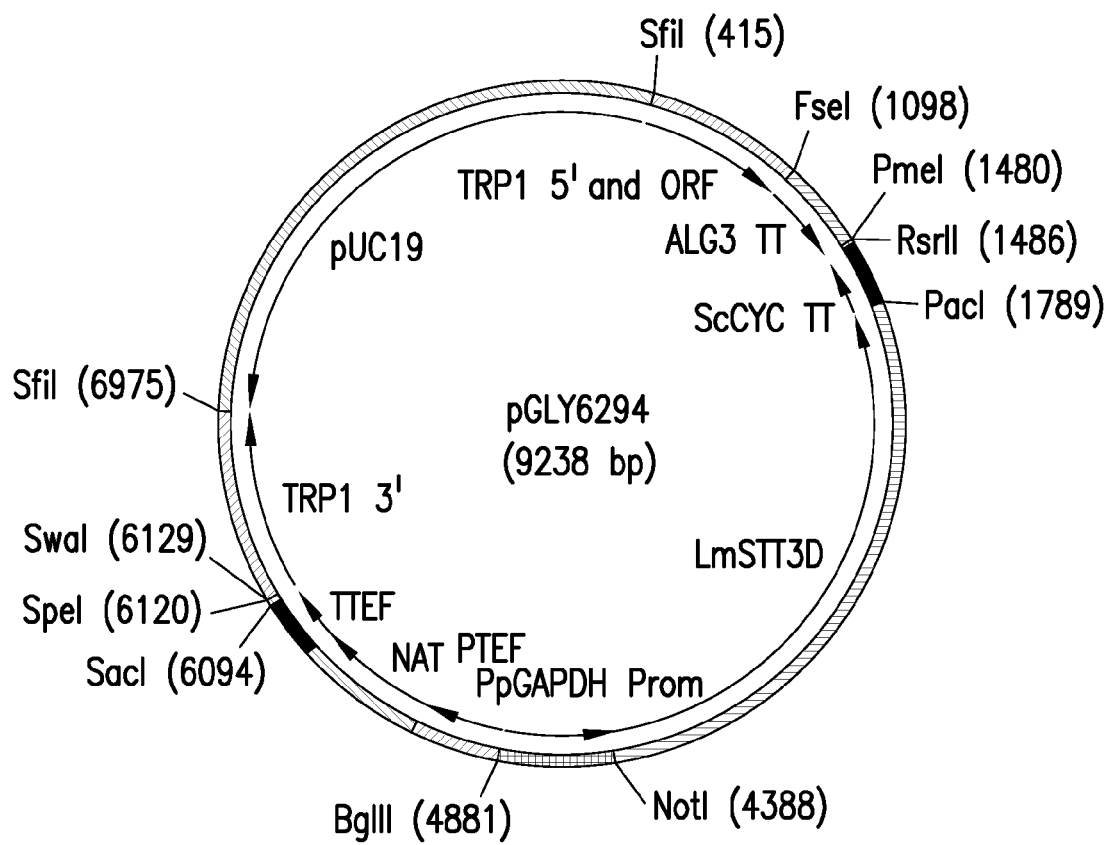
FIG. 3 shows a map of plasmid pGLY6294 encoding the LmSTT3D ORF under the control of the *P. pastoris* GAPDH promoter and *S. cerevisiae* CYC transcription termination sequence. The plasmid is a KINKO vector that targets the TRP1 locus: the 3' end of the TRP1 ORF is adjacent to the *P. pastoris* ALG3 transcription termination sequence. The selection of transformants uses nourseothricin resistance encoded by the *Streptomyces noursei* nourseothricin acetyltransferase (NAT) ORF under the control of the *Ashbya gossypii* TEF1 promoter (PTEF) and *Ashbya gossypii* TEF1 termination sequence (TTEF).

Plasmid pGLY6294 (FIG. 3) is a KINKO integration vector that targets the TRP1 locus in *P. pastoris* without disrupting expression of the locus. KINKO (Knock-In with little or No Knock-Out) integration vectors enable insertion of heterologous DNA into a targeted locus without disrupting expression of the gene at the targeted locus and have been described in U.S. Published Application No. 20090124000. The expression cassette encoding the LmSTT3D comprises a nucleic acid molecule encoding the LmSTT3D ORF operably linked at the 5' end to a nucleic acid molecule that has the constitutive *P. pastoris* GAPDH promoter sequence (SEQ ID NO:26) and at the 3' end to a nucleic acid molecule having the *S. cerevisiae* CYC transcription termination sequence (SEQ ID NO:24). For selecting transformants, the plasmid comprises an expression cassette encoding the Nourseothricin resistance (NAT[R]) ORF (originally from pAG2S from EROSCARF, Scientific Research and Development GmbH, Daimlerstrasse 13a, D-61352 Bad Homburg, Germany, See Goldstein et al., Yeast 15: 1541 (1999)); wherein the nucleic acid molecule encoding the ORF (SEQ ID NO:34) is operably linked to at the 5' end to a nucleic acid molecule having the *Ashbya gossypii* TEF1 promoter sequence (SEQ ID NO:86) and at the 3' end to a nucleic acid molecule that has the *Ashbya gossypii* TEF1 termination sequence (SEQ ID NO:87). The two expression cassettes are flanked on one side by a nucleic acid molecule comprising a nucleotide sequence from the 5' region of the ORF encoding Trp1p ending at the stop codon (SEQ ID NO:30) linked to a nucleic acid molecule having the *P. pastoris* ALG3 termination sequence (SEQ ID NO:29) and on the other side by a nucleic acid molecule comprising a nucleotide sequence from the 3' region of the TRP1 gene (SEQ ID NO:31). Plasmid pGLY6294 was constructed by cloning the DNA fragment encoding the codon-optimized LmSTT3D ORF (pGLY6287) flanked by a NoI site at the 5' end and a PacI site at the 3' end into plasmid pGLY597, which had been digested with NotI and FseI. An expression cassette comprising a nucleic acid molecule encoding the Nourseothricin resistance ORF (NAT) operably linked to the *Ashbya gossypii* TEF1 promoter (PTEF) and *Ashbya gossypii* TEF1 termination sequence (TTEF).

The above plasmids can be used to introduce the LmSTT3D expression cassettes into *P. pastoris* to increase the N-glycosylation site occupancy on glycoproteins produced therein as shown in the following examples.

EXAMPLE 2

Genetically engineered *Pichia pastoris* strain YGLY13992 is a strain that produces recombinant human anti-Her2 antibodies and *Pichia pastoris* strain YGLY14401 is a strain that produces recombinant human anti-RSV antibodies. Construction of the strains is illustrated schematically in FIG. 1A-1H. Briefly, the strains were constructed as follows.

The strain YGLY8316 was constructed from wild-type *Pichia pastoris* strain NRRL-Y 11430 using methods described earlier (See for example, U.S. Pat. Nos. 7,449,308; 7,479,389; U.S. Published Application No. 20090124000; Published PCT Application No. WO2009085135; Nett and Gerngross, Yeast 20:1279 (2003); Choi et al., Proc. Natl. Acad. Sci. USA 100:5022 (2003); Hamilton et al., Science 301:1244 (2003)). All plasmids were made in a pUC19 plasmid using standard molecular biology procedures. For nucleotide sequences that were optimized for expression in *P. pastoris*, the native nucleotide sequences were analyzed by the GENEOPTIMIZER software (GeneArt, Regensburg, Germany) and the results used to generate nucleotide sequences in which the codons were optimized for *P. pastoris* expression. Yeast strains were transformed by electroporation (using standard techniques as recommended by the manufacturer of the electroporator BioRad).

Figure 4:
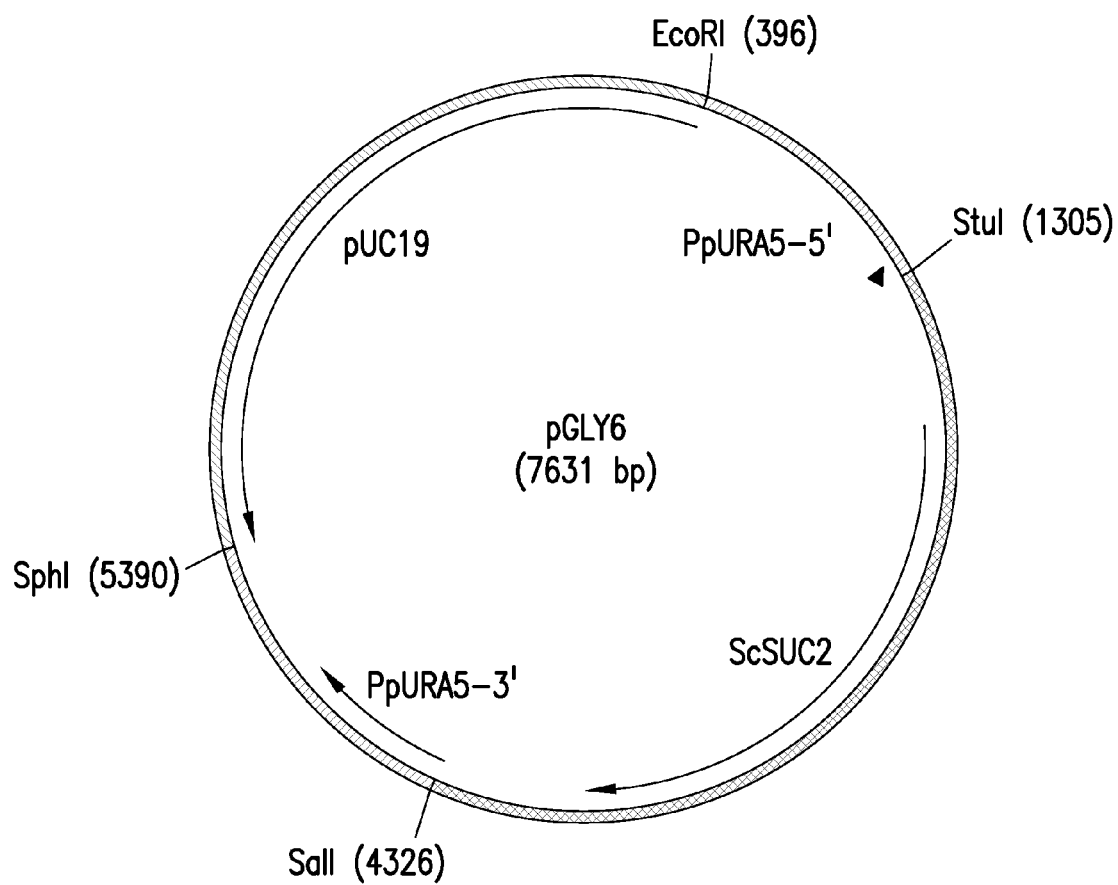
FIG. 4 shows a map of plasmid pGLY6. Plasmid pGLY6 is an integration vector that targets the URA5 locus and contains a nucleic acid molecule comprising the *S. cerevisiae* invertase gene or transcription unit (ScSUC2) flanked on one side by a nucleic acid molecule comprising a nucleotide sequence from the 5' region of the *P. pastoris* URA5 gene (PpURA5-5) and on the other side by a nucleic acid molecule comprising the a nucleotide sequence from the 3' region of the *P. pastoris* URA5 gene (PpURA5-3').

Plasmid pGLY6 (FIG. 4) is an integration vector that targets the URA5 locus. It contains a nucleic acid molecule comprising the *S. cerevisiae* invertase gene or transcription unit (ScSUC2; SEQ ID NO:38) flanked on one side by a nucleic acid molecule comprising a nucleotide sequence from the 5' region of the *P. pastoris* URA5 gene (SEQ ID NO:39) and on the other side by a nucleic acid molecule comprising the nucleotide sequence from the 3' region of the *P. pastoris* URA5 gene (SEQ ID NO:40). Plasmid pGLY6 was linearized and the linearized plasmid transformed into wild-type strain NRRL-Y 11430 to produce a number of strains in which the ScSUC2 gene was inserted into the URA5 locus by double-crossover homologous recombination. Strain YGLY1-3 was selected from the strains produced and is auxotrophic for uracil.

Figure 5:
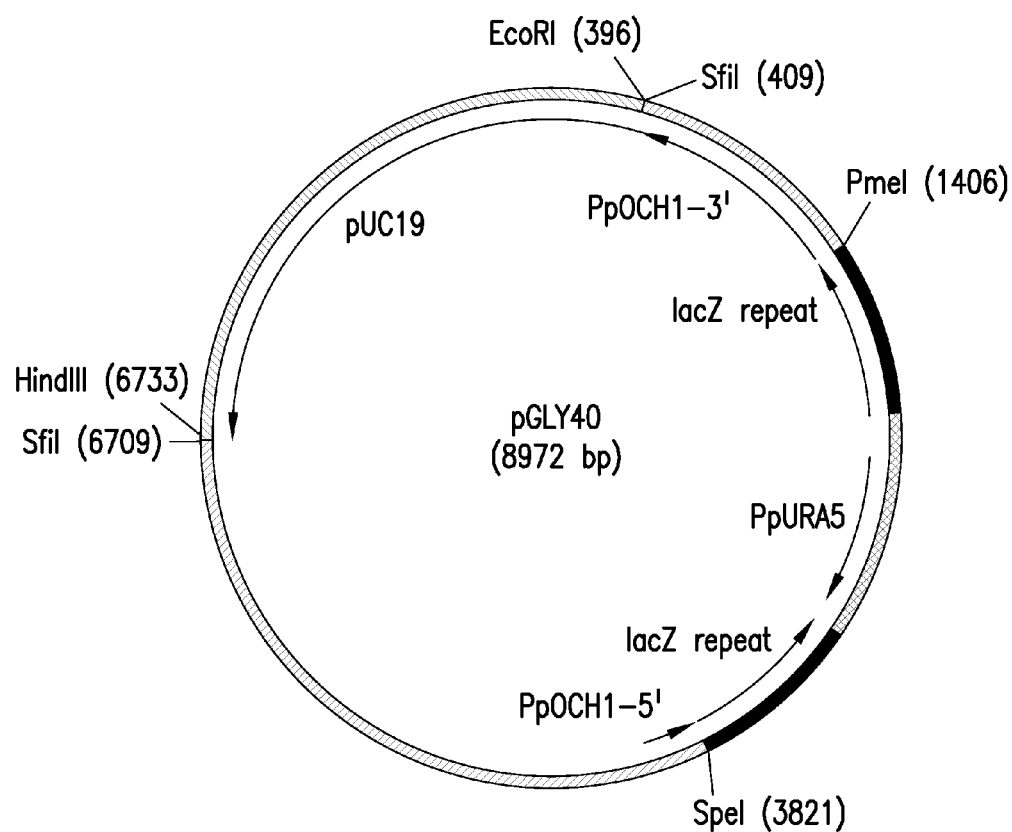
FIG. 5 shows a map of plasmid pGLY40. Plasmid pGLY40 is an integration vector that targets the OCH1 locus and contains a nucleic acid molecule comprising the *P. pastoris* URA5 gene or transcription unit (PpURA5) flanked by nucleic acid molecules comprising lacZ repeats (lacZ repeat) which in turn is flanked on one side by a nucleic acid molecule comprising a nucleotide sequence from the 5' region of the OCH1 gene (PpOCH1-5') and on the other side by a nucleic acid molecule comprising a nucleotide sequence from the 3' region of the OCH1 gene (PpOCH1-3').

Plasmid pGLY40 (FIG. 5) is an integration vector that targets the OCH1 locus and contains a nucleic acid molecule comprising the *P. pastoris* URA5 gene or transcription unit (SEQ ID NO:41) flanked by nucleic acid molecules comprising lacZ repeats (SEQ ID NO:42) which in turn is flanked on one side by a nucleic acid molecule comprising a nucleotide sequence from the 5' region of the OCH1 gene (SEQ ID NO:43) and on the other side by a nucleic acid molecule comprising a nucleotide sequence from the 3' region of the OCH1 gene (SEQ ID NO:44). Plasmid pGLY40 was linearized with SP and the linearized plasmid transformed into strain YGLY1-3 to produce a number of strains in which the URA5 gene flanked by the lacZ repeats has been inserted into the OCH1 locus by double-crossover homologous recombination. Strain YGLY2-3 was selected from the strains produced and is prototrophic for URA5. Strain YGLY2-3 was counterselected in the presence of 5-fluoroorotic acid (5-FOA) to produce a number of strains in which the URA5 gene has been lost and only the lacZ repeats remain in the OCH1 locus. This renders the strain auxotrophic for uracil. Strain YGLY4-3 was selected.

Figure 6:
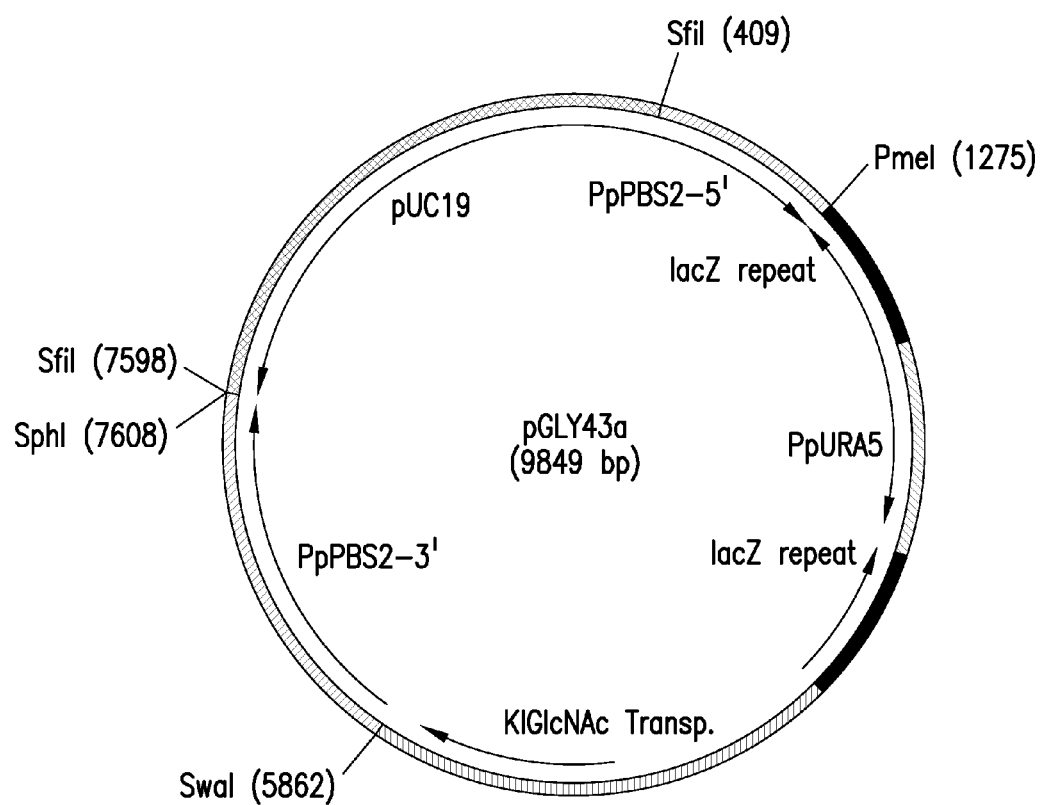
FIG. 6 shows a map of plasmid pGLY43a. Plasmid pGLY43a is an integration vector that targets the BMT2 locus and contains a nucleic acid molecule comprising the *K. lactis* UDP-N-acetylglucosamine (UDP-GlcNAc) transporter gene or transcription unit (KlGlcNAc Transp.) adjacent to a nucleic acid molecule comprising the *P. pastoris* URA5 gene or transcription unit (PpURA5) flanked by nucleic acid molecules comprising lacZ repeats (lacZ repeat). The adjacent genes are flanked on one side by a nucleic acid molecule comprising a nucleotide sequence from the 5' region of the BMT2 gene (PpPBS2-5') and on the other side by a nucleic acid molecule comprising a nucleotide sequence from the 3' region of the BMT2 gene (PpPBS2-3').

Plasmid pGLY43a (FIG. 6) is an integration vector that targets the BMT2 locus and contains a nucleic acid molecule comprising the *K. lactis* UDP-N-acetylglucosamine (UDP-GlcNAc) transporter gene or transcription unit (KlMNN2-2, SEQ ID NO:45) adjacent to a nucleic acid molecule comprising the *P. pastoris* URA5 gene or transcription unit flanked by nucleic acid molecules comprising lacZ repeats. The adjacent genes are flanked on one side by a nucleic acid molecule comprising a nucleotide sequence from the 5' region of the BMT2 gene (SEQ ID NO: 46) and on the other side by a nucleic acid molecule comprising a nucleotide sequence from the 3' region of the BMT2 gene (SEQ ID NO:47). Plasmid pGLY43a was linearized with and the linearized plasmid transformed into strain YGLY4-3 to produce to produce a number of strains in which the KlMNN2-2 gene and URA5 gene flanked by the lacZ repeats has been inserted into the BMT2 locus by double-crossover homologous recombination. The BMT2 gene has been disclosed in Mille et al., T. Biol. Chem. 283: 9724-9736 (2008) and U.S. Pat. No. 7,465,557. Strain YGLY6-3 was selected from the strains produced and is prototrophic for uracil. Strain YGLY6-3 was counterselected in the presence of 5-FOA to produce strains in which the URA5 gene has been lost and only the lacZ repeats remain. This renders the strain auxotrophic for uracil. Strain YGLY8-3 was selected.

Figure 7:
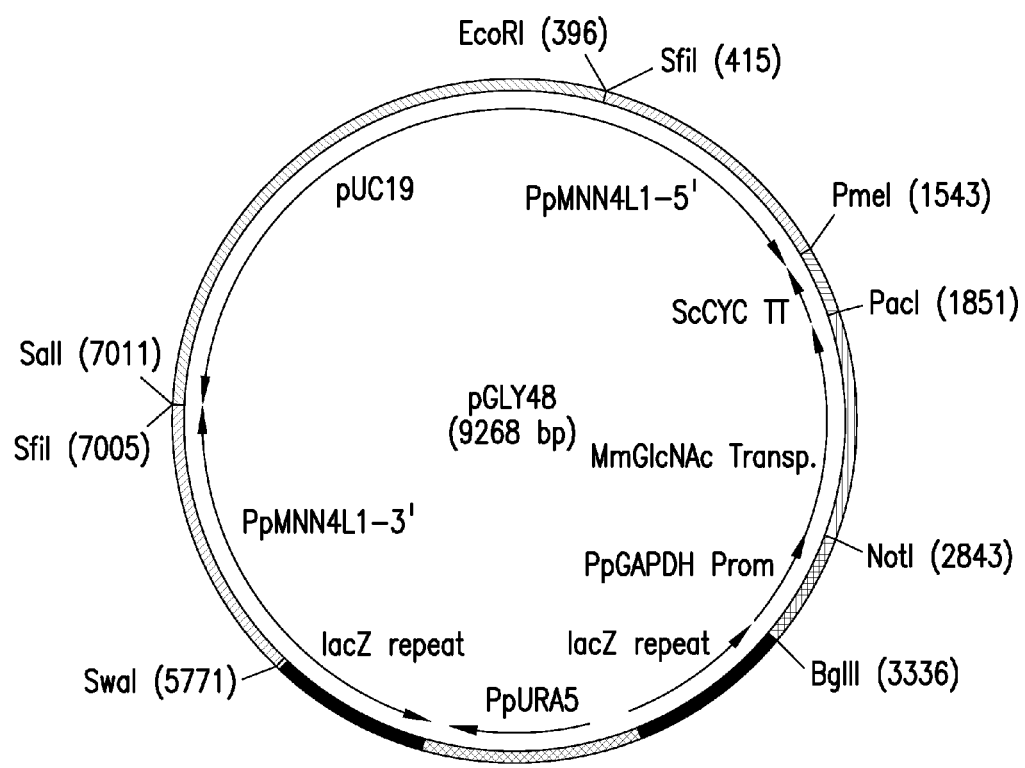
FIG. 7 shows a map of plasmid pGLY48. Plasmid pGLY48 is an integration vector that targets the MNN4L1 locus and contains an expression cassette comprising a nucleic acid molecule encoding the mouse homologue of the UDP-GlcNAc transporter (MmGlcNAc Transp.) open reading frame (ORF) operably linked at the 5' end to a nucleic acid molecule comprising the *P. pastoris* GAPDH promoter (PpGAPDH Prom) and at the 3' end to a nucleic acid molecule comprising the *S. cerevisiae* CYC termination sequence (ScCYC TT) adjacent to a nucleic acid molecule comprising the *P. pastoris* URA5 gene or transcription unit (PpURA5) flanked by lacZ repeats (lacZ repeat) and in which the expression cassettes together are flanked on one side by a nucleic acid molecule comprising a nucleotide sequence from the 5' region of the *P. pastoris* MNN4L1 gene (PpMNN4L1-5') and on the other side by a nucleic acid molecule comprising a nucleotide sequence from the 3' region of the MNN4L1 gene (PpMNN4L1-3').

Plasmid pGLY48 (FIG. 7) is an integration vector that targets the MNN4L1 locus and contains an expression cassette comprising a nucleic acid molecule encoding the mouse homologue of the UDP-GlcNAc transporter (SEQ ID NO:48) open reading frame (ORF) operably linked at the 5' end to a nucleic acid molecule comprising the *P. pastoris* GAPDH promoter (SEQ ID NO:26) and at the 3' end to a nucleic acid molecule comprising the *S. cerevisiae* CYC termination sequences (SEQ ID NO:24) adjacent to a nucleic acid molecule comprising the *P. pastoris* URA5 gene flanked by lacZ repeats and in which the expression cassettes together are flanked on one side by a nucleic acid molecule comprising a nucleotide sequence from the 5' region of the *P. pastoris* MNN4L1 gene (SEQ ID NO:49) and on the other side by a nucleic acid molecule comprising a nucleotide sequence from the 3' region of the MNN4L1 gene (SEQ ID NO:50). Plasmid pGLY48 was linearized with SfiI and the linearized plasmid transformed into strain YGLY8-3 to produce a number of strains in which the expression cassette encoding the mouse UDP-GlcNAc transporter and the URA5 gene have been inserted into the MNN4L1 locus by double-crossover homologous recombination. The MNN4L1 gene (also referred to as MNN4B) has been disclosed in U.S. Pat. No. 7,259,007. Strain YGLY10-3 was selected from the strains produced and then counterselected in the presence of 5-FOA to produce a number of strains in which the URA5 gene has been lost and only the lacZ repeats remain. Strain YGLY12-3 was selected.

Figure 8:
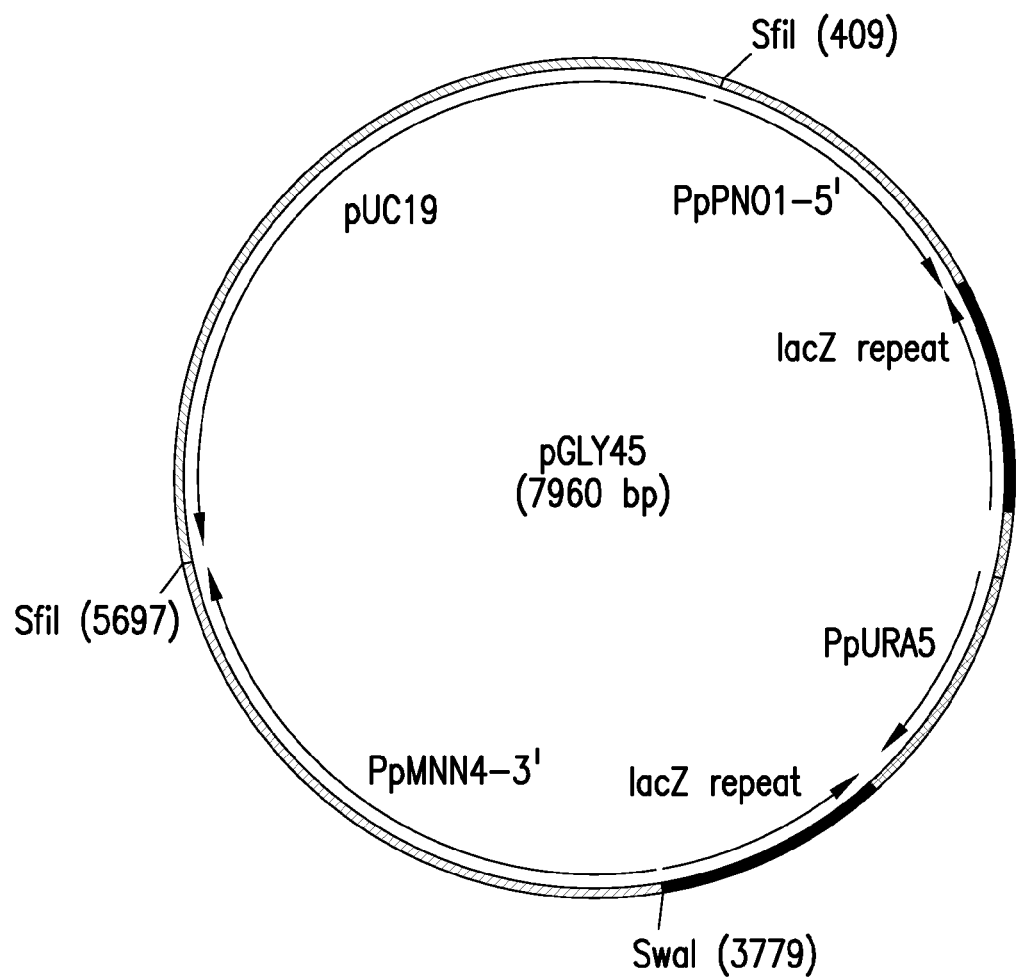
FIG. 8 shows as map of plasmid pGLY45. Plasmid pGLY45 is an integration vector that targets the PNO1/MNN4 loci contains a nucleic acid molecule comprising the *P. pastoris* URA5 gene or transcription unit (PpURA5) flanked by nucleic acid molecules comprising lacZ repeats (lacZ repeat) which in turn is flanked on one side by a nucleic acid molecule comprising a nucleotide sequence from the 5' region of the PNO1 gene (PpPNO1-5') and on the other side by a nucleic acid molecule comprising a nucleotide sequence from the 3' region of the MNN4 gene (PpMNN4-3').

Plasmid pGLY45 (FIG. 8) is an integration vector that targets the PNO1/MNN4 loci and contains a nucleic acid molecule comprising the *P. pastoris* URA5 gene or transcription unit flanked by nucleic acid molecules comprising lacZ repeats which in turn is flanked on one side by a nucleic acid molecule comprising a nucleotide sequence from the 5' region of the PNO1 gene (SEQ ID NO:51) and on the other side by a nucleic acid molecule comprising a nucleotide sequence from the 3' region of the MNN4 gene (SEQ ID NO:52). Plasmid pGLY45 was linearized with SfiI and the linearized plasmid transformed into strain YGLY12-3 to produce a number of strains in which the URA5 gene flanked by the lacZ repeats has been inserted into the PNO1MNN4 loci by double-crossover homologous recombination. The PNO1 gene has been disclosed in U.S. Pat. No. 7,198,921 and the MNN4 gene (also referred to as MNN4B) has been disclosed in U.S. Pat. No. 7,259,007. Strain YGLY14-3 was selected from the strains produced and then counterselected in the presence of 5-FOA to produce a number of strains in which the URA5 gene has been lost and only the lacZ repeats remain. Strain YGLY16-3 was selected.

Figure 9:
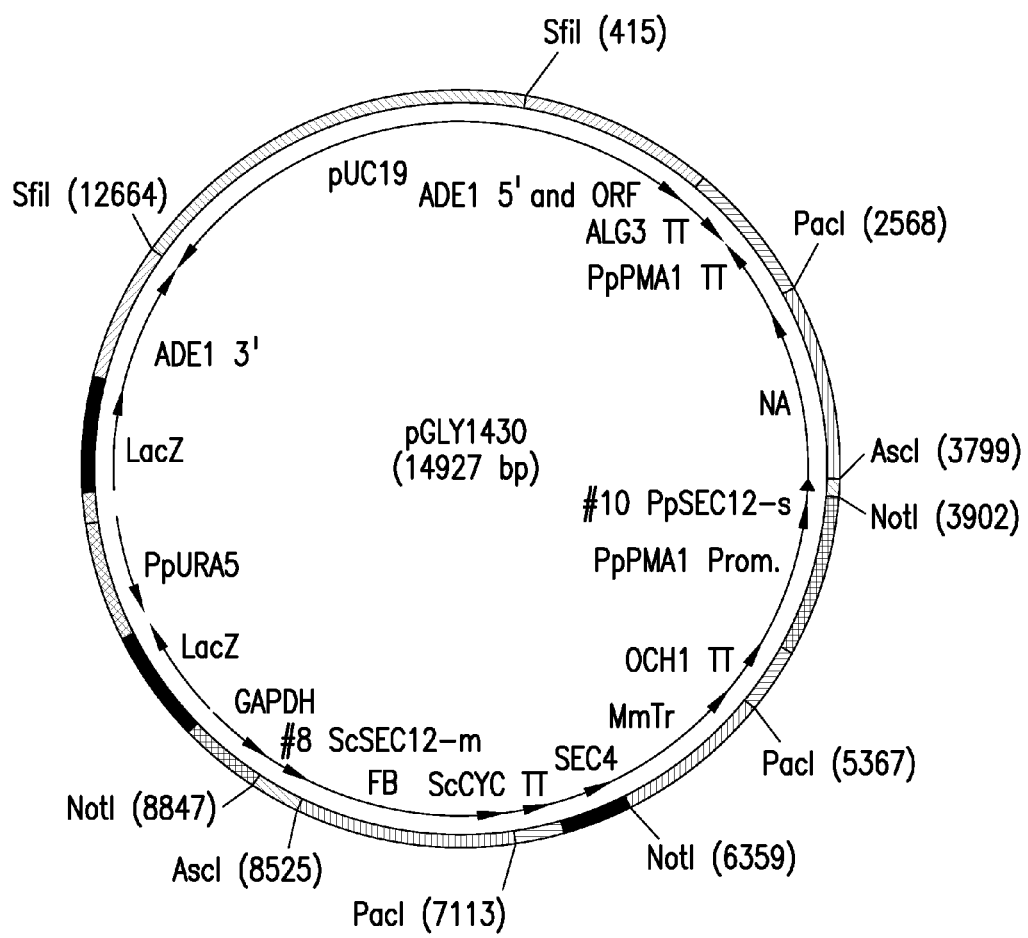
FIG. 9 shows a map of plasmid pGLY1430. Plasmid pGLY1430 is a KINKO integration vector that targets the ADE1 locus without disrupting expression of the locus and contains in tandem four expression cassettes encoding (1) the human GlcNAc transferase I catalytic domain (codon optimized) fused at the N-terminus to *P. pastoris* SEC12 leader peptide (CO-NA10), (2) mouse homologue of the UDP-GlcNAc transporter (MmTr), (3) the mouse mannosidase IA catalytic domain (FB) fused at the N-terminus to *S. cerevisiae* SEC12 leader peptide (FB8), and (4) the *P. pastoris* URA5 gene or transcription unit (PpURA5) flanked by lacZ repeats (lacZ). All flanked by the 5' region of the ADE1 gene and ORF (ADE1 5' and ORF) and the 3' region of the ADE1 gene (PpADE1-3'). PpPMA1 prom is the *P. pastoris* PMA1 promoter; PpPMA1 TT is the *P. pastoris* PMA1 termination sequence; SEC4 is the *P. pastoris* SEC4 promoter; OCH1 TT is the *P. pastoris* OCH1 termination sequence; ScCYC TT is the *S. cerevisiae* CYC termination sequence; PpOCH1 Prom is the *P. pastoris* OCH1 promoter; PpALG3 TT is the *P. pastoris* ALG3 termination sequence; and PpGAPDH is the *P. pastoris* GADPH promoter.

Plasmid pGLY1430 (FIG. 9) is a KINKO integration vector that targets the ADE1 locus without disrupting expression of the locus and contains in tandem four expression cassettes encoding (1) the human GlcNAc transferase I catalytic domain (NA) fused at the N-terminus to *P. pastoris* SEC12 leader peptide (10) to target the chimeric enzyme to the ER or Golgi, (2) mouse homologue of the UDP-GlcNAc transporter (MmTr), (3) the mouse mannosidase IA catalytic domain (FB) fused at the N-terminus to *S. cerevisiae* SEC12 leader peptide (8) to target the chimeric enzyme to the ER or Golgi, and (4) the *P. pastoris* URA5 gene or transcription unit. KINKO (Knock-In with little or No Knock-Out) integration vectors enable insertion of heterologous DNA into a targeted locus without disrupting expression of the gene at the targeted locus and have been described in U.S. Published Application No. 20090124000. The expression cassette encoding the NA10 comprises a nucleic acid molecule encoding the human GlcNAc transferase I catalytic domain codon-optimized for expression in *P. pastoris* (SEQ ID NO:53) fused at the 5' end to a nucleic acid molecule encoding the SEC12 leader 10 (SEQ ID NO:54), which is operably linked at the 5' end to a nucleic acid molecule comprising the *P. pastoris* PMA1 promoter and at the 3' end to a nucleic acid molecule comprising the *P. pastoris* PMA1 transcription termination sequence. The expression cassette encoding MmTr comprises a nucleic acid molecule encoding the mouse homologue of the UDP-GlcNAc transporter ORF operably linked at the 5' end to a nucleic acid molecule comprising the *P. pastoris* SEC4 promoter (SEQ ID NO:55) and at the 3' end to a nucleic acid molecule comprising the *P. pastoris* OCH1 termination sequences (SEQ ID NO:56). The expression cassette encoding the FBS comprises a nucleic acid molecule encoding the mouse mannosidase IA catalytic domain (SEQ ID NO:57) fused at the 5' end to a nucleic acid molecule encoding the SEC12-m leader 8 (SEQ ID NO:58), which is operably linked at the 5' end to a nucleic acid molecule comprising the *P. pastoris* GADPH promoter and at the 3' end to a nucleic acid molecule comprising the *S. cerevisiae* CYC transcription termination sequence. The URA5 expression cassette comprises a nucleic acid molecule comprising the *P. pastoris* URA5 gene or transcription unit flanked by nucleic acid molecules comprising lacZ repeats. The four tandem cassettes are flanked on one side by a nucleic acid molecule comprising a nucleotide sequence from the 5' region and complete ORF of the ADE1 gene (SEQ ID NO:59) followed by a *P. pastoris* ALG3 termination sequence (SEQ ID NO:29) and on the other side by a nucleic acid molecule comprising a nucleotide sequence from the 3' region of the ADE1 gene (SEQ ID NO:60). Plasmid pGLY1430 was linearized with SfiI and the linearized plasmid transformed into strain YGLY16-3 to produce a number of strains in which the four tandem expression cassette have been inserted into the ADE1 locus immediately following the ADE1 ORF by double-crossover homologous recombination. The strain YGLY2798 was selected from the strains produced and is auxotrophic for arginine and now prototrophic for uridine, histidine, and adenine. The strain was then counterselected in the presence of 5-FOA to produce a number of strains now auxotrophic for uridine. Strain YGLY3794 was selected and is capable of making glycoproteins that have predominantly galactose terminated N-glycans.

Figure 10:
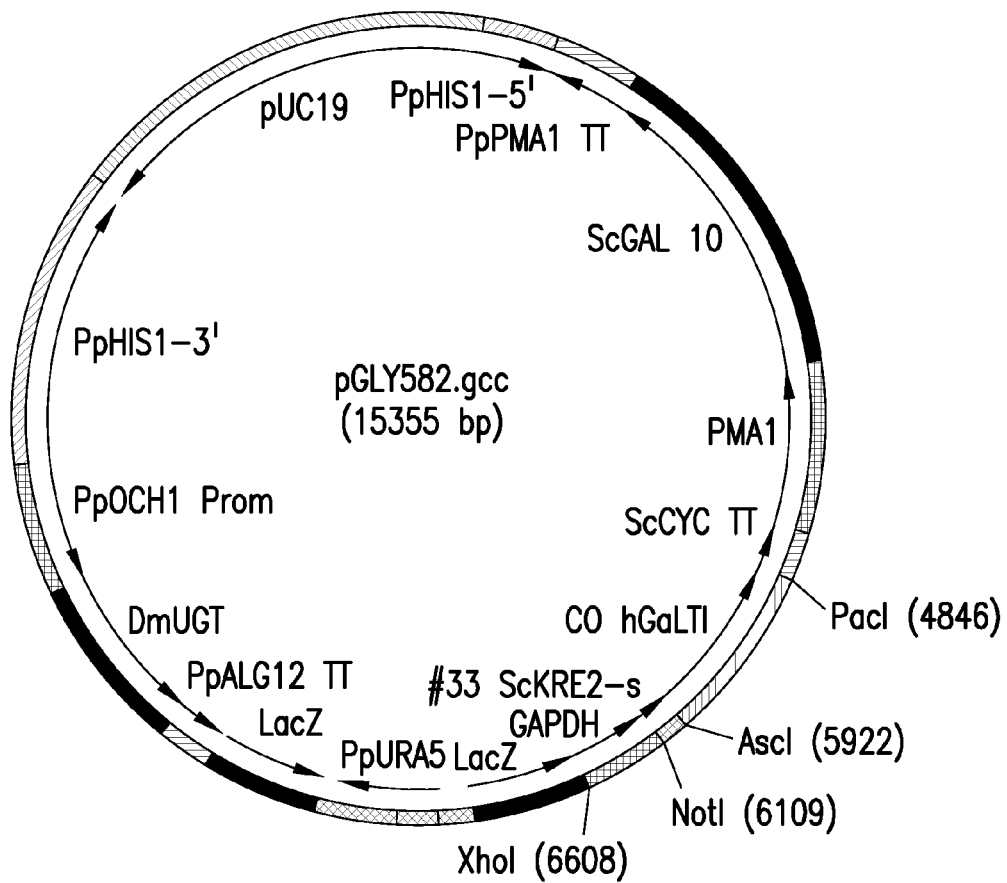
FIG. 10 shows a map of plasmid pGLY582. Plasmid pGLY582 is an integration vector that targets the HIS1 locus and contains in tandem four expression cassettes encoding (1) the *S. cerevisiae* UDP-glucose epimerase (ScGAL10), (2) the human galactosyltransferase I (hGalT) catalytic domain fused at the N-terminus to the *S. cerevisiae* KRE2-s leader peptide (33), (3) the *P. pastoris* URA5 gene or transcription unit (PpURA5) flanked by lacZ repeats (lacZ repeat), and (4) the *D. melanogaster* UDP-galactose transporter (DmUGT). All flanked by the 5' region of the HIS1 gene (PpHIS1-5') and the 3' region of the HIS1 gene (PpHIS1-3'). PMA1 is the *P. pastoris* PMA1 promoter; PpPMA1 TT is the *P. pastoris* PMA1 termination sequence; GAPDH is the *P. pastoris* GADPH promoter and ScCYC TT is the *S. cerevisiae* CYC termination sequence; PpOCH1 Prom is the *P. pastoris* OCH1 promoter and PpALG12 TT is the *P. pastoris* ALG12 termination sequence.

Plasmid pGLY582 (FIG. 10) is an integration vector that targets the HIS1 locus and contains in tandem four expression cassettes encoding (1) the *S. cerevisiae* UDP-glucose epimerase (ScGAL10), (2) the human galactosyltransferase I (hGalT) catalytic domain fused at the N-terminus to the *S. cerevisiae* KRE2-s leader peptide (33) to target the chimeric enzyme to the ER or Golgi, (3) the *P. pastoris* URA5 gene or transcription unit flanked by lacZ repeats, and (4) the *D. melanogaster* UDP-galactose transporter (DmUGT). The expression cassette encoding the ScGAL10 comprises a nucleic acid molecule encoding the ScGAL10 ORF (SEQ ID NO:61) operably linked at the 5' end to a nucleic acid molecule comprising the *P. pastoris* PMA1 promoter (SEQ ID NO:88) and operably linked at the 3' end to a nucleic acid molecule comprising the *P. pastoris* PMA1 transcription termination sequence (SEQ ID NO:62). The expression cassette encoding the chimeric galactosyltransferase I comprises a nucleic acid molecule encoding the hGalT catalytic domain codon optimized for expression in *P. pastoris* (SEQ ID NO:63) fused at the 5' end to a nucleic acid molecule encoding the KRE2-s leader 33 (SEQ ID NO:64), which is operably linked at the 5' end to a nucleic acid molecule comprising the *P. pastoris* GAPDH promoter and at the 3' end to a nucleic acid molecule comprising the *S. cerevisiae* CYC transcription termination sequence. The URA5 expression cassette comprises a nucleic acid molecule comprising the *P. pastoris* URA5 gene or transcription unit flanked by nucleic acid molecules comprising lacZ repeats. The expression cassette encoding the DmUGT comprises a nucleic acid molecule encoding the DmUGT ORF (SEQ ID NO:65) operably linked at the 5' end to a nucleic acid molecule comprising the *P. pastoris* OCH1 promoter (SEQ ID NO:66) and operably linked at the 3' end to a nucleic acid molecule comprising the *P. pastoris* ALG12 transcription termination sequence (SEQ ID NO:67). The four tandem cassettes are flanked on one side by a nucleic acid molecule comprising a nucleotide sequence from the 5' region of the HIS1 gene (SEQ ID NO:68) and on the other side by a nucleic acid molecule comprising a nucleotide sequence from the 3' region of the HIS1 gene (SEQ ID NO:69). Plasmid pGLY582 was linearized and the linearized plasmid transformed into strain YGLY3794 to produce a number of strains in which the four tandem expression cassette have been inserted into the HIS1 locus by homologous recombination. Strain YGLY3853 was selected and is auxotrophic for histidine and prototrophic for uridine.

Figure 11:
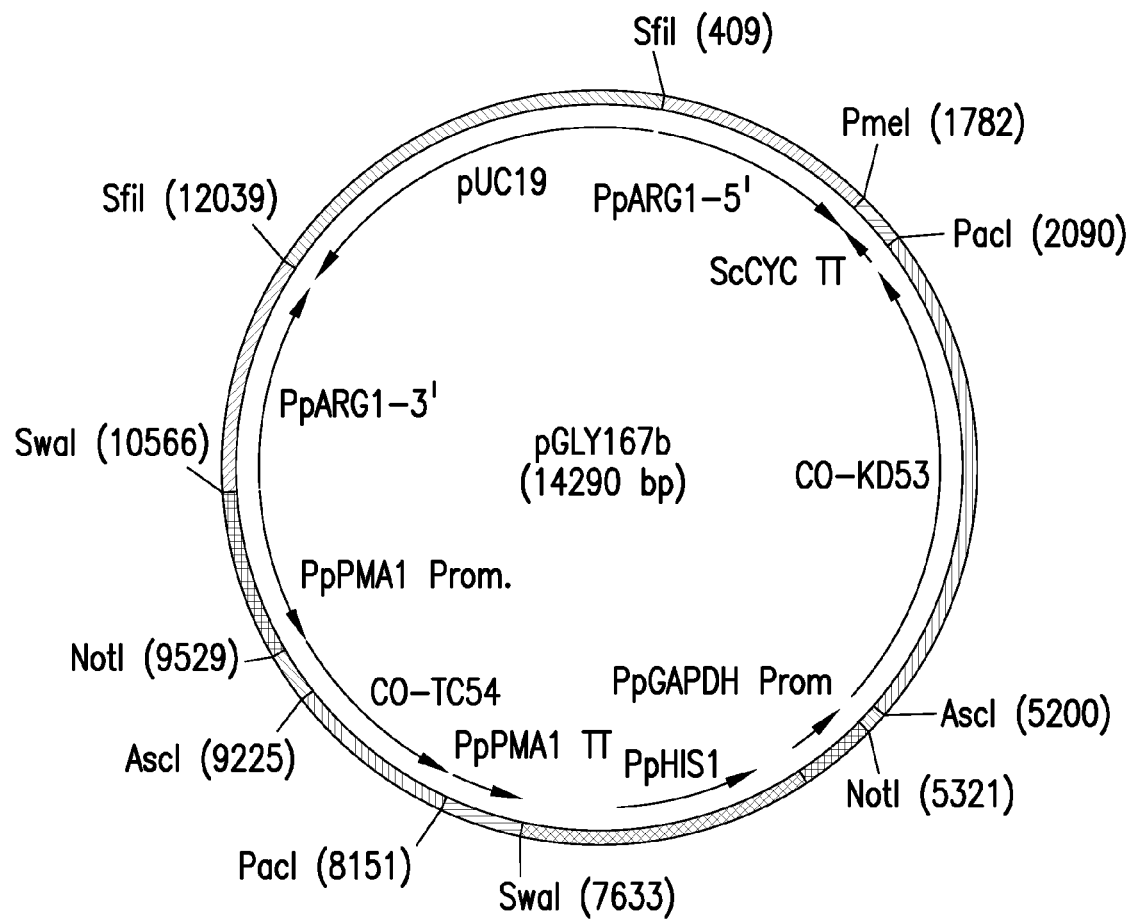
FIG. 11 shows a map of plasmid pGLY167b. Plasmid pGLY167b is an integration vector that targets the ARG1 locus and contains in tandem three expression cassettes encoding (1) the *D. melanogaster* mannosidase II catalytic domain (codon optimized) fused at the N-terminus to *S. cerevisiae* MNN2 leader peptide (CO-KD53), (2) the *P. pastoris* HIS1 gene or transcription unit, and (3) the rat N-acetylglucosamine (GlcNAc) transferase II catalytic domain (codon optimized) fused at the N-terminus to *S. cerevisiae* MNN2 leader peptide (CO-TC54). All flanked by the 5' region of the ARG1 gene (PpARG1-5') and the 3' region of the ARG1 gene (PpARG1-3'). PpPMA1 prom is the *P. pastoris* PMA1 promoter; PpPMA1 TT is the *P. pastoris* PMA1 termination sequence; PpGAPDH is the *P. pastoris* GADPH promoter; ScCYC TT is the *S. cerevisiae* CYC termination sequence; PpOCH1 Prom is the *P. pastoris* OCH1 promoter; and PpALG12 TT is the *P. pastoris* ALG12 termination sequence.

Plasmid pGLY167b (FIG. 11) is an integration vector that targets the ARG1 locus and contains in tandem three expression cassettes encoding (1) the *D. melanogaster* mannosidase II catalytic domain (KD) fused at the N-terminus to *S. cerevisiae* MNN2 leader peptide (53) to target the chimeric enzyme to the ER or Golgi, (2) the *P. pastoris* HIS1 gene or transcription unit, and (3) the rat N-acetylglucosamine (GlcNAc) transferase II catalytic domain (TC) fused at the N-terminus to *S. cerevisiae* MNN2 leader peptide (54) to target the chimeric enzyme to the ER or Golgi. The expression cassette encoding the KD53 comprises a nucleic acid molecule encoding the *D. melanogaster* mannosidase II catalytic domain codon-optimized for expression in *P. pastoris* (SEQ ID NO:70) fused at the 5' end to a nucleic acid molecule encoding the MNN2 leader 53 (SEQ ID NO:71), which is operably linked at the 5' end to a nucleic acid molecule comprising the *P. pastoris* GAPDH promoter and at the 3' end to a nucleic acid molecule comprising the *S. cerevisiae* CYC transcription termination sequence. The HIS1 expression cassette comprises a nucleic acid molecule comprising the *P. pastoris* HIS1 gene or transcription unit (SEQ ID NO:72). The expression cassette encoding the TC54 comprises a nucleic acid molecule encoding the rat GlcNAc transferase II catalytic domain codon-optimized for expression in *P. pastoris* (SEQ ID NO:73) fused at the 5' end to a nucleic acid molecule encoding the MNN2 leader 54 (SEQ ID NO:74), which is operably linked at the 5' end to a nucleic acid molecule comprising the *P. pastoris* PMA1 promoter and at the 3' end to a nucleic acid molecule comprising the *P. pastoris* PMA1 transcription termination sequence. The three tandem cassettes are flanked on one side by a nucleic acid molecule comprising a nucleotide sequence from the 5' region of the ARG1 gene (SEQ ID NO:75) and on the other side by a nucleic acid molecule comprising a nucleotide sequence from the 3' region of the ARG1 gene (SEQ ID NO:76). Plasmid pGLY167b was linearized with SfiI and the linearized plasmid transformed into strain YGLY3853 to produce a number of strains (in which the three tandem expression cassette have been inserted into the ARG1 locus by double-crossover homologous recombination. The strain YGLY4754 was selected from the strains produced and is auxotrophic for arginine and prototrophic for uridine and histidine. The strain was then counterselected in the presence of 5-FOA to produce a number of strains now auxotrophic for uridine. Strain YGLY4799 was selected.

Figure 12:
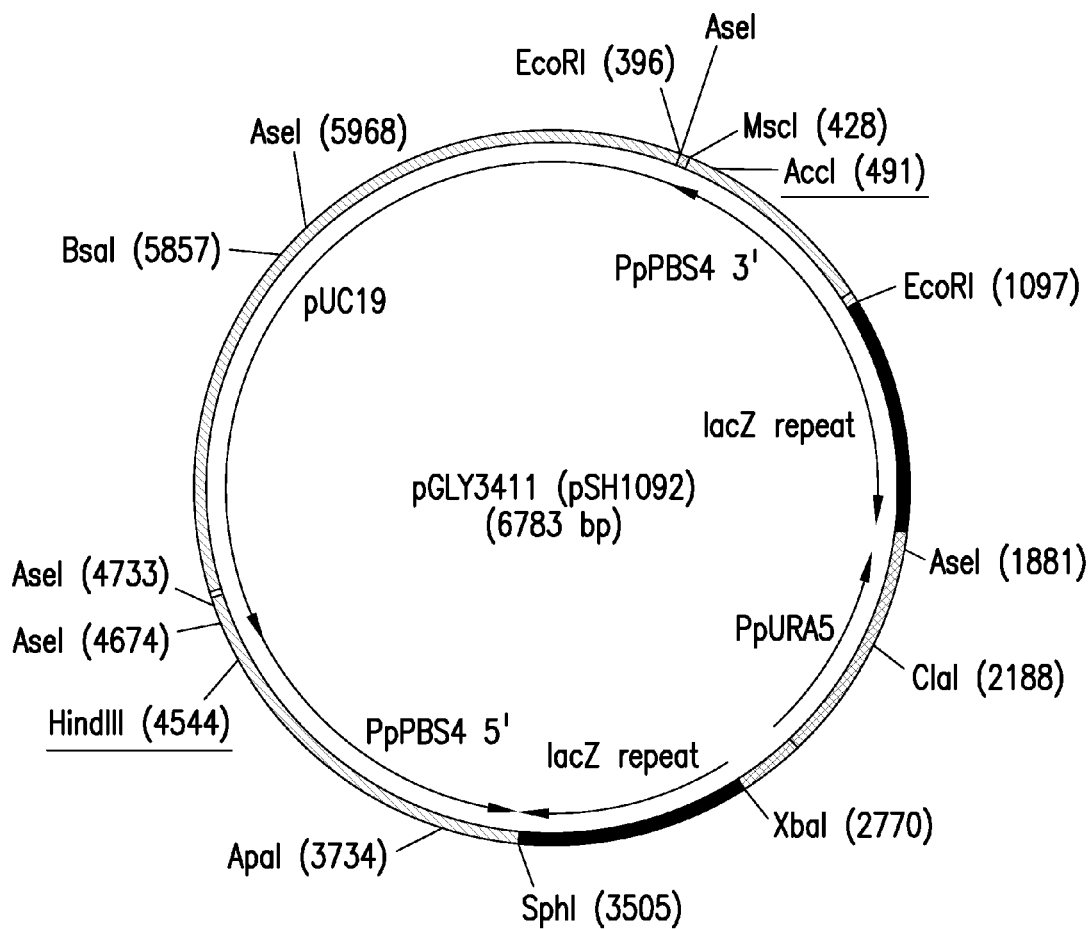
FIG. 12 shows a map of plasmid pGLY3411 (pSH1092). Plasmid pGLY3411 (pSH1092) is an integration vector that contains the expression cassette comprising the *P. pastoris* URA5 gene or transcription unit (PpURA5) flanked by lacZ repeats (lacZ repeat) flanked on one side with the 5' nucleotide sequence of the *P. pastoris* BMT4 gene (PpPBS4 5') and on the other side with the 3' nucleotide sequence of the *P. pastoris* BMT4 gene (PpPBS4 3').

Plasmid pGLY3411 (FIG. 12) is an integration vector that contains the expression cassette comprising the *P. pastoris* URA5 gene flanked by lacZ repeats flanked on one side with the 5' nucleotide sequence of the *P. pastoris* BMT4 gene (SEQ ID NO:77) and on the other side with the 3' nucleotide sequence of the *P. pastoris* BMT4 gene (SEQ ID NO:78). Plasmid pGLY3411 was linearized and the linearized plasmid transformed into YGLY4799 to produce a number of strains in which the URA5 expression cassette has been inserted into the BMT4 locus by double-crossover homologous recombination. Strain YGLY6903 was selected from the strains produced and is prototrophic for uracil, adenine, histidine, proline, arginine, and tryptophan. The strain was then counterselected in the presence of 5-FOA to produce a number of strains now auxotrophic for uridine. Strains YGLY7432 and YGLY7433 were selected.

Figure 13:
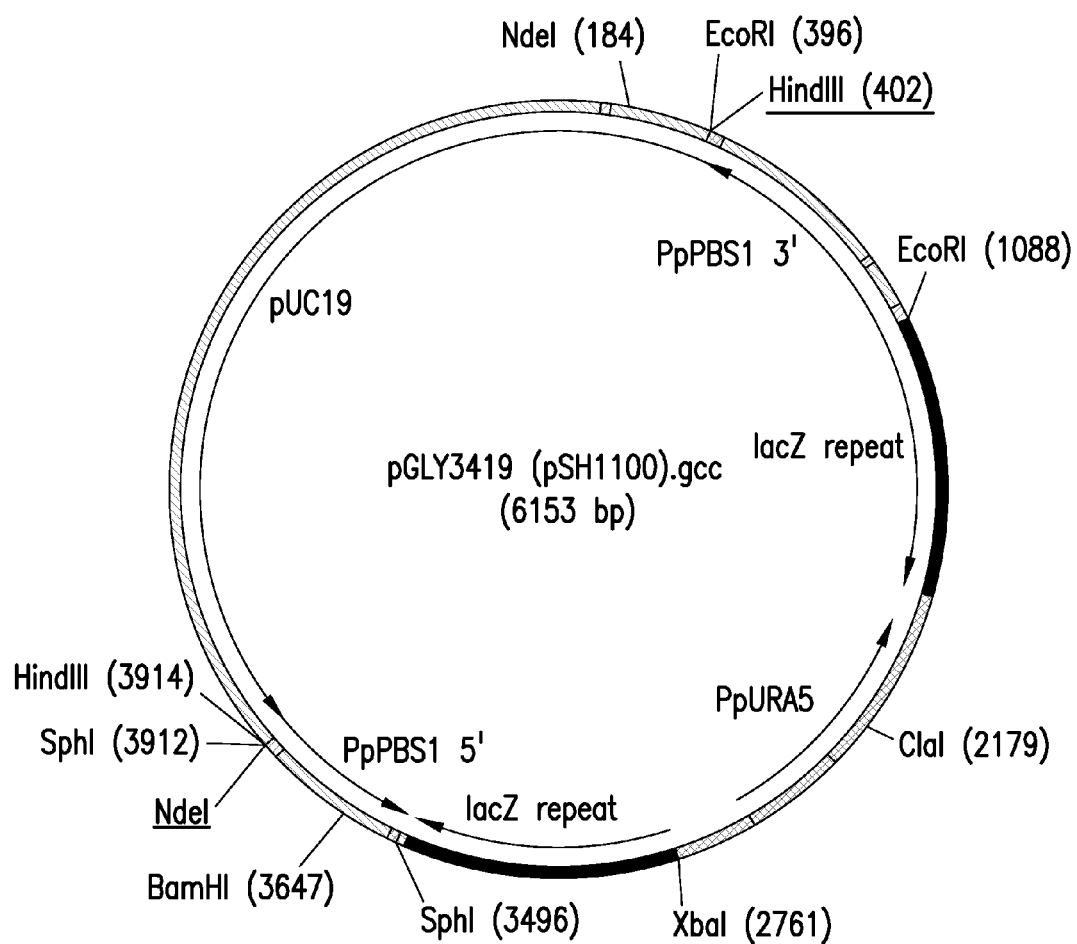
FIG. 13 shows a map of plasmid pGLY3419 (pSH1110). Plasmid pGLY3430 (pSH1115) is an integration vector that contains an expression cassette comprising the *P. pastoris* URA5 gene or transcription unit (PpURA5) flanked by lacZ repeats (lacZ repeat) flanked on one side with the 5' nucleotide sequence of the *P. pastoris* BMT1 gene (PBS1 5') and on the other side with the 3' nucleotide sequence of the *P. pastoris* BMT1 gene (PBS1 3')

Plasmid pGLY3419 (FIG. 13) is an integration vector that contains an expression cassette comprising the *P. pastoris* URA5 gene flanked by lacZ repeats flanked on one side with the 5' nucleotide sequence of the *P. pastoris* BMT1 gene (SEQ ID NO:79) and on the other side with the 3' nucleotide sequence of the *P. pastoris* BMT1 gene (SEQ ID NO:80). Plasmid pGLY3419 was linearized and the linearized plasmid transformed into strain YGLY7432 and YGLY7433 to produce a number of strains in which the URA5 expression cassette has been inserted into the BMT1 locus by double-crossover homologous recombination. The strains YGLY7656 and YGLY7651 were selected from the strains produced and are prototrophic for uracil, adenine, histidine, proline, arginine, and tryptophan. The strains were then counterselected in the presence of 5-FOA to produce a number of strains now auxotrophic for uridine. Strains YGLY7930 and YGLY7940 were selected.

Figure 14:
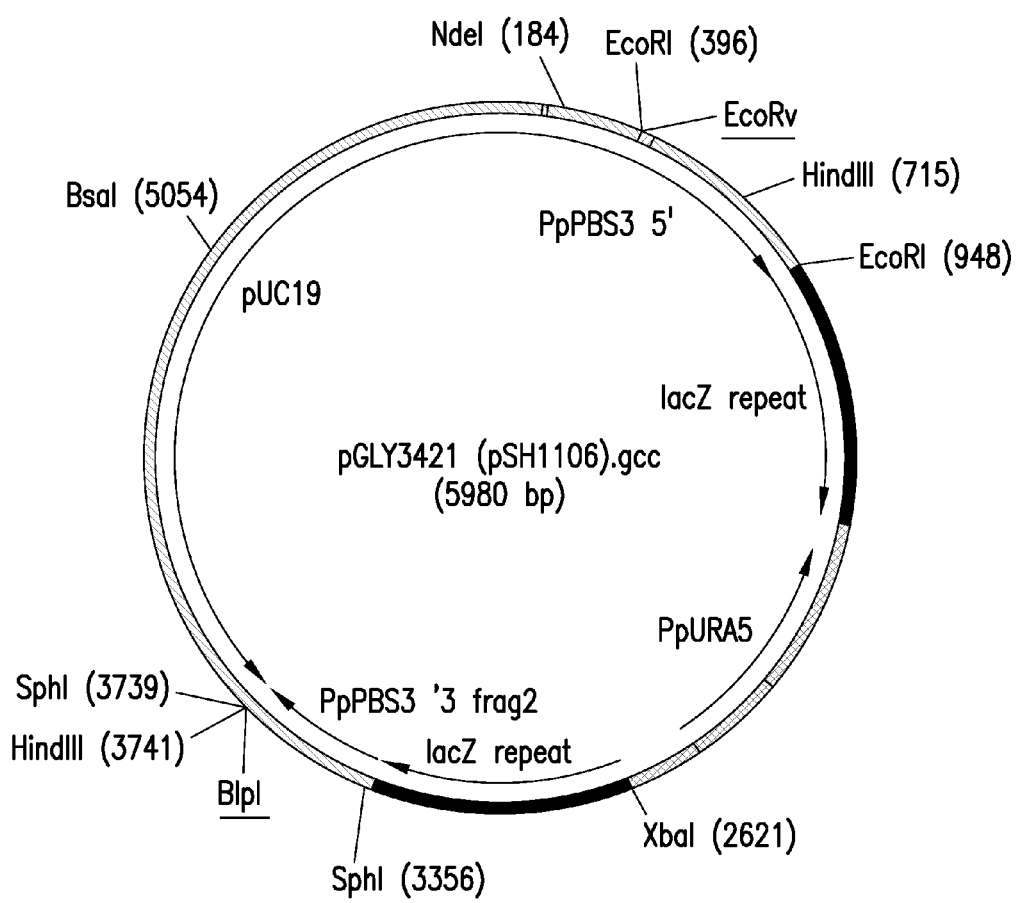
FIG. 14 shows a map of plasmid pGLY3421 (pSH1106). Plasmid pGLY4472 (pSH1186) contains an expression cassette comprising the *P. pastoris* URA5 gene or transcription unit (PpURA5) flanked by lacZ repeats (lacZ repeat) flanked on one side with the 5' nucleotide sequence of the *P. pastoris* BMT3 gene (PpPBS3 5') and on the other side with the 3' nucleotide sequence of the *P. pastoris* BMT3 gene (PpPBS3 3').

Plasmid pGLY3421 (FIG. 14) is an integration vector that contains an expression cassette comprising the *P. pastoris* URA5 gene flanked by lacZ repeats flanked on one side with the 5' nucleotide sequence of the *P. pastoris* BMT3 gene (SEQ ID NO:81) and on the other side with the 3' nucleotide sequence of the *P. pastoris* BMT3 gene (SEQ ID NO:82). Plasmid pGLY3419 was linearized and the linearized plasmid transformed into strain YGLY7930 and YGLY7940 to produce a number of strains in which the URA5 expression cassette has been inserted into the BMT1 locus by double-crossover homologous recombination. The strains YGLY7965 and YGLY7961 were selected from the strains produced and are prototrophic for uracil, adenine, histidine, proline, arginine, and tryptophan.

Figure 15:
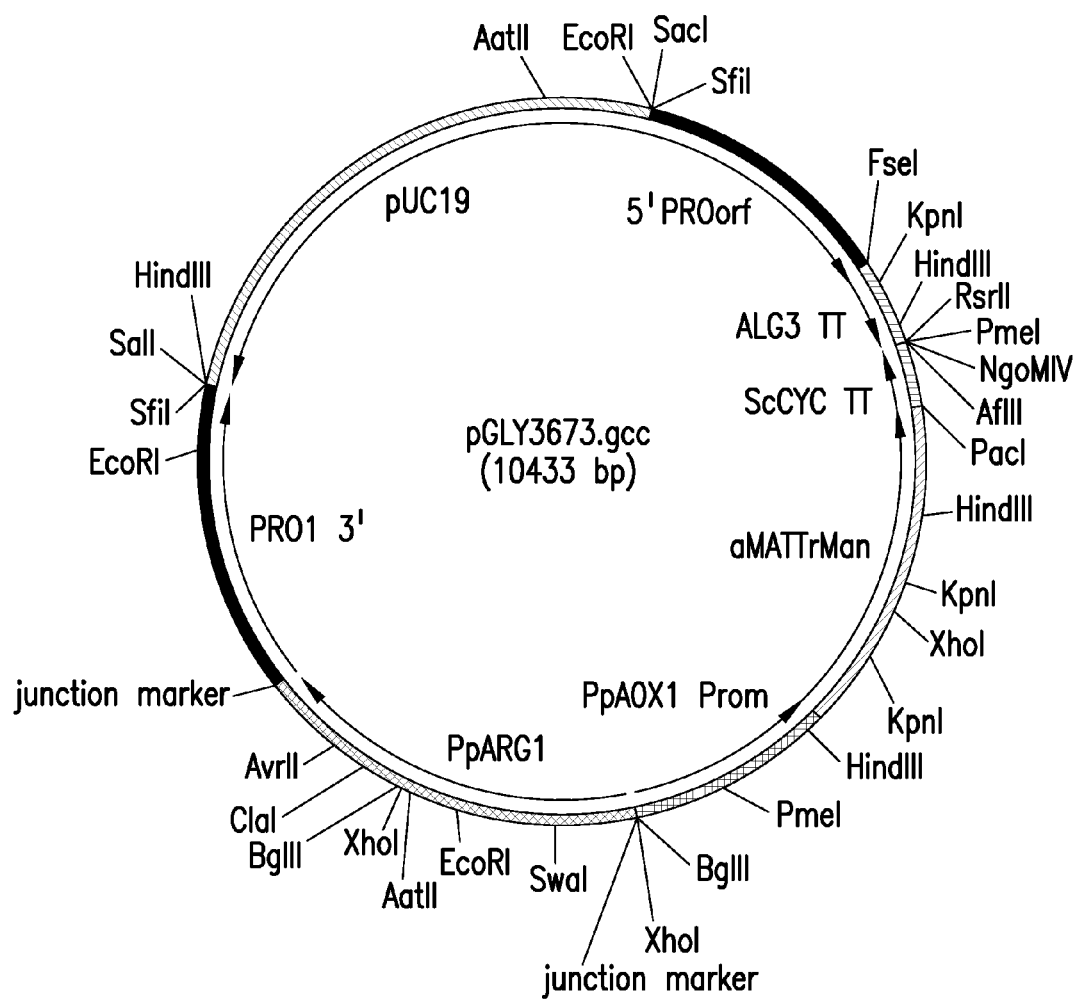
FIG. 15 shows a map of plasmid pGLY3673. Plasmid pGLY3673 is a KINKO integration vector that targets the PRO1 locus without disrupting expression of the locus and contains expression cassettes encoding the *T. reesei* α-1,2-mannosidase catalytic domain fused at the N-terminus to *S. cerevisiae* αMATpre signal peptide (aMATTrMan) to target the chimeric protein to the secretory pathway and secretion from the cell.

Plasmid pGLY3673 (FIG. 15) is a KINKO integration vector that targets the PRO1 locus without disrupting expression of the locus and contains expression cassettes encoding the *T. reesei* α-1,2-mannosidase catalytic domain fused at the N-terminus to *S. cerevisiae* αMATpre signal peptide (aMAT-TrMan) to target the chimeric protein to the secretory pathway and secretion from the cell. The expression cassette encoding the aMATTrMan comprises a nucleic acid molecule encoding the *T. reesei* catalytic domain (SEQ ID NO:83) fused at the 5' end to a nucleic acid molecule encoding the *S. cerevisiae* αMATpre signal peptide (SEQ ID NO:13), which is operably linked at the 5' end to a nucleic acid molecule comprising the *P. pastoris* AOX1 promoter (SEQ ID NO:23) and at the 3' end to a nucleic acid molecule comprising the *S. cerevisiae* CYC transcription termination sequence (SEQ ID NO:24), The cassette is flanked on one side by a nucleic acid molecule comprising a nucleotide sequence from the 5' region and complete ORF of the PRO1 gene (SEQ ID NO:89) followed by a *P. pastoris* ALG3 termination sequence and on the other side by a nucleic acid molecule comprising a nucleotide sequence from the 3' region of the PRO1 gene (SEQ ID NO:90). The plasmid contains the PpARG1 gene. Plasmid pGLY3673 was transformed into strains YGLY7965 and YGLY7961 to produce a number of strains of which strains YGLY78316 and YGLY8323 were selected from the strains produced.

Figure 16:
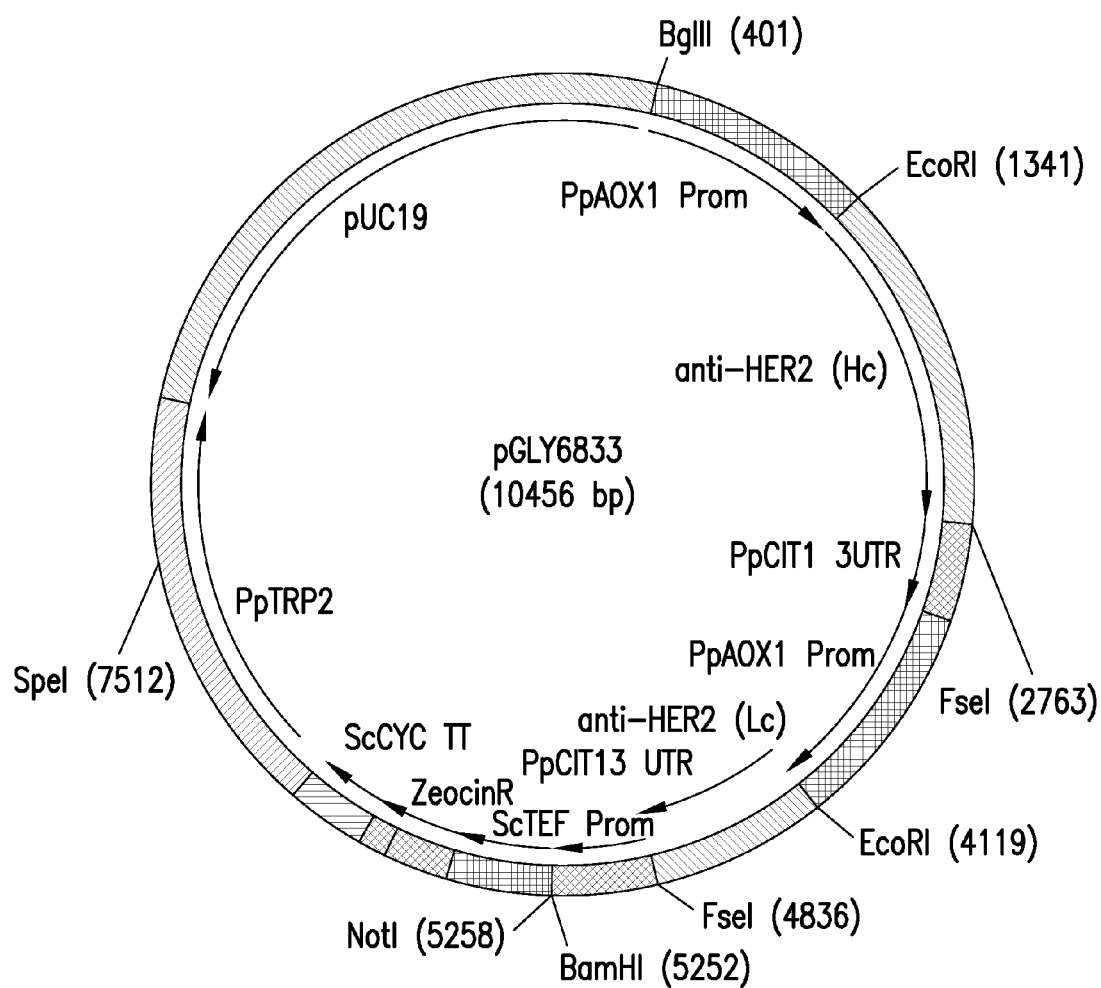
FIG. 16 shows a map of pGLY6833 encoding the light and heavy chains of an anti-Her2 antibody. The plasmid is a roll-in vector that targets the TRP2 locus. The ORFs encoding the light and heavy chains are under the control of a *P. pastoris* AOX1 promoter and the *P. pastoris* CIT1 3UTR transcription termination sequence. Selection of transformants uses zeocin resistance encoded by the zeocin resistance protein (Zeocin$^R$) ORF under the control of the *P. pastoris* TEF1 promoter and *S. cerevisiae* CYC termination sequence.

Plasmid p GLY6833 (FIG. 16) is a roll-in integration plasmid encoding the light and heavy chains of an anti-Her2 antibody that targets the TRP2 locus in *P. pastoris*. The expression cassette encoding the anti-Her2 heavy chain comprises a nucleic acid molecule encoding the heavy chain ORF codon-optimized for effective expression in *P. pastoris* (SEQ ID NO:15) operably linked at the 5' end to a nucleic acid molecule encoding the *Saccharomyces cerevisiae* mating factor pre-signal sequence (SEQ ID NO:14) which in turn is fused at its N-terminus to a nucleic acid molecule that has the inducible *P. pastoris* AOX1 promoter sequence (SEQ ID NO:23) and at the 3' end to a nucleic acid molecule that has the *P. pastoris* CIT1 transcription termination sequence (SEQ ID NO:85). The expression cassette encoding the anti-Her2 light chain comprises a nucleic acid molecule encoding the light chain ORF codon-optimized for effective expression in *P. pastoris* (SEQ ID NO:17) operably linked at the 5' end to a nucleic acid molecule encoding the *Saccharomyces cerevisiae* mating factor pre-signal sequence (SEQ ID NO:14) which in turn is fused at its N-terminus to a nucleic acid molecule that has the inducible *P. pastoris* AOX1 promoter sequence (SEQ ID NO:23) and at the 3' end to a nucleic acid molecule that has the *P. pastoris* CIT1 transcription termination sequence (SEQ ID NO:85). For selecting transformants, the plasmid comprises an expression cassette encoding the Zeocin ORF in which the nucleic acid molecule encoding the ORF (SEQ ID NO:35) is operably linked at the 5' end to a nucleic acid molecule having the *S. cerevisiae* TEF promoter sequence (SEQ ID NO:37) and at the 3' end to a nucleic acid molecule having the *S. cerevisiae* CYC transcription termination sequence (SEQ ID NO:24). The plasmid further includes a nucleic acid molecule for targeting the TRP2 locus (SEQ ID NO:91).

Figure 17:
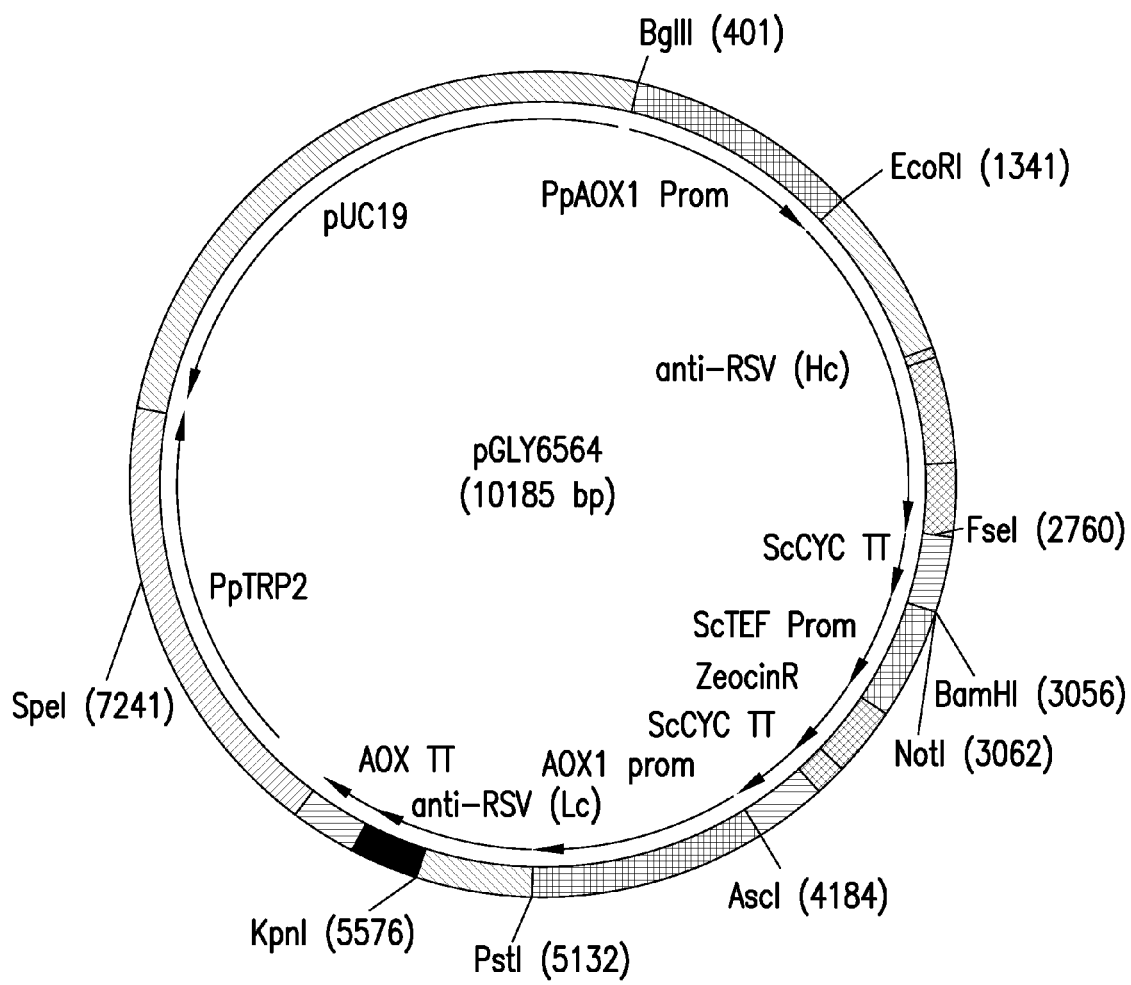
FIG. 17 shows a map of pGLY6564 encoding the light and heavy chains of an anti-RSV antibody. The plasmid is a roll-in vector that targets the TRP2 locus. The ORF encoding the heavy chain is under the control of a *P. pastoris* AOX1 promoter and the *S. cerevisiae* CYC transcription termination sequence. The ORF encoding the light chain is under the control of a *P. pastoris* AOX1 promoter and the *P. pastoris* AOX1 transcription termination sequence. Selection of transformants uses zeocin resistance encoded by the zeocin resistance protein (Zeocin$^R$) ORF under the control of the *P. pastoris* TEF1 promoter and *S. cerevisiae* CYC termination sequence.

Plasmid pGLY6564 (FIG. 17) is a roll-in integration plasmid encoding the light and heavy chains of an anti-RSV antibody that targets the TRP2 locus in *P. pastoris*. The expression cassette encoding the anti-RSV heavy chain comprises a nucleic acid molecule encoding the heavy chain ORF codon-optimized for effective expression in *P. pastoris* (SEQ ID NO:19) operably linked at the 5' end to a nucleic acid molecule encoding the *Saccharomyces cerevisiae* mating factor pre-signal sequence (SEQ ID NO:14) which in turn is fused at its N-terminus to a nucleic acid molecule that has the inducible *P. pastoris* AOX1 promoter sequence (SEQ ID NO:23) and at the 3' end to a nucleic acid molecule that has the *S. cerevisiae* CYC transcription termination sequence (SEQ ID NO:24). The expression cassette encoding the anti-RSV light chain comprises a nucleic acid molecule encoding the light chain ORF codon-optimized for effective expression in *P. pastoris* (SEQ ID NO:21) operably linked at the 5' end to a nucleic acid molecule encoding the *Saccharomyces cerevisiae* mating factor pre-signal sequence (SEQ ID NO:14) which in turn is fused at its N-terminus to a nucleic acid molecule that has the inducible *P. pastoris* AOX1 promoter sequence (SEQ ID NO:23) and at the 3' end to a nucleic acid molecule that has the *P. pastoris* AOX1 transcription termination sequence (SEQ ID NO:36). For selecting transformants, the plasmid comprises an expression cassette encoding the Zeocin ORF in which the nucleic acid molecule encoding the ORF (SEQ ID NO:35) is operably linked at the 5' end to a nucleic acid molecule having the *S. cerevisiae* TEF promoter sequence (SEQ ID NO:37) and at the 3' end to a nucleic acid molecule having the *S. cerevisiae* CYC transcription termination sequence (SEQ ID NO:24). The plasmid further includes a nucleic acid molecule for targeting the TRP2 locus (SEQ ID NO:91).

Strain YGLY13992 was generated by transforming pGLY6833, which encodes the anti-Her2 antibody, into YGLY8316. The strain YGLY13992 was selected from the strains produced. In this strain, the expression cassettes encoding the anti-Her2 heavy and light chains are targeted to the *Pichia pastoris* TRP2 locus (PpTRP2). This strain does not include the LmSTT3D expression cassette. Strain YGLY14401 was generated by transforming pGLY6564, which encodes the anti-RSV antibody, into YGLY8323. The strain YGLY14401 was selected from the strains produced. In this strain, the expression cassettes encoding the anti-RSV heavy and light chains are targeted to the *Pichia pastoris* TRP2 locus (PpTRP2). This strain does not include the LmSTT3D expression cassette.

Transformation of the appropriate strains disclosed herein with the above LmSTT3D expression/integration plasmid vectors was performed essentially as follows. Appropriate *Pichia pastoris* strains were grown in 50 mL YPD media (yeast extract (1%), peptone (2%), and dextrose (2%)) overnight to an OD of about 0.2 to 6. After incubation on ice for 30 minutes, cells were pelleted by centrifugation at 2500-3000 rpm for five minutes. Media was removed and the cells washed three times with ice cold sterile 1 M sorbitol before resuspension in 0.5 mL ice cold sterile 1 M sorbitol. Ten µL linearized DNA (5-20 µg) and 100 µL cell suspension was combined in an electroporation cuvette and incubated for 5 minutes on ice. Electroporation was in a Bio-Rad GenePulser Xcell following the preset *Pichia pastoris* protocol (2 kV, 25 µF, 200Ω), immediately followed by the addition of 1 mL YPDS recovery media (YPD media plus 1 M sorbitol). The transformed cells were allowed to recover for four hours to overnight at room temperature (24° C.) before plating the cells on selective media.

Strains YGLY13992 and YGLY14401 were each then transformed with pGLY6301, which encodes the LmSTT3D under the control of the inducible AOX1 promoter, or pGLY6294, which encodes the LmSTT3D under the control of the constitutive GAPDH promoter, as described above to produce the strains described in Example 3.

EXAMPLE 3

Integration/expression plasmid pGLY6301, which comprises the expression cassette in which the ORE encoding the LmSTT3D is operably-linked to the inducible PpAOX1 promoter, or pGLY6294, which comprises the expression cassette in which the ORE encoding the LmSTT3D is operably-linked to the constitutive PpGAPDH promoter, was linearized with SpeI or SfiI, respectively, and the linearized plasmids transformed into *Pichia pastoris* strain YGLY13992 or YGLY14401 to produce strains YGLY17351, YGLY17368, YGLY17319, and YGLY17354 shown in Table 1. Transformations were performed essentially as described in Example 2.

TABLE 1

| Strain | Antibody | LmSTT3D expression |
| --- | --- | --- |
| YGLY13992 | Anti-Her2 | none |
| YGLY17351 | Anti-Her2 | inducible |
| YGLY17368 | Anti-Her2 | constitutive |
| YGLY14401 | Anti-RSV | none |
| YGLY17319 | Anti-RSV | inducible |
| YGLY17354 | Anti-RSV | constitutive |

The genomic integration of pGLY6301 at the URA6 locus was confirmed by colony PCR (cPCR) using the primers, PpURA6out/UP (5'-CTGAGGAGTCAGATATCAGCT-CAATCTCCAT-3'; SEQ ID NO: 1) and Puc19/LP (5'-TCCG-GCTCGTATGTTGTGTGGAATTGT-3'; SEQ ID NO: 2) or ScARR3/UP (5'-GGCAATAGTCGCGAGAATCCT- TAAACCAT-3'; SEQ ID NO: 3) and PpURA6out/LP (5-CTGGATGTTTGATGGGTTCAGTTTCAGCTGGA-3'; SEQ ID NO: 4).

The genomic integration of pGLY6294 at the TRP1 locus was confirmed by cPCR using the primers, PpTRP-5'out/UP (5'-CCTCGTAAAGATCTGCGGTTTGCAAAGT-3'; SEQ ID NO: 5) and PpALG3TT/LP (5'-CCTCCCACTGGAAC-CGATGATATGGAA-3'; SEQ ID NO: 6) or PpTEFTT/UP (5'-GATGCGAAGTTAAGTGCGCAGAAAGTAATATCA-3'; SEQ ID NO: 7) and PpTRP1-3' out/LP (5'-CGTGTGTAC-CTTGAAACGTCAATGATACTTTGA-3'; SEQ ID NO: 8). Integration of the expression cassette encoding the LmSTT3D into the genome was confirmed using cPCR primers, LmSTT3D/iUP (5'-GCGACTGGTTCCAATTGA-CAAGCTT-3' (SEQ ID NO: 9) and LmSTT3D/iLP (5'-CAA-CAGTAGAACCAGAAGCCTCGTAAGTACAG-3' (SEQ ID NO: 10). The PCR conditions were one cycle of 95° C. for two minutes, 35 cycles of 95° C. for 20 seconds, 55° C. for 20 seconds, and 72° C. for one minute; followed by one cycle of 72° C. for 10 minutes.

The strains were cultivated in a Sixfor fermentor to produce the antibodies for N-glycosylation site occupancy analysis. Cell growth conditions of the transformed strains for antibody production were generally as follows.

Protein expression for the transformed yeast strains was carried out at in shake flasks at 24° C. with buffered glycerol-complex medium (BMGY) consisting of 1% yeast extract, 2% peptone, 100 mM potassium phosphate buffer pH 6.0, 1.34% yeast nitrogen base, $4 \times 10^{-5}$% biotin, and 1% glycerol. The induction medium for protein expression was buffered methanol-complex medium (BMMY) consisting of 1% methanol instead of glycerol in BMGY. Pmt inhibitor Pmti-3 in methanol was added to the growth medium to a final concentration of 18.3 μM at the time the induction medium was added. Cells were harvested and centrifuged at 2,000 rpm for five minutes.

SixFors Fermentor Screening Protocol followed the parameters shown in Table 2.

TABLE 2

SixFors Fermentor Parameters

| Parameter | Set-point | Actuated Element |
|---|---|---|
| pH | 6.5 ± 0.1 | 30% NH$_4$OH |
| Temperature | 24 ± 0.1 | Cooling Water & Heating Blanket |
| Dissolved O2 | n/a | Initial impeller speed of 550 rpm is ramped to 1200 rpm over first 10 hr, then fixed at 1200 rpm for remainder of run |

At time of about 18 hours post-inoculation, SixFors vessels containing 350 mL media A (See Table 3 below) plus 4% glycerol were inoculated with strain of interest. A small dose (0.3 mL of 0.2 mg/mL in 100% methanol) of Pmti-3 (5-[[3-(1-Phenyl-2-hydroxy)ethoxy)-4-(2-phenylethoxy)]phenyl] methylene]-4-oxo-2-thioxo-3-thiazolidineacetic Acid) (See Published International Application No. WO 2007061631) was added with inoculum. At time about 20 hour, a bolus of 17 mL 50% glycerol solution (Glycerol Fed-Batch Feed, See Table 4 below) plus a larger dose (0.3 mL of 4 mg/mL) of Pmti-3 was added per vessel. At about 26 hours, when the glycerol was consumed, as indicated by a positive spike in the dissolved oxygen (DO) concentration, a methanol feed (See Table 5 below) was initiated at 0.7 mL/hr continuously. At the same time, another dose of Pmti-3 (0.3 mL of 4 mg/mL stock) was added per vessel. At time about 48 hours, another dose (0.3 mL of 4 mg/mL) of Pmti-3 was added per vessel. Cultures were harvested and processed at time about 60 hours post-inoculation.

TABLE 3

Composition of Media A

| | |
|---|---|
| Soytone L-1 | 20 g/L |
| Yeast Extract | 10 g/L |
| KH$_2$PO4 | 11.9 g/L |
| K$_2$HPO$_4$ | 2.3 g/L |
| Sorbitol | 18.2 g/L |
| Glycerol | 40 g/L |
| Antifoam Sigma 204 | 8 drops/L |
| 10X YNB w/Ammonium Sulfate w/o Amino Acids (134 g/L) | 100 mL/L |
| 250X Biotin (0.4 g/L) | 10 mL/L |
| 500X Chloramphenicol (50 g/L) | 2 mL/L |
| 500X Kanamycin (50 g/L) | 2 mL/L |

TABLE 4

Glycerol Fed-Batch Feed

| | |
|---|---|
| Glycerol | 50% m/m |
| PTM1 Salts (see Table IV-E below) | 12.5 mL/L |
| 250X Biotin (0.4 g/L) | 12.5 mL/L |

TABLE 5

Methanol Feed

| | |
|---|---|
| Methanol | 100% m/m |
| PTM1 Salts (See Table 6) | 12.5 mL/L |
| 250X Biotin (0.4 g/L) | 12.5 mL/L |

TABLE 6

PTM1 Salts

| | |
|---|---|
| CuSO$_4$—5H$_2$O | 6 g/L |
| NaI | 80 mg/L |
| MnSO$_4$—7H$_2$O | 3 g/L |
| NaMoO$_4$—2H$_2$O | 200 mg/L |
| H$_3$BO$_3$ | 20 mg/L |
| CoCl$_2$—6H$_2$O | 500 mg/L |
| ZnCl$_2$ | 20 g/L |
| FeSO$_4$—7H$_2$O | 65 g/L |
| Biotin | 200 mg/L |
| H$_2$SO$_4$ (98%) | 5 mL/L |

The occupancy of N-glycan on anti-Her2 or anti-RSV antibodies was determined using capillary electrophoresis (CE) as follows. The antibodies were recovered from the cell culture medium and purified by protein A column chromatography. The protein A purified sample (100-200 μg) was concentrated to about 100 μL and then buffer was exchanged with 100 mM Tris-HCl pH 9.0 with 1% SDS. Then, the sample along with 2 μL of 10 kDa internal standard provided by Beckman was reduced by addition of 5 μL β-mercaptoethanol and boiled for five minutes. About 20 μL, of reduced sample was then resolved over a bare-fused silica capillary (about 70 mm, 50 μm I.D.) according to the method recommended by Beckman Coulter.

Figure 18:
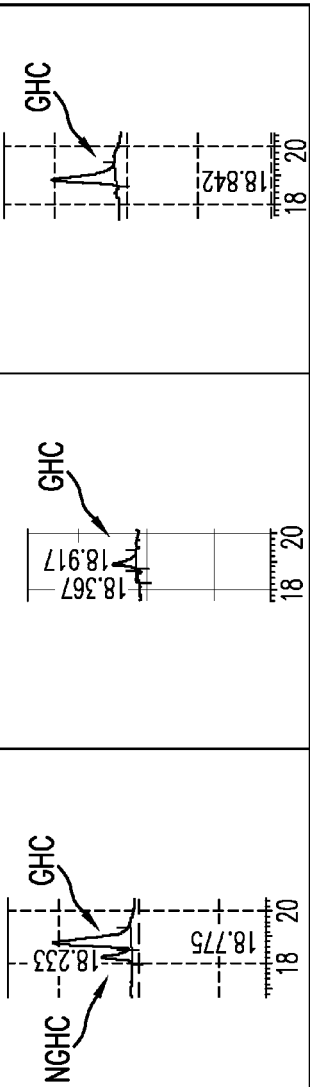
FIG. 18 shows the percent N-glycosylation site occupancy of anti-Her2 and anti-RSV antibodies produced in control strains verses strains in which the LmSTT3D is constitutively expressed (GAPDH promoter) or inducibly expressed (AOX1 promoter).

FIG. 18 shows the N-glycosylation site occupancy of heavy chains from the CE analysis. The figure shows that for both antibodies, the amount of N-linked heavy chains species increased from about 80% to about 94% when the LmSTT3D was constitutively expressed to about 99% when expression of the LmSTT3D was induced at the same time as expression of the antibodies was induced.

Table 7 shows N-glycosylation site occupancy of anti-HER2 and anti-RSV antibodies was increased for compositions in which the antibodies were obtained from host cells in which the LmSTT3D was overexpressed in the presence of the endogenous oligosaccharyltransferase (OST) complex. To determine N-glycosylation site occupancy, antibodies were reduced and the N-glycan occupancy of the heavy chains determined. The table shows that in general, overexpression of the LmSTT3D under the control of an inducible promoter effected an increase of N-glycosylation site occupancy from about 82-83% to about 99% for both antibodies tested (about a 19% increase over the N-glycosylation site occupancy in the absence of LmSTT3D overexpression). The expression of the LmSTT3D and the antibodies were under the control of the same inducible promoter. When overexpression of the LmSTT3D was under the control of a constitutive promoter the increase in N-glycosylation site occupancy was increased to about 94% for both antibodies tested (about a 13% increase over the N-glycosylation site occupancy in the absence of LmSTT3D overexpression).

TABLE 7

| Strain | LmSTT3D AOX1 Prom. (pGLY6301) (inducible) | LmSTT3D GAPDH Prom. (pGLY6294) (constitutive) | Antibody | Heavy Chain N-glycosylation site occupancy[#] (%) |
|---|---|---|---|---|
| YGLY13992 | None | None | Anti-HER2 | 83 |
| YGLY17368 | None | over-expressed | Anti-HER2 | 94 |
| YGLY17351 | over-expressed | None | Anti-HER2 | 99 |
| YGLY14401 | None | None | Anti-RSV | 82 |
| YGLY17354 | None | over-expressed | Anti-RSV | 94 |
| YGLY17319 | over-expressed | None | Anti-RSV | 99 |

[#]N-glycosylation site occupancy based upon percent glycosylation site occupancy of total heavy chains from reduced antibodies Table 8 shows the N-glycosylation site occupancy for compositions comprising whole antibodies obtained from host cells in which the LmSTT3D was overexpressed in the presence of the endogenous oligosaccharyltransferase (OST) complex based upon the determination of N-glycosylation site occupancy of the individual heavy chains from reduced antibody preparations. The formula (fraction GHC)$^2 \times 100$ will provide an estimate or approximation of the percent fully occupied antibodies based upon the determination of the fraction of heavy chains that are N-glycosylated.

TABLE 8

| Strain | LmSTT3D AOX1 Prom. (pGLY6301) (inducible) | LmSTT3D GAPDH Prom. (pGLY6294) (constitutive) | Antibody | Fully Occupied Antibodies[#] (%) |
|---|---|---|---|---|
| YGLY13992 | None | None | Anti-HER2 | 68.9 |
| YGLY17368 | None | over-expressed | Anti-HER2 | 88.4 |
| YGLY17351 | over-expressed | None | Anti-HER2 | 98.0 |
| YGLY14401 | None | None | Anti-RSV | 67.2 |
| YGLY17354 | None | over-expressed | Anti-RSV | 88.4 |
| YGLY17319 | over-expressed | None | Anti-RSV | 98.0 |

[#]based upon results obtained from Table 7.

Q-TOF Analysis

The high performance liquid chromatography (HPLC) system used consisted of an Agilent 1200 equipped with autoinjector, a column-heating compartment and a UV detector detecting at 210 and 280 nm. All LC-MS experiments performed with this system were running at 1 mL/min. The flow rate was not split for MS detection. Mass spectrometric analysis was carried out in positive ion mode on Accurate-Mass Q-TOF LC/MS 6520 (Agilent technology). The temperature of dual ESI source was set at 350° C. The nitrogen gas flow rates were set at 13 L/h for the cone and 350l/h and nebulizer was set at 45 prig with 4500 volt applied to the capillary. Reference mass of 922.009 was prepared from HP-0921 according to API-TOF reference mass solution kit for mass calibration and the protein mass measurements. The data for ion spectrum range from 300-3000 m/z were acquired and processed using Agilent Masshunter.

Sample preparation was as follows. An intact antibody sample (50 μg) was prepared 50 μL 25 mM $NH_4HCO_3$, pH 7.8. For deglycosylated antibody, a 50 μL aliquot of intact antibody sample was treated with PNGase F (10 units) for 18 hours at 37° C. Reduced antibody was prepared by adding 1 M DTT to a final concentration of 10 mM to an aliquot of either intact antibody or deglycosylated antibody and incubated for 30 min at 37° C.

Three micrograms of intact or deglycosylated antibody sample was loaded onto a Poroshell 300SB-C3 column (2.1 mm×75 mm, 5 μm) (Agilent Technologies) maintained at 70° C. The protein was first rinsed on the cartridge for 1 minute with 90% solvent A (0.1% HCOOH), 5% solvent B (90% Acetonitrile in 0.1% HCOOH). Elution was then performed using a gradient of 5-100% of B over 26 minutes followed by a three-minute regeneration at 100% B and by a final equilibration period of 10 minute at 5% B.

For reduced antibody, a three microgram sample was loaded onto a Poroshell 300SB-C3 column (2.1 mm×75 mm, 5 μm) (Agilent Technologies) maintained at 40 C. The protein was first rinsed on the cartridge for three minutes with 90% solvent A, 5% solvent B. Elution was then performed using a gradient of 5-80% of B over 20 minutes followed by a seven-minute regeneration at 80% B and by a final equilibration period of 10 minutes at 5% B.

Figure 19A:
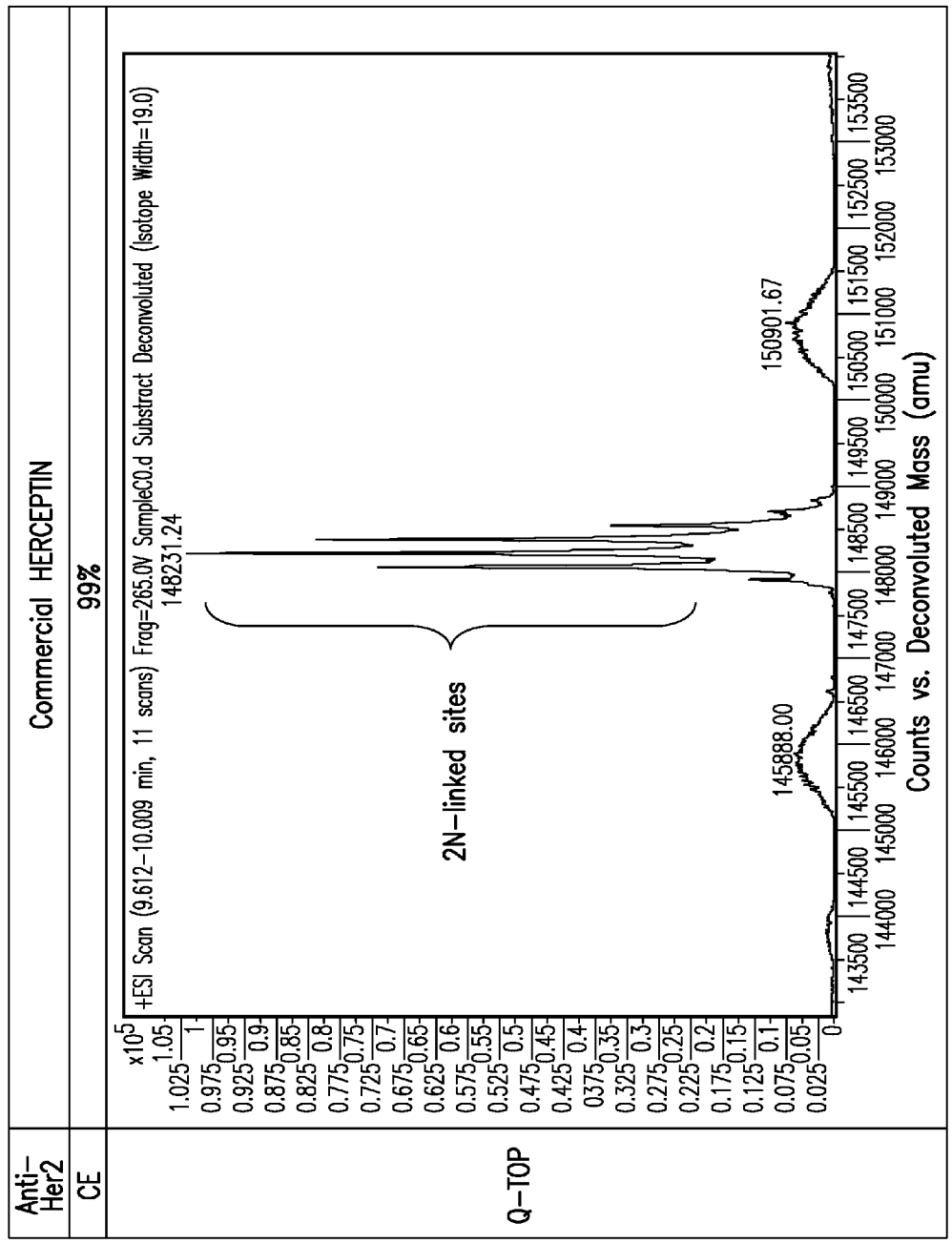
FIG. 19 shows a comparison of N-glycosylation site occupancy of the anti-Her2 antibody produced in strain YGLY13992 and strain YGLY17351 compared to N-glycosylation site occupancy of a commercially available anti-Her2 antibody produced in CHO cells (HERCEPTIN). Strain YGLY13992 does not include an expression cassette encoding the LmSTT3D whereas strain YGLY17351 includes an expression cassette encoding the LmSTT3 under the control of the inducible PpAOX1 promoter.
Figure 19B:
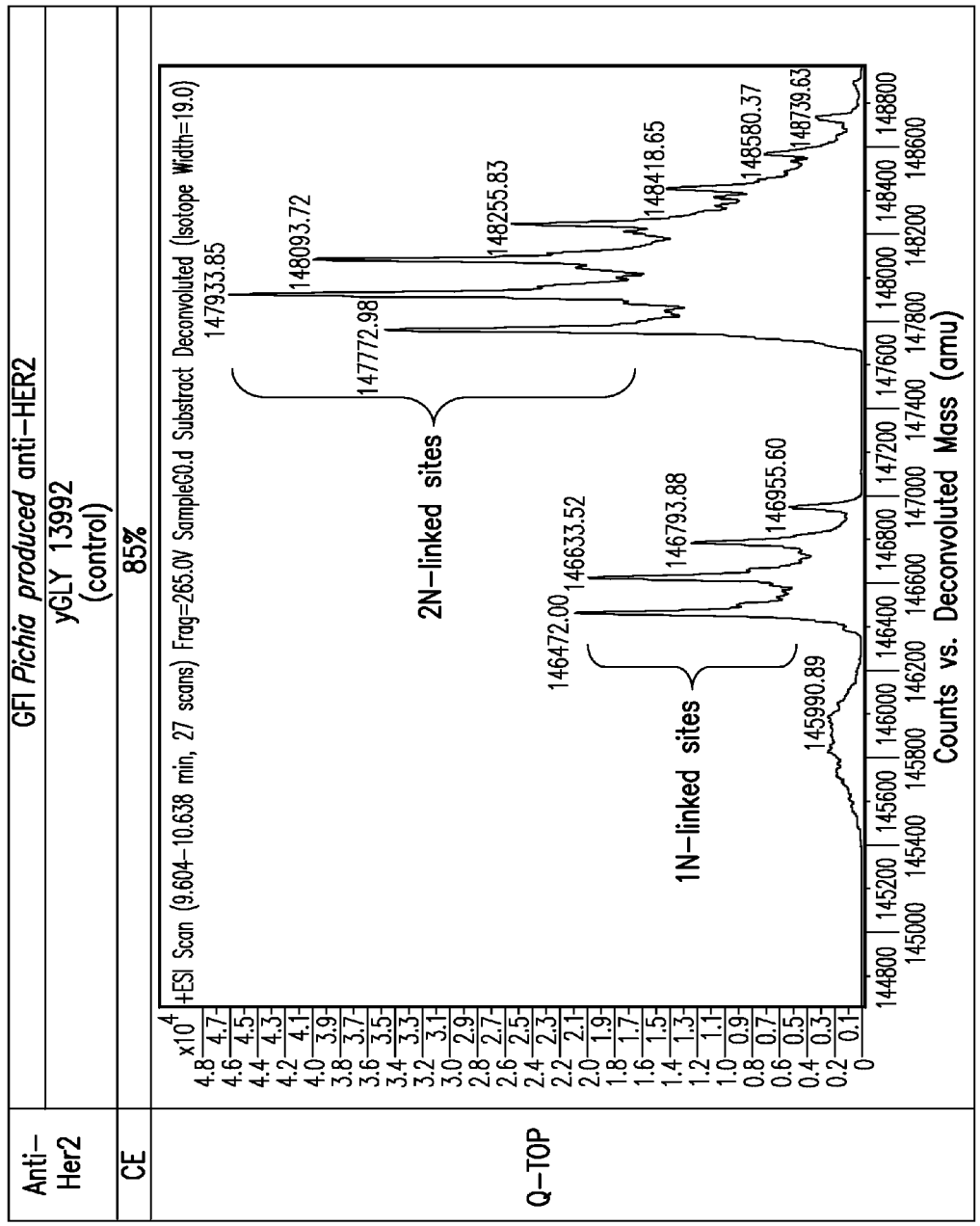
Figure 19C:
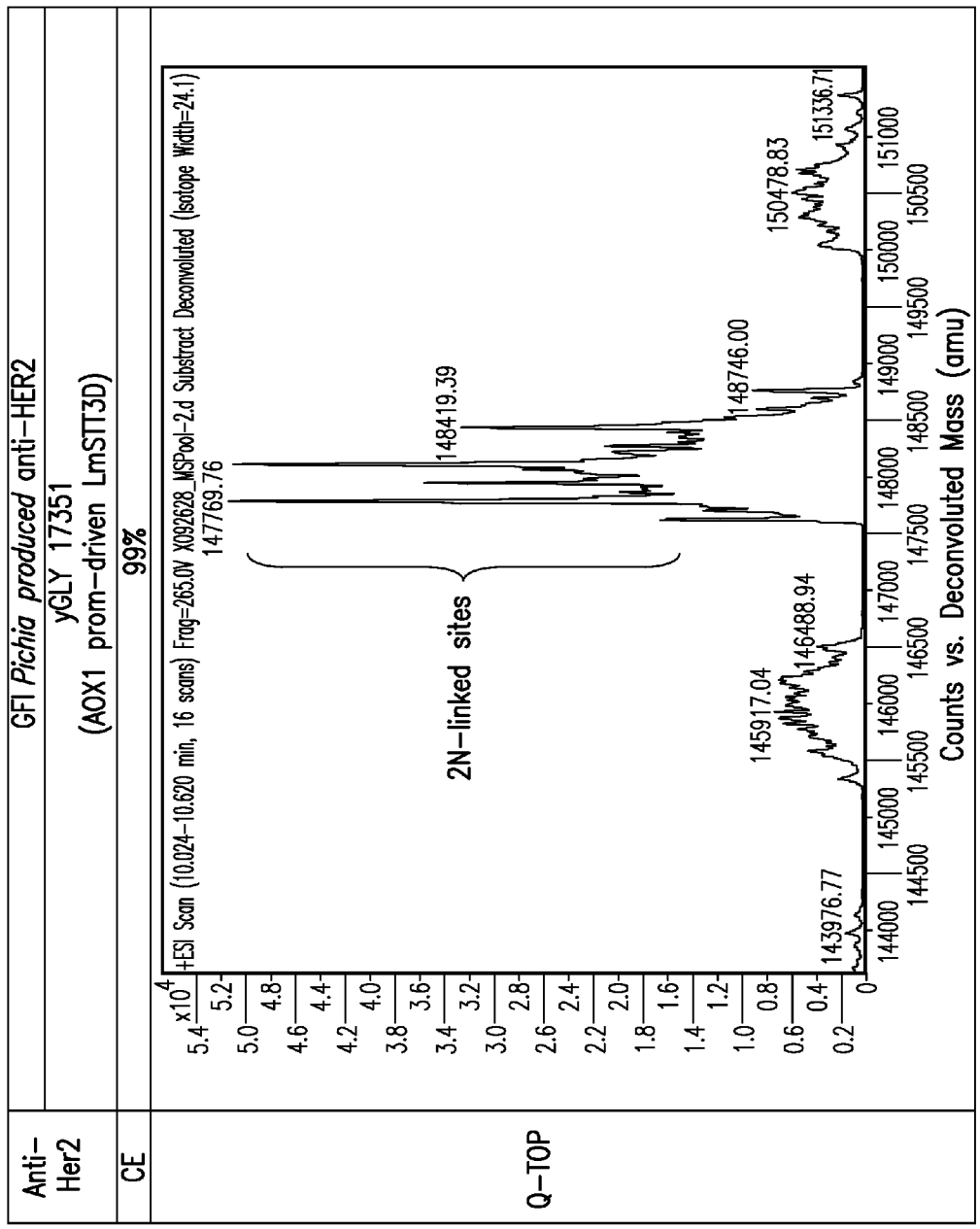

FIG. 19 shows the results of a Q-TOF analysis in which the N-glycosylation site occupancy of non-reduced anti-Her2 antibody produced in YGLY17351 was compared to N-glycosylation site occupancy of non-reduced commercially available anti-Her2 antibody produced in CHO cells (HERCEPTIN). The figure shows that anti-Her2 antibody produced in strain YGLY17351 has an N-glycosylation site occupancy that is like the N-glycosylation site occupancy of an anti-Her2 antibody made in CHO cells. The figure shows that the amount of antibodies in which only one N-glycosylation site was occupied decreased and the amount of antibodies in which both N-glycosylation sites was occupied increased when the antibodies were produced by strain YGLY17351. The results shown for anti-Her2 antibody produced in YGLY17351 were consistent with the approximated occupancy shown in Table 8.

Figure 20:
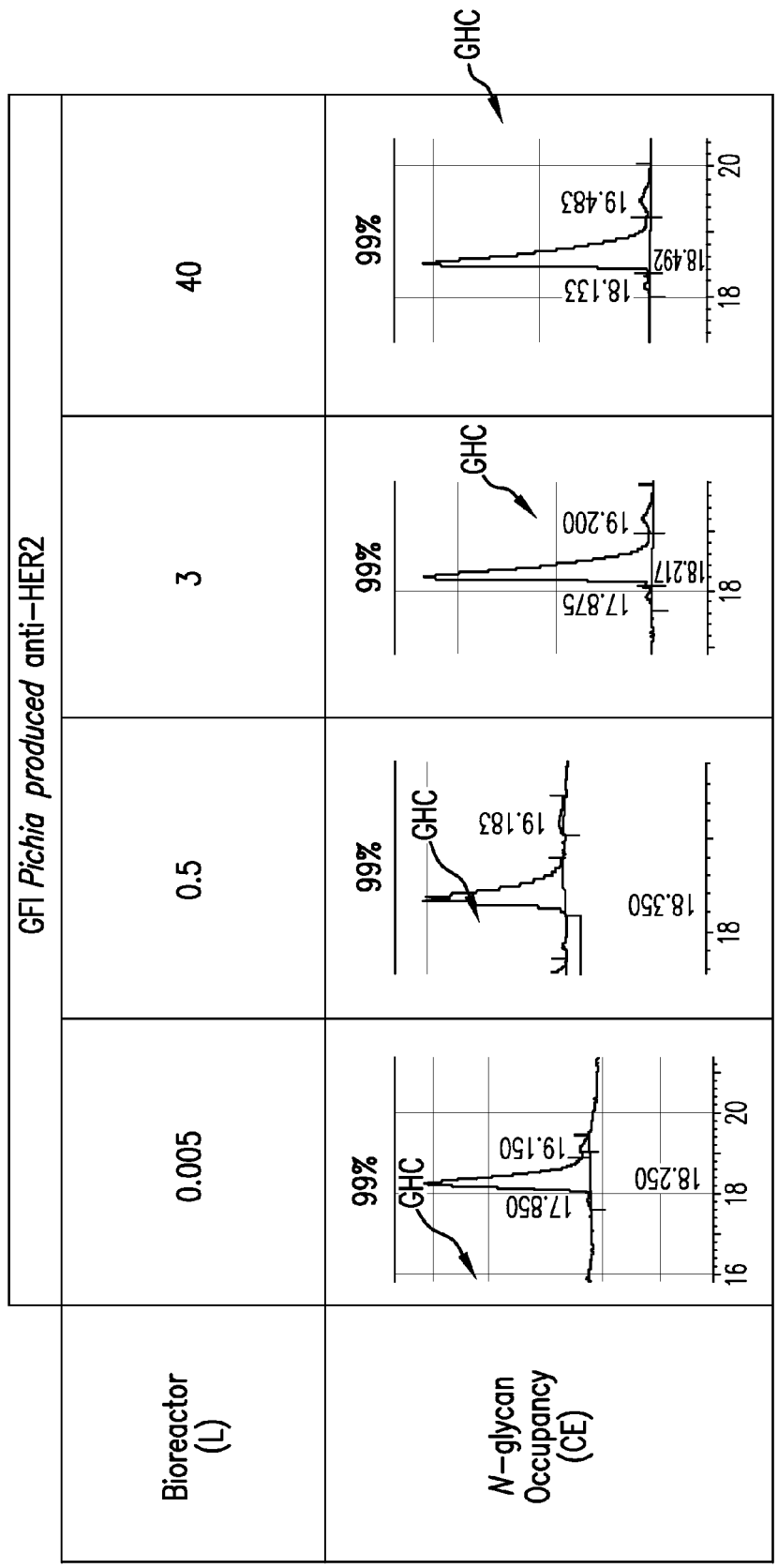
FIG. 20 shows the shows the percent N-glycosylation site occupancy of anti-Her2 antibodies produced in strain YGLY17351 grown in various bioreactors was consistent regardless of bioreactor scale.

FIG. 20 demonstrates the scalability of N-glycosylation site occupancy on anti-Her2 antibodies produced in YGLY17351. In order to evaluate scalability of N-glycan occupancy, YGLY17351 was tested in bioreactors ranging from 5 mL through 40 L. In general, N-glycosylation site occupancy of glycoproteins in glycoengineered *P. pastoris* has been observed to vary with the process conditions used to produce the glycoproteins. However, the LmSTT3D overexpressing strains showed very consistent N-glycosylation site occupancy (99%) regardless of scale of bioreactors and process conditions. Thus, the present invention provides a method in which the N-glycosylation site occupancy of glycoproteins in glycoengineered *P. pastoris* grown under small scale conditions is maintained when grown under large scale conditions.

Figure 21A:
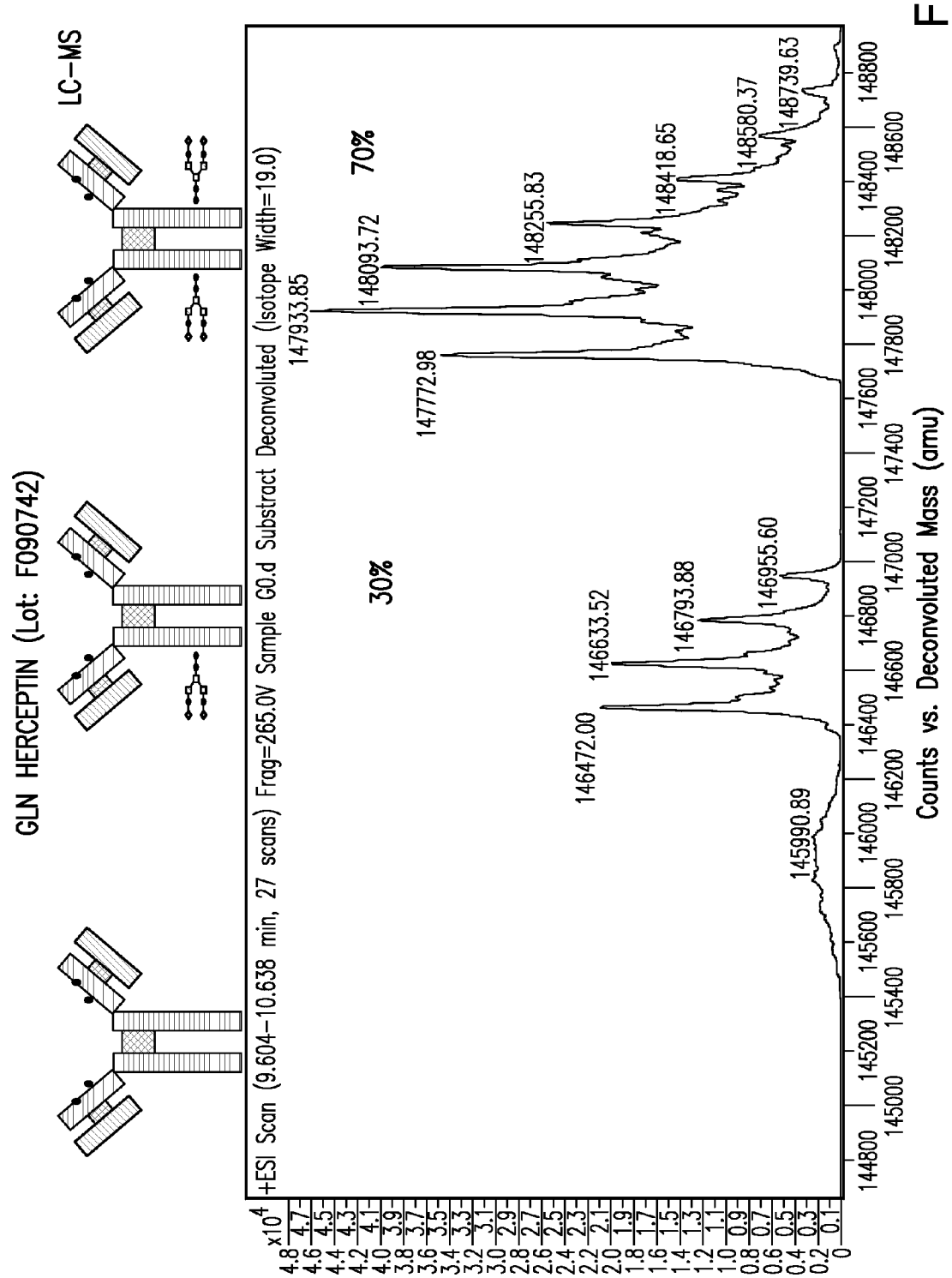
FIG. 21 shows the results of a CE and Q-TOF analysis of a commercial lot of anti-Her2 antibody (HERCEPTIN).
Figure 21B:
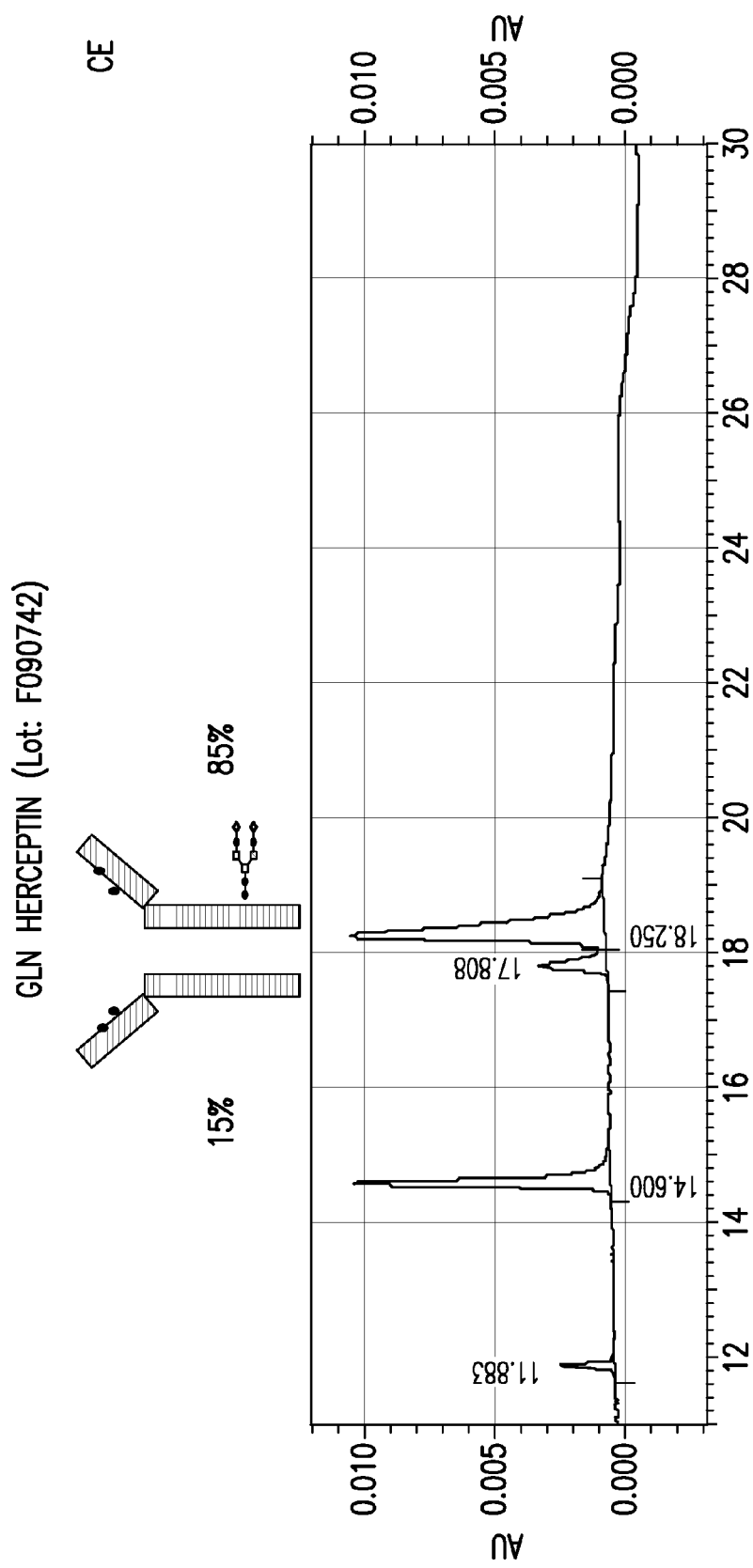
Figure 22A:
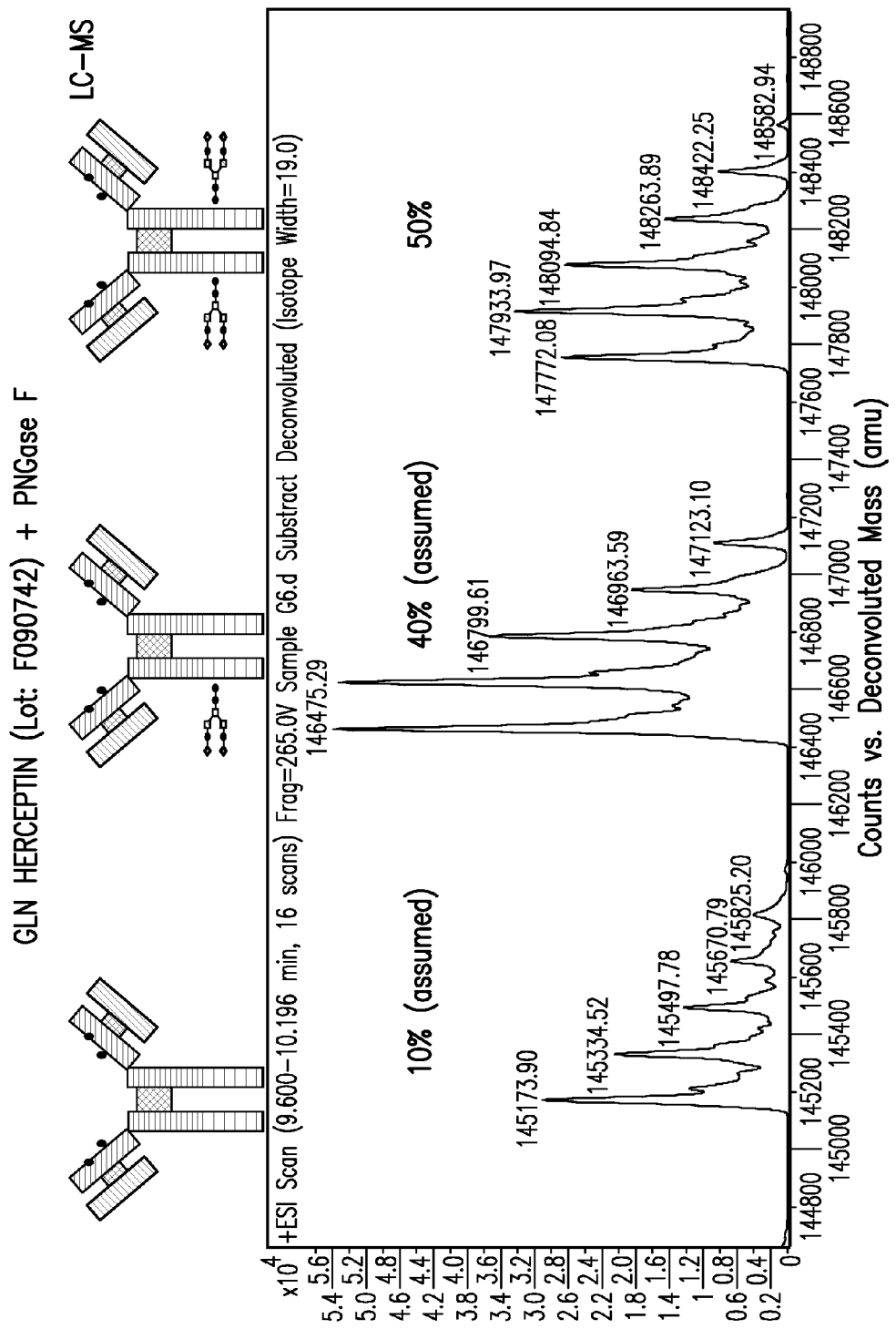
FIG. 22 shows the results of a CE and Q-TOF analysis for the same commercial lot as used for FIG. 21 but after treatment with PNGase F for a period of time.
Figure 22B:
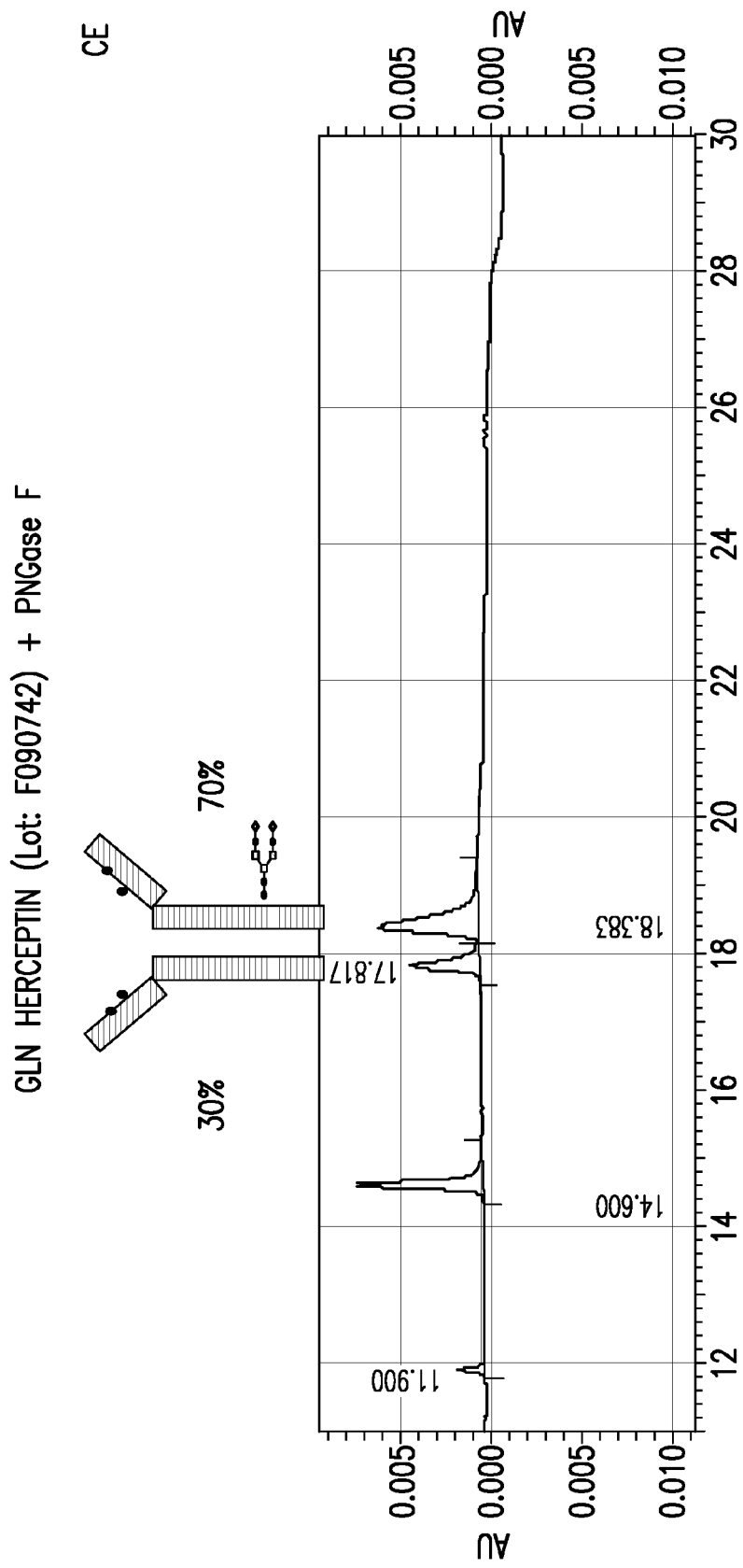

FIGS. 21 and 22 are provided for illustrative purposes. FIG. 21 shows the results of a CE and Q-TOF analysis for a commercial lot of anti-Her2 antibody produced in CHO cells (HERCEPTIN). FIG. 22 shows the results of a CE and Q-TOF analysis for the same commercial lot of anti-Her2 antibody following treatment with PNGase F for a time. The CE shows an increase in non-glycosylated heavy chain and the Q-TOF shows the presence of non-glycosylated antibody following PNGase F treatment (compare FIG. 21 to FIG. 22).

Table 9 shows the N-glycan composition of the anti-Her2 and anti-RSV antibodies produced in strains that overexpress LmSTT3D compared to strains that do not overexpress LmSTT3D. The Figure confirms that the quality of N-glycans of antibodies from LmSTT3D overexpressing strains is comparable to that from strains that do not overexpress LmSTT3D. Antibodies were produced from SixFors (0.5 L bioreactor) and N-glycans from protein A-purified antibodies were analyzed with 2AB labeling. Overall, overexpression of LmSTT3D did not appear to significantly affect the N-glycan composition of the antibodies. The glycosylation composition can vary as a function of fermentation conditions, therefore, the glycosylation composition of antibodies produced in *Pichia pastoris* strains can range from about 50-70 mole % G0, 15-25 mole % G1, 4-12% mole % G2, 5-17 mole % Man5, and 3-15 mole % hybrids.

TABLE 9

| | | N-glycans (%) | | | | |
|---|---|---|---|---|---|---|
| | LmSTT3D | G0 | G1 | G2 | Man5 | Hybrids |
| Anti-Her2 Antibody | none | 58.1 ± 1.8 | 20.5 ± 0.6 | 3.0 ± 0.9 | 14.0 ± 2.1 | 4.3 ± 1.2 |
| | overexpressed | 53.9 ± 2.0 | 22.4 ± 3.0 | 4.5 ± 1.7 | 14.7 ± 1.5 | 4.2 ± 1.5 |
| Anti-RSV Antibody | none | 51.6 ± 1.6 | 22.9 ± 2.0 | 5.3 ± 2.2 | 15.2 ± 1.1 | 4.9 ± 0.6 |
| | overexpressed | 58.4 ± 5.3 | 20.9 ± 2.8 | 3.5 ± 0.3 | 12.4 ± 0.1 | 4.7 ± 2.3 |

G0—GlcNAc$_2$Man$_3$GlcNAc$_2$
G1—GalGlcNAc$_2$Man$_3$GlcNAc$_2$
G2—Gal$_2$GlcNAc$_2$Man$_3$GlcNAc$_2$
Man5—Man$_5$GlcNAc$_2$
Hybrid—GlcNAcMan$_5$GlcNAc$_2$ and/or GalGlcNAcMan$_5$GlcNAc$_2$ Table 10 shows a comparison of the glycosylation pattern of the anti-RSV antibody produced in strain YGLY14401 compared to several commercial lots of an anti-RSV antibody produced in CHO cells and marketed as palivizumab under the tradename SYNAGIS.

TABLE 10

| Glycoform | SYNAGIS (Commercial lot 07A621) % of total | SYNAGIS (Commercial lot 09A621) % of total | Anti-RSV antibody produced in YGLY14401 % of total |
|---|---|---|---|
| Man5 | 6.4 | 6.8 | 9.5 |
| G0 | <1.0 | <1.0 | 59.9 |
| G0F | 33.9 | 30 | 0 |
| G1 | <1.0 | <1.0 | 20 |
| G1F | 41.7 | 48.8 | 0 |
| G2 | 0 | 0 | 2.8 |
| G2F | 10.9 | 12.3 | 0 |
| A2 | 5.1 | 3.7 | 0 |
| Hybrid | — | — | 7.8 |
| O-glycans occupancy (mol/mol) | 0 | 0 | 3.0 |
| Mannose (single mannose) | 0 | 0 | 96 |
| Mannobiose (two mannose residues) | 0 | 0 | 4 |

This example shows then that the present invention enables the production of recombinant glycoproteins in *Pichia pastoris* in which the N-glycosylation site occupancy of the recombinant glycoproteins is comparable to the N-glycosylation site occupancy of recombinant glycoproteins produced in mammalian expression systems such as CHO cells.

EXAMPLE 4

The *Leishmania major* STT3A protein, *Leishmania major* STT3B protein, and *Leishmania major* STT3D protein, are all examples of heterologous single-subunit oligosaccharyltransferases that have been shown to suppress the lethal phenotype of a deletion of the STT3 locus in *Saccharomyces cerevisiae* (Naseb et al., Molec. Biol. Cell 19: 3758-3768 (2008)). Naseb et al. (ibid.) further showed that the *Leishmania major* STT3D protein could suppress the lethal phenotype of a mutation of the WBP1, OST1, SWP1, or OST2 loci in *Saccharomyces cerevisiae*. Hese et al. (Glycobiology 19: 160-171 (2009)) provides data that suggest the *Leishmania major* STT3A, STT3B, and STT3D proteins can functionally complement mutations of the WBP1, OST1, SWP1, and OST2 loci. Other single-subunit heterologous oligosaccharyltransferases include but are not limited to single-subunit *Giardia* or kinetoplastid STT3 proteins, for example, the *Caenorhabditis elegans* STT3 protein, *Trypanosoma brucei* STT3 protein, *Trypanosoma cruzi* STT3 protein, and *Toxoplasma gondii* STT3 protein. In contrast to the *Leishmania major* STT3D protein, which Naseb et al. (op. cit.) teaches does not incorporate into the *Saccharomyces cerevisiae* OTase complex, Castro et al. (Proc. Natl. Acad. Sci. USA 103:

14756-14760 (2006)) teaches that the *Trypanosoma cruzi* STT3 appears to integrate into the *Saccharomyces cerevisiae* OTase complex.

In this example, host cells constructed similar to the host cells in the previous example were transformed with plasmid vectors containing expression cassettes encoding the STT3 protein from *Caenorhabditis elegans, Trypanosoma cruzi,* and *Leishmania major* STT3C operably linked to the AOX1 promoter. A vector containing an expression cassette encoding the *Pichia pastoris* Stt3p was included in the experiment. As shown in Table 11, expression of the various STT3 proteins concurrently with expression of the anti-Her2 antibody did not appear result in an increase in N-glycosylation site occupancy. However, various STT3 proteins can display substrate specificity. For example, the *Leishmania major* STT3A, B, C, and D proteins differ in substrate specificity at the level of glycosylation, which suggests that in addition to the essential N—X—S/T attachment site additional features of the substrate may influence N-linked glycosylation at a particular attachment site (Naseb et al., op cit.). The results shown in Table 9 used the anti-Her2 antibody as the substrate. The $C_{H2}$ domain of each heavy chain of an antibody contains a single site for N-linked glycosylation: this is usually at the asparagine residue 297 (Asn-297) (Kabat et al., Sequences of proteins of immunological interest, Fifth Ed., U.S. Department of Health and Human Services, NIH Publication No. 91-3242). Thus, the results shown in Table 9 suggest that the percent N-glycosylation site occupancy might be influenced by the substrate specificity of the particular single-subunit oligosaccharyltransferase being used.

TABLE 11

| STT3 (AOX1 Prom) | | Antibody | N-glycosylation site occupancy (%) |
|---|---|---|---|
| C. elegans | overexpressed | Anti-Her2 | 83 |
| T. cruzi | overexpressed | Anti-Her2 | 83 |
| L. major (STT3C) | overexpressed | Anti-Her2 | 82 |
| P. pastoris | overexpressed | Anti-Her2 | 80 |

EXAMPLE 5

A strain capable of producing sialylated N-glycans was constructed as follows. The strain was transfected with a plasmid vector encoding human GM-CSF and a plasmid vector encoding the *Leishmania major* STT3D. Construction of the strains is illustrated schematically in FIG. 23A-23D. Briefly, the strains were constructed as follows.

Figure 24:
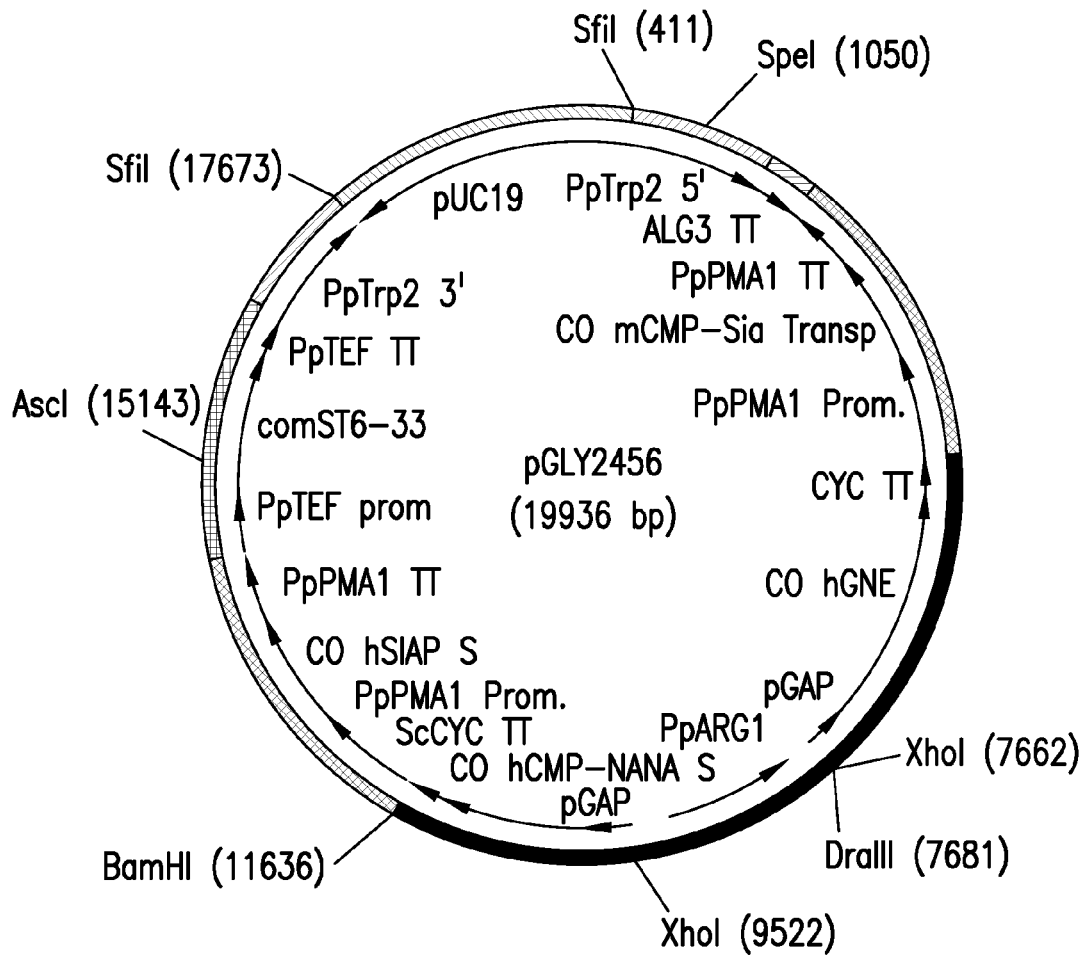
FIG. 24 shows a map of plasmid pGLY2456. Plasmid pGLY2456 is a KINKO integration vector that targets the TRP2 locus without disrupting expression of the locus and contains six expression cassettes encoding (1) the mouse CMP-sialic acid transporter codon optimized (CO mCMP-Sia Transp), (2) the human UDP-GlcNAc 2-epimerase/N-acetylmannosamine kinase codon optimized (CO hGNE), (3) the *Pichia pastoris* ARG1 gene or transcription unit, (4) the human CMP-sialic acid synthase codon optimized (CO hCMP-NANA S), (5) the human N-acetylneuraminate-9-phosphate synthase codon optimized (CO hSIAP S), and, (6) the mouse a-2,6-sialyltransferase catalytic domain codon optimized fused at the N-terminus to *S. cerevisiae* KRE2 leader peptide (comST6-33). All flanked by the 5' region of the TRP2 gene and ORF (PpTRP2 5') and the 3' region of the TRP2 gene (PpTRP2-3'). PpPMA1 prom is the *P. pastoris* PMA1 promoter; PpPMA1 TT is the *P. pastoris* PMA1 termination sequence; CYC TT is the *S. cerevisiae* CYC termination sequence; PpTEF Prom is the *P. pastoris* TEF1 promoter; PpTEF TT is the *P. pastoris* TEF1 termination sequence; PpALG3 TT is the *P. pastoris* ALG3 termination sequence; and pGAP is the *P. pastoris* GAPDH promoter.

Plasmid pGLY2456 (FIG. 24) is a KINKO integration vector that targets the TRP2 locus without disrupting expression of the locus and contains six expression cassettes encoding (1) the mouse CMP-sialic acid transporter (mCMP-Sia Transp), (2) the human UDP-GlcNAc 2-epimerase/N-acetylmannosamine kinase (hGNE), (3) the *Pichia pastoris* ARG1 gene or transcription unit, (4) the human CMP-sialic acid synthase (hCSS), (5) the human N-acetylneuraminate-9-phosphate synthase (hSPS), (6) the mouse α-2,6-sialyltransferase catalytic domain (mST6) fused at the N-terminus to *S. cerevisiae* KRE2 leader peptide (33) to target the chimeric enzyme to the ER or Golgi, and the *P. pastoris* ARG1 gene or transcription unit. The expression cassette encoding the mouse CMP-sialic acid transporter comprises a nucleic acid molecule encoding the mCMP Sia Transp ORF codon optimized for expression in *P. pastoris* (SEQ ID NO:92), which is operably linked at the 5' end to a nucleic acid molecule comprising the *P. pastoris* PMA 1 promoter and at the 3' end to a nucleic acid molecule comprising the *P. pastoris* MAI transcription termination sequence. The expression cassette encoding the human UDP-GlcNAc 2-epimerase/N-acetylmannosamine kinase comprises a nucleic acid molecule encoding the hGNE ORF codon optimized for expression in *P. pastoris* (SEQ ID NO:93), which is operably linked at the 5' end to a nucleic acid molecule comprising the *P. pastoris* GAPDH promoter and at the 3' end to a nucleic acid molecule comprising the *S. cerevisiae* CYC transcription termination sequence. The expression cassette encoding the *P. pastoris* ARG1 gene comprises (SEQ ID NO:94). The expression cassette encoding the human CMP-sialic acid synthase comprises a nucleic acid molecule encoding the hCSS ORF codon optimized for expression in *P. pastoris* (SEQ ID NO:95), which is operably linked at the 5' end to a nucleic acid molecule comprising the *P. pastoris* GAPDH promoter and at the 3' end to a nucleic acid molecule comprising the *S. cerevisiae* CYC transcription termination sequence. The expression cassette encoding the human N-acetylneuraminate-9-phosphate synthase comprises a nucleic acid molecule encoding the hSIAP S ORF codon optimized for expression in *P. pastoris* (SEQ ID NO:96), which is operably linked at the 5' end to a nucleic acid molecule comprising the *P. pastoris* PMA1 promoter and at the 3' end to a nucleic acid molecule comprising the *P. pastoris* PMA1 transcription termination sequence. The expression cassette encoding the chimeric mouse α-2,6-sialyltransferase comprises a nucleic acid molecule encoding the mST6 catalytic domain codon optimized for expression in *P. pastoris* (SEQ ID NO:97) fused at the 5' end to a nucleic acid molecule encoding the *S. cerevisiae* KRE2 signal peptide, which is operably linked at the 5' end to a nucleic acid molecule comprising the *P. pastoris* TEF promoter and at the 3' end to a nucleic acid molecule comprising the *P. pastoris* TEF transcription termination sequence. The six tandem cassettes are flanked on one side by a nucleic acid molecule comprising a nucleotide sequence from the 5' region and ORF of the TRP2 gene ending at the stop codon (SEQ ID NO:98) followed by a *P. pastoris* ALG3 termination sequence and on the other side by a nucleic acid molecule comprising a nucleotide sequence from the 3' region of the TRP2 gene (SEQ ID NO99). Plasmid pGLY2456 was linearized with SfiI and the linearized plasmid transformed into strain YGLY7961 to produce a number of strains in which the six expression cassette have been inserted into the TRP2 locus immediately following the TRP2 ORF by double-crossover homologous recombination. The strain YGLY8146 was selected from the strains produced. The strain was then counterselected in the presence of 5-FOA to produce a number of strains now auxotrophic for uridine. Strain YGLY9296 was selected.

Figure 25:
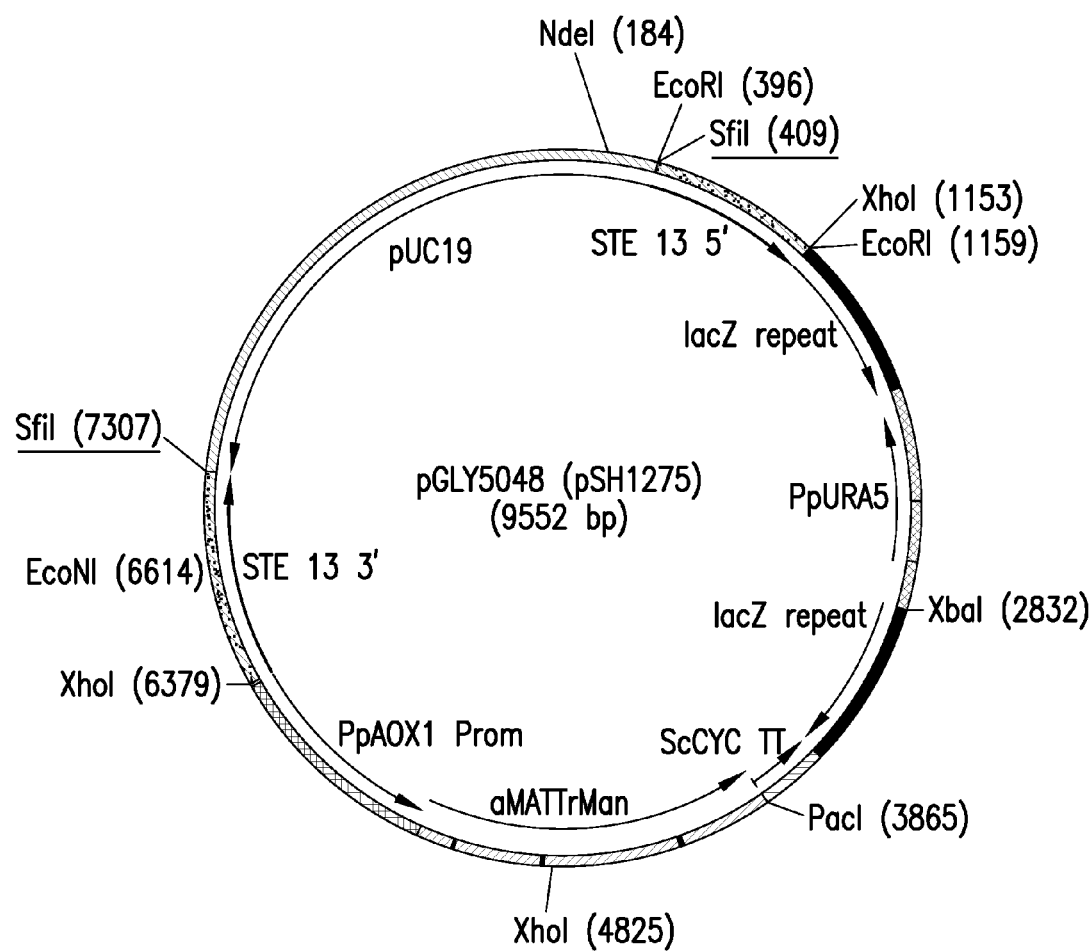
FIG. 25 shows a map of plasmid pGLY5048. Plasmid pGLY5048 is an integration vector that targets the STE13 locus and contains expression cassettes encoding (1) the *T. reesei* α-1,2-mannosidase catalytic domain fused at the N-terminus to *S. cerevisiae* αMATpre signal peptide (aMATTrMan) to target the chimeric protein to the secretory pathway and secretion from the cell and (2) the *P. pastoris* URA5 gene or transcription unit.

Plasmid pGLY5048 (FIG. 25) is an integration vector that targets the STE13 locus and contains expression cassettes encoding (1) the *T. reesei* α-1,2-mannosidase catalytic domain fused at the N-terminus to *S. cerevisiae* αMATpre signal peptide (aMATTrMan) to target the chimeric protein to the secretory pathway and secretion from the cell and (2) the *P. pastoris* URA5 gene or transcription unit. The expression cassette encoding the aMATTrMan comprises a nucleic acid molecule encoding the *T. reesei* catalytic domain (SEQ ID NO:83) fused at the 5' end to a nucleic acid molecule encoding the *S. cerevisiae* αMATpre signal peptide (SEQ ID NO:13), which is operably linked at the 5' end to a nucleic acid molecule comprising the *P. pastoris* AOX1 promoter and at the 3' end to a nucleic acid molecule comprising the *S. cerevisiae* CYC transcription termination sequence. The URA5 expression cassette comprises a nucleic acid molecule comprising the *P. pastoris* URA5 gene or transcription unit flanked by nucleic acid molecules comprising lacZ repeats.

The two tandem cassettes are flanked on one side by a nucleic acid molecule comprising a nucleotide sequence from the 5' region of the STE13 gene (SEQ ID NO:100) and on the other side by a nucleic acid molecule comprising a nucleotide sequence from the 3' region of the STE13 gene (SEQ ID NO:101). Plasmid pGLY5048 was linearized with SfiI and the linearized plasmid transformed into strain YGLY9296 to produce a number of strains. The strain YGLY9469 was selected from the strains produced. This strain is capable of producing glycoproteins that have single-mannose β-glycosylation (See Published U.S. Application No. 20090170159).

Figure 26:
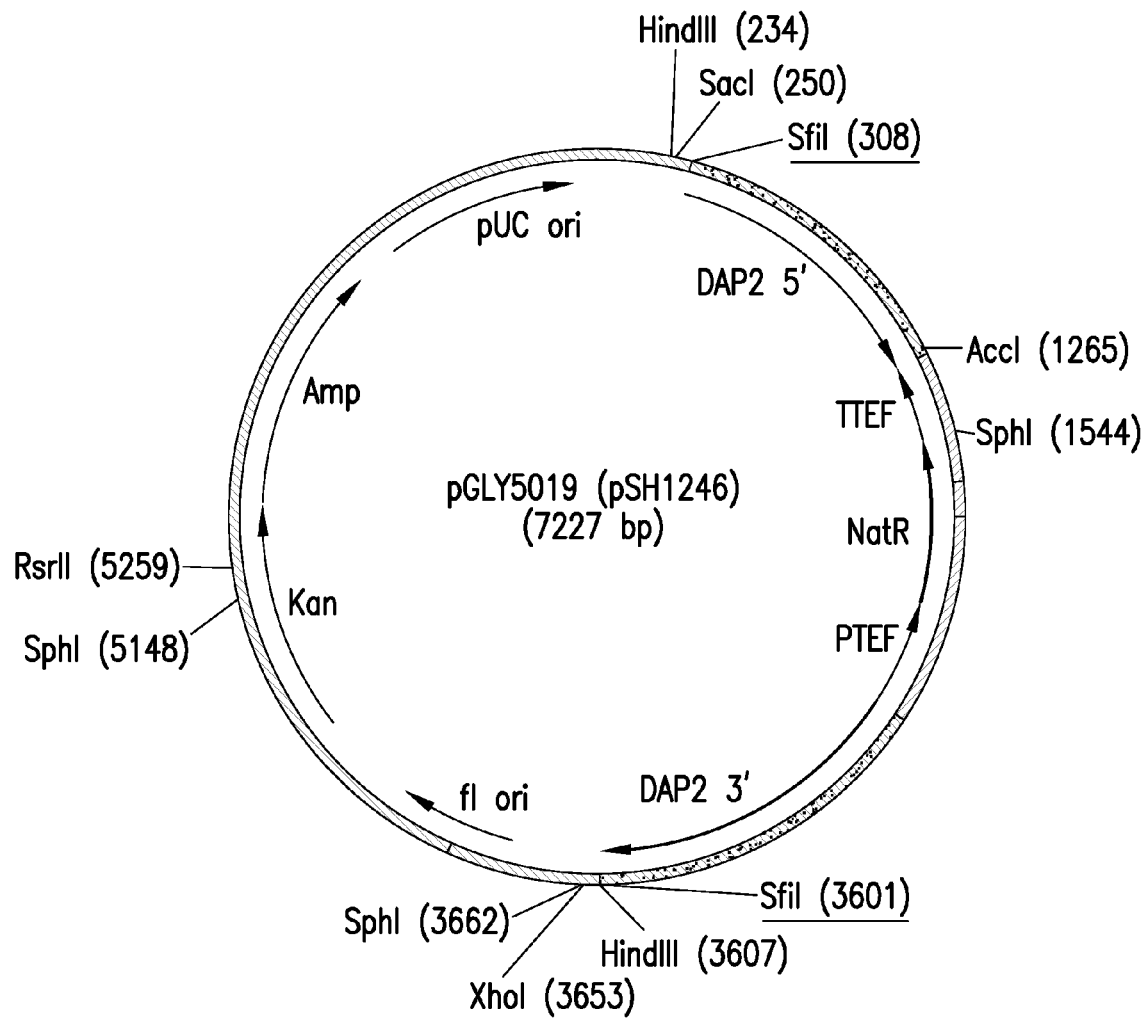
FIG. 26 shows a map of plasmid pGLY5019. Plasmid pGLY5019 is an integration vector that targets the DAP2 locus and contains an expression cassette comprising a nucleic acid molecule encoding the Nourseothricin resistance (NAT$^R$) ORF operably linked to the *Ashbya gossypii* TEF1 promoter and *A. gossypii* TEF1 termination sequences flanked one side with the 5' nucleotide sequence of the *P. pastoris* DAP2 gene and on the other side with the 3' nucleotide sequence of the *P. pastoris* DAP2 gene.

Plasmid pGLY5019 (FIG. 26) is an integration vector that targets the DAP2 locus and contains an expression cassette comprising a nucleic acid molecule encoding the Nourseothricin resistance (NATR) expression cassette (originally from pAG25 from EROSCARF, Scientific Research and Development GmbH, Daimlerstrasse 13a, D-61352 Bad Homburg, Germany, See Goldstein et al., Yeast 15: 1541 (1999)). The NAT$^R$ expression cassette (SEQ ID NO:34) is operably regulated to the *Ashbya gossypii* TEF1 promoter and *A. gossypii* TEF1 termination sequences flanked one side with the 5' nucleotide sequence of the *P. pastoris* DAP2 gene (SEQ ID NO:102) and on the other side with the 3' nucleotide sequence of the *P. pastoris* DAP2 gene (SEQ ID NO:103). Plasmid pGLY5019 was linearized and the linearized plasmid transformed into strain YGLY9469 to produce a number of strains in which the NATR expression cassette has been inserted into the DAP2 locus by double-crossover homologous recombination. The strain YGLY9797 was selected from the strains produced.

Figure 27:
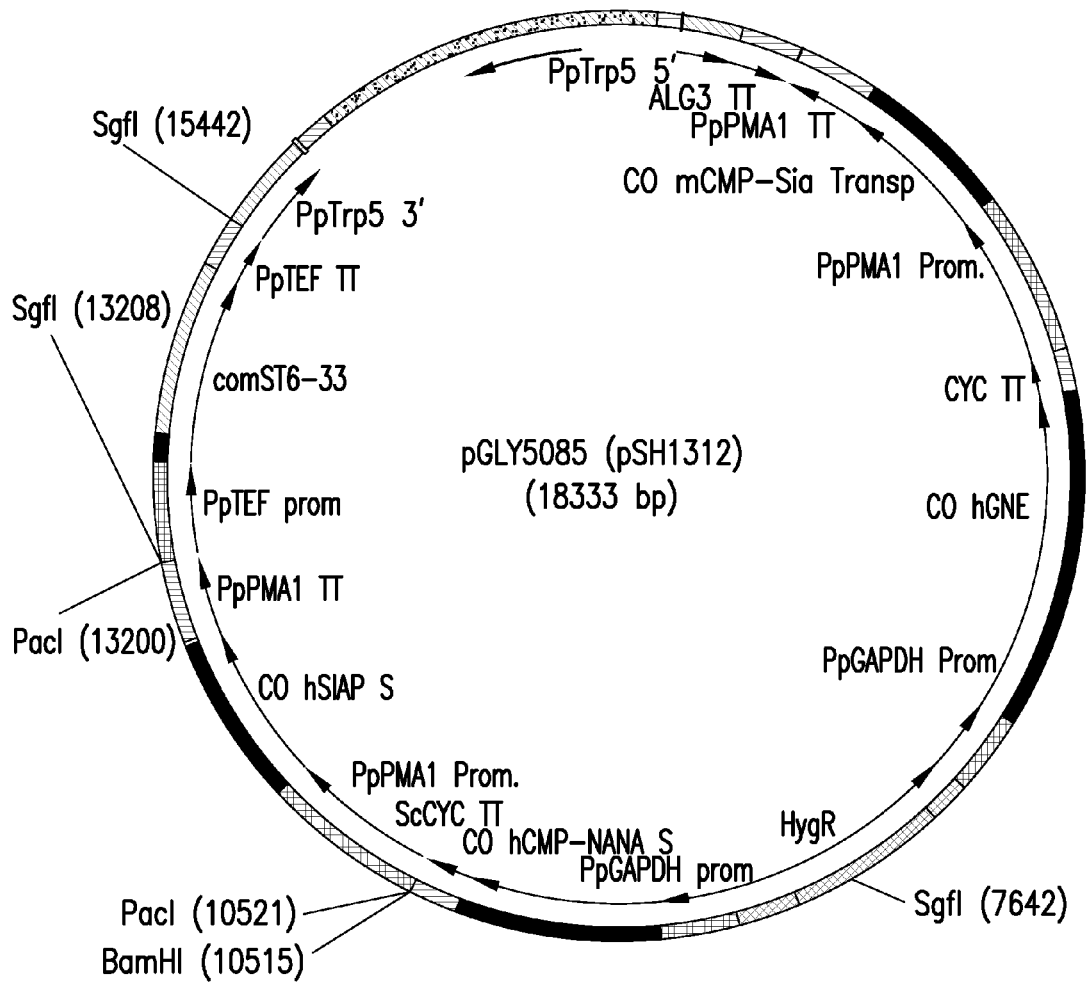
FIG. 27 shows a plasmid map of pGLY5085. Plasmid pGLY5085 is a KINKO plasmid for introducing a second set of the genes involved in producing sialylated N-glycans into *P. pastoris*. The plasmid is similar to plasmid YGLY2456 except that the *P. pastoris* ARG1 gene has been replaced with an expression cassette encoding hygromycin resistance (HygR) and the plasmid targets the *P. pastoris* TRP5 locus. The six tandem cassettes are flanked on one side by a nucleic acid molecule comprising a nucleotide sequence from the 5' region and ORF of the TRP5 gene ending at the stop codon followed by a *P. pastoris* ALG3 termination sequence and on the other side by a nucleic acid molecule comprising a nucleotide sequence from the 3' region of the TRP5 gene.

Plasmid pGLY5085 (FIG. 27) is a KINKO plasmid for introducing a second set of the genes involved in producing sialylated N-glycans into *P. pastoris*. The plasmid is similar to plasmid YGLY2456 except that the *P. pastoris* ARG1 gene has been replaced with an expression cassette encoding hygromycin resistance (HygR) and the plasmid targets the *P. pastoris* TRP5 locus. The HYG$^R$ resistance cassette is SEQ ID NO:104. The HYG$^R$ expression cassette (SEQ ID NO:104) is operably regulated to the *Ashbya gossypii* TEF1 promoter and *A. gossypii* TEF1 termination sequences (See Goldstein et al., Yeast 15: 1541 (1999)). The six tandem cassettes are flanked on one side by a nucleic acid molecule comprising a nucleotide sequence from the 5' region and ORF of the TRP5 gene ending at the stop codon (SEQ ID NO:105) followed by a *P. pastoris* ALG3 termination sequence and on the other side by a nucleic acid molecule comprising a nucleotide sequence from the 3' region of the TRP5 gene (SEQ ID NO:106). Plasmid pGLY5085 was transformed into strain YGLY9797 to produce a number of strains of which strain YGLY1200 was selected.

Figure 28:
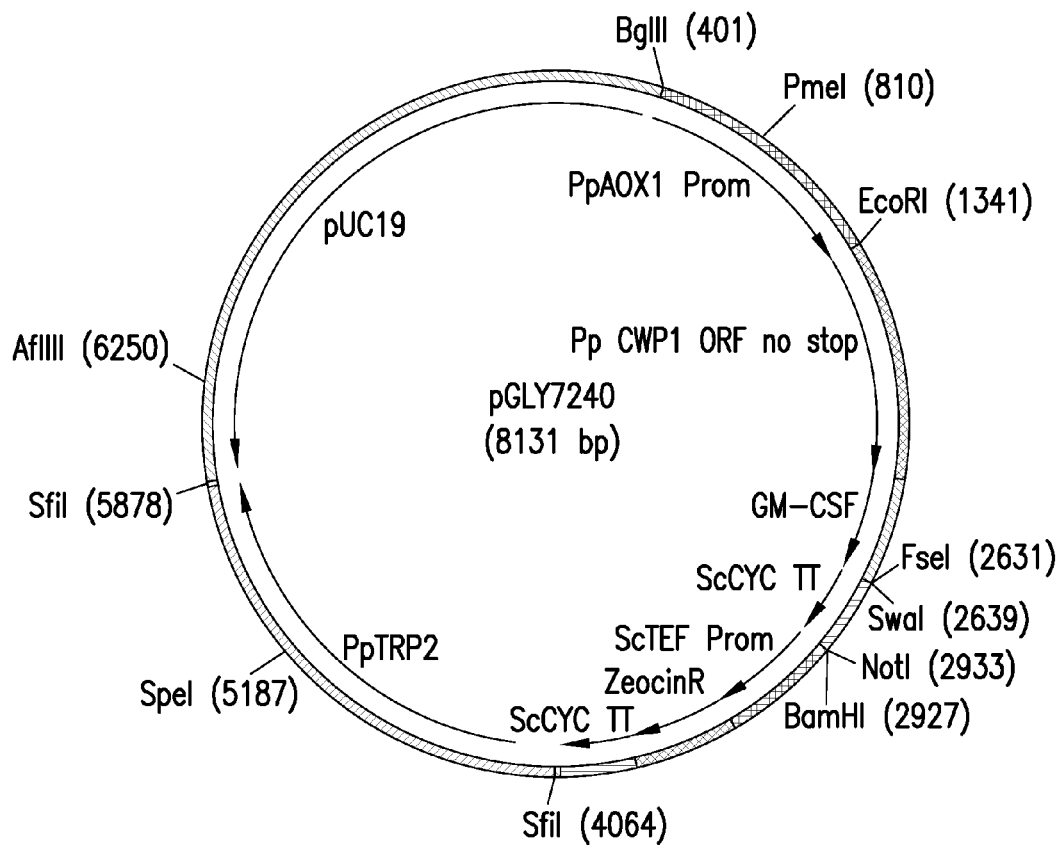
FIG. 28 shows a plasmid map of pGLY7240. The plasmid is an integration vector that targets the TRP2 locus and contains an ORF encoding the zeocin resistance protein (Zeocin$^R$) under the control of the *P. pastoris* TEF1 promoter and *S. cerevisiae* CYC termination sequence. The plasmid encodes the GM-CSF/CWP1 fusion protein operably linked at the 5' end to the *Pichia pastoris* AOX1 promoter and at the 3' end to the *S. cerevisiae* CYC transcription termination sequence.

Plasmid pGLY7240 (FIG. 28), which targets the *Pichia pastoris* TRP2 locus (PpTRP2), encodes a fusion protein comprising the human GM-CSF fused to the *Pichia pastoris* CWP1 protein via a linker containing a Kex2 cleavage site. The CWP1 protein is removed from GM-CSF in the late Golgi by the Kex2 endoprotease so that free GM-CSF is secreted into the fermentation supernatant. The human GM-CSF has the amino acid sequence shown in SEQ ID NO:108 and is encoded by the nucleotide sequence shown in SEQ ID NO:108. The fusion protein (SEQ ID NO:109) is encoded by the nucleotide sequence shown in SEQ ID NO:110. The CWP1 signal sequence is amino acids 1-18, the CWP1 amino acid sequence is from amino acids 19-289, the GGGSLVKR Kex2 linker amino acid sequence (SEQ ID NO:111) is from amino acids 290-297, and the GM-CSF amino acid sequence is from amino acids 298-424. The expression of the fusion protein is operably linked to the Pp AOX1 promoter and ScCYC termination sequences. Plasmid pGLY7240 was transformed into strain YGLY12900 to produce a number of strains of which strain YGLY15660 was selected. StrainYGLY15660 was transformed with plasmid pGLY6301 (encodes *Leishmania major* STT3D) to produce a number of strains of which YGLY16349 was selected.

Figure 29:
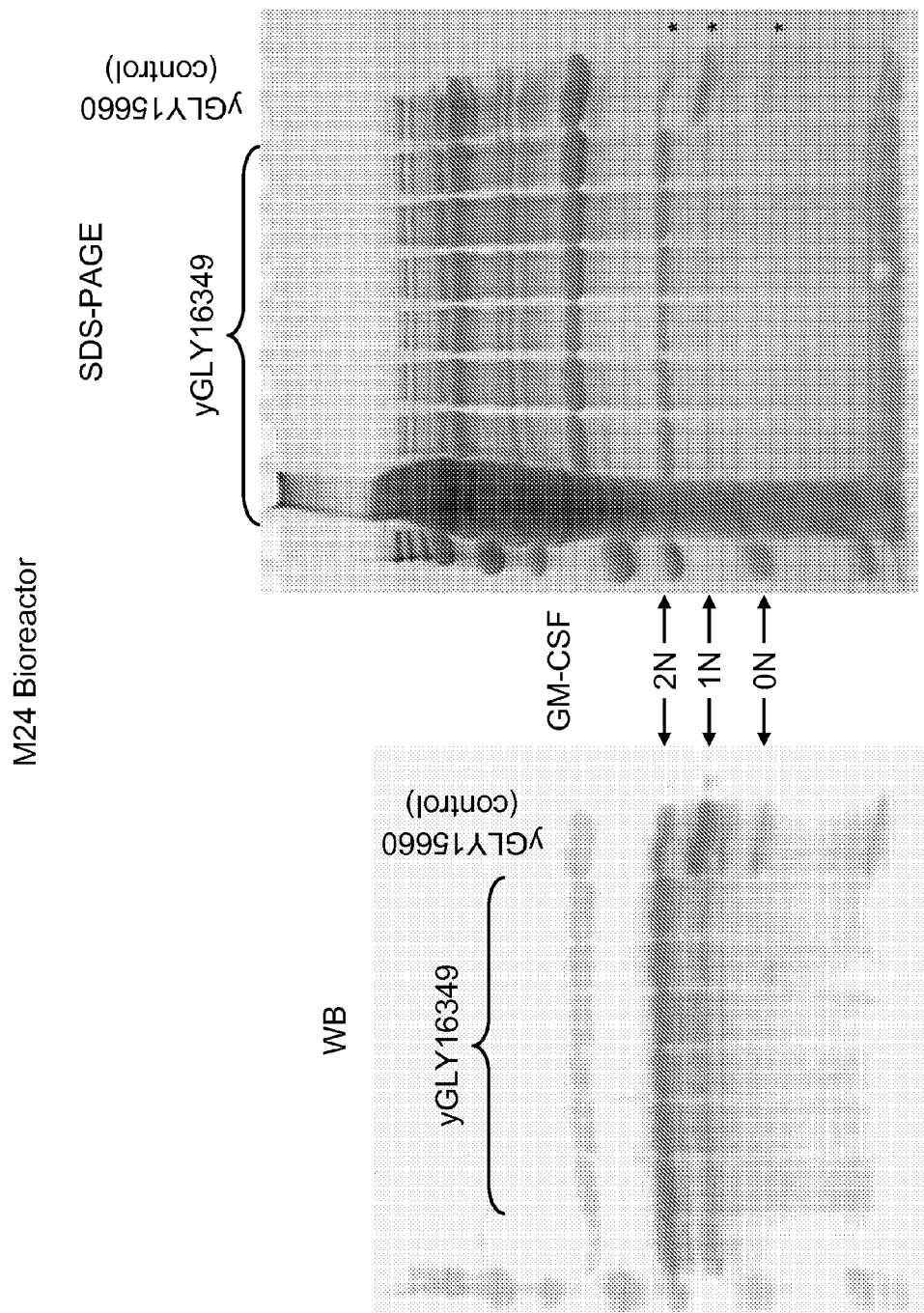
FIG. 29 shows a Western blot of GM-CSF produced in strain YGLY16349, which co-expresses LmSTT3D, that the majority of GM-CSF (Lanes 2-8) is glycosylated with 2N-linked sites in contrast to the control strain (YGLY15560, lane 9) where GM-CSF is predominantly N-glycosylated with 1 site along with the minor portions of 2 N sites and non-glycosylated.

FIG. 29 shows that LmSTT3D also improved N-glycan occupancy of non-antibody glycoprotein, GM-CSF. GM-CSF contains 2 N-linked sites and in wild-type *Pichia* 1 N-linked site on GM-CSF is predominantly glycosylated. To investigate impact of LmSTT3D on N-glycan occupancy of GM-CSF, methanol-inducible LmSTT3D was overexpressed in GM-CSF producing strain, yGLY15560. N-glycan occupancy was evaluated using Micro24 bioreactor (M24). The cell-free supernatants from M24 were analyzed for N-glycan occupancy using Western blot and 15% SDS-PAGE. As shown in Western blot detected with GM-CSF specific antibody, the majority of GM-CSF (Lanes 2-8) is glycosylated with 2N-linked sites in contrast to the control strain (yGLY15560, lane 9) where GM-CSF is predominantly N-glycosylated with 1 site along with the minor portions of 2 N sites and non-glycosylated. Taken together, this indicates that LmSTT3D can improve N-glycan occupancy of glycoproteins carrying multiple N-linked sites.

Figure 30A:
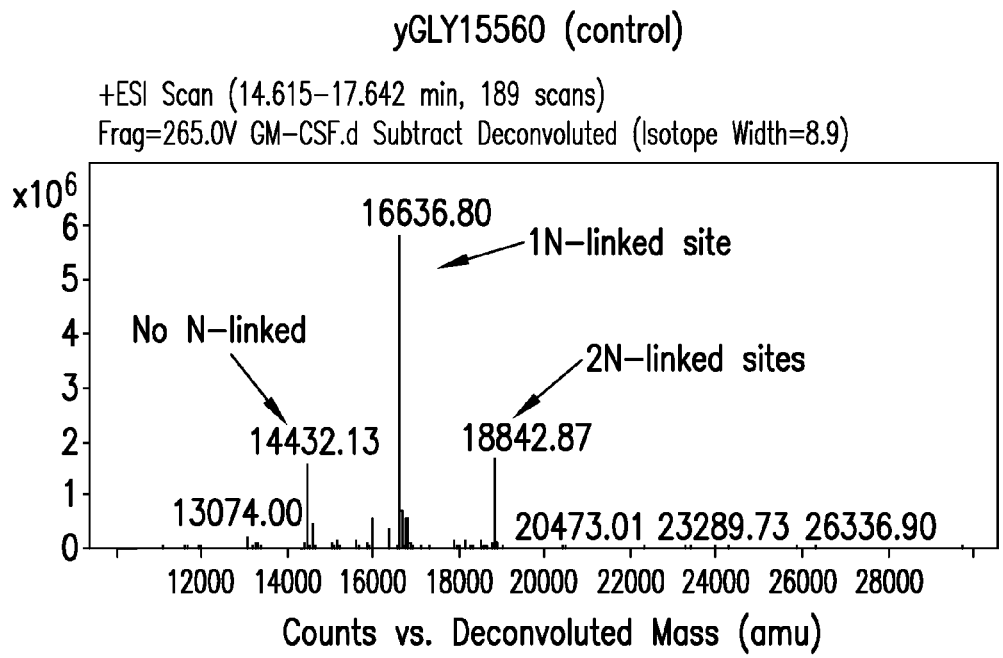
FIG. 30 shows a Q-TOP analysis of GM-CSF expressed from YGLY15560 (A) and YGLY16349 (B), respectively. Non-glycosylated GM-CSF was not detected.
Figure 30B:
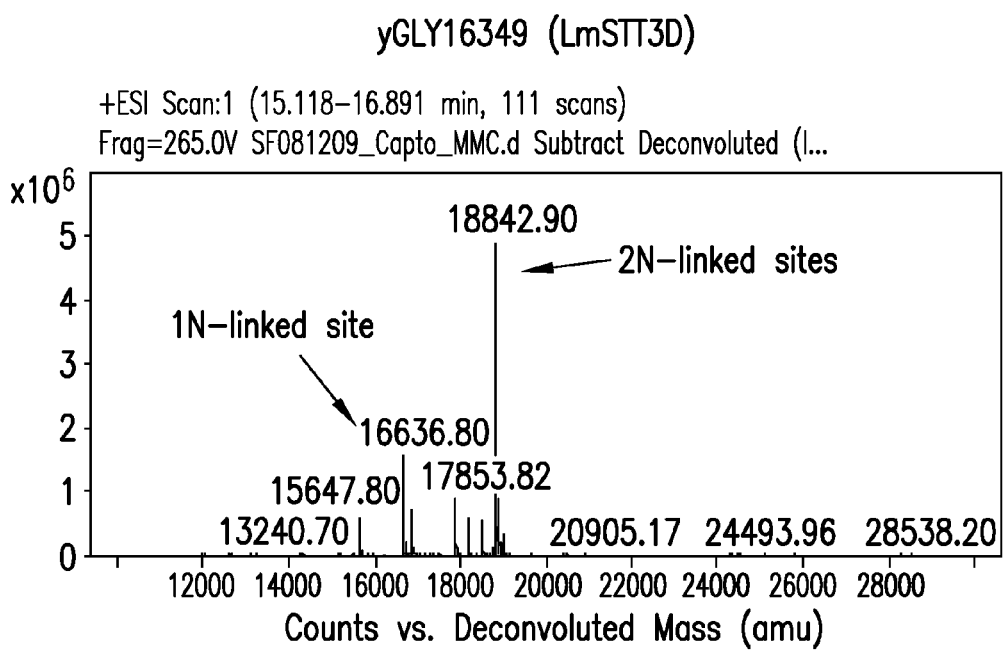

FIG. 30 shows Q-TOP analysis of GM-CSF expressed from yGLY15560 (A) and yGLY16349 (B), respectively. This analysis confirms that the majority of GM-CSF is glycosylated with 2N-linked sites in the presence of LmSTT3D as shown in FIG. 29. Non-glycosylated GM-CSF was not detected.

LC-ESI-TOF

The high performance liquid chromatography (HPLC) system used in this study consisted of an Agilent 1200 equipped with autoinjector, a column-heating compartment and a UV detector detecting at 210 and 280 nm. All LC-MS experiments performed with this system were running at 1 ml/min. The flow rate was not split for MS detection. Mass spectrometric analysis was carried out in positive ion mode on Accurate-Mass Q-TOF LC/MS 6520 (Agilent technology). The temperature of dual ESI source was set at 350° C. The nitrogen gas flow rates were set at 13 l/h for the cone and 350 l/h and nebulizer was set at 45 psig with 4500 volt applied to the capillary. eference mass of 922.009 was prepared from HP-0921 according to API-TOF reference mass solution kit for mass calibration and the protein mass measurements. The data for ion spectrum range from 300-3000 m/z were acquired and processed using Agilent Masshunter.

Sample Preparation

An intact antibody sample (50 ug) was prepared 50 ul 25 mM NH$_4$HCO$_3$, pH 7.8. For deglycosylated antibody, a 50 ul aliquot of intact antibody sample was treated with PNGase F (10 units) for 18 hr at 37C. Reduced antibody was prepared by adding 1 M DTT to a final concentration of 10 mM to an aliquot of either intact antibody or deglycosylated antibody and incubated for 30 min at 37C.

Three microgram of intact or deglycosylated antibody sample was loaded onto a Poroshell 300SB-C3 column (2.1 mm×75 mm, 5 μm) (Agilent Technologies) maintained at 70° C. The protein was first rinsed on the cartridge for 1 min with 90% solvent A (0.1% HCOOH), 5% solvent B (90% Acetonitrile in 0.1% HCOOH). Elution was then performed using an gradient of 5-100% of B over 26 min followed by a 3 min regeneration at 100% B and by a final equilibration period of 10 min at 5% B.

For reduced antibody, three microgram sample was loaded a Poroshell 300SB-C3 column (2.1 mm×75 mm, 5 μm) (Agilent Technologies) maintained at 40° C. The protein was first rinsed on the cartridge for 3 min with 90% solvent A, 5% solvent B. Elution was then performed using an gradient of 5-80% of B over 20 min followed by a 7 min regeneration at 80% B and by a final equilibration period of 10 min at 5% B.

Sequences

Sequences that were used to produce some of the strains disclosed in Examples 1-4 are provided in Table 12.

TABLE 12

BRIEF DESCRIPTION OF THE SEQUENCES

| SEQ ID NO: | Description | Sequence |
|---|---|---|
| 1 | PCR primer PpURA6out/UP | CTGAGGAGTCAGATATCAGCTCAATCTCCAT |
| 2 | PCR primer Puc19/LP | TCCGGCTCGTATGTTGTGTGGAATTGT |
| 3 | PCR primer PpURA6out/LP | CTGGATGTTTGATGGGTTCAGTTTCAGCTGGA |
| 4 | PCR primer ScARR3/UP | GGCAATAGTCGCGAGAATCCTTAAACCAT |
| 5 | PCR primer PpTRP1-5'out/UP | CCTCGTAAAGATCTGCGGTTTGCAAAGT |
| 6 | PCR primer PpALG3TT/LP | CCTCCCACTGGAACCGATGATATGGAA |
| 7 | PCR primer PpTEFTT/UP | GATGCGAAGTTAAGTGCGCAGAAAGTAATATCA |
| 8 | PCR primer PpTRP-3'1out/LP | CGTGTGTACCTTGAAACGTCAATGATACTTTGA |
| 9 | PCR primer LmSTT3D/iUP | CAGACTAAGACTGCTTCTCCACCTGCTAAG |
| 10 | PCR primer LmSTT3D/iLP | CAACAGTAGAACCAGAAGCCTCGTAAGTACAG |
| 11 | Leishmania major STT3D (DNA) | ATGGGTAAAAGAAAGGGAAACTCCTTGGGAGATTCTG GTTCTGCTGCTACTGCTTCCAGAGAGGCTTCTGCTCAA GCTGAAGATGCTGCTTCCCAGACTAAGACTGCTTCTCC ACCTGCTAAGGTTATCTTGTTGCCAAAGACTTTGACTG ACGAGAAGGACTTCATCGGTATCTTCCCATTTCCATTC TGGCCAGTTCACTTCGTTTTGACTGTTGTTGCTTTGTTC GTTTTGGCTGCTTCCTGTTTCCAGGCTTTCACTGTTAG AATGATCTCCGTTCAAATCTACGGTTACTTGATCCACG AATTTGACCCATGGTTCAACTACAGAGCTGCTGAGTA CATGTCTACTCACGGATGGAGTGCTTTTTTCTCCTGGT TCGATTACATGTCCTGGTATCCATTGGGTAGACCAGTT GGTTCTACTACTTACCCAGGATTGCAGTTGACTGCTGT TGCTATCCATAGAGCTTTGGCTGCTGCTGGAATGCCAA TGTCCTTGAACAATGTTTGTGTTTTGATGCCAGCTTGG TTTGGTGCTATCGCTACTGCTACTTTGGCTTTCTGTACT TACGAGGCTTCTGGTTCTACTGTTGCTGCTGCTGCAGC TGCTTTGTCCTTCTCCATTATCCCTGCTCACTTGATGAG ATCCATGGCTGGTGAGTTCGACAACGAGTGTATTGCT GTTGCTGCTATGTTGTTGACTTTCTACTGTTGGGTTCGT TCCTTGAGAACTAGATCCTCCTGGCCAATCGGTGTTTT GACAGGTGTTGCTTACGGTTACATGGCTGCTGCTTGGG GAGGTTACATCTTCGTTTTGAACATGGTTGCTATGCAC GCTGGTATCTCTTCTATGGTTGACTGGGCTAGAAACAC TTACAACCCATCCTTGTTGAGAGCTTACACTTTGTTCT ACGTTGTTGGTACTGCTATCGCTGTTTGTGTTCCACCA GTTGGAATGTCTCCATTCAAGTCCTTGGAGCAGTTGGG AGCTTTGTTGGTTTTGGTTTTCTTGTGTGGATTGCAAG TTTGTGAGGTTTTGAGAGCTAGAGCTGGTGTTGAAGTT AGATCCAGAGCTAATTTCAAGATCAGAGTTAGAGTTT TCTCCGTTATGGCTGGTGTTGCTGCTTTGGCTATCTCT GTTTTGGCTCCAACTGGTTACTTTGGTCCATTGTCTGTT AGAGTTAGAGCTTTGTTTGTTGAGCACACTAGAACTG GTAACCCATTGGTTGACTCCGTTGCTGAACATCAACCA GCTTCTCCAGAGGCTATGTGGGCTTTCTTGCATGTTTG TGGTGTTACTTGGGGATTGGGTTCCATTGTTTTGGCTG TTTCCACTTTCGTTCACTACTCCCCATCTAAGGTTTTCT |

TABLE 12-continued

BRIEF DESCRIPTION OF THE SEQUENCES

| SEQ ID NO: | Description | Sequence |
|---|---|---|
| | | GGTTGTTGAACTCCGGTGCTGTTTACTACTTCTCCACT
AGAATGGCTAGATTGTTGTTGTTGTCCGGTCCAGCTGC
TTGTTTGTCCACTGGTATCTTCGTTGGTACTATCTTGG
AGGCTGCTGTTCAATTGTCTTTCTGGGACTCCGATGCT
ACTAAGGCTAAGAAGCAGCAAAAGCAGGCTCAAAGA
CACCAAAGAGGTGCTGGTAAAGGTTCTGGTAGAGATG
ACGCTAAGAACGCTACTACTGCTAGAGCTTTCTGTGA
CGTTTTCGCTGGTTCTTCTTTGGCTTGGGGTCACAGAA
TGGTTTTGTCCATTGCTATGTGGGCTTTGGTTACTACT
ACTGCTGTTTCCTTCTTCTCCTCCGAATTTGCTTCTCAC
TCCACTAAGTTCGCTGAACAATCCTCCAACCCAATGAT
CGTTTTCGCTGCTGTTGTTCAGAACAGAGCTACTGGAA
AGCCAATGAACTTGTTGGTTGACGACTACTTGAAGGC
TTACGAGTGGTTGAGAGACTCTACTCCAGAGGACGCT
AGAGTTTTGGCTTGGTGGGACTACGGTTACCAAATCA
CTGGTATCGGTAACAGAACTTCCTTGGCTGATGGTAA
CACTTGGAACCACGAGCACATTGCTACTATCGGAAAG
ATGTTGACTTCCCCAGTTGTTGAAGCTCACTCCCTTGT
TAGACACATGGCTGACTACGTTTTGATTTGGGCTGGTC
AATCTGGTGACTTGATGAAGTCTCCACACATGGCTAG
AATCGGTAACTCTGTTTACCACGACATTTGTCCAGATG
ACCCATTGTGTCAGCAATTCGGTTTCCACAGAAACGA
TTACTCCAGACCAACTCCAATGATGAGAGCTTCCTTGT
TGTACAACTTGCACGAGGCTGGAAAAAGAAAGGGTGT
TAAGGTTAACCCATCTTTGTTCCAAGAGGTTTACTCCT
CCAAGTACGGACTTGTTAGAATCTTCAAGGTTATGAA
CGTTTCCGCTGAGTCTAAGAAGTGGGTTGCAGACCCA
GCTAACAGAGTTTGTCACCCACCTGGTTCTTGGATTTG
TCCTGGTCAATACCCACCTGCTAAAGAAATCCAAGAG
ATGTTGGCTCACAGAGTTCCATTCGACCAGGTTACAA
ACGCTGACAGAAAGAACAATGTTGGTTCCTACCAAGA
GGAATACATGAGAAGAATGAGAGAGTCCGAGAACAG
AAGATAATAG |
| 12 | Leishmania major STT3D (protein) | MGKRKGNSLGDSGSAATASREASAQAEDAASQTKTASP
PAKVILLPKTLTDEKDFIGIFPFPPFWPVHFVLTVVALFVLA
ASCFQAFTVRMISVQIYGYLIHEFDPWFNYRAAEYMSTH
GWSAFFSWFDYMSWYPLGRPVGSTTYPGLQLTAVAIHR
ALAAAGMPMSLNNVCVLMPAWFGAIATATLAFCTYEAS
GSTVAAAAAALSFSIIPAHLMRSMAGEFDNECIAVAAML
LTFYCWVRSLRTRSSWPIGVLTGVAYGYMAAAWGGYIF
VLNMVAMHAGISSMVDWARNTYNPSLLRAYTLFYVVG
TAIAVCVPPVGMSPFKSLEQLGALLVLVFLCGLQVCEVL
RARAGVEVRSRANFKIRVRVFSVMAGVAALAISVLAPTG
YFGPLSVRVRALFVEHTRTGNPLVDSVAEHQPASPEAM
WAFLHVCGVTWGLGSIVLAVSTFVHYSPSKVFWLLNSG
AVYYFSTRMARLLLLSGPAACLSTGIFVGTILEAAVQLSF
WDSDATKAKKQQKQAQRHQRGAGKGSGRDDAKNATT
ARAPFCDVFAGSSLAWGHRMVLSIAMWALVTTTAVSFFS
SEFASHSTKFAEQSSNPMIVFAAVVQNRATGKPMNLLVD
DYLKAYEWLRDSTPEDARVLAWWDYGYQITGIGNRTSL
ADGNTWNHEHIATIGKMLTSPVVEAHSLVRHMADYVLI
WAGQSGDLMKSPHMARIGNSVYHDICPDDPLCQQFGFH
RNDYSRPTPMMRASLLYNLHEAGKRKGVKVNPSLFQEV
YSSKYGLVRIFKVMNVSAESKKWVADPANRVCHPPGS
WICPGQYPPAKEIQEMLAHRVPFDQVTNADRKNNVGSY
QEEYMRRMRESENRR |
| 13 | Saccharomyces cerevisiae mating factor pre-signal peptide (DNA) | ATGAGATTCCCATCCATCTTCACTGCTGTTTTGTTCGC
TGCTTCTTCTGCTTTGGCT |
| 14 | Saccharomyces cerevisiae mating factor pre-signal peptide (protein) | MRFPSIFTAVLFAASSALA |

TABLE 12-continued

BRIEF DESCRIPTION OF THE SEQUENCES

| SEQ ID NO: | Description | Sequence |
|---|---|---|
| 15 | Anti-Her2 Heavy chain (VH + IgG1 constant region) (DNA) | GAGGTTCAGTTGGTTGAATCTGGAGGAGGATTGGTTC AACCTGGTGGTTCTTTGAGATTGTCCTGTGCTGCTTCC GGTTTCAACATCAAGGACACTTACATCCACTGGGTTA GACAAGCTCCAGGAAAGGGATTGGAGTGGGTTGCTAG AATCTACCCAACTAACGGTTACACAAGATACGCTGAC TCCGTTAAGGGAAGATTCACTATCTCTGCTGACACTTC CAAGAACACTGCTTACTTGCAGATGAACTCCTTGAGA GCTGAGGATACTGCTGTTTACTACTGTTCCAGATGGGG TGGTGATGGTTTCTACGCTATGGACTACGGGGTCAA GGAACTTTGGTTACTGTTTCCTCCGCTTCTACTAAGGG ACCATCTGTTTTCCCATTGGCTCCATCTTCTAAGTCTA CTTCCGGTGGTACTGCTGCTTTGGGATGTTTGGTTAAA GACTACTTCCCAGAGCCAGTTACTGTTTCTTGGAACTC CGGTGCTTTGACTTCTGGTGTTCACACTTTCCCAGCTG TTTTGCAATCTTCCGGTTTGTACTCTTTGTCCTCCGTTG TTACTGTTCCATCCTCTTCCTTGGGTACTCAGACTTAC ATCTGTAACGTTAACCACAAGCCATCCAACACTAAGG TTGACAAGAAGGTTGAGCCAAAGTCCTGTGACAAGAC ACATACTTGTCCACCATGTCCAGCTCCAGAATTGTTGG GTGGTCCATCCGTTTTCTTGTTCCCACCAAAGCCAAAG GACACTTTGATGATCTCCAGAACTCCAGAGGTTACAT GTGTTGTTGTTGACGTTTCTCACGAGGACCCAGAGGTT AAGTTCAACTGGTACGTTGACGGTGTTGAAGTTCACA ACGCTAAGACTAAGCCAAGAGAAGAGCAGTACAACT CCACTTACAGAGTTGTTTCCGTTTTGACTGTTTTGCAC CAGGACTGGTTGAACGGTAAAGAATACAAGTGTAAGG TTTCCAACAAGGCTTTGCCAGCTCCAATCGAAAAGAC TATCTCCAAGGCTAAGGGTCAACCAAGAGAGCCACAG GTTTACACTTTGCCACCATCCAGAGAAGAGATGACTA AGAACCAGGTTTCCTTGACTTGTTTGGTTAAAGGATTC TACCCATCCGACATTGCTGTTGAGTGGGAATCTAACG GTCAACCAGAGAACAACTACAAGACTACTCCACCAGT TTTGGATTCTGATGGTTCCTTCTTCTTGTACTCCAAGTT GACTGTTGACAAGTCCAGATGGCAACAGGGTAACGTT TTCTCCTGTTCCGTTATGCATGAGGCTTTGCACAACCA CTACACTCAAAAGTCCTTGTCTTTGTCCCCTGGTTAA |
| 16 | Anti-Her2 Heavy chain (VH + IgG1 constant region) (protein) | EVQLVESGGGLVQPGGSLRLSCAASGFNIKDTYIHWVRQ APGKGLEWVARIYPTNGYTRYADSVKGRFTISADTSKNT AYLQMNSLRAEDTAVYYCSRWGGDGFYAMDYWGQGT LVTVSSASTKGPSVFPLAPSSKSTSGGTAALGCLVKDYFP EPVTVSWNSGALTSGVHTFPAVLQSSGLYSLSSVVTVPSS SLGTQTYICNVNHKPSNTKVDKKVEPKSCDKTHTCPPCP APELLGGPSVFLFPPKPKDTLMISRTPEVTCVVVDVSHED PEVKFNWYVDGVEVHNAKTKPREEQYNSTYRVVSVLT VLHQDWLNGKEYKCKVSNKALPAPIEKTISKAKGQPREP QVYTLPPSREEMTKNQVSLTCLVKGFYPSDIAVEWESNG QPENNYKTTPPVLDSDGSFFLYSKLTVDKSRWQQGNVFS CSVMHEALHNHYTQKSLSLSPG |
| 17 | Anti-Her2 light chain (VL + Kappa constant region) (DNA) | GACATCCAAATGACTCAATCCCCATCTTCTTTGTCTGC TTCCGTTGGTGACAGAGTTACTATCACTTGTAGAGCTT CCCAGGACGTTAATACTGCTGTTGCTTGGTATCAACAG AAGCCAGGAAAGGCTCCAAAGTTGTTGATCTACTCCG CTTCCTTCTTGTACTCTGGTGTTCCATCCAGATTCTCTG GTTCCAGATCCGGTACTGACTTCACTTTGACTATCTCC TCCTTGCAACCAGAAGATTTCGCTACTTACTACTGTCA GCAGCACTACACTACTCCACCAACTTTCGGACAGGGT ACTAAGGTTGAGATCAAGAGAACTGTTGCTGCTCCAT CCGTTTTCATTTTCCCACCATCCGACGAACAGTTGAAG TCTGGTACAGCTTCCGTTGTTTGTTGTTGAACAACTT CTACCCAAGAGAGGCTAAGGTTCAGTGGAAGGTTGAC AACGCTTTGCAATCCGGTAACTCCCAAGAATCCGTTA CTGAGCAAGACTCTAAGGACTCCACTTACTCCTTGTCC TCCACTTTGACTTTGTCCAAGGCTGATTACGAGAAGCA CAAGGTTTACGCTTGTGAGGTTACACATCAGGGTTTGT CCTCCCCAGTTACTAAGTCCTTCAACAGAGGAGAGTG TTAA |

TABLE 12-continued

BRIEF DESCRIPTION OF THE SEQUENCES

| SEQ ID NO: | Description | Sequence |
|---|---|---|
| 18 | Anti-Her2 light chain (VL + Kappa constant region) | DIQMTQSPSSLSASVGDRVTITCRASQDVNTAVAWYQQ KPGKAPKLLIYSASFLYSGVPSRFSGSRSGTDFTLTISSLQ PEDFATYYCQQHYTTPPTFGQGTKVEIKRTVAAPSVFIFP PSDEQLKSGTASVVCLLNNFYPREAKVQWKVDNALQSG NSQESVTEQDSKDSTYSLSSTLTLSKADYEKHKVYACEV THQGLSSPVTKSFNRGEC |
| 19 | Anti-RSV Heavy chain (VH + IgG1 constant region) (DNA) | CAGGTTACATTGAGAGAATCCGGTCCAGCTTTGGTTA AGCCAACTCAGACTTTGACTTTGACTTGTACTTTCTCC GGTTTCTCCTTGTCTACTTCCGGAATGTCTGTTGGATG GATCAGACAACCACCTGGAAAGGCTTTGGAATGGCTT GCTGACATTTGGTGGGATGACAAGAAGGACTACAACC CATCCTTGAAGTCCAGATTGACTATCTCCAAGGACACT TCCAAGAATCAAGTTGTTTTGAAGGTTACAAACATGG ACCCAGCTGACACTGCTACTTACTACTGTGCTAGATCC ATGATCACTAACTGGTACTTCGATGTTTGGGGTGCTGG TACTACTGTTACTGTCTCGAGTGCTTCTACTAAGGGAC CATCCGTTTTTCCATTGGCTCCATCCTCTAAGTCTACTT CCGGTGGAACCGCTGCTTTGGGATGTTTGGTTAAAGA CTACTTCCCAGAGCCAGTTACTGTTTCTTGGAACTCCG GTGCTTTGACTTCTGGTGTTCACACTTTCCCAGCTGTTT TGCAATCTTCCGGTTTGTACTCTTTGTCCTCCGTTGTTA CTGTTCCATCCTCTTCCTTGGGTACTCAGACTTACATC TGTAACGTTAACCACAAGCCATCCAACACTAAGGTTG ACAAGAGAGTTGAGCCAAAGTCCTGTGACAAGACACA TACTTGTCCACCATGTCCAGCTCCAGAATTGTTGGGTG GTCCATCCGTTTTCTTGTTCCCACCAAAGCCAAAGGAC ACTTTGATGATCTCCAGAACTCCAGAGGTTACATGTGT TGTTGTTGACGTTTCTCACGAGGACCCAGAGGTTAAGT TCAACTGGTACGTTGACGGTGTTGAAGTTCACAACGC TAAGACTAAGCCAAGAGAAGAGCAGTACAACTCCACT TACAGAGTTGTTTCCGTTTTGACTGTTTTGCACCAGGA CTGGTTGAACGGTAAAGAATACAAGTGTAAGGTTTCC AACAAGGCTTTGCCAGCTCCAATCGAAAAGACTATCT CCAAGGCTAAGGGTCAACCAAGAGAGCCACAGGTTTA CACTTTGCCACCATCCAGAGAAGAGATGACTAAGAAC CAGGTTTCCTTGACTTGTTTGGTTAAAGGATTCTACCC ATCCGACATTGCTGTTGAGTGGGAATCTAACGGTCAA CCAGAGAACAACTACAAGACTACTCCACCAGTTTTGG ATTCTGATGGTTCCTTCTTCTTGTACTCCAAGTTGACT GTTGACAAGTCCAGATGGCAACAGGGTAACGTTTTCT CCTGTTCCGTTATGCATGAGGCTTTGCACAACCACTAC ACTCAAAAGTCCTTGTCTTTGTCCCCTGGTTAA |
| 20 | Anti-RSV Heavy chain (VH + IgG1 constant region) (protein) | QVTLRESGPALVKPTQTLTLTCTFSGFSLSTSGMSVGWIR QPPGKALEWLADIWWDDKKDYNPSLKSRLTISKDTSKN QVVLKVTNMDPADTATYYCARSMITNWYFDVWGAGTT VTVSSASTKGPSVFPLAPSSKSTSGGTAALGCLVKDYFPE PVTVSWNSGALTSGVHTFPAVLQSSGLYSLSSVVTVPSSS LGTQTYICNVNHKPSNTKVDKRVEPKSCDKTHTCPPCPA PELLGGPSVFLFPPKPKDTLMISRTPEVTCVVVDVSHEDP EVKFNWYVDGVEVHNAKTKPREEQYNSTYRVVSVLTV LHQDWLNGKEYKCKVSNKALPAPIEKTISKAKGQPREPQ VYTLPPSREEMTKNQVSLTCLVKGFYPSDIAVEWESNGQ PENNYKTTPPVLDSDGSFFLYSKLTVDKSRWQQGNVFSC SVMHEALHNHYTQKSLSLSPG |
| 21 | Anti-RSV light chain (VL + Kappa constant region (DNA) | ATGAGATTCCCATCCATCTTCACTGCTGTTTTGTTCGC TGCTTCTTCTGCTTTGGCTGACATTCAGATGACACAGT CCCCATCTACTTTGTCTGCTTCCGTTGGTGACAGAGTT ACTATCACTTGTAAGTGTCAGTTGTCCGTTGGTTACAT GCACTGGTATCAGCAAAAGCCAGGAAAGGCTCCAAA GTTGTTGATCTACGACACTTCCAAGTTGGCTTCCGGTG TTCCATCTAGATTCTCTGGTTCCGGTTCTGGTACTGAG TTCACTTTGACTATCTCTTCCTTGCAACCAGATGACTT CGCTACTTACTACTGTTTCCAGGGTTCTGGTTACCCAT TCACTTTCGGTGGTGGTACTAAGTTGGAGATCAAGAG AACTGTTGCTGCTCCATCCGTTTTCATTTTCCCACCAT CCGACGAACAATTGAAGTCCGGTACCGCTTCCGTTGTT TGTTTGTTGAACAACTTCTACCCACGTGAGGCTAAGGT |

TABLE 12-continued

BRIEF DESCRIPTION OF THE SEQUENCES

| SEQ ID NO: | Description | Sequence |
|---|---|---|
| | | TCAGTGGAAGGTTGACAACGCTTTGCAATCCGGTAAC TCCCAAGAATCCGTTACTGAGCAGGATTCTAAGGATT CCACTTACTCATTGTCCTCCACTTTGACTTTGTCCAAG GCTGATTACGAGAAGCACAAGGTTTACGCTTGCGAGG TTACACATCAGGGTTTGTCCTCCCCAGTTACTAAGTCC TTCAACAGAGGAGAGTGTTAA |
| 22 | Anti-RSV light chain (VL + Kappa constant region) (protein) | DIQMTQSPSTLSASVGDRVTITCKCQLSVGYMHWYQQK PGKAPKLLIYDTSKLASGVPSRFSGSGSGTEFTLTISSLQP DDFATYYCFQGSGYPFTFGGGTKLEIKRTVAAPSVFIFPP SDEQLKSGTASVVCLLNNFYPREAKVQWKVDNALQSGN SQESVTEQDSKDSTYSLSSTLTLSKADYEKHKVYACEVT HQGLSSPVTKSFNRGEC |
| 23 | Pp AOX1 promoter | AACATCCAAAGACGAAAGGTTGAATGAAACCTTTTTG CCATCCGACATCCACAGGTCCATTCTCACACATAAGT GCCAAACGCAACAGGAGGGGATACACTAGCAGCAGA CCGTTGCAAACGCAGGACCTCCACTCCTCTTCTCCTCA ACACCCACTTTTGCCATCGAAAAACCAGCCCAGTTATT GGGCTTGATTGGAGCTCGCTCATTCCAATTCCTTCTAT TAGGCTACTAACACCATGACTTTATTAGCCTGTCTATC CTGGCCCCCCTGGCGAGGTTCATGTTTGTTTATTTCCG AATGCAACAAGCTCCGCATTACACCCGAACATCACTC CAGATGAGGGCTTTCTGAGTGTGGGGTCAAATAGTTT CATGTTCCCCAAATGGCCCAAAACTGACAGTTTAAAC GCTGTCTTGGAACCTAATATGACAAAAGCGTGATCTC ATCCAAGATGAACTAAGTTTGGTTCGTTGAAATGCTA ACGGCCAGTTGGTCAAAAAGAAACTTCCAAAAGTCGG CATACCGTTTGTCTTGTTTGGTATTGATTGACGAATGC TCAAAAATAATCTCATTAATGCTTAGCGCAGTCTCTCT ATCGCTTCTGAACCCCGGTGCACCTGTGCCGAAACGC AAATGGGGAAACACCCGCTTTTTGGATGATTATGCAT TGTCTCCACATTGTATGCTTCCAAGATTCTGGTGGGAA TACTGCTGATAGCCTAACGTTCATGATCAAAATTTAAC TGTTCTAACCCCTACTTGACAGCAATATATAAACAGA AGGAAGCTGCCCTGTCTTAAACCTTTTTTTTTATCATC ATTATTAGCTTACTTTCATAATTGCGACTGGTTCCAAT TGACAAGCTTTTGATTTTAACGACTTTTAACGACAACT TGAGAAGATCAAAAAACAACTAATTATTCGAAACG |
| 24 | ScCYC TT | ACAGGCCCCTTTTCCTTTGTCGATATCATGTAATTAGT TATGTCACGCTTACATTCACGCCCTCCTCCCACATCCG CTCTAACCGAAAAGGAAGGAGTTAGACAACCTGAAGT CTAGGTCCCTATTTATTTTTTTAATAGTTATGTTAGTA TTAAGAACGTTATTTATATTTCAAATTTTCTTTTTTTT CTGTACAAACGCGTGTACGCATGTAACATTATACTGA AAACCTTGCTTGAGAAGGTTTTGGGACGCTCGAAGGC TTTAATTTGCAAGCTGCCGGTCTTAAG |
| 25 | PpRPL10 promoter | GTTCTTCGCTTGGTCTTGTATCTCCTTACACTGTATCTTCCC ATTTGCGTTTAGGTGGTTATCAAAAACTAAAAGGAAAAAT TTCAGATGTTTATCTCTAAGGTTTTTTCTTTTTACAGTATAA CACGTGATGCGTCACGTGGTACTAGATTACGTAAGTTATTT TGGTCCGGTGGGTAAGTGGGTAAGAATAGAAAGCATGAAG GTTTACAAAAACGCAGTCACGAATTATTGCTACTTCGAGCT TGGAACCACCCCAAAGATTATATTGTACTGATGCACTACCT TCTCGATTTTGCTCCTCCAAGAACCTACGAAAACATTTCT TGAGCCTTTTCAACCTAGACTACACATCAAGTTATTTAAGG TATGTTCCGTTAACATGTAAGAAAAGGAGAGGATAGATCG TTTATGGGGTACGTCGCCTGATTCAAGCGTGACCATTCGAA GAATAGGCCTTCGAAAGCTGAATAAAGCAAATGTCAGTTG CGATTGGTATGCTGACAAATTAGCATAAAAAGCAATAGAC TTTCTAACCACCTGTTTTTTCCTTTTACTTTATTTATATTTT GCCACCGTACTAACAAGTTCAGACAAA |
| 26 | PpGAPDH promoter | TTTTTGTAGAAATGTCTTGGTGTCCTCGTCCAATCAGG TAGCCATCTCTGAAATATCTGGCTCCGTTGCAACTCCG AACGACCTGCTGGCAACGTAAAATTCTCCGGGGTAAA ACTTAAATGTGGAGTAATGGAACCAGAAACGTCTCTT CCCTTCTCTCTCCTTCCACCGCCCGTTACCGTCCCTAG GAAATTTTACTCTGCTGGAGAGCTTCTTCTACGGCCCC CTTGCAGCAATGCTCTTCCCAGCATTACGTTGCGGGTA AAACGGAGGTCGTGTACCCGACCTAGCAGCCCAGGGA TGGAAAAGTCCCGGCCGTCGCTGGCAATAATAGCGGG |

TABLE 12-continued

BRIEF DESCRIPTION OF THE SEQUENCES

| SEQ ID NO: Description | Sequence |
|---|---|
| | CGGACGCATGTCATGAGATTATTGGAAACCACCAGAA<br>TCGAATATAAAAGGCGAACACCTTTCCCAATTTTGGTT<br>TCTCCTGACCCAAAGACTTTAAATTTAATTTATTTGTC<br>CCTATTTCAATCAATTGAACAACTATCAAAACACA |
| 27 PpTEF1 promoter | TTAAGGTTTGGAACAACACTAAACTACCTTGCGGTAC<br>TACCATTGACACTACACATCCTTAATTCCAATCCTGTC<br>TGGCCTCCTTCACCTTTTAACCATCTTGCCCATTCCAA<br>CTCGTGTCAGATTGCGTATCAAGTGAAAAAAAAAAAA<br>TTTTAAATCTTTAACCCAATCAGGTAATAACTGTCGCC<br>TCTTTTATCTGCCGCACTGCATGAGGTGTCCCCTTAGT<br>GGGAAAGAGTACTGAGCCAACCCTGGAGGACAGCAA<br>GGGAAAAATACCTACAACTTGCTTCATAATGGTCGTA<br>AAAACAATCCTTGTCGGATATAAGTGTTGTAGACTGT<br>CCCTTATCCTCTGCGATGTTCTTCCTCTCAAAGTTTGC<br>GATTTCTCTCTATCAGAATTGCCATCAAGAGACTCAGG<br>ACTAATTTCGCAGTCCCACACGCACTCGTACATGATTG<br>GCTGAAATTTCCCTAAAGAATTTCTTTTTCACGAAAAT<br>TTTTTTTTTACACAAGATTTTCAGCAGATATAAAATGG<br>AGAGCAGGACCTCCGCTGTGACTCTTCTTTTTTTTCTTT<br>TATTCTCACTACATACATTTTAGTTATTCGCCAAC |
| 28 PpTEF1 TT | ATTGCTTGAAGCTTTAATTTATTTTATTAACATAATAA<br>TAATACAAGCATGATATATTTGTATTTTGTTCGTTAAC<br>ATTGATGTTTTCTTCATTTACTGTTATTGTTTGTAACTT<br>TGATCGATTTATCTTTTCTACTTTACTGTAATATGGCTG<br>GCGGGTGAGCCTTGAACTCCCTGTATTACTTTACCTTG<br>CTATTACTTAATCTATTGACTAGCAGCGACCTCTTCAA<br>CCGAAGGGCAAGTACACAGCAAGTTCATGTCTCCGTA<br>AGTGTCATCAACCCTGGAAACAGTGGGCCATGTC |
| 29 PpALG3 TT | ATTTACAATTAGTAATATTAAGGTGGTAAAAACATTC<br>GTAGAATTGAAATGAATTAATATAGTATGACAATGGT<br>TCATGTCTATAAATCTCCGGCTTCGGTACCTTCTCCCC<br>AATTGAATACATTGTCAAAATGAATGGTTGAACTATT<br>AGGTTCGCCAGTTTCGTTATTAAGAAAACTGTTAAAAT<br>CAAATTCCATATCATCGGTTCCAGTGGGAGGACCAGT<br>TCCATCGCCAAAATCCTGTAAGAATCCATTGTCAGAA<br>CCTGTAAAGTCAGTTTGAGATGAAATTTTTCCGGTCTT<br>TGTTGACTTGGAAGCTTCGTTAAGGTTAGGTGAAACA<br>GTTTGATCAACCAGCGGCTCCCGTTTTCGTCGCTTAGT<br>AG |
| 30 PpTRP1 5' region and ORF | GCGGAAACGGCAGTAAACAATGGAGCTTCATTAGTGGGTG<br>TTATTATGGTCCCTGGCCGGGAACGAACGGTGAAACAAGA<br>GGTTGCGAGGGAAATTTCGCAGATGGTGCGGGAAAAGAGA<br>ATTTCAAAGGGCTCAAAATACTTGGATTCCAGACAACTGA<br>GGAAAGAGTGGGACGACTGTCCTCTGGAAGACTGGTTTGA<br>GTACAACGTGAAAGAAATAAACAGCAGTGGTCCATTTTTA<br>GTTGGAGTTTTTCGTAATCAAAGTATAGATGAAATCCAGCA<br>AGCTATCCACACTCATGGTTTGGATTTCGTCCAACTACATG<br>GGTCTGAGGATTTTGATTCGTATATACGCAATATCCCAGTT<br>CCTGTGATTACCAGATACACAGATAATGCCGTCGATGGTCT<br>TACCGGAGAAGACCTCGCTATAAATAGGGCCCTGGTGCTA<br>CTGGACAGCGAGCAAGGAGGTGAAGGAAAAACCATCGATT<br>GGGCTCGTGCACAAAAATTTGGAGAACGTAGAGGAAAATA<br>TTTACTAGCCGGAGGTTTGACACCTGATAATGTTGCTCATG<br>CTCGATCTCATACTGGCTGTATTGGTGTTGACGTCTCTGGT<br>GGGGTAGAAACAAATGCCTCAAAAGATATGGACAAGATCA<br>CACAATTTATCAGAAACGCTACATAA |
| 31 PpTRP1 3' region | AAGTCAATTAAATACACGCTTGAAAGGACATTACATAGCTT<br>TCGATTTAAGCAGAACCAGAAATGTAGAACCACTTGTCAA<br>TAGATTGGTCAATCTTAGCAGGAGCGGCTGGGCTAGCAGTT<br>GGAACAGCAGAGGTTGCTGAAGGTGAGAAGGATGGAGTGG<br>ATTGCAAAGTGGTGTTGGTTAAGTCAATCTCACCAGGGCTG<br>GTTTTGCCAAAAATCAACTTCTCCCAGGCTTCACGGCATTC<br>TTGAATGACCTCTTCTGCATACTTCTTGTTCTTGCATTCACC<br>AGAGAAAGCAAACTGGTTCTCAGGTTTTCCATCAGGGATCT<br>TGTAAATTCTGAACCATTCGTTGGTAGCTCTCAACAAGCCC<br>GGCATGTGCTTTTCAACATCCTCGATGTCATTGAGCTTAGG<br>AGCCAATGGGTCGTTGATGTCGATGACGATGACCTTCCAGT<br>CAGTCTCTCCCTCATCCAACAAAGCCATAACACCGAGGACC<br>TTGACTTGCTTGACCTGTCCAGTGTAACCTACGGCTTCACC |

TABLE 12-continued

BRIEF DESCRIPTION OF THE SEQUENCES

| SEQ ID NO: Description | Sequence |
|---|---|
| | AATTTCGCAAACGTCCAATGGATCATTGTCACCCTTGGCCT<br>TGGTCTCTGGATGAGTGACGTTAGGGTCTTCCCATGTCTGA<br>GGGAAGGCACCGTAGTTGTGAATGTATCCGTGGTGAGGGA<br>AACAGTTACGAACGAAACGAAGTTTTCCCTTCTTTGTGTCC<br>TGAAGAATTGGGTTCAGTTTCTCCTCCTTGGAAATCTCCAA<br>CTTGGCGTTGGTCCAACGGGGGACTTCAACAACCATGTTGA<br>GAACCTTCTTGGATTCGTCAGCATAAAGTGGGATGTCGTGG<br>AAAGGAGATACGACTT |
| 32 ScARR3 ORF | ATGTCAGAAGATCAAAAAAGTGAAAATTCCGTACCTTCTA<br>AGGTTAATATGGTGAATCGCACCGATATACTGACTACGATC<br>AAGTCATTGTCATGGCTTGACTTGATGTTGCCATTTACTAT<br>AATTCTCTCCATAATCATTGCAGTAATAATTTCTGTCTATGT<br>GCCTTCTTCCCGTCACACTTTTGACGCTGAAGGTCATCCCA<br>ATCTAATGGGAGTGTCCATTCCTTTGACTGTTGGTATGATT<br>GTAATGATGATTCCCCCGATCTGCAAAGTTTCCTGGGAGTC<br>TATTCACAAGTACTTCTACAGGAGCTATATAAGGAAGCAA<br>CTAGCCCTCTCGTTATTTTTGAATTGGGTCATCGGTCCTTTG<br>TTGATGACAGCATTGGCGTGGATGGCGCTATTCGATTATAA<br>GGAATACCGTCAAGGCATTATTATGATCGGAGTAGCTAGA<br>TGCATTGCCATGGTGCTAATTTGGAATCAGATTGCTGGAGG<br>AGACAATGATCTCTGCGTCGTGCTTGTTATTACAAACTCGC<br>TTTTACAGATGGTATTATATGCACCATTGCAGATATTTTAC<br>TGTTATGTTATTTCTCATGACCACCTGAATACTTCAAATAG<br>GGTATTATTCGAAGAGGTTGCAAAGTCTGTCGGAGTTTTTC<br>TCGGCATACCACTGGGAATTGGCATTATCATACGTTTGGGA<br>AGTCTTACCATAGCTGGTAAAAGTAATTATGAAAAATACA<br>TTTTGAGATTTATTTCTCCATGGGCAATGATCGGATTTCATT<br>ACACTTTATTTGTTATTTTTATTAGTAGAGGTTATCAATTTA<br>TCCACGAAATTGGTTCTGCAATATTGTGCTTTGTCCCATTG<br>GTGCTTTACTTCTTTATTGCATGGTTTTTGACCTTCGCATTA<br>ATGAGGTACTTATCAATATCTAGGAGTGATACACAAAGAG<br>AATGTAGCTGTGACCAAGAACTACTTTTAAAGAGGGTCTG<br>GGGAAGAAAGTCTTGTGAAGCTAGCTTTTCTATTACGATGA<br>CGCAATGTTTCACTATGGCTTCAAATAATTTTGAACTATCC<br>CTGGCAATTGCTATTTCCTTATATGGTAACAATAGCAAGCA<br>AGCAATAGCTGCAACATTTGGGCCGTTGCTAGAAGTTCCAA<br>TTTTATTGATTTTGGCAATAGTCGCGAGAATCCTTAAACCA<br>TATTATATATGGAACAATAGAAATTAA |
| 33 URA6 region | CAAATGCAAGAGGACATTAGAAATGTGTTTGGTAAGAACA<br>TGAAGCCGGAGGCATACAAACGATTCACAGATTTGAAGGA<br>GGAAAACAAACTGCATCCACCGGAAGTGCCAGCAGCCGTG<br>TATGCCAACCTTGCTCTCAAAGGCATTCCTACGGATCTGAG<br>TGGGAAATATCTGAGATTCACAGACCCACTATTGGAACAG<br>TACCAAACCTAGTTTGGCCGATCCATGATTATGTAATGCAT<br>ATAGTTTTTGTCGATGCTCACCCGTTTCGAGTCTGTCTCGTA<br>TCGTCTTACGTATAAGTTCAAGCATGTTTACCAGGTCTGTT<br>AGAAACTCCTTTGTGAGGGCAGGACCTATTCGTCTCGGTCC<br>CGTTGTTTCTAAGAGACTGTACAGCCAAGCGCAGAATGGT<br>GGCATTAACCATAAGAGGATTCTGATCGGACTTGGTCTATT<br>GGCTATTGGAACCACCCTTTACGGGACAACCAACCCTACCA<br>AGACTCCTATTGCATTTGTGGAACCAGCCACGGAAAGAGC<br>GTTTAAGGACGGAGACGTCTCTGTGATTTTTGTTCTCGGAG<br>GTCCAGGAGCTGGAAAAGGTACCCAATGTGCCAAACTAGT<br>GAGTAATTACGGATTTGTTCACCTGTCAGCTGGAGACTTGT<br>TACGTGCAGAACAGAAGAGGGAGGGGTCTAAGTATGGAGA<br>GATGATTTCCCAGTATATCAGAGATGGACTGATAGTACCTC<br>AAGAGGTCACCATTGCGCTCTTGGAGCAGGCCATGAAGGA<br>AAACTTCGAGAAAGGGAAGACACGGTTCTTGATTGATGGA<br>TTCCCTCGTAAGATGGACCAGGCCAAAACTTTTGAGGAAA<br>AAGTCGCAAAGTCCAAGGTGACACTTTTCTTTGATTGTCCC<br>GAATCAGTGCTCCTTGAGAGATTACTTAAAAGAGGACAGA<br>CAAGCGGAAGAGAGGATGATAATGCGGAGAGTATCAAAA<br>AAAGATTCAAAACATTCGTGGAAACTTCGATGCCTGTGGTG<br>GACTATTTCGGGAAGCAAGGACGCGTTTTGAAGGTATCTTG<br>TGACCACCCTGTGGATCAAGTGTATTCACAGGTTGTGTCGG<br>TGCTAAAAGAGAAGGGGATCTTTGCCGATAACGAGACGGA<br>GAATAAATAA |
| 34 NatR ORF | ATGGGTACCACTCTTGACGACACGGCTTACCGGTACC<br>GCACCAGTGTCCCGGGGGACGCCGAGGCCATCGAGGC<br>ACTGGATGGGTCCTTCACCACCGACACCGTCTTCCGC<br>GTCACCGCCACCGGGGACGGCTTCACCCTGCGGGAGG |

TABLE 12-continued

BRIEF DESCRIPTION OF THE SEQUENCES

| SEQ ID NO: | Description | Sequence |
|---|---|---|
| | | TGCCGGTGGACCCGCCCCTGACCAAGGTGTTCCCCGA CGACGAATCGGACGACGAATCGGACGACGGGGAGGA CGGCGACCCGGACTCCCGGACGTTCGTCGCGTACGGG GACGACGGCGACCTGGCGGGCTTCGTGGTCGTCTCGT ACTCCGGCTGGAACCGCCGGCTGACCGTCGAGGACAT CGAGGTCGCCCCGGAGCACCGGGGGCACGGGGTCGG GCGCGCGTTGATGGGGCTCGCGACGGAGTTCGCCCGC GAGCGGGGCGCCGGGCACCTCTGGCTGGAGGTCACCA ACGTCAACGCACCGGCGATCCACGCGTACCGGCGGAT GGGGTTCACCCTCTGCGGCCTGGACACCGCCCTGTAC GACGGCACCGCCTCGGACGGCGAGCAGGCGCTCTACA TGAGCATGCCCTGCCCCTAATCAGTACTG |
| 35 | Sequence of the Sh ble ORF (Zeocin resistance marker): | ATGGCCAAGTTGACCAGTGCCGTTCCGGTGCTCACCG CGCGCGACGTCGCCGGAGCGGTCGAGTTCTGGACCGA CCGGCTCGGGTTCTCCCGGGACTTCGTGGAGGACGAC TTCGCCGGTGTGGTCCGGGACGACGTGACCCTGTTCAT CAGCGCGGTCCAGGACCAGGTGGTGCCGGACAACACC CTGGCCTGGGTGTGGGTGCGCGGCCTGGACGAGCTGT ACGCCGAGTGGTCGGAGGTCGTGTCCACGAACTTCCG GGACGCCTCCGGGCCGGCCATGACCGAGATCGGCGAG CAGCCGTGGGGGCGGGAGTTCGCCCTGCGCGACCCGG CCGGCAACTGCGTGCACTTCGTGGCCGAGGAGCAGGA CTGA |
| 36 | PpAOX1 TT | TCAAGAGGATGTCAGAATGCCATTTGCCTGAGAGATGCAG GCTTCATTTTGATACTTTTTTATTTGTAACCTATATAGTATA GGATTTTTTTTGTCATTTTGTTTCTTCTCGTACGAGCTTGCT CCTGATCAGCCTATCTCGCAGCTGATGAATATCTTGTGGTA GGGGTTTGGGAAAATCATTCGAGTTTGATGTTTTTCTTGGT ATTTCCCACTCCTCTTCAGAGTACAGAAGATTAAGTGAGAC GTTCGTTTGTGCA |
| 37 | ScTEF1 promoter | GATCCCCCACACACCATAGCTTCAAAATGTTTCTACTC CTTTTTTACTCTTCCAGATTTTCTCGGACTCCGCGCATC GCCGTACCACTTCAAAACACCCAAGCACAGCATACTA AATTTCCCCTCTTTCTTCCTCTAGGGTGTCGTTAATTAC CCGTACTAAAGGTTTGGAAAAGAAAAAAGAGACCGC CTCGTTTCTTTTTCTTCGTCGAAAAAGGCAATAAAAAT TTTTATCACGTTTCTTTTTCTTGAAAATTTTTTTTTTTG ATTTTTTTCTCTTTCGATGACCTCCCATTGATATTTAAG TTAATAAACGGTCTTCAATTTCTCAAGTTTCAGTTTCA TTTTTTCTTGTTCTATTACAACTTTTTTTACTTCTTGCTC ATTAGAAAGAAAGCATAGCAATCTAATCTAAGTTTTA ATTACAAA |
| 38 | *S. cerevisiae* invertase gene (ScSUC2) ORF underlined | AGGCCTCGCAACAACCTATAATTGAGTTAAGTGCCTTT CCAAGCTAAAAAGTTTGAGGTTATAGGGGCTTAGCAT CCACACGTCACAATCTCGGGTATCGAGTATAGTATGT AGAATTACGGCAGGAGGTTTCCCAATGAACAAAGGAC AGGGGCACGGTGAGCTGTCGAAGGTATCCATTTTATC ATGTTTCGTTTGTACAAGCACGACATACTAAGACATTT ACCGTATGGGAGTTGTTGTCCTAGCGTAGTTCTCGCTC CCCCAGCAAAGCTCAAAAAAGTACGTCATTTAGAATA GTTTGTGAGCAAATTACCAGTCGGTATGCTACGTTAG AAAGGCCCACAGTATTCTTCTACCAAAGGCGTGCCTTT GTTGAACTCGATCCATTATGAGGGCTTCCATTATTCCC CGCATTTTTATTACTCTGAACAGGAATAAAAAGAAAA AACCCAGTTTAGGAAATTATCCGGGGCGAAGAAATA CGCGTAGCGTTAATCGACCCCACGTCCAGGGTTTTCC ATGGAGGTTTCTGGAAAAACTGACGAGGAATGTGATT ATAAATCCCTTTATGTGATGTCTAAGACTTTTAAGGTA CGCCCGATGTTTGCCTATTACCATCATAGAGACGTTTC TTTTCGAGGAATGCTTAAACGACTTTGTTTGACAAAAA TGTTGCCTAAGGGCTCTATAGTAAACCATTTGGAAGA AAGATTTGACGACTTTTTTTTTTGGATTTCGATCCTAT AATCCTTCCTCCTGAAAAGAAACATATAAATAGATAT GTATTATTCTTCAAAACATTCTCTTGTTCTTGTGCTTTT TTTTTACCATATATCTTACTTTTTTTTTTCTCTCAGAGA AACAAGCAAAACAAAAAGCTTTTCTTTTCACTAACGT ATATATGCTTTTGCAAGCTTTCCTTTTCCTTTTGGCTG GTTTTGCAGCCAAAATATCTGCATCAATGACAAACGA AACTAGCGATAGACCTTTGGTCCACTTCACACCCAAC AAGGGCTGGATGAATGACCCAAATGGGTTGTGGTACG |

TABLE 12-continued

BRIEF DESCRIPTION OF THE SEQUENCES

| SEQ ID NO: Description | Sequence |
|---|---|
| | ATGAAAAAGATGCCAAATGGCATCTGTACTTTCAATA
CAACCCAAATGACACCGTATGGGGTACGCCATTGTTT
TGGGGCCATGCTACTTCCGATGATTTGACTAATTGGGA
AGATCAACCCATTGCTATCGCTCCCAAGCGTAACGAT
TCAGGTGCTTTCTCTGGCTCCATGGTGGTTGATTACAA
CAACACGAGTGGGTTTTTCAATGATACTATTGATCCAA
GACAAAGATGCGTTGCGATTTGGACTTATAACACTCC
TGAAAGTGAAGAGCAATACATTAGCTATTCTCTTGAT
GGTGGTTACACTTTTACTGAATACCAAAAGAACCCTG
TTTTAGCTGCCAACTCCACTCAATTCAGAGATCCAAAG
GTGTTCTGGTATGAACCTTCTCAAAAATGGATTATGAC
GGCTGCCAAATCACAAGACTACAAAATTGAAATTTAC
TCCTCTGATGACTTGAAGTCCTGGAAGCTAGAATCTGC
ATTTGCCAATGAAGGTTTCTTAGGCTACCAATACGAAT
GTCCAGGTTTGATTGAAGTCCCAACTGAGCAAGATCC
TTCCAAATCTTATTGGGTCATGTTTATTTCTATCAACC
CAGGTGCACCTGCTGGCGGTTCCTTCAACCAATATTTT
GTTGGATCCTTCAATGGTACTCATTTTGAAGCGTTTGA
CAATCAATCTAGAGTGGTAGATTTTGGTAAGGACTAC
TATGCCTTGCAAACTTTCTTCAACACTGACCCAACCTA
CGGTTCAGCATTAGGTATTGCCTGGGCTTCAAACTGG
GAGTACAGTGCCTTTGTCCCAACTAACCCATGGAGAT
CATCCATGTCTTTGGTCCGCAAGTTTTCTTTGAACACT
GAATATCAAGCTAATCCAGAGACTGAATTGATCAATT
TGAAAGCCGAACCAATATTGAACATTAGTAATGCTGG
TCCCTGGTCTCGTTTTGCTACTAACACAACTCTAACTA
AGGCCAATTCTTACAATGTCGATTTGAGCAACTCGACT
GGTACCCTAGAGTTTGAGTTGGTTTACGCTGTTAACAC
CACACAAACCATATCCAAATCCGTCTTTGCCGACTTAT
CACTTTGGTTCAAGGGTTTAGAAGATCCTGAAGAATA
TTTGAGAATGGGTTTTGAAGTCAGTGCTTCTTCCTTCT
TTTTGGACCGTGGTAACTCTAAGGTCAAGTTTGTCAAG
GAGAACCCATATTTCACAAACAGAATGTCTGTCAACA
ACCAACCATTCAAGTCTGAGAACGACCTAAGTTACTA
TAAAGTGTACGGCCTACTGGATCAAAACATCTTGGAA
TTGTACTTCAACGATGGAGATGTGGTTTCTACAAATAC
CTACTTCATGACCACCGGTAACGCTCTAGGATCTGTGA
ACATGACCACTGGTGTCGATAATTTGTTCTACATTGAC
AAGTTCCAAGTAAGGGAAGTAAAATAGAGGTTATAA
AACTTATTGTCTTTTTTATTTTTTTCAAAAGCCATTCTA
AAGGGCTTTAGCTAACGAGTGACGAATGTAAAACTTT
ATGATTTCAAAGAATACCTCCAAACCATTGAAAATGT
ATTTTTATTTTTATTTTCTCCCGACCCCAGTTACCTGGA
ATTTGTTCTTTATGTACTTTATATAAGTATAATTCTCTT
AAAAATTTTTACTACTTTGCAATAGACATCATTTTTC
ACGTAATAAACCCACAATCGTAATGTAGTTGCCTTAC
ACTACTAGGATGGACCTTTTTGCCTTTATCTGTTTTGTT
ACTGACACAATGAAACCGGGTAAAGTATTAGTTATGT
GAAAATTTAAAAGCATTAAGTAGAAGTATACCATATT
GTAAAAAAAAAAAGCGTTGTCTTCTACGTAAAAGTGT
TCTCAAAAAGAAGTAGTGAGGGAAATGGATACCAAG
CTATCTGTAACAGGAGCTAAAAAATCTCAGGGAAAAG
CTTCTGGTTTGGGAAACGGTCGAC |
| 39 Sequence of the 5'-Region used for knock out of PpURA5: | ATCGGCCTTTGTTGATGCAAGTTTTACGTGGATCATGG
ACTAAGGAGTTTTATTTGGACCAAGTTCATCGTCCTAG
ACATTACGGAAAGGGTTCTGCTCCTCTTTTTGGAAACT
TTTTGGAACCTCTGAGTATGACAGCTTGGTGGATTGTA
CCCATGGTATGGCTTCCTGTGAATTTCTATTTTTTCTAC
ATTGGATTCACCAATCAAAACAAATTAGTCGCCATGG
CTTTTTGGCTTTTGGGTCTATTTGTTTGGACCTTCTTGG
AATATGCTTTGCATAGATTTTTGTTCCACTTGGACTAC
TATCTTCCAGAGAATCAAATTGCATTTACCATTCATTT
CTTATTGCATGGGATACACCACTATTTACCAATGGATA
AATACAGATTGGTGATGCCACCTACACTTTTCATTGTA
CTTTGCTACCCAATCAAGACGCTCGTCTTTTCTGTTCT
ACCATATTACATGGCTTGTTCTGGATTTGCAGGTGGAT
TCCTGGGCTATATCATGTATGATGTCACTCATTACGTT
CTGCATCACTCCAAGCTGCCTCGTTATTTCCAAGAGTT
GAAGAAATATCATTTGGAACATCACTACAAGAATTAC
GAGTTAGGCTTTGGTGTCACTTCCAAATTCTGGGACAA
AGTCTTTGGGACTTATCTGGGTCCAGACGATGTGTATC
AAAAGACAAATTAGAGTATTTATAAAGTTATGTAAGC
AAATAGGGGCTAATAGGGAAAGAAAAATTTTGGTTCT |

TABLE 12-continued

BRIEF DESCRIPTION OF THE SEQUENCES

| SEQ ID NO: | Description | Sequence |
|---|---|---|
| | | TTATCAGAGCTGGCTCGCGCGCAGTGTTTTCGTGCTC CTTTGTAATAGTCATTTTTGACTACTGTTCAGATTGAA ATCACATTGAAGATGTCACTCGAGGGGTACCAAAAAA GGTTTTTGGATGCTGCAGTGGCTTCGC |
| 40 | Sequence of the 3'-Region used for knock out of PpURA5: | GGTCTTTTCAACAAAGCTCCATTAGTGAGTCAGCTGGC TGAATCTTATGCACAGGCCATCATTAACAGCAACCTG GAGATAGACGTTGTATTTGGACCAGCTTATAAAGGTA TTCCTTTGGCTGCTATTACCGTGTTGAAGTTGTACGAG CTCGGCGGCAAAAAATACGAAAATGTCGGATATGCGT TCAATAGAAAAGAAAAGAAAGACCACGGAGAAGGTG GAAGCATCGTTGGAGAAAGTCTAAAGAATAAAAGAGT ACTGATTATCGATGATGTGATGACTGCAGGTACTGCT ATCAACGAAGCATTTGCTATAATTGGAGCTGAAGGTG GGAGAGTTGAAGGTAGTATTATTGCCCTAGATAGAAT GGAGACTACAGGAGATGACTCAAATACCAGTGCTACC CAGGCTGTTAGTCAGAGATATGGTACCCCTGTCTTGA GTATAGTGACATTGGACCATATTGTGGCCCATTTGGGC GAAACTTTCACAGCAGACGAGAAATCTCAAATGGAAA CGTATAGAAAAAGTATTTGCCCAAATAAGTATGAAT CTGCTTCGAATGAATGAATTAATCCAATTATCTTCTCA CCATTATTTTCTTCTGTTTCGGAGCTTTGGGCACGGCG GCGGGTGGTGCGGGCTCAGGTTCCCTTTCATAAACAG ATTTAGTACTTGGATGCTTAATAGTGAATGGCGAATG CAAAGGAACAATTTCGTTCATCTTTAACCCTTTCACTC GGGGTACACGTTCTGGAATGTACCCGCCCTGTTGCAA CTCAGGTGGACCGGGCAATTCTTGAACTTTCTGTAACG TTGTTGGATGTTCAACCAGAAATTGTCCTACCAACTGT ATTAGTTTCCTTTTGGTCTTATATTGTTCATCGAGATAC TTCCCACTCTCCTTGATAGCCACTCTCACTCTTCCTGG ATTACCAAAATCTTGAGGATGAGTCTTTTCAGGCTCCA GGATGCAAGGTATATCCAAGTACCTGCAAGCATCTAA TATTGTCTTTGCCAGGGGGTTCTCCACACCATACTCCT TTTGGCGCATGC |
| 41 | Sequence of the PpURA5 auxotrophic marker: | TCTAGAGGGACTTATCTGGGTCCAGACGATGTGTATC AAAAGACAAATTAGAGTATTTATAAAGTTATGTAAGC AAATAGGGGCTAATAGGGAAAGAAAAATTTTGGTTCT TTATCAGAGCTGGCTCGCGCGCAGTGTTTTCGTGCTC CTTTGTAATAGTCATTTTTGACTACTGTTCAGATTGAA ATCACATTGAAGATGTCACTGGAGGGGTACCAAAAAA GGTTTTTGGATGCTGCAGTGGCTTCGCAGGCCTTGAAG TTTGGAACTTTCACCTTGAAAAGTGGAAGACAGTCTC CATACTTCTTTAACATGGGTCTTTTCAACAAAGCTCCA TTAGTGAGTCAGCTGGCTGAATCTTATGCTCAGGCCAT CATTAACAGCAACCTGGAGATAGACGTTGTATTTGGA CCAGCTTATAAAGGTATTCCTTTGGCTGCTATTACCGT GTTGAAGTTGTACGAGCTGGGCGGCAAAAAATACGAA AATGTCGGATATGCGTTCAATAGAAAAGAAAAGAAAG ACCACGGAGAAGGTGGAAGCATCGTTGGAGAAAGTCT AAAGAATAAAAGAGTACTGATTATCGATGATGTGATG ACTGCAGGTACTGCTATCAACGAAGCATTTGCTATAA TTGGAGCTGAAGGTGGGAGAGTTGAAGGTTGTATTAT TGCCCTAGATAGAATGGAGACTACAGGAGATGACTCA AATACCAGTGCTACCCAGGCTGTTAGTCAGAGATATG GTACCCCTGTCTTGAGTATAGTGACATTGGACCATATT GTGGCCCATTTGGGCGAAACTTTCACAGCAGACGAGA AATCTCAAATGGAAACGTATAGAAAAAGTATTTGCC CAAATAAGTATGAATCTGCTTCGAATGAATGAATTAA TCCAATTATCTTCTCACCATTATTTTCTTCTGTTTCGGA GCTTTGGGCACGGCGGCGGATCC |
| 42 | Sequence of the part of the Ec lacZ gene that was used to construct the PpURA5 blaster (recyclable auxotrophic marker) | CCTGCACTGGATGGTGGCGCTGGATGGTAAGCCGCTG GCAAGCGGTGAAGTGCCTCTGGATGTCGCTCCACAAG GTAAACAGTTGATTGAACTGCCTGAACTACCGCAGCC GGGAGAGCGCCGGGCAACTCTGGCTCACAGTACGCGTA GTGCAACCGAACGCGACCGCATGGTCAGAAGCGGGC ACATCAGCGCCTGGCAGCAGTGGCGTCTGGCGGAAAA CCTCAGTGTGACGCTCCCCGCCCGCGTCCCACGCCATCC CGCATCTGACCACCAGCGAAATGGATTTTTGCATCGA GCTGGGTAATAAGCGTTGGCAATTTAACCGCCAGTCA GGCTTTCTTTCACAGATGTGGATTGGCGATAAAAAAC AACTGCTGACGCCGCTGCGCGATCAGTTCACCCGTGC ACCGCTGGATAACGACATTGGCGTAAGTGAAGCGACC |

TABLE 12-continued

BRIEF DESCRIPTION OF THE SEQUENCES

| SEQ ID NO: | Description | Sequence |
|---|---|---|
| | | CGCATTGACCCTAACGCCTGGGTCGAACGCTGGAAGG<br>CGGCGGGCCATTACCAGGCCGAAGCAGCGTTGTTGCA<br>GTGCACGGCAGATACACTTGCTGATGCGGTGCTGATT<br>ACGACCGCTCACGCGTGGCAGCATCAGGGGAAAACCT<br>TATTTATCAGCCGGAAAACCTACCGGATTGATGGTAG<br>TGGTCAAATGGCGATTACCGTTGATGTTGAAGTGGCG<br>AGCGATACACCGCATCCGGCGCGGATTGGCCTGAACT<br>GCCAG |
| 43 | Sequence of the 5'-Region used for knock out of PpOCH1: | AAAACCTTTTTTCCTATTCAAACACAAGGCATTGCTTC<br>AACACGTGTGCGTATCCTTAACACAGATACTCCATACT<br>TCTAATAATGTGATAGACGAATACAAAGATGTTCACT<br>CTGTGTTGTGTCTACAAGCATTTCTTATTCTGATTGGG<br>GATATTCTAGTTACAGCACTAAACAACTGGCGATACA<br>AACTTAAATTAAATAATCCGAATCTAGAAAATGAACT<br>TTTGGATGGTCCGCCTGTTGGTTGGATAAATCAATACC<br>GATTAAATGGATTCTATTCCAATGAGAGAGTAATCCA<br>AGACACTCTGATGTCAATAATCATTTGCTTGCAACAAC<br>AAACCCGTCATCTAATCAAAGGGTTTGATGAGGCTTA<br>CCTTCAATTGCAGATAAACTCATTGCTGTCCACTGCTG<br>TATTATGTGAGAATATGGGTGATGAATCTGGTCTTCTC<br>CACTCAGCTAACATGGCTGTTTGGGCAAAGGTGGTAC<br>AATTATACGGAGATCAGGCAATAGTGAAATTGTTGAA<br>TATGGCTACTGGACGATGCTTCAAGGATGTACGTCTA<br>GTAGGAGCCGTGGGAAGATTGCTGGCAGAACCAGTTG<br>GCACGTCGCAACAATCCCCAAGAAATGAAATAAGTGA<br>AAACGTAACGTCAAAGACAGCAATGGAGTCAATATTG<br>ATAACACCACTGGCAGAGCGGTTCGTACGTCGTTTTG<br>GAGCCGATATGAGGCTCAGCGTGCTAACAGCACGATT<br>GACAAGAAGACTCTCGAGTGACAGTAGGTTGAGTAAA<br>GTATTCGCTTAGATTCCCAACCTTCGTTTTATTCTTTCG<br>TAGACAAAGAAGCTGCATGCGAACATAGGGACAACTT<br>TTATAAATCCAATTGTCAAACCAACGTAAAACCCTCT<br>GGCACCATTTTCAACATATATTTGTGAAGCAGTACGC<br>AATATCGATAAATACTCACCGTTGTTTGTAACAGCCCC<br>AACTTGCATACGCCTTCTAATGACCTCAAATGGATAA<br>GCCGCAGCTTGTGCTAACATACCAGCAGCACCGCCCG<br>CGGTCAGCTGCGCCCACACATATAAAGGCAATCTACG<br>ATCATGGGAGGAATTAGTTTTGACCGTCAGGTCTTCA<br>AGAGTTTTGAACTCTTCTTCTTGAACTGTGTAACCTTT<br>TAAATGACGGGATCTAAATACGTCATGGATGAGATCA<br>TGTGTGTAAAAACTGACTCCAGCATATGGAATCATTC<br>CAAAGATTGTAGGAGCGAACCCACGATAAAGTTTCC<br>CAACCTTGCCAAAGTGTCTAATGCTGTGACTTGAAATC<br>TGGGTTCCTCGTTGAAGACCCTGCGTACTATGCCCAAA<br>AACTTTCCTCCACGAGCCCTATTAACTTCTCTATGAGT<br>TTCAAATGCCAAACGGACACGGATTAGGTCCAATGGG<br>TAAGTGAAAAACACAGAGCAAACCCCAGCTAATGAG<br>CCGGCCAGTAACCGTCTTGGAGCTGTTTCATAAGAGT<br>CATTAGGGATCAATAACGTTCTAATCTGTTCATAACAT<br>ACAAATTTTATGGCTGCATAGGGAAAAATTCTCAACA<br>GGGTAGCCGAATGACCCTGATATAGACCTGCGACACC<br>ATCATACCCATAGATCTGCCTGACAGCCTTAAAGAGC<br>CCGCTAAAAGACCCGGAAAACCGAGAGAACTCTGGAT<br>TAGCAGTCTGAAAAAGAATCTTCACTCTGTCTAGTGG<br>AGCAATTAATGTCTTAGCGGCACTTCCTGCTACTCCGC<br>CAGCTACTCCTGAATAGATCACATACTGCAAAGACTG<br>CTTGTCGATGACCTTGGGGTTATTTAGCTTCAAGGGCA<br>ATTTTTGGGACATTTTGGACACAGGAGACTCAGAAAC<br>AGACACAGAGCGTTCTGAGTCCTGGTGCTCCTGACGT<br>AGGCCTAGAACAGGAATTATTGGCTTTATTTGTTTGTC<br>CATTTCATAGGCTTGGGGTAATAGATAGATGACAGAG<br>AAATAGAAGACCTAATATTTTTTGTTCATGGCAAA<br>TCGCGGGTTCGCGGTCGGGTCACACACGGAGAAGTAA<br>TGAGAAGAGCTGGTAATCTGGGGTAAAAGGGTTCAAA<br>AGAAGGTCGCCTGGTAGGGATGCAATACAAGGTTGTC<br>TTGGAGTTTACATTGACCAGATGATTTGGCTTTTTCTC<br>TGTTCAATTCACATTTTTCAGCGAGAATCGGATTGACG<br>GAGAAATGGCGGGGTGTGGGGTGGATAGATGGCAGA<br>AATGCTCGCAATCACCGCGAAAGAAAGACTTTATGGA<br>ATAGAACTACTGGGTGGTGTAAGGATTACATAGCTAG<br>TCCAATGGAGTCCGTTGGAAAGGTAAGAAGAAGCTAA<br>AACCGGCTAAGTAACTAGGGAAGAATGATCAGACTTT<br>GATTTGATGAGGTCTGAAAATACTCTGCTGCTTTTTCA |

TABLE 12-continued

BRIEF DESCRIPTION OF THE SEQUENCES

| SEQ ID NO: | Description | Sequence |
|---|---|---|
| | | GTTGCTTTTTCCCTGCAACCTATCATTTTCCTTTTCATA AGCCTGCCTTTTCTGTTTTCACTTATATGAGTTCCGCC GAGACTTCCCCAAATTCTCTCCTGGAACATTCTCTATC GCTCTCCTTCCAAGTTGCGCCCCCTGGCACTGCCTAGT AATATTACCACGCGACTTATATTCAGTTCCACAATTTC CAGTGTTCGTAGCAAATATCATCAGCCATGGCGAAGG CAGATGGCAGTTTGCTCTACTATAATCCTCACAATCCA CCCAGAAGGTATTACTTCTACATGGCTATATTCGCCGT TTCTGTCATTTGCGTTTTGTACGGACCCTCACAACAAT TATCATCTCCAAAAATAGACTATGATCCATTGACGCTC CGATCACTTGATTTGAAGACTTTGGAAGCTCCTTCACA GTTGAGTCCAGGCACCGTAGAAGATAATCTTCG |
| 44 | Sequence of the 3'-Region used for knock out of PpOCH1: | AAAGCTAGAGTAAAATAGATATAGCGAGATTAGAGA ATGAATACCTTCTTCTAAGCGATCGTCCGTCATCATAG AATATCATGGACTGTATAGTTTTTTTTTTGTACATATA ATGATTAAACGGTCATCCAACATCTCGTTGACAGATCT CTCAGTACGCGAAATCCCTGACTATCAAAGCAAGAAC CGATGAAGAAAAAAACAACAGTAACCCAAACACCAC AACAAACACTTTATCTTCTCCCCCCCAACACCAATCAT CAAAGAGATGTCGGAACCAAACACCAAGAAGCAAAA ACTAACCCCATATAAAAACATCCTGGTAGATAATGCT GGTAACCCGCTCTCCTTCCATATTCTGGGCTACTTCAC GAAGTCTGACCGGTCTCAGTTGATCAACATGATCCTC GAAATGGGTGGCAAGATCGTTCCAGACCTGCCTCCTC TGGTAGATGGAGTGTTGTTTTTGACAGGGGATTACAA GTCTATTGATGAAGATACCCTAAAGCAACTGGGGGAC GTTCCAATATACAGAGACTCCTTCATCTACCAGTGTTT TGTGCACAAGACATCTCTTCCCATTGACACTTTCCGAA TTGACAAGAACGTCGACTTGGCTCAAGATTTGATCAA TAGGGCCCTTCAAGAGTCTGTGGATCATGTCACTTCTG CCAGCACAGCTGCAGCTGCTGCTGTTGTTGTCGCTACC AACGGCCTGTCTTCTAAACCAGACGCTCGTACTAGCA AAATACAGTTCACTCCCGAAGAAGATCGTTTTATTCTT GACTTTGTTAGGAGAAATCCTAAACGAAGAAACACAC ATCAACTGTACACTGAGCTCGCTCAGCACATGAAAAA CCATACGAATCATTCTATCCGCCACAGATTTCGTCGTA ATCTTTCCGCTCAACTTGATTGGGTTTATGATATCGAT CCATTGACCAACCAACCTCGAAAAGATGAAAACGGGA ACTACATCAAGGTACAAGGCCTTCCA |
| 45 | K. lactis UDP-GlcNAc transporter gene (KlMNN2-2) ORF underlined | AAACGTAACGCCTGGCACTCTATTTTCTCAAACTTCTG GGACGGAAGAGCTAAATATTGTGTTGCTTGAACAAAC CCAAAAAAACAAAAAAATGAACAAACTAAAACTACA CCTAAATAAACCGTGTGTAAAACGTAGTACCATATTA CTAGAAAAGATCACAAGTGTATCACACATGTGCATCT CATATTACATCTTTTATCCAATCCATTCTCTCTATCCCG TCTGTTCCTGTCAGATTCTTTTTCCATAAAAAGAAGAA GACCCCGAATCTCACCGGTACAATGCAAAACTGCTGA AAAAAAAGAAAGTTCACTGGATACGGGAACAGTGC CAGTAGGCTTCACCACATGGACAAAACAATTGACGAT AAAATAAGCAGGTGAGCTTCTTTTTTCAAGTCACGATC CCTTTATGTCTCAGAAACAATATATACAAGCTAAACC CTTTTGAACCAGTTCTCTCTTCATAGTTATGTTCACAT AAATTGCGGGAACAAGACTCCGCTGGCTGTCAGGTAC ACGTTGTAACGTTTTCGTCCGCCCAATTATTAGCACAA CATTGGCAAAAAGAAAAACTGCTCGTTTTCTCTACAG GTAAATTACAATTTTTTTCAGTAATTTTCGCTGAAAAA TTTAAAGGGCAGGAAAAAAAGACGATCTCGACTTTGC ATAGATGCAAGAACTGTGGTCAAAACTTGAAATAGTA ATTTTGCTGTGCGTGAACTAATAAATATATATATATAT ATATATATATATTTGTGTATTTTGTATATGTAATTGTGC ACGTCTTGGCTATTGGATATAAGATTTTCGCGGGTTGA TGACATAGAGCGTGTACTACTGTAATAGTTGTATATTC AAAAGCTGCTGCGTGGAGAAAGACTAAAATAGATAA AAAGCACACATTTTGACTTCGGTACCGTCAACTTAGTG GGACAGTCTTTTATATTTGGTGTAAGCTCATTTCTGGT ACTATTCGAAACAGAACAGTGTTTTCTGTATTACCGTC CAATCGTTTGTCATGAGTTTTGTATTGATTTTGTCGTT AGTGTTCGGAGGATGTTGTTCCAATGTGATTAGTTTCG AGCACATGGTGCAAGGCAGCAATATAAATTTGGGAAA TATTGTTACATTCACTCAATTCGTGTCTGTGACGCTAA TTCAGTTGCCCAATGCTTTGGACTTCTCTCACTTTCCGT TTAGGTTGCGACCTAGACACATTCCTCCTTAAGATCCAT |

TABLE 12-continued

BRIEF DESCRIPTION OF THE SEQUENCES

| SEQ ID NO: | Description | Sequence |
|---|---|---|
| | | ATGTTAGCTGTGTTTTTGTTCTTTACCAGTTCAGTCGCC AATAACAGTGTGTTTAAATTTGACATTTCCGTTCCGAT TCATATTATCATTAGATTTTCAGGTACCACTTTGACGA TGATAATAGGTTGGGCTGTTTGTAATAAGAGGTACTC CAAACTTCAGGTGCAATCTGCCATCATTATGACGCTTG GTGCGATTGTCGCATCATTATACCGTGACAAAGAATTT TCAATGGACAGTTTAAAGTTGAATACGGATTCAGTGG GTATGACCCAAAAATCTATGTTTGGTATCTTTGTTGTG CTAGTGGCCACTGCCTTGATGTCATTGTTGTCGTTGCT CAACGAATGGACGTATAACAAGTACGGGAAACATTGG AAAGAAACTTTGTTCTATTCGCATTTCTTGGCTCTACC GTTGTTTATGTTGGGGTACACAAGGCTCAGAGACGAA TTCAGAGACCTCTTAATTTCCTCAGACTCAATGGATAT TCCTATTGTTAAATTACCAATTGCTACGAAACTTTTCA TGCTAATAGCAAATAACGTGACCCAGTTCATTTGTATC AAAGGTGTTAACATGCTAGCTAGTAACACGGATGCTT TGACACTTTCTGTCGTGCTTCTAGTGCGTAAATTTGTT AGTCTTTTACTCAGTGTCTACATCTACAAGAACGTCCT ATCCGTGACTGCATACCTAGGGACCATCACCGTGTTCC TGGGAGCTGGTTTGTATTCATATGGTTCGGTCAAAACT GCACTGCCTCGCTGAAACAATCCACGTCTGTATGATA CTCGTTTCAGAATTTTTTGATTTTCTGCCGGATATGGT TTCTCATCTTTACAATCGCATTCTTAATTATACCAGAA CGTAATTCAATGATCCCAGTGACTCGTAACTCTTATAT GTCAATTTAAGC |
| 46 | Sequence of the 5'-Region used for knock out of PpBMT2: | GGCCGAGCGGGCCTAGATTTTCACTACAAATTTCAAA ACTACGCGGATTTATTGTCTCAGAGAGCAATTTGGCAT TTCTGAGCGTAGCAGGAGGCTTCATAAGATTGTATAG GACCGTACCAACAAATTGCCGAGGCACAACACGGTAT GCTGTGCACTTATGTGGCTACTTCCCTACAACGGAATG AAACCTTCCTCTTTCCGCTTAAACGAGAAAGTGTGTCG CAATTGAATGCAGGTGCCTGTGCGCCTTGGTGTATTGT TTTTGAGGGCCCAATTTATCAGGCGCCTTTTTTCTTGG TTGTTTTCCCTTAGCCTCAAGCAAGGTTGGTCTATTTC ATCTCCGCTTCTATACCGTGCCTGATACTGTTGGATGA GAACACGACTCAACTTCCTGCTGCTCTGTATTGCCAGT GTTTTGTCTGTGATTTGGATCGGAGTCCTCCTTACTTG GAATGATAATAATCTTGGCGGAATCTCCCTAAACGGA GGCAAGGATTCTGCCTATGATGATCTGCTATCATTGGG AAGCTTCAACGACATGGAGGTCGACTCCTATGTCACC AACATCTACGACAATGCTCCAGTGCTAGGATGTACGG ATTTGTCTTATCATGGATTGTTGAAAGTCACCCCAAAG CATGACTTAGCTTGCGATTTGGAGTTCATAAGAGCTCA GATTTTGGACATTGACGTTTACTCCGCCATAAAAGACT TAGAAGATAAAGCCTTGACTGTAAAACAAAAGGTTGA AAAACACTGGTTTACGTTTTATGGTAGTTCAGTCTTTC TGCCCGAACACGATGTGCATTACCTGGTTAGACGAGT CATCTTTTCGGCTGAAGGAAAGGCGAACTCTCCAGTA ACATC |
| 47 | Sequence of the 3'-Region used for knock out of PpBMT2: | CCATATGATGGGTGTTTGCTCACTCGTATGGATCAAAA TTCCATGGTTTCTTCTGTACAACTTGTACACTTATTTGG ACTTTTCTAACGGTTTTTCTGGTGATTTGAGAAGTCCT TATTTTGGTGTTCGCAGCTTATCCGTGATTGAACCATC AGAAATACTGCAGCTCGTTATCTAGTTTCAGAATGTGT TGTAGAATACAATCAATTCTGAGTCTAGTTTGGGTGG GTCTTGGCGACGGGACCGTTATATGCATCTATGCAGT GTTAAGGTACATAGAATGAAAATGTAGGGGTTAATCG AAAGCATCGTTAATTTCAGTAGAACGTAGTTCTATTCC CTACCCAATAATTTGCCAAGAATGCTTCGTATCCACA TACGCAGTGGACGTAGCAAATTTCACTTTGGACTGTG ACCTCAAGTCGTTATCTTCTACTTGGACATTGATGGTC ATTACGTAATCCACAAAGAATTGGATAGCCTCTCGTTT TATCTAGTGCACAGCCTAATAGCACTTAAGTAAGAGC AATGGACAAATTTGCATAGACATTGAGCTAGATACGT AACTCAGATCTTGTTCACTCATGGTGTACTCGAAGTAC TGCTGGAACCGTTACCTCTTATCATTTCGCTACTGGCT CGTGAAACTACTGGATGAAAAAAAAAAAAGAGCTGA AAGCGAGATCATCCCATTTTGTCATCATACAAATTCAC GCTTGCAGTTTTGCTTCGTTAACAAGACAAGATGTCTT TATCAAAGACCCGTTTTTTCTTCTTGAAGAATACTTCC CTGTTGAGCACATGCAAACCATATTTATCTCAGATTTC ACTCAACTTGGGTGCTTCCAAGAGAAGTAAAATTCTT |

TABLE 12-continued

BRIEF DESCRIPTION OF THE SEQUENCES

| SEQ ID NO: | Description | Sequence |
|---|---|---|
| | | CCCACTGCATCAACTTCCAAGAAACCCGTAGACCAGT<br>TTCTCTTCAGCCAAAAGAAGTTGCTCGCCGATCACCGC<br>GGTAACAGAGGAGTCAGAAGGTTTCACACCCTTCCAT<br>CCCGATTTCAAAGTCAAAGTGCTGCGTTGAACCAAGG<br>TTTTCAGGTTGCCAAAGCCCAGTCTGCAAAAACTAGTT<br>CCAAATGGCCTATTAATTCCCATAAAAGTGTTGGCTAC<br>GTATGTATCGGTACCTCCATTCTGGTATTTGCTATTGT<br>TGTCGTTGGTGGGTTGACTAGACTGACCGAATCCGGT<br>CTTTCCATAACGGAGTGGAAACCTATCACTGGTTCGGT<br>TCCCCCACTGACTGAGGAAGACTGGAAGTTGGAATTT<br>GAAAAATACAAACAAAGCCCTGAGTTTCAGGAACTAA<br>ATTCTCACATAACATTGGAAGAGTTCAAGTTTATATTT<br>TCCATGGAATGGGGACATAGATTGTTGGGAAGGGTCA<br>TCGGCCTGTCGTTTGTTCTTCCCACGTTTTACTTCATTG<br>CCCGTCGAAAGTGTTCCAAAGATGTTGCATTGAAACT<br>GCTTGCAATATGCTCTATGATAGGATTCCAAGGTTTCA<br>TCGGCTGGTGGATGGTGTATTCCGGATTGGACAAACA<br>GCAATTGGCTGAACGTAACTCCAAACCAACTGTGTCT<br>CCATATCGCTTAACTACCCATCTTGGAACTGCATTTGT<br>TATTTACTGTTACATGATTTACACAGGGCTTCAAGTTT<br>TGAAGAACTATAAGATCATGAAACAGCCTGAAGCGTA<br>TGTTCAAATTTTCAAGCAAATTGCGTCTCCAAAATTGA<br>AAACTTTCAAGAGACTCTCTTCAGTTCTATTAGGCCTG<br>GTG |
| 48 | DNA encodes MmSLC35A3 UDP-GlcNAc transporter | ATGTCTGCCAACCTAAAATATCTTTCCTTGGGAATTTT<br>GGTGTTTCAGACTACCAGTCTGGTTCTAACGATGCGGT<br>ATTCTAGGACTTTAAAAGAGGAGGGGCCTCGTTATCT<br>GTCTTCTACAGCAGTGGTTGTGGCTGAATTTTTGAAGA<br>TAATGGCCTGCATCTTTTTAGTCTACAAAGACAGTAAG<br>TGTAGTGTGAGAGCACTGAATAGAGTACTGCATGATG<br>AAATTCTTAATAAGCCCATGGAAACCCTGAAGCTCGC<br>TATCCCGTCAGGGATATATACTCTTCAGAACAACTTAC<br>TCTATGTGGCACTGTCAAACCTAGATGCAGCCACTTAC<br>CAGGTTACATATCAGTTGAAAATACTTACAACAGCAT<br>TATTTTCTGTGTCTATGCTTGGTAAAAAATTAGGTGTG<br>TACCAGTGGCTCTCCCTAGTAATTCTGATGGCAGGAGT<br>TGCTTTTGTACAGTGGCCTTCAGATTCTCAAGAGCTGA<br>ACTCTAAGGACCTTTCAACAGGCTCACAGTTTGTAGG<br>CCTCATGGCAGTTCTCACAGCCTGTTTTTCAAGTGGCT<br>TTGCTGGAGTTTATTTTGAGAAAATCTTAAAAGAAAC<br>AAAACAGTCAGTATGGATAAGGAACATTCAACTTGGT<br>TTCTTTGGAAGTATATTTGGATTAATGGGTGTATACGT<br>TTATGATGGAGAATTGGTCTCAAAGAATGGATTTTTTC<br>AGGGATATAATCAACTGACGTGGATAGTTGTTGCTCT<br>GCAGGCACTTGGAGGCCTTGTAATAGCAGCTGTCATC<br>AAATATGCAGATAACATTTTAAAAGGATTTGCGACCT<br>CCTTATCCATAATATTGTCAACAATAATATCTTATTTT<br>TGGTTGCAAGATTTTGTGCCAACCAGTGTCTTTTTCCT<br>TGGAGCCATCCTTGTAATAGCAGCTACTTTCTTGTATG<br>GTTACGATCCCAAACCTGCAGGAAATCCCACTAAAGC<br>ATAG |
| 49 | Sequence of the 5'-Region used for knock out of PpMNN4L1: | GATCTGGCCATTGTGAAACTTGACACTAAAGACAAAA<br>CTCTTAGAGTTTCCAATCACTTAGGAGACGATGTTTCC<br>TACAACGAGTACGATCCCTCATTGATCATGAGCAATTT<br>GTATGTGAAAAAAGTCATCGACCTTGACACCTTGGAT<br>AAAAGGGCTGGAGGAGGTGGAACCACCTGTGCAGGC<br>GGTCTGAAAGTGTTCAAGTACGGATCTACTACCAAAT<br>ATACATCTGGTAACCTGAACGGCGTCAGGTTAGTATA<br>CTGGAACGAAGGAAAGTTGCAAAGCTCCAAATTTGTG<br>GTTCGATCCTCTAATTACTCTCAAAAGCTTGGAGGAA<br>ACAGCAACGCCGAATCAATTGACAACAATGGTGTGGG<br>TTTTGCCTCAGCTGGAGACTCAGGCGCATGGATTCTTT<br>CCAAGCTACAAGATGTTAGGGAGTACCAGTCATTCAC<br>TGAAAAGCTAGGTGAAGCTACGATGAGCATTTTCGAT<br>TTCCACGGTCTTAAACAGGAGACTTCTACTACAGGGC<br>TTGGGGTAGTTGGTATGATTCATTCTTACGACGGTGAG<br>TTCAAACAGTTTGGTTTGTTCACTCCAATGACATCTAT<br>TCTACAAAGACTTCAACGAGTGACCAATGTAGAATGG<br>TGTGTAGCGGGTTGCGAAGATGGGGATGTGGACACTG<br>AAGGAGAACACGAATTGAGTGATTTGGAACAACTGCA<br>TATGCATAGTGATTCCGACTAGTCAGGCAAGAGAGAG<br>CCCTCAAATTTACCTCTCTGCCCCTCCTCACTCCTTTTG |

TABLE 12-continued

BRIEF DESCRIPTION OF THE SEQUENCES

| SEQ ID NO: | Description | Sequence |
|---|---|---|
| | | GTACGCATAATTGCAGTATAAAGAACTTGCTGCCAGC CAGTAATCTTATTTCATACGCAGTTCTATATAGCACAT AATCTTGCTTGTATGTATGAAATTTACCGCGTTTTAGT TGAAATTGTTTATGTTGTGTGCCTTGCATGAAATCTCT CGTTAGCCCTATCCTTACATTTAACTGGTCTCAAAACC TCTACCAATTCCATTGCTGTACAACAATATGAGGCGG CATTACTGTAGGGTTGGAAAAAAATTGTCATTCCAGC TAGAGATCACACGACTTCATCACGCTTATTGCTCCTCA TTGCTAAATCATTTACTCTTGACTTCGACCCAGAAAAG TTCGCC |
| 50 | Sequence of the 3'-Region used for knock out of PpMNN4L1: | GCATGTCAAACTTGAACACAACGACTAGATAGTTGTT TTTTCTATATAAAACGAAACGTTATCATCTTTAATAAT CATTGAGGTTTACCCTTATAGTTCCGTATTTTCGTTTCC AAACTTAGTAATCTTTTGGAAATATCATCAAAGCTGGT GCCAATCTTCTTGTTTGAAGTTTCAAACTGCTCCACCA AGCTACTTAGAGACTGTTCTAGGTCTGAAGCAACTTC GAACACAGAGACAGCTGCCGCCGATTGTTCTTTTTTGT GTTTTTCTTCTGGAAGAGGGGCATCATCTTGTATGTCC AATGCCCGTATCCTTTCTGAGTTGTCCGACACATTGTC CTTCGAAGAGTTTCCTGACATTGGGCTTCTTCTATCCG TGTATTAATTTTGGGTTAAGTTCCTCGTTTGCATAGCA GTGGATACCTCGATTTTTTTGGCTCCTATTTACCTGAC ATAATATTCTACTATAATCCAACTTGGACGCGTCATCT ATGATAACTAGGCTCTCCTTTGTTCAAAGGGGACGTCT TCATAATCCACTGGCACGAAGTAAGTCTGCAACGAGG CGGCTTTTGCAACAGAACGATAGTGTCGTTTCGTACTT GGACTATGCTAAACAAAAGGATCTGTCAAACATTTCA ACCGTGTTTCAAGGCACTCTTTACGAATTATCGACCAA GACCTTCCTAGACGAACATTTCAACATATCCAGGCTA CTGCTTCAAGGTGGTGCAAATGATAAAGGTATAGATA TTAGATGTGTTTGGGACCTAAAACAGTTCTTGCCTGAA GATTCCCTTGAGCAACAGGCTTCAATAGCCAAGTTAG AGAAGCAGTACCAAATCGGTAACAAAAGGGGAAGC ATATAAAACCTTTACTATTGCGACAAAATCCATCCTTG AAAGTAAAGCTGTTTGTTCAATGTAAAGCATACGAAA CGAAGGAGGTAGATCCTAAGATGGTTAGAGAACTTAA CGGGACATACTCCAGCTGCATCCCATATTACGATCGCT GGAAGACTTTTTTCATGTACGTATCGCCCACCAACCTT TCAAAGCAAGCTAGGTATGATTTTGACAGTTCTCACA ATCCATTGGTTTTCATGCAACTTGAAAAAACCCAACTC AAACTTCATGGGGATCCATACAATGTAAATCATTACG AGAGGGCGAGGTTGAAAAGTTTCCATTGCAATCACGT CGCATCATGGCTACTGAAAGGCCTTAAC |
| 51 | Sequence of the 5'-Region used for knock out of PpPNO1 and PpMNN4: | TCATTCTATATGTTCAAGAAAAGGGTAGTGAAAGGAA AGAAAAGGCATATAGGCGAGGGAGAGTTAGCTAGCA TACAAGATAATGAAGGATCAATAGCGGTAGTTAAAGT GCACAAGAAAAGAGCACCTGTTGAGGCTGATGATAAA GCTCCAATTACATTGCCACAGAGAAACACAGTAACAG AAATAGGAGGGGATGCACCACGAGAAGAGCATTCAG TGAACAACTTTGCCAAATTCATAACCCCAAGCGCTAA TAAGCCAATGTCAAAGTCGGCTACTAACATTAATAGT ACAACAACTATCGATTTTCAACCAGATGTTTGCAAGG ACTACAAACAGACAGGTTACTGCGGATATGGTGACAC TTGTAAGTTTTTGCACCTGAGGGATGATTTCAAACAGG GATGGAAATTAGATAGGGAGTGGGAAAATGTCCAAA AGAAGAAGCATAATACTCTCAAAGGGGTTAAGGAGAT CCAAATGTTTAATGAAGATGAGCTCAAAGATATCCCG TTTAAATGCATTATATGCAAAGGAGATTACAAATCAC CCGTGAAAACTTCTTGCAATCATTATTTTTGCGAACAA TGTTTCCTGCAACGGTCAAGAAGAAAACCAAATTGTA TTATATGTGGCAGAGACACTTTAGGAGTTGCTTTACCA GCAAAGAAGTTGTCCCAATTTCTGGCTAAGATACATA ATAATGAAAGTAATAAAGTTTAGTAATTGCATTGCGTT GACTATTGATTGCATTGATGTCGTGTGATACTTTCACC GAAAAAAAACACGAAGCGCAATAGGAGCGGTTGCAT ATTAGTCCCCAAAGCTATTTAATTGTGCCTGAAACTGT TTTTTAAGCTCATCAAGCATAATTGTATGCATTGCGAC GTAACCAACGTTTAGGCGCAGTTTAATCATAGCCCAC TGCTAAGCC |

TABLE 12-continued

BRIEF DESCRIPTION OF THE SEQUENCES

| SEQ ID NO: | Description | Sequence |
|---|---|---|
| 52 | Sequence of the 3'-Region used for knock out of PpPNO1 and PpMNN4: | CGGAGGAATGCAAATAATAATCTCCTTAATTACCCAC TGATAAGCTCAAGAGACGCGGTTTGAAAACGATATAA TGAATCATTTGGATTTTATAATAAACCCTGACAGTTTT TCCACTGTATTGTTTTAACACTCATTGGAAGCTGTATT GATTCTAAGAAGCTAGAAATCAATACGGCCATACAAA AGATGACATTGAATAAGCACCGGCTTTTTTGATTAGC ATATACCTTAAAGCATGCATTCATGGCTACATAGTTGT TAAAGGGCTTCTTCCATTATCAGTATAATGAATTACAT AATCATGCACTTATATTTGCCCATCTCTGTTCTCTCACT CTTGCCTGGGTATATTCTATGAAATTGCGTATAGCGTG TCTCCAGTTGAACCCCAAGCTTGGCGAGTTTGAAGAG AATGCTAACCTTGCGTATTCCTTGCTTCAGGAAACATT CAAGGAGAAACAGGTCAAGAAGCCAAACATTTTGATC CTTCCCGAGTTAGCATTGACTGGCTACAATTTTCAAAG CCAGCAGCGGATAGAGCCTTTTTTGGAGGAAACAACC AAGGGAGCTAGTACCCAATGGGCTCAAAAAGTATCCA AGACGTGGGATTGCTTTACTTTAATAGGATACCCAGA AAAAAGTTTAGAGAGCCCTCCCCGTATTTACAACAGT GCGGTACTTGTATCGCCTCAGGGAAAAGTAATGAACA ACTACAGAAAGTCCTTCTTGTATGAAGCTGATGAACA TTGGGGATGTTCGGAATCTTCTGATGGGTTTCAAACAG TAGATTTATTAATTGAAGGAAAGACTGTAAAGACATC ATTTGGAATTTGCATGGATTTGAATCCTTATAAATTTG AAGCTCCATTCACAGACTTCGAGTTCAGTGGCCATTGC TTGAAAACCGGTACAAGACTCATTTTGTGCCCAATGG CCTGGTTGTCCCCTCTATCGCCTTCCATTAAAAAGGAT CTTAGTGATATAGAGAAAAGCAGACTTCAAAAGTTCT ACCTTGAAAAAATAGATACCCCGGAATTTGACGTTAA TTACGAATTGAAAAAAGATGAAGTATTGCCCACCCGT ATGAATGAAACGTTGGAAACAATTGACTTTGAGCCTT CAAAACCGGACTACTCTAATATAAATTATTGGATACT AAGGTTTTTTCCCTTTCTGACTCATGTCTATAAACGAG ATGTGCTCAAAGAGAATGCAGTTGCAGTCTTATGCAA CCGAGTTGGCATTGAGAGTGATGTCTTGTACGGAGGA TCAACCACGATTCTAAACTTCAATGGTAAGTTAGCATC GACACAAGAGGAGCTGGAGTTGTACGGGCAGACTAAT AGTCTCAACCCCAGTGTGGAAGTATTGGGGGCCCTTG GCATGGGTCAACAGGGAATTCTAGTACGAGACATTGA ATTAACATAATATACAATATACAATAAACACAAATAA AGAATACAAGCCTGACAAAAATTCACAAATTATTGCC TAGACTTGTCGTTATCAGCAGCGACCTTTTTCCAATGC TCAATTTCACGATATGCCTTTTCTAGCTCTGCTTTAAG CTTCTCATTGGAATTGGCTAACTCGTTGACTGCTTGGT CAGTGATGAGTTTCTCCAAGGTCCATTTCTCGATGTTG TTGTTTTCGTTTTCCTTTAATCTCTTGATATAATCAACA GCCTTCTTTAATATCTGAGCCTTGTTCGAGTCCCCTGT TGGCAACAGAGCGGCCAGTTCCTTTATTCCGTGGTTTA TATTTTCTCTTCTACGCCTTTCTACTTCTTTGTGATTCT CTTTACGCATCTTATGCCATTCTTCAGAACCAGTGGCT GGCTTAACCGAATAGCCAGAGCCTGAAGAAGCCGCAC TAGAAGAAGCAGTGGCATTGTTGACTATGG |
| 53 | DNA encodes human GnTI catalytic domain (NA) Codon-optimized | TCAGTCAGTGCTCTTGATGGTGACCCAGCAAGTTTGAC CAGAGAAGTGATTAGATTGGCCCAAGACGCAGAGGTG GAGTTGGAGAGACAACGTGGACTGCTGCAGCAAATCG GAGATGCATTGTCTAGTCAAAGAGGTAGGGTGCCTAC CGCAGCTCCTCCAGCACAGCCTAGAGTGCATGTGACC CCTGCACCAGCTGTGATTCCTATCTTGGTCATCGCCTG TGACAGATCTACTGTTAGAAGATGTCTGGACAAGCTG TTGCATTACAGACCATCTGCTGAGTTGTTCCCTATCAT CGTTAGTCAAGACTGTGGTCACGAGGAGACTGCCCAA GCCATCGCCTCCTACGGATCTGCTGTCACTCACATCAG ACAGCCTGACCTGTCATCTATTGCTGTGCCACCAGACC ACAGAAAGTTCCAAGGTTACTACAAGATCGCTAGACA CTACAGATGGGCATTGGGTCAAGTCTTCAGACAGTTT AGATTCCCTGCTGCTGTGGTGGTGGAGGATGACTTGG AGGTGGCTCCTGACTTCTTTGAGTACTTTAGAGCAACC TATCCATTGCTGAAGGCAGACCCATCCCTGTGGTGTGT CTCTGCCTGGAATGACAACGGTAAGGAGCAAATGGTG GACGCTTCTAGGCCTGAGCTGTTGTACAGAACCGACT TCTTTCCTGGTCTGGGATGGTTGCTGTTGGCTGAGTTG TGGGCTGAGTTGGAGCCTAAGTGGCCAAAGGCATTCT GGGACGACTGGATGAGAAGACCTGAGCAAAGACAGG GTAGAGCCTGTATCAGACCTGAGATCTCAAGAACCAT |

TABLE 12-continued

BRIEF DESCRIPTION OF THE SEQUENCES

| SEQ ID NO: | Description | Sequence |
|---|---|---|
| | | GACCTTTGGTAGAAAGGGAGTGTCTCACGGTCAATTC<br>TTTGACCAACACTTGAAGTTTATCAAGCTGAACCAGC<br>AATTTGTGCACTTCACCCAACTGGACCTGTCTTACTTG<br>CAGAGAGAGGCCTATGACAGAGATTTCCTAGCTAGAG<br>TCTACGGAGCTCCTCAACTGCAAGTGGAGAAAGTGAG<br>GACCAATGACAGAAAGGAGTTGGGAGAGGTGAGAGT<br>GCAGTACACTGGTAGGGACTCCTTTAAGGCTTTCGCTA<br>AGGCTCTGGGTGTCATGGATGACCTTAAGTCTGGAGT<br>TCCTAGAGCTGGTTACAGAGGTATTGTCACCTTTCAAT<br>TCAGAGGTAGAAGAGTCCACTTGGCTCCTCCACCTAC<br>TTGGGAGGGTTATGATCCTTCTTGGAATTAG |
| 54 | DNA encodes Pp SEC12 (10) The last 9 nucleotides are the linker containing the AscI restriction site used for fusion to proteins of interest. | ATGCCCAGAAAATATTTAACTACTTCATTTTGACTGT<br>ATTCATGGCAATTCTTGCTATTGTTTTACAATGGTCTA<br>TAGAGAATGGACATGGGCGCGCC |
| 55 | Sequence of the PpSEC4 promoter: | GAAGTAAAGTTGGCGAAACTTTGGGAACCTTTGGTTA<br>AAACTTTGTAATTTTTGTCGCTACCCATTAGGCAGAAT<br>CTGCATCTTGGGAGGGGGATGTGGTGGCGTTCTGAGA<br>TGTACGCGAAGAATGAAGAGCCAGTGGTAACAACAG<br>GCCTAGAGAGATACGGGCATAATGGGTATAACCTACA<br>AGTTAAGAATGTAGCAGCCCTGGAAACCAGATTGAAA<br>CGAAAAACGAAATCATTTAAACTGTAGGATGTTTTGG<br>CTCATTGTCTGGAAGGCTGGCTGTTTATTGCCCTGTTC<br>TTTGCATGGGAATAAGCTATTATATCCCTCACATAATC<br>CCAGAAAATAGATTGAAGCAACGCGAAATCCTTACGT<br>ATCGAAGTAGCCTTCTTACACATTCACGTTGTACGGAT<br>AAGAAAACTACTCAAACGAACAATC |
| 56 | Sequence of the PpOCH1 terminator: | AATAGATATAGCGAGATTAGAGAATGAATACCTTCTT<br>CTAAGCGATCGTCCGTCATCATAGAATATCATGGACT<br>GTATAGTTTTTTTTTTGTACATATAATGATTAAACGGT<br>CATCCAACATCTCGTTGACAGATCTCTCAGTACGCGA<br>AATCCCTGACTATCAAAGCAAGAACCGATGAAGAAAA<br>AAACAACAGTAACCCAAACACCACAACAAACACTTTA<br>TCTTCTCCCCCCCAACACCAATCATCAAAGAGATGTC<br>GGAACACAAACACCAAGAAGCAAAAACTAACCCCAT<br>ATAAAAACATCCTGGTAGATAATGCTGGTAACCCGCT<br>CTCCTTCCATATTCTGGGCTACTTCACGAAGTCTGACC<br>GGTCTCAGTTGATCAACATGATCCTCGAAATGG |
| 57 | DNA encodes Mm ManI catalytic domain (FB) | GAGCCCGCTGACGCCACCATCCGTGAGAAGAGGGCAA<br>AGATCAAAGAGATGATGACCCATGCTTGGAATAATTA<br>TAAACGCTATGCGTGGGGCTTGAACGAACTGAAACCT<br>ATATCAAAAGAAGGCCATTCAAGCAGTTTGTTTGGCA<br>ACATCAAAGGAGCTACAATAGTAGATGCCCTGGATAC<br>CCTTTTCATTATGGGCATGAAGACTGAATTTCAAGAA<br>GCTAAATCGTGGATTAAAAAATATTTAGATTTTAATGT<br>GAATGCTGAAGTTTCTGTTTTTGAAGTCAACATACGCT<br>TCGTCGGTGGACTGCTGTCAGCCTACTATTTGTCCGGA<br>GAGGAGATATTTCGAAAGAAAGCAGTGGAACTTGGGG<br>TAAAATTGCTACCTGCATTTCATACTCCCTCTGGAATA<br>CCTTGGGCATTGCTGAATATGAAAAGTGGGATCGGGC<br>GGAACTGGCCCTGGGCCTCTGGAGGCAGCAGTATCCT<br>GGCCGAATTTGGAACTCTGCATTTAGAGTTTATGCACT<br>TGTCCCACTTATCAGGAGACCCAGTCTTTGCCGAAAA<br>GGTTATGAAAATTCGAACAGTGTTGAACAAACTGGAC<br>AAACCAGAAGGCCTTTATCCTAACTATCTGAACCCCA<br>GTAGTGGACAGTGGGTCAACATCATGTGTCGGTTGG<br>AGGACTTGGAGACAGCTTTTATGAATATTTGCTTAAG<br>GCGTGGTTAATGTCTGACAAGACAGATCTCGAAGCCA<br>AGAAGATGTATTTTGATGCTGTTCAGGCCATCGAGAC<br>TCACTTGATCCGCAAGTCAAGTGGGGACTAACGTAC<br>ATCGCAGAGTGGAAGGGGGGCCTCCTGGAACACAAG<br>ATGGGCCACCTGACGTGCTTTGCAGGAGGCATGTTTG<br>CACTTGGGGCAGATGGAGCTCCGGAAGCCCGGGCCCA |

TABLE 12-continued

BRIEF DESCRIPTION OF THE SEQUENCES

| SEQ ID NO: | Description | Sequence |
|---|---|---|
| | | ACACTACCTTGAACTCGGAGCTGAAATTGCCCGCACT<br>TGTCATGAATCTTATAATCGTACATATGTGAAGTTGGG<br>ACCGGAAGCGTTTCGATTTGATGGCGGTGTGGAAGCT<br>ATTGCCACGAGGCAAAATGAAAAGTATTACATCTTAC<br>GGCCCGAGGTCATCGAGACATACATGTACATGTGGCG<br>ACTGACTCACGACCCCAAGTACAGGACCTGGGCCTGG<br>GAAGCCGTGGAGGCTCTAGAAAGTCACTGCAGAGTGA<br>ACGGAGGCTACTCAGGCTTACGGGATGTTTACATTGC<br>CCGTGAGAGTTATGACGATGTCCAGCAAAGTTTCTTCC<br>TGGCAGAGACACTGAAGTATTTGTACTTGATATTTTCC<br>GATGATGACCTTCTTCCACTAGAACACTGGATCTTCAA<br>CACCGAGGCTCATCCTTTCCCTATACTCCGTGAACAGA<br>AGAAGGAAATTGATGGCAAAGAGAAATGA |
| 58 | DNA encodes ScSEC12 (8) The last 9 nucleotides are the linker containing the AscI restriction site used for fusion to proteins of interest | ATGAACACTATCCACATAATAAAATTACCGCTTAACT<br>ACGCCAACTACACCTCAATGAAACAAAAAATCTCTAA<br>ATTTTTCACCAACTTCATCCTTATTGTGCTGCTTTCTTA<br>CATTTTACAGTTCTCCTATAAGCACAATTTGCATTCCA<br>TGCTTTTCAATTACGCGAAGGACAATTTTCTAACGAAA<br>AGAGACACCATCTCTTCGCCCTACGTAGTTGATGAAG<br>ACTTACATCAAACAACTTTGTTTGGCAACCACGGTAC<br>AAAAACATCTGTACCTAGCGTAGATTCCATAAAAGTG<br>CATGGCGTGGGGCGCGCC |
| 59 | Sequence of the 5'-region that was used to knock into the PpADE1 locus: | GAGTCGGCCAAGAGATGATAACTGTTACTAAGCTTCT<br>CCGTAATTAGTGGTATTTTGTAACTTTTACCAATAATC<br>GTTTATGAATACGGATATTTTTCGACCTTATCCAGTGC<br>CAAATCACGTAACTTAATCATGGTTTAAATACTCCACT<br>TGAACGATTCATTATTCAGAAAAAAGTCAGGTTGGCA<br>GAAACACTTGGGCGCTTTGAAGAGTATAAGAGTATTA<br>AGCATTAAACATCTGAACTTTCACCGCCCCAATATACT<br>ACTCTAGGAAACTCGAAAAATTCCTTTCCATGTGTCAT<br>CGCTTCCAACACACTTTGCTGTATCCTTCCAAGTATGT<br>CCATTGTGAACACTGATCTGGACGGAATCCTACCTTTA<br>ATCGCCAAAGGAAAGGTTAGAGACATTTATGCAGTCG<br>ATGAGAACAACTTGCTGTTCGTCGCAACTGACCGTAT<br>CTCCGCTTACGATGTGATTATGACAAACGGTATTCCTG<br>ATAAGGGAAAGATTTTGACTCAGCTCTCAGTTTTCTGG<br>TTTGATTTTTTGGCACCCTACATAAAGAATCATTTGGT<br>TGCTTCTAATGACAAGGAAGTCTTTGCTTTACTACCAT<br>CAAAACTGTCTGAAGAAAAaTACAAATCTCAATTAGA<br>GGGACGATCCTTGATAGTAAAAAAGCACAGACTGATA<br>CCTTTGGAAGCCATTGTCAGAGGTTACATCACTGGAA<br>GTGCATGGAAAGAGTACAAGAACTCAAAAACTGTCCA<br>TGGAGTCAAGGTTGAAAACGAGAACCTTCAAGAGAGC<br>GACGCCTTTCCAACTCCGATTTTCACACCTTCAACGAA<br>AGCTGAACAGGGTGAACACGATGAAAACATCTCTATT<br>GAACAAGCTGCTGAGATTGTAGGTAAAGACATTTGTG<br>AGAAGGTCGCTGTCAAGGCGGTCGAGTTGTATTCTGC<br>TGCAAAAAACCTCGCCCTTTTGAAGGGGATCATTATT<br>GCTGATACGAAATTCGAATTTGGACTGGACGAAAACA<br>ATGAATTGGTACTAGTAGATGAAGTTTTAACTCCAGA<br>TTCTTCTAGATTTTGGAATCAAAAGACTTACCAAGTGG<br>GTAAATCGCAAGAGAGTTACGATAAGCAGTTTCTCAG<br>AGATTGGTTGACGGCCAACGGATTGAATGGCAAAGAG<br>GGCGTAGCCATGGATGCAGAAATTGCTATCAAGAGTA<br>AAGAAAAGTATATTGAAGCTTATGAAGCAATTACTGG<br>CAAGAAATGGGCTTGA |
| 60 | Sequence of the 3'-region that was used to knock into the PpADE1 locus: | ATGATTAGTACCCTCCTCGCCTTTTTCAGACATCTGAA<br>ATTTCCCTTATTCTTCCAATTCCATATAAAATCCTATTT<br>AGGTAATTAGTAAACAATGATCATAAAGTGAAATCAT<br>TCAAGTAACCATTCCGTTTATCGTTGATTTAAAATCAA<br>TAACGAATGAATGTCGGTCTGAGTAGTCAATTTGTTGC<br>CTTGGAGCTCATTGGCAGGGGGTCTTTTGGCTCAGTAT<br>GGAAGGTTGAAAGGAAAACAGATGGAAAGTGGTTCG<br>TCAGAAAAGAGGTATCCTACATGAAGATGAATGCCAA<br>AGAGATATCTCAAGTGATAGCTGAGTTCAGAATTCTT<br>AGTGAGTTAAGCCATCCCAACATTGTGAAGTACCTTC<br>ATCACGAACATATTTCTGAGAATAAAACTGTCAATTT<br>ATACATGGAATACTGTGATGGTGGAGATCTCTCCAAG<br>CTGATTCGAACACATAGAAGGAACAAAGAGTACATTT |

TABLE 12-continued

BRIEF DESCRIPTION OF THE SEQUENCES

| SEQ ID NO: Description | Sequence |
|---|---|
| | CAGAAGAAAAAATATGGAGTATTTTTACGCAGGTTTT<br>ATTAGCATTGTATCGTTGTCATTATGGAACTGATTTCA<br>CGGCTTCAAAGGAGTTTGAATCGCTCAATAAAGGTAA<br>TAGACGAACCCAGAATCCTTCGTGGGTAGACTCGACA<br>AGAGTTATTATTCACAGGGATATAAAACCCGACAACA<br>TCTTTCTGATGAACAATTCAAACCTTGTCAAACTGGGA<br>GATTTTGGATTAGCAAAAATTCTGGACCAAGAAAACG<br>ATTTTGCCAAAACATACGTCGGTACGCCGTATTACATG<br>TCTCCTGAAGTGCTGTTGGACCAACCCTACTCACCATT<br>ATGTGATATATGGTCTCTTGGGTGCGTCATGTATGAGC<br>TATGTGCATTGAGGCCTCCTT |
| 61 DNA encodes ScGAL10 | ATGACAGCTCAGTTACAAAGTGAAAGTACTTCTAAAA<br>TTGTTTTGGTTACAGGTGGTGCTGGATACATTGGTTCA<br>CACACTGTGGTAGAGCTAATTGAGAATGGATATGACT<br>GTGTTGTTGCTGATAACCTGTCGAATTCAACTTATGAT<br>TCTGTAGCCAGGTTAGAGGTCTTGACCAAGCATCACA<br>TTCCCTTCTATGAGGTTGATTTGTGTGACCGAAAAGGT<br>CTGGAAAAGGTTTTCAAAGAATATAAAATTGATTCGG<br>TAATTCACTTTGCTGGTTTAAAGGCTGTAGGTGAATCT<br>ACACAAATCCCGCTGAGATACTATCACAATAACATTT<br>TGGGAACTGTCGTTTTATTAGAGTTAATGCAACAATAC<br>AACGTTTCCAAATTTGTTTTTTCATCTTCTGCTACTGTC<br>TATGGTGATGCTACGAGATTCCCAAATATGATTCCTAT<br>CCCAGAAGAATGTCCCTTAGGGCCTACTAATCCGTAT<br>GGTCATACGAAATACGCCATTGAGAATATCTTGAATG<br>ATCTTTACAATAGCGACAAAAAAAGTTGGAAGTTTGC<br>TATCTTGCGTTATTTTAACCCAATTGGCGCACATCCCT<br>CTGGATTAATCGGAGAAGATCCGCTAGGTATACCAAA<br>CAATTTGTTGCCATATATGGCTCAAGTAGCTGTTGGTA<br>GGCGCGAGAAGCTTTACATCTTCGGAGACGATTATGA<br>TTCCAGAGATGGTACCCCGATCAGGGATTATATCCAC<br>GTAGTTGATCTAGCAAAAGGTCATATTGCAGCCCTGC<br>AATACCTAGAGGCCTACAATGAAAATGAAGGTTTGTG<br>TCGTGAGTGGAACTTGGGTTCCGGTAAAGGTTCTACA<br>GTTTTTGAAGTTTATCATGCATTCTGCAAAGCTTCTGG<br>TATTGATCTTCCATACAAAGTTACGGGCAGAAGAGCA<br>GGTGATGTTTTGAACTTGACGGCTAAACCAGATAGGG<br>CCAAACGCGAACTGAAATGGCAGACCGAGTTGCAGGT<br>TGAAGACTCCTGCAAGGATTATGGAAATGGACTACT<br>GAGAATCCTTTTGGTTACCAGTTAAGGGGTGTCGAGG<br>CCAGATTTTCCGCTGAAGATATGCGTTATGACGCAAG<br>ATTTGTGACTATTGGTGCCGGCACCAGATTTCAAGCCA<br>CGTTTGCCAATTTGGGCGCCAGCATTGTTGACCTGAAA<br>GTGAACGGACAATCAGTTGTTCTTGGCTATGAAAATG<br>AGGAAGGGTATTTGAATCCTGATAGTGCTTATATAGG<br>CGCCACGATCGGCAGGTATGCTAATCGTATTTCGAAG<br>GGTAAGTTTAGTTTATGCAACAAAGACTATCAGTTAA<br>CCGTTAATAACGGCGTTAATGCGAATCATAGTAGTAT<br>CGGTTCTTTCCACAGAAAAAGATTTTTGGGACCCATCA<br>TTCAAAATCCTTCAAAGGATGTTTTTACCGCCGAGTAC<br>ATGCTGATAGATAATGAGAAGGACACCGAATTTCCAG<br>GTGATCTATTGGTAACCATACAGTATACTGTGAACGTT<br>GCCCAAAAAAGTTTGGAAATGGTATATAAAGGTAAAT<br>TGACTGCTGGTGAAGCGACGCCAATAAATTTAACAAA<br>TCATAGTTATTTCAATCTGAACAAGCCATATGGAGAC<br>ACTATTGAGGGTACGGAGATTATGGTGCGTTCAAAAA<br>AATCTGTTGATGTCGACAAAAACATGATTCCTACGGG<br>TAATATCGTCGATAGAGAAATTGCTACCTTTAACTCTA<br>CAAAGCCAACGGTCTTAGGCCCAAAAATCCCCAGTT<br>TGATTGTTGTTTTGTGGTGGATGAAAATGCTAAGCCAA<br>GTCAAATCAATACTCTAAACAATGAATTGACGCTTATT<br>GTCAAGGCTTTTCATCCCGATTCCAATATTACATTAGA<br>AGTTTTAAGTACAGAGCCAACTTATCAATTTTATACCG<br>GTGATTTCTTGTCTGCTGGTTACGAAGCAAGACAAGG<br>TTTTGCAATTGAGCCTGGTAGATACATTGATGCTATCA<br>ATCAAGAGAACTGGAAAGATTGTGTAACCTTGAAAAA<br>CGGTGAAACTTACGGGTCCAAGATTGTCTACAGATTTT<br>CCTGA |

TABLE 12-continued

BRIEF DESCRIPTION OF THE SEQUENCES

| SEQ ID NO: | Description | Sequence |
|---|---|---|
| 62 | Sequence of the PpPMA1 terminator: | TAAGCTTCACGATTTGTGTTCCAGTTTATCCCCCCTTT ATATACCGTTAACCCTTTCCCTGTTGAGCTGACTGTTG TTGTATTACCGCAATTTTTCCAAGTTTGCCATGCTTTTC GTGTTATTTGACCGATGTCTTTTTTCCCAAATCAAACT ATATTTGTTACCATTTAAACCAAGTTATCTTTTGTATT AAGAGTCTAAGTTTGTTCCCAGGCTTCATGTGAGAGT GATAACCATCCAGACTATGATTCTTGTTTTTTATTGGG TTTGTTTGTGTGATACATCTGAGTTGTGATTCGTAAAG TATGTCAGTCTATCTAGATTTTTAATAGTTAATTGGTA ATCAATGACTTGTTTGTTTTAACTTTTAAATTGTGGGT CGTATCCACGCGTTTAGTATAGCTGTTCATGGCTGTTA GAGGAGGGCGATGTTTATATACAGAGGACAAGAATGA GGAGGCGGCGTGTATTTTTAAAATGGAGACGCGACTC CTGTACACCTTATCGGTTGG |
| 63 | hGalT codon optimized (XB) | GGTAGAGATTTGTCTAGATTGCCACAGTTGGTTGGTGT TTCCACTCCATTGCAAGGAGGTTCTAACTCTGCTGCTG CTATTGGTCAATCTTCCGGTGAGTTGAGAACTGGTGG AGCTAGACCACCTCCACCATTGGGAGCTTCCTCTCAA CCAAGACCAGGTGGTGATTCTTCTCCAGTTGTTGACTC TGGTCCAGGTCCAGCTTCTAACTTGACTTCCGTTCCAG TTCCACACACTACTGCTTTGTCCTTGCCAGCTTGTCCA GAAGAATCCCCATTGTTGGTTGGTCCAATGTTGATCGA GTTCAACATGCCAGTTGACTTGGGAGTTGGTTGCTAAGC AGAACCCAAACGTTAAGATGGGTGGTAGATACGCTCC AAGAGACTGTGTTTCCCCACACAAAGTTGCTATCATC ATCCCATTCAGAAACAGACAGGAGCACTTGAAGTACT GGTTGTACTACTTGCACCCAGTTTTGCAAAGACAGCA GTTGGACTACGGTATCTACGTTATCAACCAGGCTGGT GACACTATTTTCAACAGAGCTAAGTTGTTGAATGTTGG TTTCCAGGAGGCTTTGAAGGATTACGACTACACTTGTT TCGTTTTCTCCGACGTTGACTTGATTCCAATGAACGAC CACAACGCTTACAGATGTTTCTCCCAGCCAAGACACA TTTCTGTTGCTATGGACAAGTTCGGTTTCTCCTTGCCA TACGTTCAATACTTCGGTGGTGTTTCCGCTTTGTCCAA GCAGCAGTTCTTGACTATCAACGGTTTCCCAAACAATT ACTGGGGATGGGGTGGTGAAGATGACGACATCTTTAA CAGATTGGTTTTCAGAGGAATGTCCATCTCTAGACCA AACGCTGTTGTTGGTAGATGTAGAATGATCAGACACT CCAGAGACAAGAAGAACGAGCCAAACCCACAAAGAT TCGACAGAATCGCTCACACTAAGGAAACTATGTTGTC CGACGGATTGAACTCCTTGACTTACCAGGTTTTGGACG TTCAGAGATACCCATTGTACACTCAGATCACTGTTGAC ATCGGTACTCCATCCTAG |
| 64 | DNA encodes ScMnt1 (Kre2) (33) | ATGGCCCTCTTTCTCAGTAAGAGACTGTTGAGATTTAC CGTCATTGCAGGTGCGGTTATTGTTCTCCTCCTAACAT TGAATTCCAACAGTAGAACTCAGCAATATATTCCGAG TTCCATCTCCGCTGCATTTGATTTTACCTCAGGATCTA TATCCCCTGAACAACAAGTCATCGGGCGCGCC |
| 65 | DNA encodes DmUGT | ATGAATAGCATACACATGAACGCCAATACGCTGAAGT ACATCAGCCTGCTGACGCTGACCCTGCAGAATGCCAT CCTGGGCCTCAGCATGCGCTACGCCCGCACCCGGCCA GGCGACATCTTCCTCAGCTCCACGGCCGTACTCATGG CAGAGTTCGCCAAACTGATCACGTGCCTGTTCCTGGTC TTCAACGAGGAGGGCAAGGATGCCCAGAAGTTTGTAC GCTCGCTGCACAAGACCATCATTGCGAATCCCATGGA CACGCTGAAGGTGTGCGTCCCCTCGCTGGTCTATATCG TTCAAAACAATCTGCTGTACGTCTCTGCCTCCCATTTG GATGCGGCCACCTACCAGGTGACGTACCAGCTGAAGA TTCTCACCACGGCCATGTTCGCGGTTGTCATTCTGCGC CGCAAGCTGCTGAACACGCAGTGGGTGCGCTGCTGC TCCTGGTGATGGGCATCGTCCTGGTGCAGTTGGCCCA AACGGAGGGTCCGACGAGTGGCTCAGCCGGTGGTGCC GCAGCTGCAGCCACGGCCGCCTCCTCTGGCGGTGCTC CCGAGCAGAACAGGATGCTCGGACTGTGGGCCGCACT GGGCGCCTGCTTCCTCTCCGGATTCGCGGGCATCTACT TGAGAAGATCCTCAAGGGTGCCGAGATCTCCGTGTG GATGCGGAATGTGCAGTTGAGTCTGCTCAGCATTCCCT TCGGCCTGCTCACCTGTTTCGTTAACGACGGCAGTAGG ATCTTCGACCAGGGATTCTTCAAGGGCTACGATCTGTT TGTCTGGTACCTGGTCCTGCTGCAGGCCGGCGGTGGA TTGATCGTTGCCGTGGTGGTCAAGTACGCGGATAACA |

TABLE 12-continued

BRIEF DESCRIPTION OF THE SEQUENCES

| SEQ ID NO: | Description | Sequence |
|---|---|---|
| | | TTCTCAAGGGCTTCGCCACCTCGCTGGCCATCATCATC TCGTGCGTGGCCTCCATATACATCTTCGACTTCAATCT CACGCTGCAGTTCAGCTTCGGAGCTGGCCTGGTCATC GCCTCCATATTTCTCTACGGCTACGATCCGGCCAGGTC GGCGCCGAAGCCAACTATGCATGGTCCTGGCGGCGAT GAGGAGAAGCTGCTGCCGCGCGTCTAG |
| 66 | Sequence of the PpOCH1 promoter: | TGGACACAGGAGACTCAGAAACAGACACAGAGCGTT CTGAGTCCTGGTGCTCCTGACGTAGGCCTAGAACAGG AATTATTGGCTTTATTTGTTTGTCCATTTCATAGGCTTG GGGTAATAGATAGATGACAGAGAAATAGAGAAGACC TAATATTTTTTGTTCATGGCAAATCGCGGGTTCGCGGT CGGGTCACACACGGAGAAGTAATGAGAAGAGCTGGT AATCTGGGGTAAAAGGGTTCAAAAGAAGGTCGCCTGG TAGGGATGCAATACAAGGTTGTCTTGGAGTTTACATT GACCAGATGATTTGGCTTTTTCTCTGTTCAATTCACAT TTTTCAGCGAGAATCGGATTGACGGAGAAATGGCGGG GTGTGGGGTGGATAGATGGCAGAAATGCTCGCAATCA CCGCGAAAGAAAGACTTTATGGAATAGAACTACTGGG TGGTGTAAGGATTACATAGCTAGTCCAATGGAGTCCG TTGGAAAGGTAAGAAGAAGCTAAAACCGGCTAAGTA ACTAGGGAAGAATGATCAGACTTTGATTTGATGAGGT CTGAAAATACTCTGCTGCTTTTTCAGTTGCTTTTTCCCT GCAACCTATCATTTTCCTTTTCATAAGCCTGCCTTTTCT GTTTTCACTTATATGAGTTCCGCCGAGACTTCCCCAAA TTCTCTCCTGGAACATTCTCTATCGCTCTCCTTCCAAG TTGCGCCCCTGGCACTGCCTAGTAATATTACCACGCG ACTTATATTCAGTTCCACAATTTCCAGTGTTCGTAGCA AATATCATCAGCC |
| 67 | Sequence of the PpALG12 terminator: | AATATATACCTCATTTGTTCAATTTGGTGTAAAGAGTG TGGCGGATAGACTTCTTGTAAATCAGGAAAGCTACAA TTCCAATTGCTGCAAAAAATACCAATGCCCATAAACC AGTATGAGCGGTGCCTTCGACGGATTGCTTACTTTCCG ACCCTTTGTCGTTTGATTCTTCTGCCTTTGGTGAGTCA GTTTGTTTCGACTTTATATCTGACTCATCAACTTCCTTT ACGGTTGCGTTTTTAATCATAATTTTAGCCGTTGGCTT ATTATCCCTTGAGTTGGTAGGAGTTTTGATGATGCTG |
| 68 | Sequence of the 5'-Region used for knock out of PpHIS1: | TAACTGGCCCTTTGACGTTTCTGACAATAGTTCTAGAG GAGTCGTCCAAAAACTCAACTCTGACTTGGGTGACAC CACCACGGGATCCGGTTCTTCCGAGGACCTTGATGAC CTTGGCTAATGTAACTGGAGTTTTAGTATCCATTTTAA GATGTGTGTTTCTGTAGGTTCTGGGTTGGAAAAAAATT TTAGACACCAGAAGAGAGGAGTGAACTGGTTTGCGTG GGTTTAGACTGTGTAAGGCACTACTCTGTCGAAGTTTT AGATAGGGGTTACCCGCTCCGATGCATGGGAAGCGAT TAGCCCGGCTGTTGCCCGTTTGGTTTTTGAAGGGTAAT TTTCAATATCTCTGTTTGAGTCATCAATTTCATATTCA AAGATTCAAAACAAATCTGGTCCAAGGAGCGCATT TAGGATTATGGAGTTGGCGAATCACTTGAACGATAGA CTATTATTTGC |
| 69 | Sequence of the 3'-Region used for knock out of PpHIS1: | GTGACATTCTTGTCTTTGAGATCAGTAATTGTAGAGCA TAGATAGAATAATATTCAAGACCAACGGCTTCTCTTC GGAAGCTCCAAGTAGCTTATAGTGATGAGTACCGGCA TATATTTATAGGCTTAAAATTTCGAGGGTTCACTATAT TCGTTTAGTGGGAAGAGTTCCTTTCACTCTTGTTATCT ATATTGTCAGCGTGGACTGTTTATAACTGTACCAACTT AGTTTCTTTCAACTCCAGGTTAAGAGACATAAATGTCC TTTGATGCTGACAATAATCAGTGGAATTCAAGGAAGG ACAATCCCGACCTCAATCTGTTCATTAATGAAGAGTTC GAATCGTCCTTAAATCAAGCGCTAGACTCAATTGTCA ATGAGAACCCTTTCTTTGACCAAGAAACTATAAATAG ATCGAATGACAAAGTTGGAAATGAGTCCATTAGCTTA CATGATATTGAGCAGGCAGACCAAAATAAACCGTCCT TTGAGAGCGATATTGATGGTTCGGCGCCGTTGATAAG AGACGACAAATTGCCAAAGAAACAAAGCTGGGGGCT GAGCAATTTTTTTTCAAGAAGAAATAGCATATGTTTAC CACTACATGAAAATGATTCAAGTGTTGTTAAGACCGA AAGATCTATTGCAGTGGGAACACCCCATCTTCAATAC TGCTTCAATGGAATCTCCAATGCCAAGTACAATGCATT TACCTTTTTCCCAGTCATCCTATACGAGCAATTCAAAT TTTTTTTCAATTTATACTTTACTTTAGTGGCTCTCTCTC |

TABLE 12-continued

BRIEF DESCRIPTION OF THE SEQUENCES

| SEQ ID NO: Description | Sequence |
|---|---|
| | AAGCGATACCGCAACTTCGCATTGGATATCTTTCTTCG<br>TATGTCGTCCCACTTTTGTTTGTACTCATAGTGACCAT<br>GTCAAAAGAGGCGATGGATGATATTCAACGCCGAAGA<br>AGGGATAGAGAACAGAACAATGAACCATATGAGGTT<br>CTGTCCAGCCCATCACCAGTTTTGTCCAAAAACTTAAA<br>ATGTGGTCACTTGGTTCGATTGCATAAGGGAATGAGA<br>GTGCCCGCAGATATGGTTCTTGTCCAGTCAAGCGAAT<br>CCACCGGAGAGTCATTTATCAAGACAGATCAGCTGGA<br>TGGTGAGACTGATTGGAAGCTTCGGATTGTTTCTCCAG<br>TTACACAATCGTTACCAATGACTGAACTTCAAAATGTC<br>GCCATCACTGCAAGCGCACCCTCAAAATCAATTCACT<br>CCTTTCTTGGAAGATTGACCTACAATGGGCAATCATAT<br>GGTCTTACGATAGACAACACAATGTGGTGTAATACTG<br>TATTAGCTTCTGGTTCAGCAATTGGTTGTATAATTTAC<br>ACAGGTAAAGATACTCGACAATCGATGAACACAACTC<br>AGCCCAAACTGAAAACGGGCTTGTTAGAACTGGAAAT<br>CAATAGTTTGTCCAAGATCTTATGTGTTTGTGTGTTTG<br>CATTATCTGTCATCTTAGTGCTATTCCAAGGAATAGCT<br>GATGATTGGTACGTCGATATCATGCGGTTTCTCATTCT<br>ATTCTCCACTATTATCCCAGTGTCTCTGAGAGTTAACC<br>TTGATCTTGGAAAGTCAGTCCATGCTCATCAAATAGA<br>AACTGATAGCTCAATACCTGAAACCGTTGTTAGAACT<br>AGTACAATACCGGAAGACCTGGGAAGAATTGAATACC<br>TATTAAGTGACAAAACTGGAACTCTTACTCAAAATGA<br>TATGGAAATGAAAAAACTACACCTAGGAACAGTCTCT<br>TATGCTGGTGATACCATGGATATTATTTCTGATCATGT<br>TAAAGGTCTTAATAACGCTAAAACATCGAGGAAAGAT<br>CTTGGTATGGAGAATAAGAGATTTGGTTACAACTCTGG<br>CCATCTG |
| 70 DNA encodes *Drosophila melanogaster* ManII codon-optimized (KD) | AGAGACGATCCAATTAGACCTCCATTGAAGGTTGCTA<br>GATCCCCAAGACCAGGTCAATGTCAAGATGTTGTTCA<br>GGACGTCCCAAACGTTGATGTCCAGATGTTGGAGTTG<br>TACGATAGAATGTCCTTCAAGGACATTGATGGTGGTG<br>TTTGGAAGCAGGGTTGGAACATTAAGTACGATCCATT<br>GAAGTACAACGCTCATCACAAGTTGAAGGTCTTCGTT<br>GTCCCACACTCCCACAACGATCCTGGTTGGATTCAGA<br>CCTTCGAGGAATACTACCAGCACGACACCAAGCACAT<br>CTTGTCCAACGCTTTGAGACATTTGCACGACAACCCA<br>GAGATGAAGTTCATCTGGGCTGAAATCTCCTACTTCGC<br>TAGATTCTACCACGATTTGGGTGAGAACAAGAAGTTG<br>CAGATGAAGTCCATCGTCAAGAACGGTCAGTTGGAAT<br>TCGTCACTGGTGGATGGGTCATGCCAGACGAGGCTAA<br>CTCCCACTGGAGAAACGTTTTGTTGCAGTTGACCGAA<br>GGTCAAACTTGGTTGAAGCAATTCATGAACGTCACTC<br>CAACTGCTTCCTGGGCTATCGATCCATTCGGACACTCT<br>CCAACTATGCCATACATTTTGCAGAAGTCTGGTTTCAA<br>GAATATGTTGATCCAGAGAACCCACTACTCCGTTAAG<br>AAGGAGTTGGCTCAACAGAGACAGTTGGAGTTCTTGT<br>GGAGACAGATCTGGGACAACAAAGGTGACACTGCTTT<br>GTTCACCCACATGATGCCATTCTACTCTTACGACATTC<br>CTCATACCTGTGGTCCAGATCCAAAGGTTTGTTGTCAG<br>TTCGATTTCAAAAGAATGGGTTCCTTCGGTTTGTCTTG<br>TCCATGGAAGGTTCCACCTAGAACTATCTCTGATCAA<br>AATGTTGCTGCTAGATCCGATTTGTTGGTTGATCAGTG<br>GAAGAAGAAGGCTGAGTTGTACAGAACCAACGTCTTG<br>TTGATTCCATTGGGTGACGACTTCAGATTCAAGCAGA<br>ACACCGAGTGGGATGTTCAGAGAGTCAACTACGAAAG<br>ATTGTTCGAACACATCAACTCTCAGGCTCACTTCAATG<br>TCCAGGCTCAGTTCGGTACTTTGCAGGAATACTTCGAT<br>GCTGTTCACCAGGCTGAAAGAGCTGGACAAGCTGAGT<br>TCCCAACCTTGTCTGGTGACTTCTTCACTTACGCTGAT<br>AGATCTGATAACTACTGGTCTGGTTACTACACTTCCAG<br>ACCATACCATAAGAGAATGGACAGAGTCTTGATGCAC<br>TACGTTAGAGCTGCTGAAATGTTGTCCGCTTGGCACTC<br>CTGGGACGGTATGGCTAGAATCGAGGAAAGATTGGAG<br>CAGGCTAGAAGAGAGTTGTCCTTGTTCCAGCACCACG<br>ACGGTATTACTGGTACTGCTAAAACTCACGTTGTCGTC<br>GACTACGAGCAAAGAATGCAGGAAGCTTTGAAAGCTT<br>GTCAAATGGTCATGCAACAGTCTGTCTACAGATTGTTG<br>ACTAAGCCATCCATCTACTCTCCAGACTTCTCCTTCTC<br>CTACTTCACTTTGGACGACTCCAGATGGCCAGGTTCTG<br>GTGTTGAGGACTCTAGAACTACCATCATCTTGGGTGA<br>GGATATCTTGCCATCCAAGCATGTTGTCATGCACAAC |

TABLE 12-continued

BRIEF DESCRIPTION OF THE SEQUENCES

| SEQ ID NO: | Description | Sequence |
|---|---|---|
| | | ACCTTGCCACACTGGAGAGAGCAGTTGGTTGACTTCT ACGTCTCCTCTCCATTCGTTTCTGTTACCGACTTGGCT AACAATCCAGTTGAGGCTCAGGTTTCTCCAGTTTGGTC TTGGCACCACGACACTTTGACTAAGACTATCCACCCA CAAGGTTCCACCACCAAGTACAGAATCATCTTCAAGG CTAGAGTTCCACCAATGGGTTTGGCTACCTACGTTTTG ACCATCTCCGATTCCAAGCCAGAGCACACCTCCTACG CTTCCAATTTGTTGCTTAGAAAGAACCCAACTTCCTTG CCATTGGGTCAATACCCAGAGGATGTCAAGTTCGGTG ATCCAAGAGAGATCTCCTTGAGAGTTGGTAACGGTCC AACCTTGGCTTTCTCTGAGCAGGGTTTGTTGAAGTCCA TTCAGTTGACTCAGGATTCTCCACATGTTCCAGTTCAC TTCAAGTTCTTGAAGTACGGTGTTAGATCTCATGGTGA TAGATCTGGTGCTTACTTGTTCTTGCCAAATGGTCCAG CTTCTCCAGTCGAGTTGGGTCAGCCAGTTGTCTTGGTC ACTAAGGGTAAATTGGAGTCTTCCGTTTCTGTTGGTTT GCCATCTGTCGTTCACCAGACCATCATGAGAGGTGGT GCTCCAGAGATTAGAAATTTGGTCGATATTGGTTCTTT GGACAACACTGAGATCGTCATGAGATTGGAGACTCAT ATCGACTCTGGTGATATCTTCTACACTGATTTGAATGG ATTGCAATTCATCAAGAGGAGAAGATTGGACAAGTTG CCATTGCAGGCTAACTACTACCCAATTCCATCTGGTAT GTTCATTGAGGATGCTAATACCAGATTGACTTTGTTGA CCGGTCAACCATTGGGTGGATCTTCTTTGGCTTCTGGT GAGTTGGAGATTATGCAAGATAGAAGATTGGCTTCTG ATGATGAAAGAGGTTTGGGTCAGGGTGTTTTGGACAA CAAGCCAGTTTTGCATATTTACAGATTGGTCTTGGAGA AGGTTAACAACTGTGTCAGACCATCTAAGTTGCATCC AGCTGGTTACTTGACTTCTGCTGCTCACAAAGCTTCTC AGTCTTTGTTGGATCCATTGGACAAGTTCATCTTCGCT GAAAATGAGTGGATCGGTGCTCAGGGTCAATTCGGTG GTGATCATCCATCTGCTAGAGAGGATTTGGATGTCTCT GTCATGAGAAGATTGACCAAGTCTTCTGCTAAAACCC AGAGAGTTGGTTACGTTTTGCACAGAACCAATTTGAT GCAATGTGGTACTCCAGAGGAGCATACTCAGAAGTTG GATGTCTGTCACTTGTTGCCAAATGTTGCTAGATGTGA GAGAACTACCTTGACTTTCTTGCAGAATTTGGAGCACT TGGATGGTATGGTTGCTCCAGAAGTTTGTCCAATGGA AACCGCTGCTTACGTCTCTTCTCACTCTTCTTGA |
| 71 | DNA encodes Mnn2 leader (53) | ATGCTGCTTACCAAAAGGTTTTCAAAGCTGTTCAAGCT GACGTTCATAGTTTTGATATTGTGCGGGCTGTTCGTCA TTACAAACAAATACATGGATGAGAACACGTCG |
| 72 | Sequence of the PpHIS1 auxotrophic marker: | CAAGTTGCGTCCGGTATACGTAACGTCTCACGATGAT CAAAGATAATACTTAATCTTCATGGTCTACTGAATAAC TCATTTAAACAATTGACTAATTGTACATTATATTGAAC TTATGCATCCTATTAACGTAATCTTCTGGCTTCTCTCTC AGACTCCATCAGACACAGAATATCGTTCTCTCTAACTG GTCCTTTGACGTTTCTGACAATAGTTCTAGAGGAGTCG TCCAAAAACTCAACTCTGACTTGGGTGACACCACCAC GGGATCCGGTTCTTCCGAGGACCTTGATGACCTTGGCT AATGTAACTGGAGTTTTAGTATCCATTTTAAGATGTGT GTTTCTGTAGGTTCTGGGTTGGAAAAAAATTTTAGACA CCAGAAGAGAGGAGTGAACTGGTTTGCGTGGGTTTAG ACTGTGTAAGGCACTACTCTGTCGAAGTTTTAGATAG GGGTTACCCGCTCCGATGCATGGGAAGCGATTAGCCC GGCTGTTGCCCGTTTGGTTTTTGAAGGGTAATTTTCAA TATCTCTGTTTGAGTCATCAATTTCATATTCAAAGATT CAAAAACAAAATCTGGTCCAAGGAGCGCATTTAGGAT TATGGAGTTGGCGAATCACTTGAACGATAGACTATTA TTTGCTGTTCCTAAAGAGGGCAGATTGTATGAGAAAT GCGTTGAATTACTTAGGGGATCAGATATTCAGTTTCGA AGATCCAGTAGATTGGATATAGCTTTGTGCACTAACCT GCCCCTGGCATTGGTTTTCCTTCCAGCTGCTGACATTC CCACGTTTGTAGGAGAGGGTAAATGTGATTTGGGTAT AACTGGTATTGACCAGGTTCAGGAAAGTGACGTAGAT GTCATACCTTTATTAGACTTGAATTTCGGTAAGTGCAA GTTGCAGATTCAAGTTCCCGAGAATGGTGACTTGAAA GAACCTAAACAGCTAATTGGTAAAGAAATTGTTTCCT CCTTTTACTAGCTTAACCACCAGGTACTTTGAACAACTG GAAGGAGTTAAGCCTGGTGAGCCACTAAAGACAAAA ATCAAATATGTTGGAGGGTCTGTTGAGGCCTCTTGTGC CCTAGGAGTTGCCGATGCTATTGTGGATCTTGTTGAGA |

TABLE 12-continued

BRIEF DESCRIPTION OF THE SEQUENCES

| SEQ ID NO: | Description | Sequence |
|---|---|---|
| | | GTGGAGAAACCATGAAAGCGGCAGGGCTGATCGATAT<br>TGAAACTGTTCTTTCTACTTCCGCTTACCTGATCTCTTC<br>GAAGCATCCTCAACACCCAGAACTGATGGATACTATC<br>AAGGAGAGAATTGAAGGTGTACTGACTGCTCAGAAGT<br>ATGTCTTGTGTAATTACAACGCACCTAGAGGTAACCTT<br>CCTCAGCTGCTAAAACTGACTCCAGGCAAGAGAGCTG<br>CTACCGTTTCTCCATTAGATGAAGAAGATTGGGTGGG<br>AGTGTCCTCGATGGTAGAGAAGAAAGATGTTGGAAGA<br>ATCATGGACGAATTAAAGAAACAAGGTGCCAGTGACA<br>TTCTTGTCTTTGAGATCAGTAATTGTAGAGCATAGATA<br>GAATAATATTCAAGACCAACGGCTTCTCTTCGGAAGC<br>TCCAAGTAGCTTATAGTGATGAGTACCGGCATATATTT<br>ATAGGCTTAAAATTTCGAGGGTTCACTATATTCGTTTA<br>GTGGGAAGAGTTCCTTTCACTCTTGTTATCTATATTGT<br>CAGCGTGGACTGTTTATAACTGTACCAACTTAGTTTCT<br>TTCAACTCCAGGTTAAGAGACATAAATGTCCTTTGATGC |
| 73 | DNA encodes Rat GnT II (TC) Codon-optimized | TCCTTGGTTTACCAATTGAACTTCGACCAGATGTTGAG<br>AAACGTTGACAAGGACGGTACTTGGTCTCCTGGTGAG<br>TTGGTTTTGGTTGTTCAGGTTCACAACAGACCAGAGTA<br>CTTGAGATTGTTGATCGACTCCTTGAGAAAGGCTCAA<br>GGTATCAGAGAGGTTTTGGTTATCTTCTCCCACGATTT<br>CTGGTCTGCTGAGATCAACTCCTTGATCTCCTCCGTTG<br>ACTTCTGTCCAGTTTTGCAGGTTTTCTTCCCATTCTCCA<br>TCCAATTGTACCCATCTGAGTTCCCAGGTTCTGATCCA<br>AGAGACTGTCCAAGAGACTTGAAGAAGAACGCTGCTT<br>TGAAGTTGGGTTGTATCAACGCTGAATACCCAGATTCT<br>TTCGGTCACTACAGAGAGGCTAAGTTCTCCCAAACTA<br>AGCATCATTGGTGGTGGAAGTTGCACTTTGTTTGGGA<br>GAGAGTTAAGGTTTTGCAGGACTACACTGGATTGATC<br>TTGTTCTTGGAGGAGGATCATTACTTGGCTCCAGACTT<br>CTACCACGTTTTCAAGAAGATGTGGAAGTTGAAGCAA<br>CAAGAGTGTCCAGGTTGTGACGTTTTGTCCTTGGGAAC<br>TTACACTACTATCAGATCCTTCTACGGTATCGCTGACA<br>AGGTTGACGTTAAGACTTGGAAGTCCACTGAACACAA<br>CATGGGATTGGCTTTGACTAGAGATGCTTACCAGAAG<br>TTGATCGAGTGTACTGACACTTTCTGTACTTACGACGA<br>CTACAACTGGGACTGGACTTTGCAGTACTTGACTTTGG<br>CTTGTTTGCCAAAAGTTTGGAAGGTTTTGGTTCCACAG<br>GCTCCAAGAATTTTCCACGCTGGTGACTGTGGAATGC<br>ACCACAAGAAAACTTGTAGACCATCCACTCAGTCCGC<br>TCAAATTGAGTCCTTGTTGAACAACAACAAGCAGTAC<br>TTGTTCCCAGAGACTTTGGTTATCGGAGAGAAGTTTCC<br>AATGGCTGCTATTTCCCCACCAAGAAAGAATGGTGGA<br>TGGGGTGATATTAGAGACCACGAGTTGTGTAAATCCT<br>ACAGAAGATTGCAGTAG |
| 74 | DNA encodes Mnn2 leader (54) The last 9 nucleotides are the linker containing the AscI restriction site) | ATGCTGCTTACCAAAAGGTTTTCAAAGCTGTTCAAGCT<br>GACGTTCATAGTTTTGATATTGTGCGGGCTGTTCGTCA<br>TTACAAACAAATACATGGATGAGAACACGTCGGTCAA<br>GGAGTACAAGGAGTACTTAGACAGATATGTCCAGAGT<br>TACTCCAATAAGTATTCATCTTCCTCAGACGCCGCCAG<br>CGCTGACGATTCAACCCCATTGAGGGACAATGATGAG<br>GCAGGCAATGAAAAGTTGAAAAGCTTCTACAACAACG<br>TTTTCAACTTTCTAATGGTTGATTCGCCCGGGCGCGCC |
| 75 | Sequence of the 5'-Region used for knock out of PpARG1: | GATCTGGCCTTCCCTGAATTTTTACGTCCAGCTATACG<br>ATCCGTTGTGACTGTATTTCCTGAAATGAAGTTTCAAC<br>CTAAAGTTTTGGTTGTACTTGCTCCACCTACCACGGAA<br>ACTAATATCGAAACCAATGAAAAAGTAGAACTGGAAT<br>CGTCAATCGAAATTCGCAACCAAGTGGAACCCAAAGA<br>CTTGAATCTTTCTAAAGTCTATTCTAGTGACACTAATG<br>GCAACAGAAGATTTGAGCTGACTTTTCAAATGAATCT<br>CAATAATGCAATATCAACATCAGACAATCAATGGGCT<br>TTGTCTAGTGACACAGGATCAATTATAGTAGTGTCTTC<br>TGCAGGAAGAATAACTTCCCCGATCCTAGAAGTCGGG<br>GCATCCGTCTGTGTCTTAAGATCGTACAACGAACACCT<br>TTTGGCAATAACTTGTGAAGGAACATGCTTTTCATGGA<br>ATTTAAAGAAGCAAGAATGTGTTCTAAACAGCATTTC<br>ATTAGCACCTATAGTCAATTCACACATGCTAGTTAAG<br>AAAGTTGGAGATGCAAGGAACTATTCTATTGTATCTG<br>CCGAAGGAGACAACAATCCGTTACCCCAGATTCTAGA<br>CTGCGAACTTTCCAAAAATGGCGCTCCAATTGTGGCTC |

| SEQ ID NO: | Description | Sequence |
|---|---|---|
| | | TTAGCACGAAAGACATCTACTCTTATTCAAAGAAAAT GAAATGCTGGATCCATTTGATTGATTCGAAATACTTTG AATTGTTGGGTGCTGACAATGCACTGTTTGAGTGTGTG GAAGCGCTAGAAGGTCCAATTGGAATGCTAATTCATA GATTGGTAGATGAGTTCTTCCATGAAAACACTGCCGG TAAAAAACTCAAACTTTACAACAAGCGAGTACTGGAG GACCTTTCAAATTCACTTGAAGAACTAGGTGAAAATG CGTCTCAATTAAGAGAGAAACTTGACAAACTCTATGG TGATGAGGTTGAGGCTTCTTGACCTCTTCTCTCTATCT GCGTTTCTTTTTTTTTTTTTTTTTTTTTTTCAGTTG AGCCAGACCGCGCTAAACGCATACCAATTGCCAAATC AGGCAATTGTGAGACAGTGGTAAAAAAGATGCCTGCA AAGTTAGATTCACACAGTAAGAGAGATCCTACTCATA AATGAGGCGCTTATTTAGTAGCTAGTGATAGCCACTG CGGTTCTGCTTTATGCTATTTGTTGTATGCCTTACTATC TTTGTTTGGCTCCTTTTTCTTGACGTTTTCCGTTGGAGG GACTCCCTATTCTGAGTCATGAGCCGCACAGATTATCG CCCAAAATTGACAAAATCTTCTGGCGAAAAAGTATA AAAGGAGAAAAAGCTCACCCTTTTCCAGCGTAGAAA GTATATATCAGTCATTGAAGAC |
| 76 | Sequence of the 3'-Region used for knock out of PpARG1: | GGGACTTTAACTCAAGTAAAAGGATAGTTGTACAATT ATATATACGAAGAATAAATCATTACAAAAAGTATTCG TTTCTTTGATTCTTAACAGGATTCATTTTCTGGGTGTCA TCAGGTACAGCGCTGAATATCTTGAAGTTAACATCGA GCTCATCATCGACGTTCATCACACTAGCCACGTTTCCG CAACGGTAGCAATAATTAGGAGCGGACCACACAGTGA CGACATCTTTCTCTTTGAAATGGTATCTGAAGCCTTCC ATGACCAATTGATGGGCTCTAGCGATGAGTTGCAAGT TATTAATGTGGTTGAACTCACGTGCTACTCGAGCACCG AATAACCAGCCAGCTCCACGAGGAGAAACAGCCCAA CTGTCGACTTCATCTGGGTCAGACCAAACCAAGTCAC AAAATCCTCCTTCATGAGGGACCTCTTGCGCTCGGCTG AGAACTCTGATTTGATCTAACATGCGAATATCGGGAG AGAGACCACCATGGATACATAATATTTTACCATCAAT GATGGCACTAAGGGTTAAAAAGTCGAACACCTGGCAA CAGTACTTCCAGACAGTGGTGGAACCATATTTATTGA GACATTCCTCATAAAATCCATAAACCTGAGTGATCTGT CTGGATTCATGATTTCCCCTTACCAATGTGATATGTTG AGGAAACTTAATTTTTAAAATCATGAGTAACGTGAAC GTCTCCAACGAGAAATAGCCTCTATCCACATAGTCTCC TAGGAAGATATAGTTCTGTTTTATTCCATTAGAGGAGG ATCCGGGAAACCCACCACTAATCTTGAAAAGTTCCAG TAGATCGTGAAATTGGCCGTGAATATCTCCGCATACT GTCACTGGACTCTGCACTGGCTGTATATTGGATTCCTC CATCAGCAAATCCTTCACCCGTTCGCAAAGATGCTTCA TATCATTTTCACTTAAAGCCTTGCAGCTTTTGACTTCTT CAAACCACTGATCTGGTCCTCTTTCTGGCATGATTAAG GTCTATAATATTTCTGAGCTGAGATGTAAAAAAAAAT AATAAAAATGGGGAGTGAAAAGTGTGTAGCTTTTAG GAGTTTGGGATTGATACCCCAAAATGATCTTTATGAG AATTAAAAGGTAGATACGCTTTTAATAAGAACACCTA TCTATAGTACTTTGTGGTCTTGAGTAATTGAGATGTTC AGCTTCTGAGGTTTGCCGTTATTCTGGGATAGTAGTGC GCGACCAAACAACCCGCCAGGCAAAGTGTGTTGTGCT CGAAGACGATTGCCAGAAGAGTAAGTCCGTCCTGCCT CAGATGTTACACACTTTCTTCCCTAGACAGTCGATGCA TCATCGGATTTAAACCTGAAACTTTGATGCCATGATAC GCCTAGTCACGTCGACTGAGATTTTAGATAAGCCCCG ATCCCTTTAGTACATTCCTGTTATCCATGGATGGAATG GCCTGATA |
| 77 | Sequence of the 5'-Region used for knock out of BMT4 | AAGCTTGTTCACCGTTGGGACTTTTCCGTGGACAATGT TGACTACTCCAGGAGGGATTCCAGCTTTCTCTACTAGC TCAGCAATAATCAATGCAGCCCCAGGCGCCCGTTCTG ATGGCTTGATGACCGTTGTATTGCCTGTCACTATAGCC AGGGGTAGGGTCCATAAAGGAATCATAGCAGGGAAA TTAAAAGGGCATATTGATGCAATCACTCCCAATGGCT CTCTTGCCATTGAAGTCTCCATATCAGCACTAACTTCC AAGAAGGACCCCTTCAAGTCTGACGTGATAGAGCACG CTTGCTCTGCCACCTGTAGTCCTCTCAAAACGTCACCT TGTGCATCAGCAAAGACTTTACCTTGCTCCAATACTAT GACGGAGGCAATTCTGTCAAAATTCTCTCTCAGCAATT CAACCAACTTGAAAGCAAATTGCTGTCTCTTGATGAT |

TABLE 12-continued

BRIEF DESCRIPTION OF THE SEQUENCES

| SEQ ID NO: Description | Sequence |
| --- | --- |
| | GGAGACTTTTTTCCAAGATTGAAATGCAATGTGGGAC |
| | GACTCAATTGCTTCTTCCAGCTCCTCTTCGGTTGATTG |
| | AGGAACTTTTGAAACCACAAAATTGGTCGTTGGGTCA |
| | TGTACATCAAACCATTCTGTAGATTTAGATTCGACGAA |
| | AGCGTTGTTGATGAAGGAAAAGGTTGGATACGGTTTG |
| | TCGGTCTCTTTGGTATGGCCGGTGGGGTATGCAATTGC |
| | AGTAGAAGATAATTGGACAGCCATTGTTGAAGGTAGA |
| | GAAAAGGTCAGGGAACTTGGGGGTTATTTATACCATT |
| | TTACCCCACAAATAACAACTGAAAAGTACCCATTCCA |
| | TAGTGAGAGGTAACCGACGGAAAAAGACGGGCCCAT |
| | GTTCTGGGACCAATAGAACTGTGTAATCCATTGGGAC |
| | TAATCAACAGACGATTGGCAATATAATGAAATAGTTC |
| | GTTGAAAAGCCACGTCAGCTGTCTTTTCATTAACTTTG |
| | GTCGGACACAACATTTTCTACTGTTGTATCTGTCCTAC |
| | TTTGCTTATCATCTGCCACAGGGCAAGTGGATTTCCTT |
| | CTCGCGCGGCTGGGTGAAAACGGTTAACGTGAA |
| 78 Sequence of the 3'-Region used for knock out of BMT4 | GCCTTGGGGGACTTCAAGTCTTTGCTAGAAACTAGAT GAGGTCAGGCCCTCTTATGGTTGTGTCCCAATTGGGCA ATTTCACTCACCTAAAAAGCATGACAATTATTTAGCG AAATAGGTAGTATATTTTCCCTCATCTCCCAAGCAGTT TCGTTTTTGCATCCATATCTCTCAAATGAGCAGCTACG ACTCATTAGAACCAGAGTCAAGTAGGGGTGAGCTCAG TCATCAGCCTTCGTTTCTAAAACGATTGAGTTCTTTTG TTGCTACAGGAAGCGCCCTAGGGAACTTTCGCACTTT GGAAATAGATTTTGATGACCAAGAGCGGGAGTTGATA TTAGAGAGGCTGTCCAAAGTACATGGGATCAGGCCGG CCAAATTGATTGGTGTGACTAAACCATTGTGTACTTGG ACACTCTATTACAAAAGCGAAGATGATTTGAAGTATT ACAAGTCCCGAAGTGTTAGAGGATTCTATCGAGCCCA GAATGAAATCATCAACCGTTATCAGCAGATTGATAAA CTCTTGGAAAGCGGTATCCCATTTTCATTATTGAAGAA CTACGATAATGAAGATGTGAGAGACGGCGACCCTCTG AACGTAGACGAAGAAACAAATCTACTTTTGGGGTACA ATAGAGAAAGTGAATCAAGGGAGGTATTTGTGGCCAT AATACTCAACTCTATCATTAATG |
| 79 Sequence of the 5'-Region used for knock out of BMT1 | CATATGGTGAGAGCCGTTCTGCACAACTAGATGTTTTC GAGCTTCGCATTGTTTCCTGCAGCTCGACTATTGAATT AAGATTTCCGGATATCTCCAATCTCACAAAAACTTATG TTGACCACGTGCTTTCCTGAGGCGAGGTGTTTTATATG CAAGCTGCCAAAAATGGAAAACGAATGGCCATTTTTC GCCCAGGCAAATTATTCGATTACTGCTGTCATAAAGA CAGTGTTGCAAGGCTCACATTTTTTTTAGGATCCGAG ATAAAGTGAATACAGGACAGCTTATCTCTATATCTTGT ACCATTCGTGAATCTTAAGAGTTCGGTTAGGGGGACT CTAGTTGAGGGTTGGCACTCACGTATGGCTGGGCGCA GAAATAAAATTCAGGCGCAGCAGCACTTATCGATG |
| 80 Sequence of the 3'-Region used for knock out of BMT1 | GAATTCACAGTTATAAATAAAAACAAAAACTCAAAAA GTTTGGGCTCCACAAAATAACTTAATTTAAATTTTTGT CTAATAAATGAATGTAATTCCAAGATTATGTGATGCA AGCACAGTATGCTTCAGCCCTATGCAGCTACTAATGTC AATCTCGCCTGCGAGCGGGCCTAGATTTTCACTACAA ATTTCAAAACTACGCGGATTTATTGTCTCAGAGAGCA ATTTGGCATTTCTGAGCGTAGCAGGAGGCTTCATAAG ATTGTATAGGACCGTACCAACAAATTGCCGAGGCACA ACACGGTATGCTGTGCACTTATGTGGCTACTTCCCTAC AACGGAATGAAACCTTCCTCTTTCCGCTTAAACGAGA AAGTGTGTCGCAATTGAATGCAGGTGCCTGTGCGCCT TGGTGTATTGTTTTTGAGGGCCCAATTTATCAGGCGCC TTTTTTCTTGGTTGTTTTCCCTTAGCCTCAAGCAAGGTT GGTCTATTTCATCTCCGCTTCTATACCGTGCCTGATAC TGTTGGATGAGAACACGACTCAACTTCCTGCTGCTCTG TATTGCCAGTGTTTTGTCTGTGATTTGGATCGGAGTCC TCCTTACTTGGAATGATAATAATCTTGGCGGAATCTCC CTAAACGGAGGCAAGGATTCTGCCTATGATGATCTGC TATCATTGGGAAGCTT |

TABLE 12-continued

BRIEF DESCRIPTION OF THE SEQUENCES

| SEQ ID NO: | Description | Sequence |
|---|---|---|
| 81 | Sequence of the 5'-Region used for knock out of BMT3 | GATATCTCCCTGGGGACAATATGTGTTGCAACTGTTCG TTGTTGGTGCCCCAGTCCCCCAACCGGTACTAATCGGT CTATGTTCCCGTAACTCATATTCGGTTAGAACTAGAAC AATAAGTGCATCATTGTTCAACATTGTGGTTCAATTGT CGAACATTGCTGGTGCTTATATCTACAGGGAAGACGA TAAGCCTTTGTACAAGAGAGGTAACAGACAGTTAATT GGTATTTCTTTGGGAGTCGTTGCCCTCTACGTTGTCTC CAAGACATACTACATTCTGAGAAACAGATGGAAGACT CAAAAATGGGAGAAGCTTAGTGAAGAAGAGAAAGTT GCCTACTTGGACAGAGCTGAGAAGGAGAACCTGGGTT CTAAGAGGCTGGACTTTTTGTTCGAGAGTTAAACTGC ATAATTTTTTCTAAGTAAATTTCATAGTTATGAAATTT CTGCAGCTTAGTGTTTACTGCATCGTTTACTGCATCAC CCTGTAAATAATGTGAGCTTTTTTCCTTCCATTGCTTG GTATCTTCCTTGCTGCTGTTT |
| 82 | Sequence of the 3'-Region used for knock out of BMT3 | ACAAAACAGTCATGTACAGAACTAACGCCTTTAAGAT GCAGACCACTGAAAAGAATTGGGTCCCATTTTTCTTG AAAGACGACCAGGAATCTGTCCATTTTGTTTACTCGTT CAATCCTCTGAGAGTACTCAACTGCAGTCTTGATAAC GGTGCATGTGATGTTCTATTTGAGTTACCACATGATTT TGGCATGTCTTCCGAGCTACGTGGTGCCACTCCTATGC TCAATCTTCCTCAGGCAATCCCGATGGCAGACGACAA AGAAATTTGGGTTTCATTCCCAAGAACGAGAATATCA GATTGCGGGTGTTCTGAAACAATGTACAGGCCAATGT TAATGCTTTTTGTTAGAGAAGGAACAAACTTTTTTGCT GAGC |
| 83 | DNA encodes Tr ManI catalytic domain | CGCGCCGGATCTCCCAACCCTACGAGGGCGGCAGCAG TCAAGGCCGCATTCCAGACGTCGTGGAACGCTTACCA CCATTTTGCCTTTCCCCATGACGACCTCCACCCGGTCA GCAACAGCTTTGATGATGAGAGAAACGGCTGGGGCTC GTCGGCAATCGATGGCTTGGACACGGCTATCCTCATG GGGGATGCCGACATTGTGAACACGATCCTTCAGTATG TACCGCAGATCAACTTCACCACGACTGCGGTTGCCAA CCAAGGCATCTCCGTGTTCGAGACCAACATTCGGTAC CTCGGTGGCCTGCTTTCTGCCTATGACCTGTTGCGAGG TCCTTTCAGCTCCTTGGCGACAAACCAGACCCTGGTAA ACAGCCTTCTGAGGCAGGCTCAAACACTGGCCAACGG CCTCAAGGTTGCGTTCACCACTCCCAGCGGTGTCCCG GACCCTACCGTCTTCTTCAACCCTACTGTCCGGAGAAG TGGTGCATCTAGCAACAACGTCGCTGAAATTGGAAGC CTGGTGCTCGAGTGGACACGGTTGAGCGACCTGACGG GAAACCCGCAGTATGCCCAGCTTGCGCAGAAGGGCGA GTCGTATCTCCTGAATCCAAAGGGAAGCCCGGAGGCA TGGCCTGGCCTGATTGGAACGTTTGTCAGCACGAGCA ACGGTACCTTTCAGGATAGCAGCGGCAGCTGGTCCGG CCTCATGGACAGCTTCTACGAGTACCTGATCAAGATG TACCTGTACGACCCGGTTGCGTTTGCACACTACAAGG ATCGCTGGGTCCTTGCTGCCGACTCGACCATTGCGCAT CTCGCCTCTCACCCGTCGACGCGCAAGGACTTGACCTT TTTGTCTTCGTACAACGGACAGTCTACGTCGCCAAACT CAGGACATTTGGCCAGTTTTGCCGGTGGCAACTTCATC TTGGGAGGCATTCTCCTGAACGAGCAAAAGTACATTG ACTTTGGAATCAAGCTTGCCAGCTCGTACTTTGCCACG TACAACCAGACGGCTTCTGGAATCGGCCCCGAAGGCT TCGCGTGGGTGGACAGCGTGACGGGCGCCGGCGGCTC GCCGCCCTCGTCCCAGTCCGGGTTCTACTCGTCGGCAG GATTCTGGGTGACGGCACCGTATTACATCCTGCGGCC GGGAGACGCTGGAGAGCTTGTACTACGCATACCGCGTC ACGGGCGACTCCAAGTGGCAGGACCTGGCGTGGGAA GCGTTCAGTGCCATTGAGGACGCATGCCGCGCCGGCA GCGCGTACTCGTCCATCAACGACGTGACGCAGGCCAA CGGCGGGGTGCCTCTGACGATATGGAGAGCTTCTGG TTTGCCGAGGCGCTCAAGTATGCGTACCTGATCTTTGC GGAGGAGTCGGATGTGCAGGTGCAGGCCAACGGCGG GAACAAATTTGTCTTTAACACGGAGGCGCACCCCTTT AGCATCCGTTCATCATCACGACGGGGCGGCCACCTTG CTTAA |

TABLE 12-continued

BRIEF DESCRIPTION OF THE SEQUENCES

| SEQ ID NO: Description | Sequence |
|---|---|
| 84 5'ARG1 and ORF | TACCAATTGCCAAATCAGGCAATTGTGAGACAGTGGTAAA<br>AAAGATGCCTGCAAAGTTAGATTCACACAGTAAGAGAGAT<br>CCTACTCATAAATGAGGCGCTTATTTAGTAGCTAGTGATAG<br>CCACTGCGGTTCTGCTTTATGCTATTTGTTGTATGCCTTACT<br>ATCTTTGTTTGGCTCCTTTTTCTTGACGTTTTCCGTTGGAGG<br>GACTCCCTATTCTGAGTCATGAGCCGCACAGATTATCGCCC<br>AAAATTGACAAAATCTTCTGGCGAAAAAAGTATAAAAGGA<br>GAAAAAAGCTCACCCTTTTCCAGCGTAGAAAGTATATATCA<br>GTCATTGAAGACTATTATTTAAATAACACAATGTCTAAAGG<br>AAAAGTTTGTTTGGCCTACTCCGGTGGTTTGGATACCTCCA<br>TCATCCTAGCTTGGTTGTTGGAGCAGGGATACGAAGTCGTT<br>GCCTTTTTAGCCAACATTGGTCAAGAGGAAGACTTTGAGGC<br>TGCTAGAGAGAAAGCTCTGAAGATCGGTGCTACCAAGTTT<br>ATCGTCAGTGACGTTAGGAAGGAATTTGTTGAGGAAGTTTT<br>GTTCCCAGCAGTCCAAGTTAACGCTATCTACGAGAACGTCT<br>ACTTACTGGGTACCTCTTTGGCCAGACCAGTCATTGCCAAG<br>GCCCAAATAGAGGTTGCTGAACAAGAAGGTTGTTTTGCTGT<br>TGCCCACGGTTGTACCGGAAAGGGTAACGATCAGGTTAGA<br>TTTGAGCTTTCCTTTTATGCTCTGAAGCCTGACGTTGTCTGT<br>ATCGCCCCATGGAGAGACCCAGAATTCTTCGAAAGATTCG<br>CTGGTAGAAATGACTTGCTGAATTACGCTGCTGAGAAGGA<br>TATTCCAGTTGCTCAGACTAAAGCCAAGCCATGGTCTACTG<br>ATGAGAACATGGCTCACATCTCCTTCGAGGCTGGTATTCTA<br>GAAGATCCAAACACTACTCCTCCAAAGGACATGTGGAAGC<br>TCACTGTTGACCCAGAAGATGCACCAGACAAGCCAGAGTT<br>CTTTGACGTCCACTTTGAGAAGGGTAAGCCAGTTAAATTAG<br>TTCTCGAGAACAAAACTGAGGTCACCGATCCGGTTGAGAT<br>CTTTTTGACTGCTAACGCCATTGCTAGAAGAAACGGTGTTG<br>GTAGAATTGACATTGTCGAGAACAGATTCATCGGAATCAA<br>GTCCAGAGGTTGTTATGAAACTCCAGGTTTGACTCTACTGA<br>GAACCACTCACATCGACTTGGAAGGTCTTACCGTTGACCGT<br>GAAGTTAGATCGATCAGAGACACTTTTGTTACCCCAACCTA<br>CTCTAAGTTGTTATACAACGGGTTGTACTTTACCCCAGAAG<br>GTGAGTACGTCAGAACTATGATTCAGCCTTCTCAAACACC<br>GTCAACGGTGTTGTTAGAGCCAAGGCCTACAAAGGTAATG<br>TGTATAACCTAGGAAGATACTCTGAAACCGAGAAATTGTA<br>CGATGCTACCGAATCTTCCATGGATGAGTTGACCGGATTCC<br>ACCCTCAAGAAGCTGGAGGATTATCACAACACAAGCCAT<br>CAGAATCAAGAAGTACGGAGAAAGTGTCAGAGAGAAGGG<br>AAAGTTTTTGGGACTTTAACTCAAGTAAAAGGATAGTTGTA<br>CAATTATATATACGAAGAATAAATCATTACAAAAAGTATT<br>CGTTTCTTTGATTCTTAACAGGATTCATTTTCTGGGTGTCAT<br>CAGGTACAGCGCTGAATATCTTGAAGTTAACATCGAGCTCA<br>TCATCGACGTTCATCACACTAGCCACGTTTCCGCAACGGTAG |
| 85 PpCITI TT | CCGGCCATTTAAATATGTGACGACTGGGTGATCCGGGTTAG<br>TGAGTTGTTCTCCCATCTGTATATTTTTCATTTACGATGAAT<br>ACGAAATGAGTATTAAGAAATCAGGCGTAGCAATATGGGC<br>AGTGTTCAGTCCTGTCATAGATGGCAAGCACTGGCACATCC<br>TTAATAGGTTAGAGAAAATCATTGAATCATTTGGGTGGTGA<br>AAAAAAATTGATGTAAACAAGCCACCCACGCTGGGAGTCG<br>AACCCAGAATCTTTTGATTAGAAGTCAAACGCGTTAACCAT<br>TACGCTACGCAGGCATGTTTCACGTCCATTTTTGATTGCTTT<br>CTATCATAATCTAAAGATGTGAACTCAATTAGTTGCAATTT<br>GACCAATTCTTCCATTACAAGTCGTGCTTCCTCCGTTGATG<br>CAAC |
| 86 Ashbya gossypii TEF1 promoter | GATCTGTTTAGCTTGCCTCGTCCCCGCCGGGTCACCCG<br>GCCAGCGACATGGAGGCCCAGAATACCCTCCTTGACA<br>GTCTTGACGTGCGCAGCTCAGGGGCATGATGTGACTG<br>TCGCCCGTACATTTAGCCCCATACATCCCCATGTATAAT<br>CATTTGCATCCATACATTTTGATGGCCGCACGGCGCGA<br>AGCAAAAATTACGGCTCCTCGCTGCAGACCTGCGAGC<br>AGGGAAACGCTCCCCTCACAGACGCGTTGAATTGTCC<br>CCACGCCGCGCCCCTGTAGAGAAATATAAAAGGTTAG<br>GATTTGCCACTGAGGTTCTTCTTTCATATACTTCCTTTT<br>AAAATCTTGCTAGGATACAGTTCTCACATCACATCCG<br>AACATAAACAACC |

TABLE 12-continued

BRIEF DESCRIPTION OF THE SEQUENCES

| SEQ ID NO: | Description | Sequence |
|---|---|---|
| 87 | *Ashbya gossypii* TEF1 termination sequence | TAATCAGTACTGACAATAAAAAGATTCTTGTTTTCAAG AACTTGTCATTTGTATAGTTTTTTTATATTGTAGTTGTT CTATTTTAATCAAATGTTAGCGTGATTTATATTTTTTT CGCCTCGACATCATCTGCCCAGATGCGAAGTTAAGTG CGCAGAAAGTAATATCATGCGTCAATCGTATGTGAAT GCTGGTCGCTATACTGCTGTCGATTCGATACTAACGCC GCCATCCAGTGTCGAAAAC |
| 88 | Sequence of the PpPMA1 promoter: | AAATGCGTACCTCTTCTACGAGATTCAAGCGAATGAG AATAATGTAATATGCAAGATCAGAAAGAATGAAAGG AGTTGAAAAAAAAAACCGTTGCGTTTTGACCTTGAAT GGGGTGGAGGTTTCCATTCAAAGTAAAGCCTGTGTCT TGGTATTTTCGGCGGCACAAGAAATCGTAATTTTCATC TTCTAAACGATGAAGATCGCAGCCCAACCTGTATGTA GTTAACCGGTCGGAATTATAAGAAAGATTTTCGATCA ACAAACCCTAGCAAATAGAAAGCAGGGTTACAACTTT AAACCGAAGTCACAAACGATAAACCACTCAGCTCCCA CCCAAATTCATTCCCACTAGCAGAAAGGAATTATTTA ATCCCTCAGGAAACCTCGATGATTCTCCCGTTCTTCCA TGGGCGGGTATCGCAAAATGAGGAATTTTTCAAATTT CTCTATTGTCAAGACTGTTTATTATCTAAGAAATAGCC CAATCCGAAGCTCAGTTTTGAAAAAATCACTTCCGCG TTTCTTTTTTACAGCCCGATGAATATCCAAATTTGGAA TATGGATTACTCTATCGGGACTGCAGATAATATGACA ACAACGCAGATTACATTTTAGGTAAGGCATAAACACC AGCCAGAAATGAAACGCCCACTAGCCATGGTCGAATA GTCCAATGAATTCAGATAGCTATGGTCTAAAAGCTGA TGTTTTTTATTGGGTAATGGCGAAGAGTCCAGTACGAC TTCCAGCAGAGCTGAGATGGCCATTTTTGGGGGTATT AGTAACTTTTTGAGCTCTTTTCACTTCGATGAAGTGTC CCATTCGGGATATAATCGGATCGCGTCGTTTTCTCGAA AATACAGCTTAGCGTCGTCCGCTTGTTGTAAAAGCAG CACCACATTCCTAATCTCTTATATAAACAAAACAACCC AAATTATCAGTGCTGTTTTCCCACCAGATATAAGTTTC TTTTCTCTTCCGCTTTTTGATTTTTTATCTCTTTCCTTTA AAAACTTCTTTACCTTAAAGGGCGGCC |
| 89 | Sequence of the 5'-region that was used to knock into the PpPRO1 locus: | GAAGGGCCATCGAATTGTCATCGTCTCCTCAGGTGCC ATCGCTGTGGGCATGAAGAGAGTCAACATGAAGCGGA AACCAAAAAAGTTACAGCAAGTGCAGGCATTGGCTGC TATAGGACAAGGCCGTTTGATAGGACTTTGGGACGAC CTTTTCCGTCAGTTGAATCAGCCTATTGCGCAGATTTT ACTGACTAGAACGGATTTGGTCGATTACACCCAGTTT AAGAACGCTGAAAATACATTGGAACAGCTTATTAAAA TGGGTATTATTCCTATTGTCAATGAGAATGACACCCTA TCCATTCAAGAAATCAAATTTGGTGACAATGACACCT TATCCGCCATAACAGCTGGTATGTGTCATGCAGACTA CCTGTTTTTGGTGACTGATGTGGACTGTCTTTACACGG ATAACCCTCGTACGAATCCGGACGCTGAGCCAATCGT GTTAGTTAGAAATATGAGGAATCTAAACGTCAATACC GAAAGTGGAGGTTCCGCCGTAGGAACAGGAGGAATG ACAACTAAATTGATCGCAGCTGATTTGGGTGTATCTGC AGGTGTTACAACGATTATTTGCAAAAGTGAACATCCC GAGCAGATTTTGGACATTGTAGAGTACAGTATCCGTG CTGATAGAGTCGAAAATGAGGCTAAATATCTGGTCAT CAACGAAGAGGAAACTGTGGAACAATTTCAAGAGATC AATCGGTCAGAACTGAGGGAGTTGAACAAGCTGGACA TTCCTTTGCATACACGTTTCGTTGGCCACAGTTTTAAT GCTGTTAATAACAAAGAGTTTTGGTTACTCCATGGACT AAAGGCCAACGGAGCCATTATCATTGATCCAGGTTGT TATAAGGCTATCACTAGAAAAAACAAAGCTGGTATTC TTCCAGCTGGAATTATTTCCGTAGAGGGTAATTTCCAT GAATACGAGTGTGTTGATGTTAAGGTAGGACTAAGAG ATCCAGATGACCCACATTCACTAGACCCCAATGAAGA ACTTTACGTCGTTGGCCGTGCCCGTTGTAATTACCCCA GCAATCAAATCAACAAAATTAAGGGTCTACAAAGCTC GCAGATCGAGCAGGTTCTAGGTTACGCTGACGGTGAG TATGTTGTTCACAGGGACAACTTGGCTTTCCCAGTATT TGCCGATCCAGAACTGTTGGATGTTGTTGAGAGTACC CTGTCTGAACAGGAGAGAGAATCCAAACCAAATAAAT AG |

TABLE 12-continued

BRIEF DESCRIPTION OF THE SEQUENCES

| SEQ ID NO: Description | Sequence |
|---|---|
| 90 Sequence of the 3'-region that was used to knock into the PpPRO1 locus: | AATTTCACATATGCTGCTTGATTATGTAATTATACCTT GCGTTCGATGGCATCGATTTCCTCTTCTGTCAATCGCG CATCGCATTAAAAGTATACTTTTTTTTTTTTCCTATAGT ACTATTCGCCTTATTATAAACTTTGCTAGTATGAGTTC TACCCCCAAGAAAGAGCCTGATTTGACTCCTAAGAAG AGTCAGCCTCCAAAGAATAGTCTCGGTGGGGGTAAAG GCTTTAGTGAGGAGGGTTTCTCCCAAGGGGACTTCAG CGCTAAGCATATACTAAATCGTCGCCCTAACACCGAA GGCTCTTCTGTGGCTTCGAACGTCATCAGTTCGTCATC ATTGCAAAGGTTACCATCCTCTGGATCTGGAAGCGTT GCTGTGGGAAGTGTGTTGGGATCTTCGCCATTAACTCT TTCTGGAGGGTTCCACGGGCTTGATCCAACCAAGAAT AAAATAGACGTTCCAAAGTCGAAACAGTCAAGGAGA CAAAGTGTTCTTTCTGACATGATTTCCACTTCTCATGC AGCTAGAAATGATCACTCAGAGCAGCAGTTACAAACT GGACAACAATCAGAACAAAAAGAAGAAGATGGTAGT CGATCTTCTTTTTCTGTTTCTTCCCCCGCAAGAGATATC CGGCACCCAGATGTACTGAAAACTGTCGAGAAACATC TTGCCAATGACAGCGAGATCGACTCATCTTTACAACTT CAAGGTGGAGATGTCACTAGAGGCATTTATCAATGGG TAACTGGAGAAAGTAGTCAAAAAGATAACCCGCCTTT GAAACGAGCAAATAGTTTTAATGATTTTTCTTCTGTGC ATGGTGACGAGGTAGGCAAGGCAGATGCTGACCACG ATCGTGAAAGCGTATTCGACGAGGATGATATCTCCAT TGATGATATCAAAGTTCCGGGAGGGATGCGTCGAAGT TTTTTATTACAAAAGCATAGAGACCAACAACTTTCTGG ACTGAATAAAACGGCTCACCAACCAAAACAACTTACT AAACCTAATTTCTTCACGAACAACTTTATAGAGTTTTT GGCATTGTATGGGCATTTTGCAGGTGAAGATTTGGAG GAAGACGAAGATGAAGATTTAGACAGTGGTTCCGAAT CAGTCGCAGTCAGTGATAGTGAGGGAGAATTCAGTGA GGCTGACAACAATTTGTTGTATGATGAAGAGTCTCTCC TATTAGCACCTAGTACCTCCAACTATGCGAGATCAAG AATAGGAAGTATTCGTACTCCTACTTATGGATCTTTCA GTTCAAATGTTGGTTCTTCGTCTATTCATCAGCAGTTA ATGAAAAGTCAAATCCCGAAGCTGAAGAAACGTGGA CAGCACAAGCATAAAACACAATCAAAAATACGCTCGA AGAAGCAAACTACCACCGTAAAAGCAGTGTTGCTGCT ATTAAA |
| 91 Sequence of the PpTRP2 gene integration locus: | GGTTTCTCAATTACTATATACTACTAACCATTTACCTG TAGCGTATTTCTTTTCCCTCTTCGCAAAGCTCAAGGG CATCTTCTTGACTCATGAAAAATATCTGGATTTCTTCT GACAGATCATCACCCTTGAGCCCAACTCTCTAGCCTAT GAGTGTAAGTGATAGTCATCTTGCAACAGATTATTTTG GAACGCAACTAACAAAGCAGATACACCCTTCAGCAGA ATCCTTTCTGGATATTGTGAAGAATGATCGCCAAAGTC ACAGTCCTGAGACAGTTCCTAATCTTTACCCCATTTAC AAGTTCATCCAATCAGACTTCTTAACGCCTCATCTGGC TTATATCAAGCTTACCAACAGTTCAGAAACTCCCAGTC CAAGTTTCTTGCTTGAAAGTGCGAAGAATGGTGACAC CGTTGACAGGTACACCTTTATGGGACATTCCCCCAGA AAAATAATCAAGACTGGGCCTTTAGAGGGTGCTGAAG TTGACCCCTTGGTGCTTCTGGAAAAAGAACTGAAGGG CACCAGACAAGCGCAACTTCCTGGTATTCCTCGTCTAA GTGGTGGTGCCATAGGATACATCTCGTACGATTGTATT AAGTACTTTGAACCAAAAACTGAAAGAAAACTGAAA GATGTTTTGCAACTTCCGGAAGCAGCTTTGATGTTGTT CGACACGATCGTGGCTTTTGACAATGTTTATCAAAGAT TCCAGGTAATTGGAAACGTTTCTCTATCCGTTGATGAC TCGGACGAAGCTATTCTTGAGAAATATTATAAGACAA GAGAAGAAGTGGAAAAGATCAGTAAAGTGGTATTTGA CAATAAAACTGTTCCCTACTATGAACAGAAAGATATT ATTCAAGGCCAAACGTTCACCTCTAATATTGGTCAGG AAGGGTATGAAAACCATGTTCGCAAGCTGAAAGAACA TATTCTGAAAGGAGACATCTTCCAAGCTGTTCCCTCTC AAAGGGTAGCCAGGCCGACCTCATTGCACCCTTTCAA CATCTATCGTCATTTGAGAACTGTCAATCCTTCTCCAT ACATGTTCTATATTGACTATCTAGACTTCCAAGTTGTT GGTGCTTCACCTGAATTACTAGTTAAATCCGACAACA ACAACAAAATCATCACACATCCTATTGCTGGAACTCTT CCCAGAGGTAAAACTATCGAAGAGGACGACAATTATG CTAAGCAATTGAAGTCGTCTTTGAAAGACAGGGCCGA GCACGTCATGCTGGTAGATTTGGCCAGAAATGATATT |

TABLE 12-continued

BRIEF DESCRIPTION OF THE SEQUENCES

| SEQ ID NO: | Description | Sequence |
|---|---|---|
| | | AACCGTGTGTGTGAGCCCACCAGTACCACGGTTGATC GTTTATTGACTGTGGAGAGATTTTCTCATGTGATGCAT CTTGTGTCAGAAGTCAGTGGAACATTGAGACCAAACA AGACTCGCTTCGATGCTTTCAGATCCATTTTCCCAGCA GGAACCGTCTCCGGTGCTCCGAAGGTAAGAGCAATGC AACTCATAGGAGAATTGGAAGGAGAAAAGAGAGGTG TTTATGCGGGGGCCGTAGGACACTGGTCGTACGATGG AAAATCGATGGACACATGTATTGCCTTAAGAACAATG GTCGTCAAGGACGGTGTCGCTTACCTTCAAGCCGGAG GTGGAATTGTCTACGATTCTGACCCCTATGACGAGTAC ATCGAAACCATGAACAAAATGAGATCCAACAATAACA CCATCTTGGAGGCTGAGAAAATCTGGACCGATAGGTT GGCCAGAGACGAGAATCAAAGTGAATCCGAAGAAAA CGATCAATGAACGGAGGACGTAAGTAGGAATTTATG |
| 92 | Human UDP-GlcNAc 2-epimerase/N-acetylmannosamine kinase (HsGNE) codon opitimized | ATGGAAAAGAACGGTAACAACAGAAAGTTGAGAGTTT GTGTTGCTACTTGTAACAGAGCTGACTACTCCAAGTTG GCTCCAATCATGTTCGGTATCAAGACTGAGCCAGAGT TCTTCGAGTTGGACGTTGTTGTTTTGGGTTCCCACTTG ATTGATGACTACGGTAACACTTACAGAATGATCGAGC AGGACGACTTCGACATCAACACTAGATTGCACACTAT TGTTAGAGGAGAGGACGAAGCTGCTATGGTTGAATCT GTTGGATTGGCTTTGGTTAAGTTGCCAGACGTTTTGAA CAGATTGAAGCCAGACATCATGATTGTTCACGGTGAC AGATTCGATGCTTTGGCTTTGGCTACTTCCGCTGCTTT GATGAACATTAGAATCTTGCACATCGAGGGTGGTGAA GTTTCTGGTACTATCGACGACTCCATCAGACACGCTAT CACTAAGTTGGCTCACTACCATGTTTGTTGTACTAGAT CCGCTGAGCAACACTTGATTTCCATGTGTGAGGACCA CGACAGAATTTTGTTGGCTGGTTGTCCATCTTACGACA AGTTGTTGTCCGCTAAGAACAAGGACTACATGTCCAT CATCAGAATGTGGTTGGGTGACGACGTTAAGTCTAAG GACTACATCGTTGCTTTGCAGCACCCAGTTACTACTGA CATCAAGCACTCCATCAAGATGTTCGAGTTGACTTTGG ACGCTTTGATCTCCTTCAACAAGAGAACTTTGGTTTTG TTCCCAAACATTGACGCTGGTTCCAAAGAGATGGTTA GAGTTATGAGAAGAAGGGTATCGAACACCACCCAA ACTTCAGAGCTGTTAAGCACGTTCCATTCGACCAATTC ATCCAGTTGGTTGCTCATGCTGGTTGTATGATCGGTAA CTCCTCCTGTGGTGTTAGAGAAGTTGGTGCTTTCGGTA CTCCAGTTATCAACTTGGGTACTAGACAGATCGGTAG AGAGACTGGAGAAAACGTTTTGCATGTTAGAGATGCT GACACTCAGGACAAGATTTTGCAGGCTTTGCACTTGC AATTCGGAAAGCAGTACCCATGTTCCAAAATCTACGG TGACGGTAACGCTGTTCCAAGAATCTTGAAGTTTTTGA AGTCCATCGACTTGCAAGAGCCATTGCAGAAGAAGTT CTGTTTCCCACCAGTTAAGGAGAACATCTCCCAGGAC ATTGACCACATCTTGGAGACATTGTCCGCTTTGGCTGT TGATTTGGGTGGAACTAACTTGAGAGTTGCTATCGTTT CCATGAAGGGAGAGATCGTTAAGAAGTACACTCAGTT CAACCCAAAGACTTACGAGGAGAGAATCAACTTGATC TTGCAGATGTGTGTTGAAGCTGCTGCTGAGGCTGTTAA GTTGAACTGTAGAATCTTGGGTGTTGGTATCTCTACTG GTGGTAGAGTTAATCCAAGAGAGGGTATCGTTTTGCA CTCCACTAAGTTGATTCAGGAGTGGAACTCCGTTGATT TGAGAACTCCATTGTCCGACACATTGCACTTGCCAGTT TGGGTTGACAACGACGGTAATTGTGCTGCTTTGGCTG AGAGAAAGTTCGGTCAAGGAAAGGGATTGGAGAACTT CGTTACTTTGATCACTGGTACTGGTATTGGTGGTGGTA TCATTCACCAGCACGAGTTGATTCACGGTTCTTCCTTC TGTGCTGCTGAATTGGGACACTTGGTTGTTTCTTTGGA CGGTCCAGACTGTTCTTGTGGTTCCCACGGTTGTATTG AAGCTTACGCATCAGGAATGGCATTGCAGAGAGAGGC TAAGAAGTTGCACGACGAGGACTTGTTGTTGGTTGAG GGAATGTCTGTTCCAAAGGACGAGGCTGTTGGTGCTT TGCATTTGATCCAGGCTGCTAAGTTGGGTAATGCTAA GGCTCAGTCCATCTTGAGAACTGCTGGTACTGCTTTGG GATTGGGTGTTGTTAATATCTTGCACACTATGAACCCA TCCTTGGTTATCTTGTCCGGTGTTTTGGCTTCTCACTAC ATCCACATCGTTAAGGACGTTATCAGACAGCAAGCTT TGTCCTCCGTTCAAGACGTTGATGTTGTTGTTTCCGAC TTGGTTGACCCAGCTTTGTTGGGTGCTGCTTCCATGGT TTTGGACTACACTACTAGAAGAATCTACTAATAG |

TABLE 12-continued

BRIEF DESCRIPTION OF THE SEQUENCES

| SEQ ID NO: | Description | Sequence |
|---|---|---|
| 93 | Sequence of the PpARG1 auxotrophic marker: | CAGTTGAGCCAGACCGCGCTAAACGCATACCAATTGC<br>CAAATCAGGCAATTGTGAGACAGTGGTAAAAAAGATG<br>CCTGCAAAGTTAGATTCACACAGTAAGAGAGATCCTA<br>CTCATAAATGAGGCGCTTATTTAGTAGCTAGTGATAG<br>CCACTGCGGTTCTGCTTTATGCTATTTGTTGTATGCCTT<br>ACTATCTTTGTTTGGCTCCTTTTTCTTGACGTTTTCCGT<br>TGGAGGGACTCCCTATTCTGAGTCATGAGCCGCACAG<br>ATTATCGCCCAAAATTGACAAAATCTTCTGGCGAAAA<br>AAGTATAAAAGGAGAAAAAAGCTCACCCTTTTCCAGC<br>GTAGAAAGTATATATCAGTCATTGAAGACTATTATTTA<br>AATAACACAATGTCTAAAGGAAAAGTTTGTTTGGCCT<br>ACTCCGGTGGTTTGGATACCTCCATCATCCTAGCTTGG<br>TTGTTGGAGCAGGGATACGAAGTCGTTGCCTTTTTAGC<br>CAACATTGGTCAAGAGGAAGACTTTGAGGCTGCTAGA<br>GAGAAAGCTCTGAAGATCGGTGCTACCAAGTTTATCG<br>TCAGTGACGTTAGGAAGGAATTTGTTGAGGAAGTTTT<br>GTTCCCAGCAGTCCAAGTTAACGCTATCTACGAGAAC<br>GTCTACTTACTGGGTACCTCTTTGGCCAGACCAGTCAT<br>TGCCAAGGCCCAAATAGAGGTTGCTGAACAAGAAGGT<br>TGTTTTGCTGTTGCCCACGGTTGTACCGGAAAGGGTAA<br>CGATCAGGTTAGATTTGAGCTTTCCTTTTATGCTCTGA<br>AGCCTGACGTTGTCTGTATCGCCCCATGGAGAGACCC<br>AGAATTCTTCGAAAGATTCGCTGGTAGAAATGACTTG<br>CTGAATTACGCTGCTGAGAAGGATATTCCAGTTGCTC<br>AGACTAAAGCCAAGCCATGGTCTACTGATGAGAACAT<br>GGCTCACATCTCCTTCGAGGCTGGTATTCTAGAAGATC<br>CAAACACTACTCCTCCAAAGGACATGTGGAAGCTCAC<br>TGTTGACCCAGAAGATGCACCAGACAAGCCAGAGTTC<br>TTTGACGTCCACTTTGAGAAGGGTAAGCCAGTTAAAT<br>TAGTTCTCGAGAACAAAACTGAGGTCACCGATCCGGT<br>TGAGATCTTTTTGACTGCTAACGCCATTGCTAGAAGAA<br>ACGGTGTTGGTAGAATTGACATTGTCGAGAACAGATT<br>CATCGGAATCAAGTCCAGAGGTTGTTATGAAACTCCA<br>GGTTTGACTCTACTGAGAACCACTCACATCGACTTGG<br>AAGGTCTTACCGTTGACCGTGAAGTTAGATCGATCAG<br>AGACACTTTTGTTACCCCAACCTACTCTAAGTTGTTAT<br>ACAACGGGTTGTACTTTACCCCAGAAGGTGAGTACGT<br>CAGAACTATGATTCAGCCTTCTCAAAACACCGTCAAC<br>GGTGTTGTTAGAGCCAAGGCCTACAAAGGTAATGTGT<br>ATAACCTAGGAAGATACTCTGAAACCGAGAAATTGTA<br>CGATGCTACCGAATCTTCCATGGATGAGTTGACCGGA<br>TTCCACCCTCAAGAAGCTGGAGGATTTATCACAACAC<br>AAGCCATCAGAATCAAGAAGTACGGAGAAAGTGTCA<br>GAGAGAAGGGAAAGTTTTTGGGACTTTAACTCAAGTA<br>AAAGGATAGTTGTACAATTATATATACGAAGAATAAA<br>TCATTACAAAAGTATTCGTTTCTTTGATTCTTAACAG<br>GATTCATTTTCTGGGTGTCATCAGGTACAGCGCTGAAT<br>ATCTTGAAGTTAACATCGAGCTCATCATCGACGTTCAT<br>CACACTAGCCACGTTTCCGCAACGGTAGCAATAATTA<br>GGAGCGGACCACACAGTGACGACATC |
| 94 | Human CMP-sialic acid synthase (HsCSS) codon optimized | ATGGACTCTGTTGAAAAGGGTGCTGCTACTTCTGTTTC<br>CAACCCAAGAGGTAGACCATCCAGAGGTAGACCTCCT<br>AAGTTGCAGAGAAACTCCAGAGGTGGTCAAGGTAGA<br>GGTGTTGAAAAGCCACCACACTTGGCTGCTTTGATCTT<br>GGCTAGAGGAGGTTCTAAGGGTATCCCATTGAAGAAC<br>ATCAAGCACTTGGCTGGTGTTCCATTGATTGGATGGGT<br>TTTGAGAGCTGCTTTGGACTCTGGTGCTTTCCAATCTG<br>TTTGGGTTTCCACTGACCACGACGAGATTGAGAACGT<br>TGCTAAGCAATTCGGTGCTCAGGTTCACAGAAGATCC<br>TCTGAGGTTTCCAAGGACTCTTCTACTTCCTTGGACGC<br>TATCATCGAGTTCTTGAACTACCACAACGAGGTTGAC<br>ATCGTTGGTAACATCCAAGCTACTTCCCCATGTTTGCA<br>CCCAACTGACTTGCAAAAAGTTGCTGAGATGATCAGA<br>GAAGAGGGTTACGACTCCGTTTTCTCCGTTGTTAGAAG<br>GCACCAGTTCAGATGGTCCGAGATTCAGAAGGGTGTT<br>AGAGAGGTTACAGAGCCATTGAACTTGAACCCAGCTA<br>AAAGACCAAGAAGGCAGGATTGGGACGGTGAATTGT<br>ACGAAAACGGTTCCTTCTACTTCGCTAAGAGACACTT<br>GATCGAGATGGGATACTTGCAAGGTGGAAAGATGGCT<br>TACTACGAGATGAGAGCTGAACACTCCGTTGACATCG<br>ACGTTGATATCGACTGGCCAATTGCTGAGCAGAGAGT<br>TTTGAGATACGGTTACTTCGGAAAGGAGAAGTTGAAG<br>GAGATCAAGTTGTTGGTTTGTAACATCGACGGTTGTTT |

TABLE 12-continued

BRIEF DESCRIPTION OF THE SEQUENCES

| SEQ ID NO: | Description | Sequence |
|---|---|---|
| | | GACTAACGGTCACATCTACGTTTCTGGTGACCAGAAG GAGATTATCTCCTACGACGTTAAGGACGCTATTGGTAT CTCCTTGTTGAAGAAGTCCGGTATCGAAGTTAGATTG ATCTCCGAGAGAGCTTGTTCCAAGCAAACATTGTCCTC TTTGAAGTTGGACTGTAAGATGGAGGTTTCCGTTTCTG ACAAGTTGGCTGTTGTTGACGAATGGAGAAAGGAGAT GGGTTTGTGTTGGAAGGAAGTTGCTTACTTGGGTAAC GAAGTTTCTGACGAGGAGTGTTTGAAGAGAGTTGGTT TGTCTGGTGCTCCAGCTGATGCTTGTTCCACTGCTCAA AAGGCTGTTGGTTACATCTGTAAGTGTAACGGTGGTA GAGGTGCTATTAGAGAGTTCGCTGAGCACATCTGTTT GTTGATGGAGAAAGTTAATAACTCCTGTCAGAAGTAG TAG |
| 95 | Human N-acetylneuraminate-9-phosphate synthase (HsSPS) codon optimized | ATGCCATTGGAATTGGAGTTGTGTCCTGGTAGATGGG TTGGTGGTCAACACCCATGTTTCATCATCGCTGAGATC GGTCAAAACCACCAAGGAGACTTGGACGTTGCTAAGA GAATGATCAGAATGGCTAAGGAATGTGGTGCTGACTG TGCTAAGTTCCAGAAGTCCGAGTTGGAGTTCAAGTTC AACAGAAAGGCTTTGGAAAGACCATACACTTCCAAGC ACTCTTGGGGAAAGACTTACGGAGAACACAAGAGAC ACTTGGAGTTCTCTCACGACCAATACAGAGAGTTGCA GAGATACGCTGAGGAAGTTGGTATCTTCTTCACTGCTT CTGGAATGGACGAAATGGCTGTTGAGTTCTTGCACGA GTTGAACGTTCCATTCTTCAAAGTTGGTTCCGGTGACA CTAACAACTTCCCATACTTGGAAAAGACTGCTAAGAA AGGTAGACCAATGGTTATCTCCTCTGGAATGCAGTCT ATGGACACTATGAAGCAGGTTTACCAGATCGTTAAGC CATTGAACCCAAACTTTTGTTTCTTGCAGTGTACTTCC GCTTACCCATTGCAACCAGAGGACGTTAATTTGAGAG TTATCTCCGAGTACCAGAAGTTGTTCCCAGACATCCCA ATTGGTTACTCTGGTCACGAGACTGGTATTGCTATTTC CGTTGCTGCTGTTGCTTTGGGTGCTAAGGTTTTGGAGA GACACATCACTTTGGACAAGACTTGGAAGGGTTCTGA TCACTCTGCTTCTTTGGAACCTGGTGAGTTGGCTGAAC TTGTTAGATCAGTTAGATTGGTTGAGAGAGCTTTGGGT TCCCCAACTAAGCAATTGTTGCCATGTGAGATGGCTTG TAACGAGAAGTTGGGAAAGTCCGTTGTTGCTAAGGTT AAGATCCCAGAGGGTACTATCTTGACTATGGACATGT TGACTGTTAAAGTTGGAGAGCCAAAGGGTTACCCACC AGAGGACATCTTTAACTTGGTTGGTAAAAAGGTTTTG GTTACTGTTGAGGAGGACGACACTATTATGGAGGAGT TGGTTGACAACCACGGAAAGAAGATCAAGTCCTAG |
| 96 | Mouse alpha-2,6-sialyl transferase catalytic domain (MmmST6) codon optimized | GTTTTTCAAATGCCAAAGTCCCAGGAGAAAGTTGCTG TTGGTCCAGCTCCACAAGCTGTTTTCTCCAACTCCAAG CAAGATCCAAAGGAGGGTGTTCAAATCTTGTCCTACC CAAGAGTTACTGCTAAGGTTAAGCCACAACCATCCTT GCAAGTTTGGGACAAGGACTCCACTTACTCCAAGTTG AACCCAAGATTGTTGAAGATTTGGAGAAACTACTTGA ACATGAACAAGTACAAGGTTTCCTACAAGGGTCCAGG TCCAGGTGTTAAGTTCTCCGTTGAGGCTTTGAGATGTC ACTTGAGAGACCACGTTAACGTTTCCATGATCGAGGC TACTGACTTCCCATTCAACACTACTGAATGGGAGGGA TACTTGCCAAAGGAGAACTTCAGAACTAAGGCTGGTC CATGGCATAAGTGTGCTGTTGTTTCTTCTGCTGGTTCC TTGAAGAACTCCCAGTTGGGTAGAGAAATTGACAACC ACGACGCTGTTTTGAGATTCAACGGTGCTCCAACTGA CAACTTCCAGCAGGATGTTGGTACTAAGACTACTATC AGATTGGTTAACTCCCAATTGGTTACTACTGAAGAGA GATTCTTGAAGGACTCCTTGTACACTGAGGGAATCTTG ATTTTGTGGGACCCATCTGTTTACCACGCTGACATTCC ACAATGGTATCAGAAGCCAGACTACAACTTCTTCGAG ACTTACAAGTCCTACAGAAGATTGCACCCATCCCAGC CATTCTACATCTTGAAGCCACAAATGCCATGGGAATT GTGGGACATCATCCAGGAAATTTCCCCAGACTTGATC CAACCAAACCCACCATCTTCTGGAATGTTGGGTATCAT CATCATGATGACTTTGTGTGACCAGGTTGACATCTACG AGTTCTTGCCATCCAAGAGAAAGACTGATGTTTGTTAC TACCACCAGAAGTTCTTCGACTCCGCTTGTACTATGGG AGCTTACCACCCATTGTTGTTCGAGAAGAACATGGTT AAGCACTTGAACGAAGGTACTGACGAGGACATCTACT TGTTCGGAAAGGCTACTTTGTCCGGTTTCAGAAACAA CAGATGTTAG |

TABLE 12-continued

BRIEF DESCRIPTION OF THE SEQUENCES

| SEQ ID NO: | Description | Sequence |
|---|---|---|
| 97 | Human UDP-GlcNAc 2-epimerase/N-acetylmannosamine kinase (HsGNE) codon opitimized | ATGGAAAAGAACGGTAACAACAGAAAGTTGAGAGTTT GTGTTGCTACTTGTAACAGAGCTGACTACTCCAAGTTG GCTCCAATCATGTTCGGTATCAAGACTGAGCCAGAGT TCTTCGAGTTGGACGTTGTTGTTTTGGGTTCCCACTTG ATTGATGACTACGGTAACACTTACAGAATGATCGAGC AGGACGACTTCGACATCAACACTAGATTGCACACTAT TGTTAGAGGAGAGGACGAAGCTGCTATGGTTGAATCT GTTGGATTGGCTTTGGTTAAGTTGCCAGACGTTTTGAA CAGATTGAAGCCAGACATCATGATTGTTCACGGTGAC AGATTCGATGCTTTGGCTTTGGCTACTTCCGCTGCTTT GATGAACATTAGAATCTTGCACATCGAGGGTGGTGAA GTTTCTGGTACTATCGACGACTCCATCAGACACGCTAT CACTAAGTTGGCTCACTACCATGTTTGTTGTACTAGAT CCGCTGAGCAACACTTGATTTCCATGTGTGAGGACCA CGACAGAATTTTGTTGGCTGGTTGTCCATCTTACGACA AGTTGTTGTCCGCTAAGAACAAGGACTACATGTCCAT CATCAGAATGTGGTTGGGTGACGACGTTAAGTCTAAG GACTACATCGTTGCTTTGCAGCACCCAGTTACTACTGA CATCAAGCACTCCATCAAGATGTTCGAGTTGACTTTGG ACGCTTTGATCTCCTTCAACAAGAGAACTTTGGTTTTG TTCCCAAACATTGACGCTGGTTCCAAAGAGATGGTTA GAGTTATGAGAAAGAAGGGTATCAACACCACCCAA ACTTCAGAGCTGTTAAGCACGTTCCATTCGACCAATTC ATCCAGTTGGTTGCTCATGCTGGTTGTATGATCGGTAA CTCCTCCTGTGGTGTTAGAGAAGTTGGTGCTTTCGGTA CTCCAGTTATCAACTTGGGTACTAGACAGATCGGTAG AGAGACTGGAGAAAACGTTTTGCATGTTAGAGATGCT GACACTCAGGACAAGATTTTGCAGGCTTTTGCACTTGC AATTCGGAAAGCAGTACCCATGTTCCAAAATCTACGG TGACGGTAACGCTGTTCCAAGAATCTTGAAGTTTTTGA AGTCCATCGACTTGCAAGAGCCATTGCAGAAGAAGTT CTGTTTCCCACCAGTTAAGGAGAACATCTCCCAGGAC ATTGACCACATCTTGGAGACATTGTCCGCTTTGGCTGT TGATTTGGGTGGAACTAACTTGAGAGTTGCTATCGTTT CCATGAAGGGAGAGATCGTTAAGAAGTACACTCAGTT CAACCCAAAGACTTACGAGGAGAGAATCAACTTGATC TTGCAGATGTGTGTTGAAGCTGCTGCTGAGGCTGTTAA GTTGAACTGTAGAATCTTGGGTGTTGGTATCTCTACTG GTGGTAGAGTTAATCCAAGAGAGGGTATCGTTTTGCA CTCCACTAAGTTGATTCAGGAGTGGAACTCCGTTGATT TGAGAACTCCATTGTCCGACACATTGCACTTGCCAGTT TGGGTTGACAACGACGGTAATTGTGCTGCTTTGGCTG AGAGAAAGTTCGGTCAAGGAAAGGGATTGGAGAACTT CGTTACTTTGATCACTGGTACTGGTATTGGTGGTGGTA TCATTCACCAGCACGAGTTGATTCACGGTTCTTCCTTC TGTGCTGCTGAATTGGGACACTTGGTTGTTTCTTTGGA CGGTCCAGACTGTTCTTGTGGTTCCCACGGTTGTATTG AAGCTTACGCATCAGGAATGGCATTGCAGAGAGAGGC TAAGAAGTTGCACGACGAGGACTTGTTGTTGGTTGAG GGAATGTCTGTTCCAAAGGACGAGGCTGTTGGTGCTT TGCATTTGATCCAGGCTGCTAAGTTGGGTAATGCTAA GGCTCAGTCCATCTTGAGAACTGCTGGTACTGCTTTGG GATTGGGTGTTGTTAATATCTTGCACACTATGAACCCA TCCTTGGTTATCTTGTCCGGTGTTTTGGCTTCTCACTAC ATCCACATCGTTAAGGACGTTATCAGACAGCAAGCTT TGTCCTCCGTTCAAGACGTTGATGTTGTTGTTTCCGAC TTGGTTGACCCAGCTTTGTTGGGTGCTGCTTCCATGGT TTTGGACTACACTACTAGAAGAATCTACTAATAG |
| 98 | Pp TRP2: 5' and ORF | ACTGGGCCTTTAGAGGGTGCTGAAGTTGACCCCTTGG TGCTTCTGGAAAAAGAACTGAAGGGCACCAGACAAGC GCAACTTCCTGGTATTCCTCGTCTAAGTGGTGGTGCCA TAGGATACATCTCGTACGATTGTATTAAGTACTTTGAA CCAAAAACTGAAAGAAAACTGAAAGATGTTTTGCAAC TTCCGGAAGCAGCTTTGATGTTGTTCGACACGATCGTG GCTTTTGACAATGTTTATCAAAGATTCCAGGTAATTGG AAACGTTTCTCTATCCGTTGATGACTCGGACGAAGCTA TTCTTGAGAAATATTATAAGACAAGAGAAGAAGTGGA AAAGATCAGTAAAGTGGTATTTGACAATAAAACTGTT CCCTACTATGAACAGAAAGATATTATTCAAGGCCAAA CGTTCACCTCTAATATTGGTCAGGAAGGGTATGAAAA CCATGTTCGCAAGCTGAAAGAACATATTCTGAAGGA GACATCTTCCAAGCTGTTCCCTCTCAAAGGGTAGCCA |

TABLE 12-continued

BRIEF DESCRIPTION OF THE SEQUENCES

| SEQ ID NO: | Description | Sequence |
|---|---|---|
| | | GGCCGACCTCATTGCACCCTTTCAACATCTATCGTCAT
TTGAGAACTGTCAATCCTTCTCCATACATGTTCTATAT
TGACTATCTAGACTTCCAAGTTGTTGGTGCTTCACCTG
AATTACTAGTTAAATCCGACAACAACAACAAAATCAT
CACACATCCTATTGCTGGAACTCTTCCCAGAGGTAAA
ACTATCGAAGAGGACGACAATTATGCTAAGCAATTGA
AGTCGTCTTTGAAAGACAGGGCCGAGCACGTCATGCT
GGTAGATTTGGCCAGAAATGATATTAACCGTGTGTCT
GAGCCCACCAGTACCACGGTTGATCGTTTATTGACTGT
GGAGAGATTTTCTCATGTGATGCATCTTGTGTCAGAAG
TCAGTGGAACATTGAGACCAAACAAGACTCGCTTCGA
TGCTTTCAGATCCATTTTCCCAGCAGGTACCGTCTCCG
GTGCTCCGAAGGTAAGAGCAATGCAACTCATAGGAGA
ATTGGAAGGAGAAAAGAGAGGTGTTTATGCGGGGGCC
GTAGGACACTGGTCGTACGATGGAAAATCGATGGACA
CATGTATTGCCTTAAGAACAATGGTCGTCAAGGACGG
TGTCGCTTACCTTCAAGCCGGAGGTGGAATTGTCTACG
ATTCTGACCCCTATGACGAGTACATCGAAACCATGAA
CAAAATGAGATCCAACAATAACACCATCTTGGAGGCT
GAGAAAATCTGGACCGATAGGTTGGCCAGAGACGAG
AATCAAAGTGAATCCGAAGAAAACGATCAATGA |
| 99 | PpTRP2 3' region | ACGGAGGACGTAAGTAGGAATTTATGTAATCATGCCA
ATACATCTTTAGATTTCTTCCTCTTCTTTTTAACGAAAG
ACCTCCAGTTTTGCACTCTCGACTCTCTAGTATCTTCC
CATTTCTGTTGCTGCAACCTCTTGCCTTCTGTTTCCTTC
AATTGTTCTTCTTTCTTCTGTTGCACTTGGCCTTCTTCC
TCCATCTTTCGTTTTTTTTCAAGCCTTTTCAGCAGTTCT
TCTTCCAAGAGCAGTTCTTTGATTTTCTCTCTCCAATCC
ACCAAAAAACTGGATGAATTCAACCGGGCATCATCAA
TGTTCCACTTTCTTTCTCTTATCAATAATCTACGTGCTT
CGGCATACGAGGAATCCAGTTGCTCCCTAATCGAGTC
ATCCACAAGGTTAGCATGGGCCTTTTTCAGGGTGTCA
AAAGCATCTGGAGCTCGTTTATTCGGAGTCTTGTCTGG
ATGGATCAGCAAAGACTTTTTGCGGAAAGTCTTTCTTA
TATCTTCCGGAGAACAACCTGGTTTCAAATCCAAGAT
GGCATAGCTGTCCAATTTGAAAGTGGAAAGAATCCTG
CCAATTTCCTTCTCTCGTGTCAGCTCGTTCTCCTCCTTT
TGCAACAGGTCCACTTCATCTGGCATTTTTCTTTATGT
TAACTTTAATTATTATTAATTATAAAGTTGATTATCGT
TATCAAAATAATCATATTCGAGAAATAATCCGTCCAT
GCAATATATAAATAAGAATTCATAATAATGTAATGAT
AACAGTACCTCTGATGACCTTTGATGAACCGCAATTTT
CTTTCCAATGACAAGACATCCCTATAATACAATTATAC
AGTTTATATATCACAAATAATCACCTTTTTATAAGAAA
ACCGTCCTCTCCGTAACAGAACTTATTATCCGCACGTT
ATGGTTAACACACTACTAATACCGATATAGTGTATGA
AGTCGCTACGAGATAGCCATCCAGGAAACTTACCAAT
TCATCAGCACTTTCATGATCCGATTGTTGGCTTTATTC
TTTGCGAGACAGATACTTGCCAATGAAATAACTGATC
CCACAGATGAGAATCCGGTGCTCGT |
| 100 | Sequence of the 5'-Region used for knock out of STE13 | TTGGGGGCCTCCAGGACTTGCTGAAATTTGCTGACTCA
TCTTCGCCATCCAAGGATAATGAGTTAGCTAATGTGA
CAGTTAATGAGTCGTCTTGACTAACGGGGAACATTTC
ATTATTTATATCCAGAGTCAATTTGATAGCAGAGTTTG
TGGTTGAAATACCTATGATTCGGGAGACTTTGTTGTAA
CGACCATTATCCACAGTTTGGACCGTGAAAATGTCAT
CGAAGAGAGCAGACGACATATTATCTATTGTGGTAAG
TGATAGTTGGAAGTCCGACTAAGGCATGAAAATGAGA
AGACTGAAAATTTAAAGTTTTTGAAAACACTAATCGG
GTAATAACTTGGAAATTACGTTTACGTGCCTTTAGCTC
TTGTCCTTACCCCTGATAATCTATCCATTTCCCGAGAG
ACAATGACATCTCGGACAGCTGAGAACCCGTTCGATA
TAGAGCTTCAAGAGAATCTAAGTCCACGTTCTTCCAAT
TCGTCCATATTGGAAAACATTAATGAGTATGCTAGAA
GACATCGCAATGATTCGCTTTCCCAAGAATGTGATAA
TGAAGATGAGAACGAAAATCTCAATTATACTGATAAC
TTGGCCAAGTTTTCAAAGTCTGGAGTATCAAGAAAGA
GCTGTATGCTAATATTTGGTATTTGCTTTGTTATCTGG
CTGTTTCTCTTTGCCTTGTATGCGAGGGACAATCGATT
TTCCAATTTGAACGAGTACGTTCCAGATTCAAACAG |

TABLE 12-continued

BRIEF DESCRIPTION OF THE SEQUENCES

| SEQ ID NO: | Description | Sequence |
|---|---|---|
| 101 | Sequence of the 3'-Region used for knock out of STE13 | CTACTGGGAACCACGAGACATCACTGCAGTAGTTTCC AAGTGGATTTCAGATCACTCATTTGTGAATCCTGACAA AACTGCGATATGGGGGTGGTCTTACGGTGGGTTCACT ACGCTTAAGACATTGGAATATGATTCTGGAGAGGTTT TCAAATATGGTATGGCTGTTGCTCCAGTAACTAATTGG CTTTTGTATGACTCCATCTACACTGAAAGATACATGAA CCTTCCAAAGGACAATGTTGAAGGCTACAGTGAACAC AGCGTCATTAAGAAGGTTTCCAATTTTAAGAATGTAA ACCGATTCTTGGTTTGTCACGGGACTACTGATGATAAC GTGCATTTTCAGAACACACTAACCTTACTGGACCAGTT CAATATTAATGGTGTTGTGAATTACGATCTTCAGGTGT ATCCCGACAGTGAACATAGCATTGCCCATCACAACGC AAATAAAGTGATCTACGAGAGGTTATTCAAGTGGTTA GAGCGGGCATTTAACGATAGATTTTTGTAACATTCCGT ACTTCATGCCATACTATATATCCTGCAAGGTTTCCCTT TCAGACACAATAATTGCTTTGCAATTTTACATACCACC AATTGGCAAAATAATCTCTTCAGTAAGTTGAATGCTT TTCAAGCCAGCACCGTGAGAAATTGCTACAGCGCGCA TTCTAACATCACTTTAAAATTCCCTCGCCGGTGCTCAC TGGAGTTTCCAACCCTTAGCTTATCAAAATCGGGTGAT AACTCTGAGTTTTTTTTTTCACTTCTATTCCTAAACCTT CGCCCAATGCTACCACCTCCAATCAACATCCCGAAAT GGATAGAAGAGAATGGACATCTCTTGCAACCTCCGGT TAATAATTACTGTCTCCACAGAGGAGGATTTACGGTA ATGATTGTAGGTGGGCCTAATG |
| 102 | Sequence of the 5'-Region used for knock out of DAP2 | CACCTGGGCCTGTTGCTGCTGGTACTGCTGTTGGAACT GTTGGTATTGTTGCTGATCTAAGGCCGCCTGTTCCACA CCGTGTGTATCGAATGCTTGGGCAAAATCATCGCCTG CCGGAGGCCCCACTACCGCTTGTTCCTCCTGCTCTTGT TTGTTTTGCTCATTGATGATATCGGCGTCAATGAATTG ATCCTCAATCGTGTGGTGGTGGTGTCGTGATTCCTCTT CTTTCTTGAGTGCCTTATCCATATTCCTATCTTAGTCTA CCAATAATTTTGTTAAACACACGCTGTTGTTTATGAAA AGTCGTCAAAAGGTTAAAAATTCTACTTGGTGTGTGTC AGAGAAAGTAGTGCAGACCCCCAGTTTGTTGACTAGT TGAGAAGGCGGCTCACTATTGCGCGAATAGCATGAGA AATTTGCAAACATCTGGCAAAGTGGTCAATACCTGCC AACCTGCCAATCTTCGCGACGGAGGCTGTTAAGCGGG TTGGGTTCCCAAAGTGAATGGATATTACGGGCAGGAA AAACAGCCCCTTCCACACTAGTCTTTGCTACTGACATC TTCCCTCTCATGTATCCCGAACACAAGTATCGGGAGTA TCAACGGAGGGTGCCCTTATGGCAGTACTCCCTGTTG GTGATTGTACTGCTATACGGGTCTCATTTGCTTATCAG CACCATCAACTTGATACACTATAACCACAAAAATTAT CATGCACACCCAGTCAATAGTGGTATCGTTCTTAATGA GTTTGCTGATGACGATTCATTCTCTTTGAATGGCACTC TGAACTTGGAGAACTGGAGAAATGGTACCTTTTCCCC TAAATTTCATTCCATTCAGTGGACCGAAATAGGTCAG GAAGATGACCAGGGATATTACATTCTCTCTTCCAATTC CTCTTACATAGTAAAGTCTTTATCCGACCCAGACTTTG AATCTGTTCTATTCAACGAGTCTACAATCACTTACAACG |
| 103 | Sequence of the 3'-Region used for knock out of DAP2 | GGCAGCAAAGCCTTACGTTGATGAGAATAGACTGGCC ATTTGGGGTTGGTCTTATGGAGGTTACATGACGCTAA AGGTTTTAGAACAGGATAAAGGTGAAACATTCAAATA TGGAATGTCTGTTGCCCCTGTGACGAATTGGAAATTCT ATGATTCTATCTACACAGAAAGATACATGCACACTCC TCAGGACAATCCAAACTATTATAATTCGTCAATCCATG AGATTGATAATTTGAAGGGAGTGAAGAGGTTCTTGCT AATGCACGGAACTGGTGACGACAATGTTCACTTCCAA AATACACTCAAAGTTCTAGATTTATTTGATTTACATGG TCTTGAAAACTATGATATCCACGTGTTCCCTGATAGTG ATCACAGTATTAGATATCACAACGGTAATGTTATAGT GTATGATAAGCTATTCCATTGGATTAGGCGTGCATTCA AGGCTGGCAAATAAATAGGTGCAAAAATATTATTAGA CTTTTTTTTTCGTTCGCAAGTTATTACTGTGTACCATAC CGATCCAATCCGTATTGTAATTCATGTTCTAGATCCAA AATTTGGGACTCTAATTCATGAGGTCTAGGAAGATGA TCATCTCTATAGTTTTCAGCGGGGGGCTCGATTTGCGG TTGGTCAAAGCTAACATCAAAATGTTTGTCAGGTTCA GTGAATGGTAACTGCTGCTCTTGAATTGGTCGTCTGAC AAATTCTCTAAGTGATAGCACTTCATCTACAATCATTT GCTTCATCGTTTCTATATCGTCCACGACCTCAAACGAG |

| SEQ ID NO: | Description | Sequence |
|---|---|---|
| | | AAATCGAATTTGGAAGAACAGACGGGCTCATCGTTAG<br>GATCATGCCAAACCTTGAGATATGGATGCTCTAAAGC<br>CTCAGTAACTGTAATTCTGTGAGTGGGATCTACCGTGA<br>GCATTCGATCCAGTAAGTCTATCGCTTCAGGGTTGGCA<br>CCGGGAAATAACTGGCTGAATGGGATCTTGGGCATGA<br>ATGGCAGGGAGCGAACATAATCCTGGGCACGCTCTGA<br>TCTGATAGACTGAAGTGTCTCTTCCGAAACAGTACCC<br>AGCGTACTCAAAATCAAGTTCAATTGATCCACATAGT<br>CTCTTCCTCTAAAAATGGGTCGGCCACCTA |
| 104 | HYG$^R$ resistance cassette | GATCTGTTTAGCTTGCCTCGTCCCCGCCGGGTCACCCG<br>GCCAGCGACATGGAGGCCCAGAATACCCTCCTTGACA<br>GTCTTGACGTGCGCAGCTCAGGGGCATGATGTGACTG<br>TCGCCCGTACATTTAGCCCATACATCCCCATGTATAAT<br>CATTTGCATCCATACATTTTGATGGCCGCACGGCGCGA<br>AGCAAAAATTACGGCTCCTCGCTGCGGACCTGCGAGC<br>AGGGAAACGCTCCCCTCACAGACGCGTTGAATTGTCC<br>CCACGCCGCGCCCCTGTAGAGAAATATAAAAGGTTAG<br>GATTTGCCACTGAGGTTCTTCTTTCATATACTTCCTTTT<br>AAAATCTTGCTAGGATACAGTTCTCACATCACATCCG<br>AACATAAACAACCATGGGTAAAAAGCCTGAACTCACC<br>GCGACGTCTGTCGAGAAGTTTCTGATCGAAAAGTTCG<br>ACAGCGTCTCCGACCTGATGCAGCTCTCGGAGGGCGA<br>AGAATCTCGTGCTTTCAGCTTCGATGTAGGAGGGCGT<br>GGATATGTCCTGCGGGTAAATAGCTGCGCCGATGGTT<br>TCTACAAAGATCGTTATGTTTATCGGCACTTTGCATCG<br>GCCGCGCTCCCGATTCCGGAAGTGCTTGACATTGGGG<br>AATTCAGCGAGAGCCTGACCTATTGCATCTCCCGCCGT<br>GCACAGGGTGTCACGTTGCAAGACCTGCCTGAAACCG<br>AACTGCCCGCTGTTCTGCAGCCGGTCGCGGAGGCCAT<br>GGATGCGATCGCTGCGGCCGATCTTAGCCAGACGAGC<br>GGGTTCGGCCCATTCGGACCGCAAGGAATCGGTCAAT<br>ACACTACATGGCGTGATTTCATATGCGCGATTGCTGAT<br>CCCCATGTGTATCACTGGCAAACTGTGATGGACGACA<br>CCGTCAGTGCGTCCGTCGCGCAGGCTCTCGATGAGCT<br>GATGCTTTGGGCCGAGGACTGCCCCGAAGTCCGGCAC<br>CTCGTGCACGCGGATTTCGGCTCCAACAATGTCCTGAC<br>GGACAATGGCCGCATAACAGCGGTCATTGACTGGAGC<br>GAGGCGATGTTCGGGGATTCCCAATACGAGGTCGCCA<br>ACATCTTCTTCTGGAGGCCGTGGTTGGCTTGTATGGAG<br>CAGCAGACGCGCTACTTCGAGCGGAGGCATCCGGAGC<br>TTGCAGGATCGCCGCGGCTCCGGGCGTATATGCTCCG<br>CATTGGTCTTGACCAACTCTATCAGAGCTTGGTTGACG<br>GCAATTTCGATGATGCAGCTTGGGCGCAGGGTCGATG<br>CGACGCAATCGTCCGATCCGGAGCCGGGACTGTCGGG<br>CGTACACAAATCGCCCGCAGAAGCGCGGCCGTCTGGA<br>CCGATGGCTGTGTAGAAGTACTCGCCGATAGTGGAAA<br>CCGACGCCCCAGCACTCGTCCGAGGGCAAAGGAATAA<br>TCAGTACTGACAATAAAAAGATTCTTGTTTTCAAGAA<br>CTTGTCATTTGTATAGTTTTTTTATATTGTAGTTGTTCT<br>ATTTTAATCAAATGTTAGCGTGATTTATATTTTTTTCG<br>CCTCGACATCATCTGCCCAGATGCGAAGTTAAGTGCG<br>CAGAAAGTAATATCATGCGTCAATCGTATGTGAATGC<br>TGGTCGCTATACTGCTGTCGATTCGATACTAACGCCGC<br>CATCCAGTGTCGAAAACGAGCT |
| 105 | Sequence of PpTRP5 5' integration fragment | ACGACGGCCAAATTCATGATACACACTCTGTTTCAGCT<br>GGTTTGGACTACCCTGGAGTTGGTCCTGAATTGGCTGC<br>CTGGAAAGCAAATGGTAGAGCCCAATTTTCCGCTGTA<br>ACTGATGCCCAAGCATTAGAGGGATTCAAAATCCTGT<br>CTCAATTGGAAGGGATCATTCCAGCACTAGAGTCTAG<br>TCATGCAATCTACGCGCATTGCAAATTGCAAAGACT<br>ATGTCTTCGGACCAGTCCTTAGTTATTAATGTATCTGG<br>AAGGGGTGATAAGGACGTCCAGAGTGTAGCTGAGATT<br>TTACCTAAATTGGGACCTCAAATTGGATGGGATTTGC<br>GTTTCAGCGAAGACATTACTAAAGAGTGA |
| 106 | Sequence of PpTRP5 3' integration fragment | TCGATAGCACAATATTCAACTTGACTGGGTGTTAAGA<br>ACTAAGAGCTCTGGGAAACTTTGTATTTATTACTACCA<br>ACACAGTCAAATTATTGGATGTGTTTTTTTTCCAGTA<br>CATTTCACTGAGCAGTTTGTTATACTCGGTCTTTAATC<br>TCCATATACATGCAGATTGTAATACAGATCTGAACAG<br>TTTGATTCTGATTGATCTTGCCACCAATATTCTATTTTT<br>GTATCAAGTAACAGAGTCAATGATCATTGGTAACGTA |

TABLE 12-continued

BRIEF DESCRIPTION OF THE SEQUENCES

| SEQ ID NO: | Description | Sequence |
|---|---|---|
| | | ACGGTTTTCGTGTATAGTAGTTAGAGCCCATCTTGTAA CCTCATTTCCTCCCATATTAAAGTATCAGTGATTCGCT GGAACGATTAACTAAGAAAAAAAAAATATCTGCACAT ACTCATCAGTCTGTAAATCTAAGTCAAAACTGCTGTAT CCAATAGAAATCGGGATATACCTGGATGTTTTTTCCAC ATAAACAAACGGGAGTTCAGCTTACTTATGGTGTTGA TGCAATTCAGTATGATCCTACCAATAAAACGAAACTT TGGGATTTTGGCTGTTTGAGGGATCAAAAGCTGCACC TTTACAAGATTGACGGATCGACCATTAGACCAAAGCA AATGGCCACCAA |
| 107 | DNA encodes GM-CSF | CCAGCTAGATCTCCATCTCCATCCACTCAACCATGGGAACA CGTTAACGCTATCCAAGAGGCTTTGAGATTGTTGAACTTGT CCAGAGACACTGCTGCTGAAATGAACGAGACTGTTGAGGT TATCTCCGAGATGTTCGACTTGCAAGAGCCAACTTGTTTGC AGACTAGATTGGAGTTGTACAAGCAGGGATTGAGAGGATC CTTGACTAAGTTGAAGGGACCATTGACTATGATGGCTTCCC ACTACAAGCAACACTGTCCACCAACTCCAGAAACATCCTGT GCTACTCAGATCATCACTTTCGAGTCCTT CAAAGAGAACTTGAAGGACTTCTTGTTGGTTATCCCATTCG ACTGTTGGGAACCAGTTCAAGAATAATAA |
| 108 | GM-CSF | PARSPSPSTQPWEHVNAIQEALRLLNLSRDTAAEMNETVEVIS EMFDLQEPTCLQTRLELYKQGLRGSLTKLKGPLTMMASHYK QHCPPTPETSCATQIITFESFKENLKDFLLVIPFDCWEPVQE |
| 109 | DNA encodes CWP1-GMCSF fusion protein | ATGTTCAACCTGAAAACTATTCTCATCTCAACACTTGC ATCGATCGCTGTTGCCGACCAAACCTTCGGTGTCCTTC TAATCCGGAGTGGATCCCCATATCACTATTCGACTCTC ACTAATAGAGACGAAAAGATTGTTGCTGGAGGTGGCA ACAAAAAAGTGACCCTCACAGATGAGGGAGCTCTGAA GTATGATGGTGGTAAATGGATAGGTCTTGATGATGAT GGCTATGCGGTACAGACCGACAAACCAGTTACAGGTT GGAGCACTAACGGTGGATACCTCTATTTTGACCAAGG CTTAATTGTTTGCACGGAGGACTATATCGGATATGTGA AGAAACATGGTGAATGCAAAGGTGACAGCTATGGTAT GGCTTGGAAGGTACTCCCAGCCGACGATGACAAGGAT GATGACAAGGATGATGATAAAGATGATGACAAGGATT ATGACGATGACAATGACCACGGTGATGGTGATTACTA TTGCTCGATCACAGGAACCTATGCCATCAAATCCAAA GGCAGTAAGCATCAATACGAGGCCATCAAAAAAGTTG ATGCACATCCTCATGTCTTCTCTGTAGGAGGAGATCAG GGAAACGATCTGATTGTGACTTTCCAAAAGGATTGTT CGCTGGTAGATCAAGATAACAGAGGCGTATATGTTGA CCCTAATTCTGGAGAAGTCGGAAACGTTGACCCTTGG GGAGAACTCACGCCATCTGTTAAATGGGATATTGACG ACGGATACCTGATCTTTAATGGTGAGTCCAATTTCAGG TCATGTCCATCTGGTAATGGATATTCATTGTCTATCAA GGATTGTGTTGGGGGAACTGACATTGGCCTTAAAGTA TGGGAGAAAGGTGGAGGTTCTTTGGTTAAGAGGGCTC CAGCTAGATCTCCATCTCCATCCACTCAACCATGGGA ACACGTTAACGCTATCCAAGAGGCTTTGAGATTGTTG AACTTGTCCAGAGACACTGCTGCTGAAATGAACGAGA CTGTTGAGGTTATCTCCGAGATGTTCGACTTGCAAGAG CCAACTTGTTTGCAGACTAGATTGGAGTTGTACAAGC AGGGATTGAGAGGATCCTTGACTAAGTTGAAGGGACC ATTGACTATGATGGCTTCCCACTACAAGCAACACTGTC CACCAACTCCAGAAACATCCTGTGCTACTCAGATCAT CACTTTCGAGTCCTTCAAAGAGAACTTGAAGGACTTCT TGTTGGTTATCCCATTCGACTGTTGGGAACCAGTTCAA GAATAA |
| 110 | CWP1-GMCSF fusion protein | MFNLKTILISTLASIAVADQTFGVLLIRSGSPYHYSTLTNR DEKIVAGGGNKKVTLTDEGALKYDGGKWIGLDDDGYA VQTDKPVTGWSTNGGYLYFDQGLIVCTEDYIGYVKKHG ECKGDSYGMAWKVLPADDDKDDDKDDDKDDDKDYDD DNDHGDGDYYCSITGTYAIKSKGSKHQYEAIKKVDAHP HVFSVGGDQGNDLIVTFQKDCSLVDQDNRGVYVDPNSG EVGNVDPWGELTPSVKWDIDDGYLIFNGESNFRSCPSGN GYSLSIKDCVGGTDIGLKVWEKGGGSLVKRAPARSPSPS TQPWEHVNAIQEALRLLNLSRDTAAEMNETVEVISEMFD LQEPTCLQTRLELYKQGLRGSLTKLKGPLTMMASHYKQ HCPPTPETSCATQIITFESFKENLKDFLLVIPFDCWEPVQE |

TABLE 12-continued

BRIEF DESCRIPTION OF THE SEQUENCES

| SEQ ID NO: | Description | Sequence |
|---|---|---|
| 111 | Kex2 linker amino acid sequence | GGGSLVKR |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

What is claimed:

1. A method for producing a heterologous glycoprotein in a yeast or filamentous fungus host cell, comprising:
   (a) providing a yeast or filamentous fungus host cell that includes at least one nucleic acid molecule encoding a heterologous single-subunit oligosaccharyltransferase and a nucleic acid molecule encoding the heterologous glycoprotein, and wherein the endogenous host cell genes encoding the proteins comprising the endogenous OTase complex are expressed; and
   (b) culturing the host cell under conditions for expressing the heterologous glycoprotein to produce the heterologous glycoprotein.

2. The method of claim 1, wherein the single-subunit oligosaccharyltransferase is the *Leishmania* sp. STT3A protein, STT3B protein, STT3C protein, STT3D protein or combinations thereof.

3. The method of claim 1, wherein the single-subunit oligosaccharyltransferase is the *Leishmania major* STT3D protein.

4. The method of claim 1, wherein at least 70% of the heterologous glycoproteins produced by the host cell have fully occupied N-glycosylation sites.

5. The method of claim 1, wherein the host cell is genetically engineered to produce glycoproteins comprising one or more mammalian- or human-like N-glycans.

6. The method of claim 1, wherein the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia sp., Saccharomyces cerevisiae, Saccharomyces sp., Hansenula polymorphs, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum*, and *Neurospora crassa*.

7. The method of claim 1, wherein the host cell is *P. pastoris* genetically engineered to be an och1 mutant that lacks α1,6-mannosyltransferase activity.

8. A method for producing a glycoprotein composition in which at least 70% of the N-glycosylation sites on the glycoproteins in the composition are occupied with an N-glycan, comprising:
   (a) providing a recombinant yeast or filamentous fungus host cell that includes at least one nucleic acid molecule encoding a heterologous single-subunit oligosaccharyltransferase and a nucleic acid molecule encoding the glycoprotein, and wherein the host cell genes encoding the endogenous OTase complex are expressed; and
   (b) culturing the recombinant host cell under conditions for expressing the glycoprotein to produce the composition in which at least 70% of the N-glycosylation sites on the glycoproteins in the composition are occupied with the N-glycan.

9. The method of claim 8, wherein the single-subunit oligosaccharyltransferase is the *Leishmania* sp. STT3A protein, STT3B protein, STT3C protein, STT3D protein or combinations thereof.

10. The method of claim 8, wherein the single-subunit oligosaccharyltransferase is the *Leishmania major* STT3D protein.

11. A yeast or filamentous fungus host cell, comprising:
    (a) a first nucleic acid molecule encoding at least one heterologous single-subunit oligosaccharyltransferase; and
    (b) a second nucleic acid molecule encoding a heterologous glycoprotein; and
    the host cell expresses the genes encoding the proteins comprising the endogenous oligosaccharyltransferase (OTase) complex.

12. The host cell of claim 11, wherein the single-subunit oligosaccharyltransferase is the *Leishmania* sp. STT3A protein, STT3B protein, STT3C protein, or STT3D protein.

13. The host cell of claim 11, wherein the single-subunit oligosaccharyltransferase is the *Leishmania major* STT3D protein.

14. The host cell of claim 11, wherein the host cell is genetically engineered to produce glycoproteins comprising one or more mammalian- or human-like N-glycans.

15. The host cell of claim 11, wherein the heterologous glycoprotein is erythropoietin (EPO); cytokines such as interferon α, interferon β, interferon γ, and interferon ω; and granulocyte-colony stimulating factor (GCSF); granulocyte macrophage-colony stimulating factor (GM-CSF); coagulation factors such as factor VIII, factor IX, and human protein C; antithrombin III; thrombin,; soluble IgE receptor α-chain; immunoglobulins such as IgG, IgG fragments, IgG fusions, and IgM; immunoadhesions and other Fc fusion proteins such as soluble TNF receptor-Fc fusion proteins; RAGE-Fc fusion proteins; interleukins; urokinase; chymase; urea trypsin inhibitor; IGF-binding protein; epidermal growth factor; growth hormone-releasing factor; annexin V fusion protein; angiostatin; vascular endothelial growth factor-2; myeloid progenitor inhibitory factor-1; osteoprotegerin; α-1-antitrypsin; α-feto proteins; DNase II; kringle 3 of human plasminogen; glucocerebrosidase; TNF binding protein 1; follicle stimulating hormone; cytotoxic T lymphocyte associated antigen 4-Ig; transmembrane activator and calcium modulator and cyclophilin ligand; glucagon like protein 1; or IL-2 receptor agonist.

16. The host cell of claim 11, wherein the heterologous glycoprotein is an anti-Her2 antibody, anti-RSV (respiratory syncytial virus) antibody, anti-TNFα antibody, anti-VEGF antibody, anti-CD3 receptor antibody, anti-CD41 7E3 antibody, anti-CD25 antibody, anti-CD52 antibody, anti-CD33 antibody, anti-IgE antibody, anti-CD11 α antibody, anti-EGF receptor antibody, or anti-CD20 antibody.

17. The host cell of claim 11, wherein the host cell is selected from the group consisting of *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia minuta (Ogataea minuta, Pichia lindneri), Pichia* sp., *Saccharomyces cerevisiae, Saccharomyces* sp., *Hansenula polymorphs, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum*, and *Neurospora crassa*.

18. The method of claim 11, wherein the host cell is *P. pastoris* genetically engineered to be an och1 mutant that lacks α1,6-mannosyltransferase activity.

* * * * *

SEQUENCE LISTING

```
<160> NUMBER OF SEQ ID NOS: 111

<210> SEQ ID NO 1
<211> LENGTH: 31
<212> TYPE: DNA
<213> ORGANISM: Artificial Sequence
<220> FEATURE:
<223> OTHER INFORMATION: PCR primer PpURA6out/UP

<400> SEQUENCE: 1
ctgaggagtc agatatcagc tcaatctcca t                              31

<210> SEQ ID NO 2
<211> LENGTH: 27
<212> TYPE: DNA
<213> ORGANISM: Artificial Sequence
<220> FEATURE:
<223> OTHER INFORMATION: PCR primer Puc19/LP

<400> SEQUENCE: 2
tccggctcgt atgttgtgtg gaattgt                                   27

<210> SEQ ID NO 3
<211> LENGTH: 32
<212> TYPE: DNA
<213> ORGANISM: Artificial Sequence
<220> FEATURE:
<223> OTHER INFORMATION: PCR primer PpURA6out/LP

<400> SEQUENCE: 3
ctggatgttt gatgggttca gtttcagctg ga                             32

<210> SEQ ID NO 4
<211> LENGTH: 29
<212> TYPE: DNA
<213> ORGANISM: Artificial Sequence
<220> FEATURE:
<223> OTHER INFORMATION: PCR primer ScARR3/UP

<400> SEQUENCE: 4
ggcaatagtc gcgagaatcc ttaaaccat                                 29

<210> SEQ ID NO 5
<211> LENGTH: 28
<212> TYPE: DNA
```

```
<213> ORGANISM: Artificial Sequence
<220> FEATURE:
<223> OTHER INFORMATION: PCR primer PpTRP1-5'out/UP

<400> SEQUENCE: 5
cctcgtaaag atctgcggtt tgcaaagt                                          28

<210> SEQ ID NO 6
<211> LENGTH: 27
<212> TYPE: DNA
<213> ORGANISM: Artificial Sequence
<220> FEATURE:
<223> OTHER INFORMATION: PCR primer PpALG3TT/LP

<400> SEQUENCE: 6
cctcccactg gaaccgatga tatggaa                                           27

<210> SEQ ID NO 7
<211> LENGTH: 33
<212> TYPE: DNA
<213> ORGANISM: Artificial Sequence
<220> FEATURE:
<223> OTHER INFORMATION: PCR primer PpTEFTT/UP

<400> SEQUENCE: 7
gatgcgaagt taagtgcgca gaaagtaata tca                                    33

<210> SEQ ID NO 8
<211> LENGTH: 33
<212> TYPE: DNA
<213> ORGANISM: Artificial Sequence
<220> FEATURE:
<223> OTHER INFORMATION: PCR primer PpTRP-3'1out/LP

<400> SEQUENCE: 8
cgtgtgtacc ttgaaacgtc aatgatactt tga                                    33

<210> SEQ ID NO 9
<211> LENGTH: 30
<212> TYPE: DNA
<213> ORGANISM: Artificial Sequence
<220> FEATURE:
<223> OTHER INFORMATION: PCR primer LmSTT3D/iUP

<400> SEQUENCE: 9
cagactaaga ctgcttctcc acctgctaag                                        30

<210> SEQ ID NO 10
<211> LENGTH: 32
<212> TYPE: DNA
<213> ORGANISM: Artificial Sequence
<220> FEATURE:
<223> OTHER INFORMATION: PCR primer LmSTT3D/iLP

<400> SEQUENCE: 10
caacagtaga accagaagcc tcgtaagtac ag                                     32

<210> SEQ ID NO 11
<211> LENGTH: 2577
<212> TYPE: DNA
<213> ORGANISM: Leishmania major

<400> SEQUENCE: 11
atgggtaaaa gaaagggaaa ctccttggga gattctggtt ctgctgctac tgcttccaga       60
gaggcttctg ctcaagctga agatgctgct tcccagacta agactgcttc tccacctgct      120
```

-continued

```
aaggttatct tgttgccaaa gactttgact gacgagaagg acttcatcgg tatcttccca    180
tttccattct ggccagttca cttcgttttg actgttgttg ctttgttcgt tttggctgct    240
tcctgtttcc aggctttcac tgttagaatg atctccgttc aaatctacgg ttacttgatc    300
cacgaatttg acccatggtt caactacaga gctgctgagt acatgtctac tcacggatgg    360
agtgctttt  tctcctggtt cgattacatg tcctggtatc cattgggtag accagttggt    420
tctactactt acccaggatt gcagttgact gctgttgcta tccatagagc tttggctgct    480
gctggaatgc caatgtcctt gaacaatgtt tgtgttttga tgccagcttg gtttggtgct    540
atcgctactc tactttggc tttctgtact tacgaggctt ctggttctac tgttgctgct    600
gctgcagctg ctttgtcctt ctccattatc cctgctcact tgatgagatc catggctggt    660
gagttcgaca acgagtgtat tgctgttgct gctatgttgt tgactttcta ctgttgggtt    720
cgttccttga gaactagatc ctcctggcca atcggtgttt tgacaggtgt tgcttacggt    780
tacatggctg ctgcttgggg aggttacatc ttcgttttga acatggttgc tatgcacgct    840
ggtatctctt ctatggttga ctgggctaga aacacttaca acccatcctt gttgagagct    900
tacactttgt tctacgttgt tggtactgct atcgctgttt gtgttccacc agttggaatg    960
tctccattca agtccttgga gcagttggga gctttgttgg ttttggtttt cttgtgtgga   1020
ttgcaagttt gtgaggtttt gagagctaga gctggtgttg aagttagatc cagagctaat   1080
ttcaagatca gagttagagt tttctccgtt atggctggtg ttgctgcttt ggctatctct   1140
gttttggctc caactggtta ctttggtcca ttgtctgtta gagttagagc tttgtttgtt   1200
gagcacacta gaactggtaa cccattggtt gactccgttg ctgaacatca accagcttct   1260
ccagaggcta tgtgggcttt cttgcatgtt tgtggtgtta cttggggatt gggttccatt   1320
gttttggctg tttccacttt cgttcactac tccccatcta aggttttctg gttgttgaac   1380
tccggtgctg tttactactt ctccactaga atggctagat tgttgttgtt gtccggtcca   1440
gctgcttgtt tgtccactgg tatcttcgtt ggtactatct tggaggctgc tgttcaattg   1500
tctttctggg actccgatgc tactaaggct aagaagcagc aaaagcaggc tcaaagacac   1560
caaagaggtg ctggtaaagg ttctggtaga gatgacgcta agaacgctac tactgctaga   1620
gctttctgtg acgttttcgc tggttcttct ttggcttggg gtcacagaat ggttttgtcc   1680
attgctatgt gggctttggt tactactact gctgtttcct tcttctcctc cgaatttgct   1740
tctcactcca ctaagttcgc tgaacaatcc tccaacccaa tgatcgtttt cgctgctgtt   1800
gttcagaaca gagctactgg aaagccaatg aacttgttgg ttgacgacta cttgaaggct   1860
tacgagtggt tgagagactc tactccagag gacgctagag ttttggcttg gtgggactac   1920
ggttaccaaa tcactggtat cggtaacaga acttccttgg ctgatggtaa cacttggaac   1980
cacgagcaca ttgctactat cggaaagatg ttgacttccc cagttgttga agctcactcc   2040
cttgttagac acatggctga ctacgttttg atttgggctg tcaatctggg tgacttgatg   2100
aagtctccac acatggctag aatcggtaac tctgttacc acgacatttg tccagatgac   2160
ccattgtgtc agcaattcgg tttccacaga aacgattact ccagaccaac tccaatgatg   2220
agagcttcct tgttgtacaa cttgcacgag gctggaaaaa gaagggtgt taaggttaac   2280
ccatctttgt tccaagaggt ttactcctcc aagtacggac ttgttagaat cttcaaggtt   2340
atgaacgttt ccgctgagtc taagaagtgg gttgcagacc cagctaacag agtttgtcac   2400
ccacctggtt cttggatttg tcctggtcaa tacccacctg ctaaagaaat ccaagagatg   2460
ttggctcaca gagttccatt cgaccaggtt acaaacgctg acagaaagaa caatgttggt   2520
```

```
tcctaccaag aggaatacat gagaagaatg agagagtccg agaacagaag ataatag        2577
```

<210> SEQ ID NO 12
<211> LENGTH: 857
<212> TYPE: PRT
<213> ORGANISM: Leishmania major

<400> SEQUENCE: 12

| Met | Gly | Lys | Arg | Lys | Gly | Asn | Ser | Leu | Gly | Asp | Ser | Gly | Ser | Ala | Ala |
|---|---|---|---|---|---|---|---|---|---|---|---|---|---|---|---|
| 1 | | | | 5 | | | | | 10 | | | | | 15 | |

| Thr | Ala | Ser | Arg | Glu | Ala | Ser | Ala | Gln | Ala | Glu | Asp | Ala | Ala | Ser | Gln |
| | | | 20 | | | | | 25 | | | | | 30 | | |

| Thr | Lys | Thr | Ala | Ser | Pro | Pro | Ala | Lys | Val | Ile | Leu | Leu | Pro | Lys | Thr |
| | | | 35 | | | | | 40 | | | | | 45 | | |

| Leu | Thr | Asp | Glu | Lys | Asp | Phe | Ile | Gly | Ile | Phe | Pro | Phe | Pro | Phe | Trp |
| | 50 | | | | | 55 | | | | | 60 | | | | |

| Pro | Val | His | Phe | Val | Leu | Thr | Val | Val | Ala | Leu | Phe | Val | Leu | Ala | Ala |
| 65 | | | | | 70 | | | | | 75 | | | | | 80 |

| Ser | Cys | Phe | Gln | Ala | Phe | Thr | Val | Arg | Met | Ile | Ser | Val | Gln | Ile | Tyr |
| | | | | 85 | | | | | 90 | | | | | 95 | |

| Gly | Tyr | Leu | Ile | His | Glu | Phe | Asp | Pro | Trp | Phe | Asn | Tyr | Arg | Ala | Ala |
| | | | 100 | | | | | 105 | | | | | 110 | | |

| Glu | Tyr | Met | Ser | Thr | His | Gly | Trp | Ser | Ala | Phe | Phe | Ser | Trp | Phe | Asp |
| | | | 115 | | | | | 120 | | | | | 125 | | |

| Tyr | Met | Ser | Trp | Tyr | Pro | Leu | Gly | Arg | Pro | Val | Gly | Ser | Thr | Thr | Tyr |
| | 130 | | | | | 135 | | | | | 140 | | | | |

| Pro | Gly | Leu | Gln | Leu | Thr | Ala | Val | Ala | Ile | His | Arg | Ala | Leu | Ala | Ala |
| 145 | | | | | 150 | | | | | 155 | | | | | 160 |

| Ala | Gly | Met | Pro | Met | Ser | Leu | Asn | Asn | Val | Cys | Val | Leu | Met | Pro | Ala |
| | | | | 165 | | | | | 170 | | | | | 175 | |

| Trp | Phe | Gly | Ala | Ile | Ala | Thr | Ala | Thr | Leu | Ala | Phe | Cys | Thr | Tyr | Glu |
| | | | 180 | | | | | 185 | | | | | 190 | | |

| Ala | Ser | Gly | Ser | Thr | Val | Ala | Ala | Ala | Ala | Ala | Leu | Ser | Phe | Ser |
| | | | 195 | | | | | 200 | | | | | 205 | | |

| Ile | Ile | Pro | Ala | His | Leu | Met | Arg | Ser | Met | Ala | Gly | Glu | Phe | Asp | Asn |
| | 210 | | | | | 215 | | | | | 220 | | | | |

| Glu | Cys | Ile | Ala | Val | Ala | Ala | Met | Leu | Leu | Thr | Phe | Tyr | Cys | Trp | Val |
| 225 | | | | | 230 | | | | | 235 | | | | | 240 |

| Arg | Ser | Leu | Arg | Thr | Arg | Ser | Ser | Trp | Pro | Ile | Gly | Val | Leu | Thr | Gly |
| | | | | 245 | | | | | 250 | | | | | 255 | |

| Val | Ala | Tyr | Gly | Tyr | Met | Ala | Ala | Trp | Gly | Gly | Tyr | Ile | Phe | Val |
| | | | 260 | | | | | 265 | | | | | 270 | | |

| Leu | Asn | Met | Val | Ala | Met | His | Ala | Gly | Ile | Ser | Ser | Met | Val | Asp | Trp |
| | | | 275 | | | | | 280 | | | | | 285 | | |

| Ala | Arg | Asn | Thr | Tyr | Asn | Pro | Ser | Leu | Leu | Arg | Ala | Tyr | Thr | Leu | Phe |
| | 290 | | | | | 295 | | | | | 300 | | | | |

| Tyr | Val | Val | Gly | Thr | Ala | Ile | Ala | Val | Cys | Val | Pro | Pro | Val | Gly | Met |
| 305 | | | | | 310 | | | | | 315 | | | | | 320 |

| Ser | Pro | Phe | Lys | Ser | Leu | Glu | Gln | Leu | Gly | Ala | Leu | Leu | Val | Leu | Val |
| | | | | 325 | | | | | 330 | | | | | 335 | |

| Phe | Leu | Cys | Gly | Leu | Gln | Val | Cys | Glu | Val | Leu | Arg | Ala | Arg | Ala | Gly |
| | | | 340 | | | | | 345 | | | | | 350 | | |

| Val | Glu | Val | Arg | Ser | Arg | Ala | Asn | Phe | Lys | Ile | Arg | Val | Arg | Val | Phe |
| | | | 355 | | | | | 360 | | | | | 365 | | |

| Ser | Val | Met | Ala | Gly | Val | Ala | Ala | Leu | Ala | Ile | Ser | Val | Leu | Ala | Pro |

```
                 370                 375                 380
Thr Gly Tyr Phe Gly Pro Leu Ser Val Arg Val Arg Ala Leu Phe Val
385                 390                 395                 400

Glu His Thr Arg Thr Gly Asn Pro Leu Val Asp Ser Val Ala Glu His
                405                 410                 415

Gln Pro Ala Ser Pro Glu Ala Met Trp Ala Phe Leu His Val Cys Gly
                420                 425                 430

Val Thr Trp Gly Leu Gly Ser Ile Val Leu Ala Val Ser Thr Phe Val
                435                 440                 445

His Tyr Ser Pro Ser Lys Val Phe Trp Leu Leu Asn Ser Gly Ala Val
                450                 455                 460

Tyr Tyr Phe Ser Thr Arg Met Ala Arg Leu Leu Leu Ser Gly Pro
465                 470                 475                 480

Ala Ala Cys Leu Ser Thr Gly Ile Phe Val Gly Thr Ile Leu Glu Ala
                485                 490                 495

Ala Val Gln Leu Ser Phe Trp Asp Ser Asp Ala Thr Lys Ala Lys Lys
                500                 505                 510

Gln Gln Lys Gln Ala Gln Arg His Gln Arg Gly Ala Gly Lys Gly Ser
                515                 520                 525

Gly Arg Asp Asp Ala Lys Asn Ala Thr Thr Ala Arg Ala Phe Cys Asp
530                 535                 540

Val Phe Ala Gly Ser Ser Leu Ala Trp Gly His Arg Met Val Leu Ser
545                 550                 555                 560

Ile Ala Met Trp Ala Leu Val Thr Thr Thr Ala Val Ser Phe Phe Ser
                565                 570                 575

Ser Glu Phe Ala Ser His Ser Thr Lys Phe Ala Glu Gln Ser Ser Asn
                580                 585                 590

Pro Met Ile Val Phe Ala Ala Val Gln Asn Arg Ala Thr Gly Lys
            595                 600                 605

Pro Met Asn Leu Leu Val Asp Asp Tyr Leu Lys Ala Tyr Glu Trp Leu
                610                 615                 620

Arg Asp Ser Thr Pro Glu Asp Ala Arg Val Leu Ala Trp Trp Asp Tyr
625                 630                 635                 640

Gly Tyr Gln Ile Thr Gly Ile Gly Asn Arg Thr Ser Leu Ala Asp Gly
                645                 650                 655

Asn Thr Trp Asn His Glu His Ile Ala Thr Ile Gly Lys Met Leu Thr
                660                 665                 670

Ser Pro Val Val Glu Ala His Ser Leu Val Arg His Met Ala Asp Tyr
            675                 680                 685

Val Leu Ile Trp Ala Gly Gln Ser Gly Asp Leu Met Lys Ser Pro His
            690                 695                 700

Met Ala Arg Ile Gly Asn Ser Val Tyr His Asp Ile Cys Pro Asp Asp
705                 710                 715                 720

Pro Leu Cys Gln Gln Phe Gly Phe His Arg Asn Asp Tyr Ser Arg Pro
                725                 730                 735

Thr Pro Met Met Arg Ala Ser Leu Leu Tyr Asn Leu His Glu Ala Gly
                740                 745                 750

Lys Arg Lys Gly Val Lys Val Asn Pro Ser Leu Phe Gln Glu Val Tyr
            755                 760                 765

Ser Ser Lys Tyr Gly Leu Val Arg Ile Phe Lys Val Met Asn Val Ser
            770                 775                 780

Ala Glu Ser Lys Lys Trp Val Ala Asp Pro Ala Asn Arg Val Cys His
785                 790                 795                 800
```

```
Pro Pro Gly Ser Trp Ile Cys Pro Gly Gln Tyr Pro Pro Ala Lys Glu
            805                 810                 815

Ile Gln Glu Met Leu Ala His Arg Val Pro Phe Asp Gln Val Thr Asn
        820                 825                 830

Ala Asp Arg Lys Asn Asn Val Gly Ser Tyr Gln Glu Gly Tyr Met Arg
        835                 840                 845

Arg Met Arg Glu Ser Glu Asn Arg Arg
    850                 855

<210> SEQ ID NO 13
<211> LENGTH: 57
<212> TYPE: DNA
<213> ORGANISM: Artificial Sequence
<220> FEATURE:
<223> OTHER INFORMATION: Saccharomyces cerevisiae mating factor
      pre-signal peptide (DNA)

<400> SEQUENCE: 13
atgagattcc catccatctt cactgctgtt ttgttcgctg cttcttctgc tttggct      57

<210> SEQ ID NO 14
<211> LENGTH: 19
<212> TYPE: PRT
<213> ORGANISM: Artificial Sequence
<220> FEATURE:
<223> OTHER INFORMATION: Saccharomyces cerevisiae mating factor
      pre-signal peptide

<400> SEQUENCE: 14

Met Arg Phe Pro Ser Ile Phe Thr Ala Val Leu Phe Ala Ala Ser Ser
  1               5                  10                  15

Ala Leu Ala

<210> SEQ ID NO 15
<211> LENGTH: 1350
<212> TYPE: DNA
<213> ORGANISM: Artificial Sequence
<220> FEATURE:
<223> OTHER INFORMATION: Anti-Her2 Heavy chain (VH + IgG1 constant
      region) (DNA)

<400> SEQUENCE: 15
gaggttcagt tggttgaatc tggaggagga ttggttcaac tggtggttc tttgagattg      60 tcctgtgctg cttccggttt caacatcaag gacacttaca tccactgggt tagacaagct    120
ccaggaaagg gattggagtg ggttgctaga atctacccaa ctaacggtta cacaagatac    180
gctgactccg ttaagggaag attcactatc tctgctgaca cttccaagaa cactgcttac    240
ttgcagatga actccttgag agctgaggat actgctgttt actactgttc cagatggggt    300
ggtgatggtt tctacgctat ggactactgg ggtcaaggaa cttttggtta cgtttcctcc    360
gcttctacta agggaccatc tgttttccca ttggctccat tctctaagtc tacttccggt    420
ggtactgctg ctttgggatg tttggttaaa gactacttcc cagagccagt tactgtttct    480
tggaactccg gtgctttgac ttctggtgtt cacactttcc cagctgtttt gcaatcttcc    540
ggtttgtact ctttgtcctc cgttgttact gttccatcct cttccttggg tactcagact    600
tacatctgta acgttaacca caagccatcc aacactaagg ttgacaagaa ggttgagcca    660
aagtcctgtg acaagacaca tacttgtcca ccatgtccag ctccagaatt gttgggtggt    720
ccatccgttt tcttgttccc accaaagcca aaggacactt tgatgatctc cagaactcca    780
gaggttacat gtgttgttgt tgacgttct cacgaggacc cagaggttaa gttcaactgg    840
```

-continued

```
tacgttgacg gtgttgaagt tcacaacgct aagactaagc caagagaaga gcagtacaac    900
tccacttaca gagttgtttc cgttttgact gttttgcacc aggactggtt gaacggtaaa    960
gaatacaagt gtaaggtttc caacaaggct ttgccagctc caatcgaaaa gactatctcc    1020
aaggctaagg tcaaccaag agagccacag gtttacactt tgccaccatc cagagaagag    1080
atgactaaga accaggtttc cttgacttgt ttggttaaag gattctaccc atccgacatt    1140
gctgttgagt gggaatctaa cggtcaacca gagaacaact acaagactac tccaccagtt    1200
ttggattctg atggttcctt cttcttgtac tccaagttga ctgttgacaa gtccagatgg    1260
caacagggta acgttttctc ctgttccgtt atgcatgagg ctttgcacaa ccactacact    1320
caaaagtcct tgtctttgtc ccctggttaa                                     1350
```

<210> SEQ ID NO 16
<211> LENGTH: 449
<212> TYPE: PRT
<213> ORGANISM: Artificial Sequence
<220> FEATURE:
<223> OTHER INFORMATION: Anti-Her2 Heavy chain (VH + IgG1 constant region)

<400> SEQUENCE: 16

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
           100                 105                 110

Gly Thr Leu Val Thr Val Ser Ser Ala Ser Thr Lys Gly Pro Ser Val
       115                 120                 125

Phe Pro Leu Ala Pro Ser Ser Lys Ser Thr Ser Gly Gly Thr Ala Ala
   130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
               165                 170                 175

Leu Gln Ser Ser Gly Leu Tyr Ser Leu Ser Ser Val Val Thr Val Pro
           180                 185                 190

Ser Ser Ser Leu Gly Thr Gln Thr Tyr Ile Cys Asn Val Asn His Lys
       195                 200                 205

Pro Ser Asn Thr Lys Val Asp Lys Lys Val Glu Pro Lys Ser Cys Asp
   210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
               245                 250                 255

Ser Arg Thr Pro Glu Val Thr Cys Val Val Val Asp Val Ser His Glu
           260                 265                 270
```

```
Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 17
<211> LENGTH: 645
<212> TYPE: DNA
<213> ORGANISM: Artificial Sequence
<220> FEATURE:
<223> OTHER INFORMATION: Anti-Her2 light chain (VL + Kappa constant
      region) (DNA)

<400> SEQUENCE: 17
gacatccaaa tgactcaatc cccatcttct ttgtctgctt ccgttggtga cagagttact      60
atcacttgta gagcttccca ggacgttaat actgctgttg cttggtatca acagaagcca     120
ggaaaggctc caaagttgtt gatctactcc gcttccttct tgtactctgg tgttccatcc     180
agattctctg gttccagatc cggtactgac ttcactttga ctatctcctc cttgcaacca     240
gaagatttcg ctacttacta ctgtcagcag cactacacta ctccaccaac tttcggacag     300
ggtactaagg ttgagatcaa agaactgttg ctgctccat ccgttttcat ttcccacca      360 tccgacgaac agttgaagtc tggtacagct tccgttgttt gtttgttgaa caacttctac     420
ccaagagagg ctaaggttca gtggaaggtt gacaacgctt gcaatccgg taactcccaa     480 gaatccgtta ctgagcaaga ctctaaggac tccacttact ccttgtcctc cactttgact     540
ttgtccaagg ctgattacga aagcacaag gtttacgctt gtgaggttac acatcaggt    600 ttgtcctccc cagttactaa gtccttcaac agaggagagt gttaa                     645

<210> SEQ ID NO 18
<211> LENGTH: 214
<212> TYPE: PRT
<213> ORGANISM: Artificial Sequence
<220> FEATURE:
<223> OTHER INFORMATION: Anti-Her2 light chain (VL + Kappa constant
      region)

<400> SEQUENCE: 18

Asp Ile Gln Met Thr Gln Ser Pro Ser Ser Leu Ser Ala Ser Val Gly
```

```
                  1               5                  10                  15
Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
                 35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
               100                 105                 110

Pro Ser Val Phe Ile Phe Pro Pro Ser Asp Glu Gln Leu Lys Ser Gly
               115                 120                 125

Thr Ala Ser Val Val Cys Leu Leu Asn Asn Phe Tyr Pro Arg Glu Ala
           130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
               165                 170                 175

Ser Thr Leu Thr Leu Ser Lys Ala Asp Tyr Glu Lys His Lys Val Tyr
           180                 185                 190

Ala Cys Glu Val Thr His Gln Gly Leu Ser Ser Pro Val Thr Lys Ser
           195                 200                 205

Phe Asn Arg Gly Glu Cys
    210

<210> SEQ ID NO 19
<211> LENGTH: 1350
<212> TYPE: DNA
<213> ORGANISM: Artificial Sequence
<220> FEATURE:
<223> OTHER INFORMATION: Anti-RSV Heavy chain (VH + IgG1 constant
      region) (DNA)

<400> SEQUENCE: 19
caggttacat tgagagaatc cggtccagct ttggttaagc caactcagac tttgactttg       60
acttgtactt tctccggttt ctccttgtct acttccggaa tgtctgttgg atggatcaga     120
caaccacctg aaaggctttg gaatggcttg ctgacatttg gtgggatgaa caagaaggac     180
tacaacccat ccttgaagtc cagattgact atctccaagg acacttccaa gaatcaagtt     240
gttttgaagg ttacaaacat ggacccagct gacactgcta cttactactg tgctagatcc     300
atgatcacta actggtactt cgatgttggg ggtgctggta ctactgttac tgtctcgagt     360
gcttctacta agggaccatc cgttttttcca ttggctccat cctctaagtc tacttccggt     420
ggaaccgctg ctttgggatg tttggttaaa gactacttcc cagagccagt tactgttttct     480 tggaactccg gtgctttgac ttctggtgtt cacacttttcc cagctgtttt gcaatcttcc     540
ggtttgtact ctttgtcctc cgttgttact gttccatcct cttccttggg tactcagact     600
tacatctgta acgttaacca caagccatcc aacactaagg ttgacaagag agttgagcca     660
aagtcctgtg acaagacaca tacttgtcca ccatgtccag ctccagaatt gttgggtggt     720
ccatccgttt tcttgttccc accaaagcca aaggacactt tgatgatctc agaactccaa     780
gaggttacat gtgttgttgt tgacgttcct cacgaggacc cagaggttaa gttcaactgg     840
```

-continued

```
tacgttgacg gtgttgaagt tcacaacgct aagactaagc caagagaaga gcagtacaac   900
tccacttaca gagttgtttc cgttttgact gttttgcacc aggactggtt gaacggtaaa   960
gaatacaagt gtaaggtttc caacaaggct ttgccagctc caatcgaaaa gactatctcc  1020
aaggctaagg tcaaccaag agagccacag gtttacactt tgccaccatc cagagaagag   1080
atgactaaga accaggtttc cttgacttgt ttggttaaag gattctaccc atccgacatt  1140
gctgttgagt gggaatctaa cggtcaacca gagaacaact acaagactac tccaccagtt  1200
ttggattctg atggttcctt cttcttgtac tccaagttga ctgttgacaa gtccagatgg  1260
caacagggta acgttttctc ctgttccgtt atgcatgagg ctttgcacaa ccactacact  1320
caaaagtcct tgtctttgtc ccctggttaa                                   1350
```

<210> SEQ ID NO 20
<211> LENGTH: 449
<212> TYPE: PRT
<213> ORGANISM: Artificial Sequence
<220> FEATURE:
<223> OTHER INFORMATION: Anti-RSV Heavy chain (VH + IgG1 constant region)

<400> SEQUENCE: 20

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Ser Val Gly Trp Ile Arg Gln Pro Pro Gly Lys Ala Leu Glu
         35                  40                  45

Trp Leu Ala Asp Ile Trp Trp Asp Asp Lys Lys Asp Tyr Asn Pro Ser
     50                  55                  60

Leu Lys Ser Arg Leu Thr Ile Ser Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala Arg Ser Met Ile Thr Asn Trp Tyr Phe Asp Val Trp Gly Ala
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

-continued

```
Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly
```

```
<210> SEQ ID NO 21
<211> LENGTH: 699
<212> TYPE: DNA
<213> ORGANISM: Artificial Sequence
<220> FEATURE:
<223> OTHER INFORMATION: Anti-RSV light chain (VL + Kappa constant
      region (DNA)

<400> SEQUENCE: 21
atgagattcc catccatctt cactgctgtt tgttcgctg cttcttctgc tttggctgac      60
attcagatga cacagtcccc atctactttg tctgcttccg ttggtgacag agttactatc     120
acttgtaagt gtcagttgtc cgttggttac atgcactggt atcagcaaaa gccaggaaag     180
gctccaaagt tgttgatcta cgacacttcc aagttggctt ccggtgttcc atctagattc     240
tctggttccg gttctggtac tgagttcact ttgactatct cttccttgca accagatgac     300
ttcgctactt actactgttt ccagggttct ggttacccat tcacttttcgg tggtggtact     360 aagttggaga tcaagagaac tgttgctgct ccatccgttt tcatttttccc accatccgac     420 gaacaattga gtccggtac cgcttccgtt gtttgttttgt tgaacaactt ctacccacgt     480
gaggctaagg ttcagtggaa ggttgacaac gctttgcaat ccggtaactc ccaagaatcc     540
gttactgagc aggattctaa ggattccact tactcattgt cctccacttt gactttgtcc     600
aaggctgatt acgagaagca caaggtttac gcttgcgagg ttacacatca gggtttgtcc     660
tccccagtta ctaagtcctt caacagagga gagtgttaa                              699
```

```
<210> SEQ ID NO 22
<211> LENGTH: 213
<212> TYPE: PRT
<213> ORGANISM: Artificial Sequence
<220> FEATURE:
<223> OTHER INFORMATION: Anti-RSV light chain (VL + Kappa constant
      region

<400> SEQUENCE: 22
```

```
Asp Ile Gln Met Thr Gln Ser Pro Ser Thr Leu Ser Ala Ser Val Gly
  1               5                  10                  15

Asp Arg Val Thr Ile Thr Cys Lys Cys Gln Leu Ser Val Gly Tyr Met
             20                  25                  30

His Trp Tyr Gln Gln Lys Pro Gly Lys Ala Pro Lys Leu Leu Ile Tyr
         35                  40                  45

Asp Thr Ser Lys Leu Ala Ser Gly Val Pro Ser Arg Phe Ser Gly Ser
     50                  55                  60

Gly Ser Gly Thr Glu Phe Thr Leu Thr Ile Ser Ser Leu Gln Pro Asp
 65                  70                  75                  80

Asp Phe Ala Thr Tyr Tyr Cys Phe Gln Gly Ser Gly Tyr Pro Phe Thr
                 85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 23
<211> LENGTH: 934
<212> TYPE: DNA
<213> ORGANISM: Artificial Sequence
<220> FEATURE:
<223> OTHER INFORMATION: Pp AOX1 promoter

<400> SEQUENCE: 23

```
aacatccaaa gacgaaaggt tgaatgaaac cttttttgcca tccgacatcc acaggtccat    60
tctcacacat aagtgccaaa cgcaacagga ggggatacac tagcagcaga ccgttgcaaa   120
cgcaggacct ccactcctct tctcctcaac acccactttt gccatcgaaa accagcccaa   180
gttattgggc ttgattggag ctcgctcatt ccaattcctt ctattaggct actaacacca   240
tgactttatt agcctgtcta tcctggcccc cctggcgagg ttcatgtttg tttatttccg   300
aatgcaacaa gctccgcatt acacccgaac atcactccag atgagggctt tctgagtgtg   360
gggtcaaata gtttcatgtt ccccaaatgg cccaaaactg acagtttaaa cgctgtcttg   420
gaacctaata tgacaaaagc gtgatctcat ccaagatgaa ctaagtttgg ttcgttgaaa   480
tgctaacggc cagttggtca aaagaaaact tccaaaagtc ggcataccgt tgtcttgtt    540
tggtattgat tgacgaatgc tcaaaaataa tctcattaat gcttagcgca gtctctctat   600
cgcttctgaa ccccggtgca cctgtgccga aacgcaaatg gggaaacacc cgcttttttgg  660
atgattatgc attgtctcca cattgtatgc ttccaagatt ctggtgggaa tactgctgat   720
agcctaacgt tcatgatcaa aatttaactg ttctaacccc tacttgacag caatatataa   780
acagaaggaa gctgccctgt cttaaacctt ttttttttatc atcattatta gcttactttc   840
```

```
ataattgcga ctggttccaa ttgacaagct tttgatttta acgactttta acgacaactt    900
gagaagatca aaaacaact aattattcga aacg                                 934
```

<210> SEQ ID NO 24
<211> LENGTH: 293
<212> TYPE: DNA
<213> ORGANISM: Artificial Sequence
<220> FEATURE:
<223> OTHER INFORMATION: ScCYC TT

<400> SEQUENCE: 24

```
acaggcccct ttcctttgt cgatatcatg taattagtta tgtcacgctt acattcacgc     60
cctcctccca catccgctct aaccgaaaag gaaggagtta gacaacctga agtctaggtc   120
cctatttatt tttttaata gttatgttag tattaagaac gttatttata tttcaaattt    180
ttcttttttt tctgtacaaa cgcgtgtacg catgtaacat tatactgaaa accttgcttg   240
agaaggtttt gggacgctcg aaggctttaa tttgcaagct gccggctctt aag          293
```

<210> SEQ ID NO 25
<211> LENGTH: 600
<212> TYPE: DNA
<213> ORGANISM: Artificial Sequence
<220> FEATURE:
<223> OTHER INFORMATION: PpRPL10 promoter

<400> SEQUENCE: 25

```
gttcttcgct tggtcttgta tctccttaca ctgtatcttc ccatttgcgt ttaggtggtt    60
atcaaaaact aaaaggaaaa atttcagatg tttatctcta aggttttttc tttttacagt   120
ataacacgtg atgcgtcacg tggtactaga ttacgtaagt tattttggtc cggtgggtaa   180
gtgggtaaga atagaaagca tgaaggttta caaaaacgca gtcacgaatt attgctactt   240
cgagcttgga accaccccaa agattatatt gtactgatgc actaccttct cgattttgct   300
cctccaagaa cctacgaaaa acatttcttg agccttttca acctagacta cacatcaagt   360
tatttaaggt atgttccgtt aacatgtaag aaaaggagag gatagatcgt ttatggggta   420
cgtcgcctga ttcaagcgtg accattcgaa gaataggcct tcgaaagctg aataaagcaa   480
atgtcagttg cgattggtat gctgacaaat tagcataaaa agcaatagac tttctaacca   540
cctgtttttt tccttttact ttatttatat tttgccaccg tactaacaag ttcagacaaa   600
```

<210> SEQ ID NO 26
<211> LENGTH: 486
<212> TYPE: DNA
<213> ORGANISM: Artificial Sequence
<220> FEATURE:
<223> OTHER INFORMATION: PpGAPDH promoter

<400> SEQUENCE: 26

```
tttttgtaga aatgtcttgg tgtcctcgtc caatcaggta gccatctctg aaatatctgg    60
ctccgttgca actccgaacg acctgctggc aacgtaaaat tctccggggt aaaacttaaa   120
tgtggagtaa tggaaccaga aacgtctctt cccttctctc tccttccacc gcccgttacc   180
gtccctagga aattttactc tgctggagag cttcttctac ggccccttg cagcaatgct    240 cttcccagca ttacgttgcg ggtaaaacgg aggtcgtgta cccgacctag cagcccaggg   300
atggaaaagt cccggccgtc gctggcaata atagcgggcg gacgcatgtc atgagattat   360
tggaaaccac cagaatcgaa tataaaaggc gaacaccttt cccaatttg gtttctcctg    420 acccaaagac tttaaattta atttatttgt ccctatttca atcaattgaa caactatcaa   480
```

```
aacaca                                                              486

<210> SEQ ID NO 27
<211> LENGTH: 600
<212> TYPE: DNA
<213> ORGANISM: Artificial Sequence
<220> FEATURE:
<223> OTHER INFORMATION: PpTEF1 promoter

<400> SEQUENCE: 27
ttaaggtttg gaacaacact aaactacctt gcggtactac cattgacact acacatcctt    60
aattccaatc ctgtctggcc tccttcacct tttaaccatc ttgcccattc caactcgtgt   120
cagattgcgt atcaagtgaa aaaaaaaaaa ttttaaatct ttaacccaat caggtaataa   180
ctgtcgcctc ttttatctgc cgcactgcat gaggtgtccc cttagtggga aagagtactg   240
agccaaccct ggaggacagc aagggaaaaa tacctacaac ttgcttcata atggtcgtaa   300
aaacaatcct tgtcggatat aagtgttgta gactgtccct tatcctctgc gatgttcttc   360
ctctcaaagt ttgcgatttc tctctatcag aattgccatc aagagactca ggactaattt   420
cgcagtccca cacgcactcg tacatgattg gctgaaattt ccctaaagaa tttcttttc    480 acgaaaattt ttttttaca caagatttc agcagatata aatggagag caggacctcc     540 gctgtgactc tcttttttt tcttttattc tcactacata cattttagtt attcgccaac   600

<210> SEQ ID NO 28
<211> LENGTH: 301
<212> TYPE: DNA
<213> ORGANISM: Artificial Sequence
<220> FEATURE:
<223> OTHER INFORMATION: PpTEF1 TT

<400> SEQUENCE: 28
attgcttgaa gctttaattt attttattaa cataataata atacaagcat gatatatttg    60
tattttgttc gttaacattg atgttttctt catttactgt tattgtttgt aactttgatc   120
gatttatctt ttctacttta ctgtaatatg gctggcgggt gagccttgaa ctccctgtat   180
tactttacct tgctattact taatctattg actagcagcg acctcttcaa ccgaagggca   240
agtacacagc aagttcatgt ctccgtaagt gtcatcaacc ctggaaacag tgggccatgt   300
c                                                                   301

<210> SEQ ID NO 29
<211> LENGTH: 376
<212> TYPE: DNA
<213> ORGANISM: Artificial Sequence
<220> FEATURE:
<223> OTHER INFORMATION: PpALG3 TT

<400> SEQUENCE: 29
atttacaatt agtaatatta aggtggtaaa aacattcgta gaattgaaat gaattaatat    60
agtatgacaa tggttcatgt ctataaatct ccggcttcgg taccttctcc ccaattgaat   120
acattgtcaa aatgaatggt tgaactatta ggttcgccag tttcgttatt aagaaaactg   180
ttaaaatcaa attccatatc atcggttcca gtgggaggac cagttccatc gccaaaatcc   240
tgtaagaatc cattgtcaga acctgtaaag tcagtttgag atgaaatttt tccggtcttt   300
gttgacttgg aagcttcgtt aaggttaggt gaaacagttt gatcaaccag cggctcccgt   360
tttcgtcgct tagtag                                                   376
```

<210> SEQ ID NO 30
<211> LENGTH: 672
<212> TYPE: DNA
<213> ORGANISM: Artificial Sequence
<220> FEATURE:
<223> OTHER INFORMATION: PpTRP1 5' region and ORF

<400> SEQUENCE: 30

```
gcggaaacgg cagtaaacaa tggagcttca ttagtgggtg ttattatggt ccctggccgg      60
gaacgaacgg tgaaacaaga ggttgcgagg gaaatttcgc agatggtgcg ggaaaagaga     120
atttcaaagg gctcaaaata cttggattcc agacaactga ggaaagagtg ggacgactgt     180
cctctggaag actggtttga gtacaacgtg aagaaataa acagcagtgg tccattttta     240
gttggagttt ttcgtaatca agtatagat gaaatccagc aagctatcca cactcatggt     300
ttggatttcg tccaactaca tgggtctgag gattttgatt cgtatatacg caatatccca     360
gttcctgtga ttaccagata cacagataat gccgtcgatg tcttaccgg agaagacctc      420
gctataaata gggccctggt gctactggac agcgagcaag gaggtgaagg aaaaaccatc     480
gattgggctc gtgcacaaaa atttggagaa cgtagaggaa atatttact agccggaggt      540
ttgacacctg ataatgttgc tcatgctcga tctcatactg ctgtattgg tgttgacgtc      600
tctggtgggg tagaaacaaa tgcctcaaaa gatatggaca agatcacaca atttatcaga     660
aacgctacat aa                                                         672
```

<210> SEQ ID NO 31
<211> LENGTH: 834
<212> TYPE: DNA
<213> ORGANISM: Artificial Sequence
<220> FEATURE:
<223> OTHER INFORMATION: PpTRP1 3' region

<400> SEQUENCE: 31

```
aagtcaatta atacacgct tgaaaggaca ttacatagct ttcgatttaa gcagaaccag       60
aaaatgtagaa ccacttgtca atagattggt caatcttagc aggagcggct gggctagcag    120
ttggaacagc agaggttgct gaaggtgaga aggatggagt ggattgcaaa gtggtgttgg    180
ttaagtcaat ctcaccaggg ctggttttgc caaaaatcaa cttctcccag gcttcacggc     240
attcttgaat gacctcttct gcatacttct tgttcttgca ttcaccagag aaagcaaact    300
ggttctcagg ttttccatca gggatcttgt aaattctgaa ccattcgttg gtagctctca    360
acaagcccgg catgtgcttt tcaacatcct cgatgtcatt gagcttagga gccaatgggt    420
cgttgatgtc gatgacgatg accttccagt cagtctctcc ctcatccaac aaagccataa    480
caccgaggac cttgacttgc ttgacctgtc cagtgtaacc tacggcttca ccaatttcgc    540
aaacgtccaa tggatcattg tcacccttgg ccttggtctc tggatgagtg acgttagggt    600
cttcccatgt ctgagggaag gcaccgtagt tgtgaatgta tccgtggtga gggaaacagt    660
tacgaacgaa acgaagtttt cccttctttg tgtcctgaag aattgggttc agtttctcct    720
ccttggaaat ctccaacttg gcgttggtcc aacggggac ttcaacaacc atgttgagaa     780
ccttcttgga ttcgtcagca taagtgggga tgtcgtggaa aggagatacg actt          834
```

<210> SEQ ID NO 32
<211> LENGTH: 1215
<212> TYPE: DNA
<213> ORGANISM: Artificial Sequence
<220> FEATURE:
<223> OTHER INFORMATION: ScARR3 ORF

<400> SEQUENCE: 32

```
atgtcagaag atcaaaaaag tgaaaattcc gtaccttcta aggttaatat ggtgaatcgc    60
accgatatac tgactacgat caagtcattg tcatggcttg acttgatgtt gccatttact   120
ataattctct ccataatcat tgcagtaata atttctgtct atgtgccttc ttcccgtcac   180
acttttgacg ctgaaggtca tcccaatcta atgggagtgt ccattccttt gactgttggt   240
atgattgtaa tgatgattcc cccgatctgc aaagtttcct gggagtctat tcacaagtac   300
ttctacagga gctatataag gaagcaacta gccctctcgt tattttttgaa ttgggtcatc   360 ggtcctttgt tgatgacagc attggcgtgg atggcgctat tcgattataa ggaataccgt   420
caaggcatta ttatgatcgg agtagctaga tgcattgcca tggtgctaat ttggaatcag   480
attgctggag gagacaatga tctctgcgtc gtgcttgtta ttacaaactc gcttttacag   540
atggtattat atgcaccatt gcagatattt tactgttatg ttatttctca tgaccacctg   600
aatacttcaa atagggtatt attcgaagag gttgcaaagt ctgtcggagt ttttctcggc   660
ataccactgg gaattggcat tatcatacgt ttgggaagtc ttaccatagc tggtaaaagt   720
aattatgaaa aatacatttt gagatttatt tctccatggg caatgatcgg atttcattac   780
actttatttg ttattttat tagtagaggt tatcaattta tccacgaaat tggttctgca   840
atattgtgct tgtcccatt ggtgctttac ttctttattg catggttttt gaccttcgca   900
ttaatgaggt acttatcaat atctaggagt gatacacaaa gagaatgtag ctgtgaccaa   960
gaactacttt taagagggt ctggggaaga aagtcttgtg aagctagctt ttctattacg  1020
atgacgcaat gtttcactat ggcttcaaat aattttgaac tatccctggc aattgctatt  1080
tccttatatg gtaacaatag caagcaagca atagctgcaa catttgggcc gttgctagaa  1140
gttccaattt tattgatttt ggcaatagtc gcgagaatcc ttaaaccata ttatatatgg  1200
aacaatagaa attaa                                                   1215
```

<210> SEQ ID NO 33
<211> LENGTH: 1144
<212> TYPE: DNA
<213> ORGANISM: Artificial Sequence
<220> FEATURE:
<223> OTHER INFORMATION: URA6 region

<400> SEQUENCE: 33

```
caaatgcaag aggacattag aaatgtgttt ggtaagaaca tgaagccgga ggcatacaaa    60
cgattcacag atttgaagga ggaaaacaaa ctgcatccac cggaagtgcc agcagccgtg   120
tatgccaacc ttgctctcaa aggcattcct acggatctga gtgggaaata tctgagattc   180
acagacccac tattggaaca gtaccaaacc tagtttggcc gatccatgat tatgtaatgc   240
atatagtttt tgtcgatgct cacccgtttc gagtctgtct cgtatcgtct tacgtataag   300
ttcaagcatg tttaccaggt ctgttagaaa ctcctttgtg agggcaggac ctattcgtct   360
cggtcccgtt gtttctaaga gactgtacag ccaagcgcag aatggtggca ttaaccataa   420
gaggattctg atcggacttg gtctattggc tattggaacc accctttacg ggacaaccaa   480
ccctaccaag actcctattg catttgtgga accagccacg gaaagagcgt ttaaggacgg   540
agacgtctct gtgattttttg ttctcggagg tccaggagct ggaaaaggta cccaatgtgc   600
caaactagtg agtaattacg gatttgttca cctgtcagct ggagacttgt tacgtgcaga   660
acagaagagg gaggggtcta agtatggaga tgatttcc cagtatatca gagatggact   720
gatagtacct caagaggtca ccattgcgct cttggagcag gccatgaagg aaaacttcga   780
gaaagggaag acacggttct tgattgatgg attccctcgt aagatggacc aggccaaaac   840
```

```
ttttgaggaa aaagtcgcaa agtccaaggt gacactttc tttgattgtc ccgaatcagt    900
gctccttgag agattactta aaagaggaca gacaagcgga agagaggatg ataatgcgga    960
gagtatcaaa aaaagattca aaacattcgt ggaaacttcg atgcctgtgg tggactattt   1020
cgggaagcaa ggacgcgttt tgaaggtatc ttgtgaccac cctgtggatc aagtgtattc   1080
acaggttgtg tcggtgctaa aagagaaggg gatctttgcc gataacgaga cggagaataa   1140
ataa                                                                1144
```

<210> SEQ ID NO 34
<211> LENGTH: 582
<212> TYPE: DNA
<213> ORGANISM: Artificial Sequence
<220> FEATURE:
<223> OTHER INFORMATION: NatR ORF

<400> SEQUENCE: 34

```
atgggtacca ctcttgacga cacggcttac cggtaccgca ccagtgtccc gggggacgcc     60
gaggccatcg aggcactgga tgggtccttc accaccgaca ccgtcttccg cgtcaccgcc    120
accggggacg gcttcaccct gcgggaggtg ccggtgaccc cgccctgac caaggtgttc    180 cccgacgacg aatcggacga cgaatcggac gacggggagg acggcgaccc ggactcccgg    240
acgttcgtcg cgtacgggga cgacggcgac ctggcgggct tcgtggtcgt ctcgtactcc    300
ggctggaacc gccggctgac cgtcgaggac atcgaggtcg ccccggagca ccgggggcac    360
ggggtcgggc gcgcgttgat ggggctcgcg acggagttcg cccgcgagcg gggcgccggg    420
cacctctggc tggaggtcac caacgtcaac gcaccggcga tccacgcgta ccggcggatg    480
gggttcaccc tctgcggcct ggacaccgcc ctgtacgacg caccgcctc ggacggcgag    540 caggcgctct acatgagcat gccctgcccc taatcagtac tg                      582
```

<210> SEQ ID NO 35
<211> LENGTH: 375
<212> TYPE: DNA
<213> ORGANISM: Artificial Sequence
<220> FEATURE:
<223> OTHER INFORMATION: Sequence of the Sh ble ORF (Zeocin resistance
      marker):

<400> SEQUENCE: 35

```
atggccaagt tgaccagtgc cgttccggtg ctcaccgcgc gcgacgtcgc cggagcggtc     60
gagttctgga ccgaccggct cgggttctcc cggggacttcg tggaggacga cttcgccggt    120
gtggtccggg acgacgtgac cctgttcatc agcgcggtcc aggaccaggt ggtgccggac    180
aacaccctgg cctgggtgtg gtgcgcggc ctggacgagc tgtacgccga gtggtcggag    240
gtcgtgtcca cgaacttccg ggacgcctcc gggccggcca tgaccgagat cggcgagcag    300
ccgtgggggc gggagttcgc cctgcgcgac ccggccggca actgcgtgca cttcgtggcc    360
gaggagcagg actga                                                    375
```

<210> SEQ ID NO 36
<211> LENGTH: 260
<212> TYPE: DNA
<213> ORGANISM: Artificial Sequence
<220> FEATURE:
<223> OTHER INFORMATION: PpAOX1 TT

<400> SEQUENCE: 36

```
tcaagaggat gtcagaatgc catttgcctg agagatgcag gcttcatttt gatactttt     60
```

```
tatttgtaac ctatatagta taggattttt tttgtcattt tgtttcttct cgtacgagct    120
tgctcctgat cagcctatct cgcagctgat gaatatcttg tggtaggggt ttgggaaaat    180
cattcgagtt tgatgttttt cttggtattt cccactcctc ttcagagtac agaagattaa    240
gtgagacgtt cgtttgtgca                                                260

<210> SEQ ID NO 37
<211> LENGTH: 427
<212> TYPE: DNA
<213> ORGANISM: Artificial Sequence
<220> FEATURE:
<223> OTHER INFORMATION: ScTEF1 promoter

<400> SEQUENCE: 37
gatcccccac acaccatagc ttcaaaatgt ttctactcct tttttactct tccagatttt     60
ctcggactcc gcgcatcgcc gtaccacttc aaaacaccca agcacagcat actaaatttc    120
ccctctttct tcctctaggg tgtcgttaat tacccgtact aaaggtttgg aaaagaaaaa    180
agagaccgcc tcgtttcttt ttcttcgtcg aaaaaggcaa taaaaatttt tatcacgttt    240 cttttcttg  aaaattttttt  tttttgattt tttttctcttt cgatgacctc ccattgatat    300
ttaagttaat aaacggtctt caatttctca agtttcagtt tcattttttct tgttctatta    360 caacttttt tacttcttgc tcattagaaa gaaagcatag caatctaatc taagttttaa    420
ttacaaa                                                              427

<210> SEQ ID NO 38
<211> LENGTH: 3029
<212> TYPE: DNA
<213> ORGANISM: Saccharomyces cerevisiea

<400> SEQUENCE: 38
aggcctcgca acaacctata attgagttaa gtgcctttcc aagctaaaaa gtttgaggtt     60 atagggctt agcatccaca cgtcacaatc tcgggtatcg agtatagtat gtagaattac    120
ggcaggaggt ttcccaatga acaaaggaca ggggcacggt gagctgtcga aggtatccat    180
tttatcatgt ttcgtttgta caagcacgac atactaagac atttaccgta tgggagttgt    240
tgtcctagcg tagttctcgc tccccccagca aagctcaaaa aagtacgtca tttagaatag    300
tttgtgagca aattaccagt cggtatgcta cgttagaaag gcccacagta ttcttctacc    360
aaaggcgtgc ctttgttgaa ctcgatccat tatgagggct tccattattc cccgcatttt    420
tattactctg aacaggaata aaaagaaaaa acccagttta ggaaattatc cggggcgaa    480 gaaatacgcg tagcgttaat cgaccccacg tccagggttt ttccatggag gtttctggaa    540
aaactgacga ggaatgtgat tataaatccc tttatgtgat gtctaagact tttaaggtac    600
gcccgatgtt tgcctattac catcatagag acgtttcttt tcgaggaatg cttaaacgac    660
tttgtttgac aaaaatgttg cctaagggct ctatagtaaa ccatttggaa gaaagatttg    720 acgactttt  tttttggat ttcgatccta taatccttcc tcctgaaaag aaacatataa    780
atagatatgt attattcttc aaaacattct cttgttcttg tgcttttttt ttaccatata    840
tcttactttt tttttctct cagagaaaca agcaaaacaa aaagcttttc ttttcactaa    900
cgtatatgat gcttttgcaa gctttccttt tccttttggc tggttttgca gccaaaatat    960
ctgcatcaat gacaaacgaa actagcgata gacctttggt ccacttcaca cccaacaagg   1020
gctggatgaa tgacccaaat gggttgtggt acgatgaaaa agatgccaaa tggcatctgt   1080
actttcaata caacccaaat gacaccgtat ggggtacgcc attgttttgg ggccatgcta   1140
```

```
cttccgatga tttgactaat tgggaagatc aacccattgc tatcgctccc aagcgtaacg   1200
attcaggtgc tttctctggc tccatggtgg ttgattacaa caacacgagt gggtttttca   1260
atgatactat tgatccaaga caaagatgcg ttgcgatttg gacttataac actcctgaaa   1320
gtgaagagca atacattagc tattctcttg atggtggtta cacttttact gaataccaaa   1380
agaaccctgt tttagctgcc aactccactc aattcagaga tccaaaggtg ttctggtatg   1440
aaccttctca aaatggatt atgacggctg ccaaatcaca agactacaaa attgaaattt    1500
actcctctga tgacttgaag tcctggaagc tagaatctgc atttgccaat gaaggtttct   1560
taggctacca atacgaatgt ccaggtttga ttgaagtccc aactgagcaa gatccttcca   1620
aatcttattg ggtcatgttt atttctatca acccaggtgc acctgctggc ggttccttca   1680
accaatattt tgttggatcc ttcaatggta ctcattttga agcgtttgac aatcaatcta   1740
gagtggtaga ttttggtaag gactactatg ccttgcaaac tttcttcaac actgacccaa   1800
cctacggttc agcattaggt attgcctggg cttcaaactg ggagtacagt gcctttgtcc   1860
caactaaccc atggagatca tccatgtctt tggtccgcaa gttttctttg aacactgaat   1920
atcaagctaa tccagagact gaattgatca atttgaaagc cgaaccaata ttgaacatta   1980
gtaatgctgg tccctggtct cgttttgcta ctaacacaac tctaactaag gccaattctt   2040
acaatgtcga tttgagcaac tcgactggta ccctagagtt tgagttggtt tacgctgtta   2100
acaccacaca aaccatatcc aaatccgtct ttgccgactt atcactttgg ttcaagggtt   2160
tagaagatcc tgaagaatat ttgagaatgg gttttgaagt cagtgcttct tccttctttt   2220
tggaccgtgg taactctaag gtcaagtttg tcaaggagaa cccatatttc acaaacagaa   2280
tgtctgtcaa caaccaacca ttcaagtctg agaacgacct aagttactat aaagtgtacg   2340
gcctactgga tcaaaacatc ttggaattgt acttcaacga tggagatgtg gtttctacaa   2400 ataccctactt catgaccacc ggtaacgctc taggatctgt gaacatgacc actggtgtcg   2460
ataatttgtt ctacattgac aagttccaag taagggaagt aaaatagagg ttataaaact   2520
tattgtcttt tttattttttt tcaaaagcca ttctaaaggg ctttagctaa cgagtgacga   2580
atgtaaaact ttatgatttc aaagaatacc tccaaaccat tgaaaatgta ttttatttt    2640 tattttctcc cgaccccagt tacctggaat ttgttcttta tgtactttat ataagtataa   2700
ttctcttaaa aatttttact acttttgcaat agacatcatt ttttcacgta ataaacccac   2760
aatcgtaatg tagttgcctt acactactag gatggacctt tttgcctta tctgttttgt    2820 tactgacaca atgaaaccgg gtaaagtatt agttatgtga aaatttaaaa gcattaagta   2880
gaagtatacc atattgtaaa aaaaaaagc gttgtcttct acgtaaaagt gttctcaaaa    2940
agaagtagtg agggaaatgg ataccaagct atctgtaaca ggagctaaaa aatctcaggg   3000
aaaagcttct ggtttgggaa acggtcgac                                    3029
```

<210> SEQ ID NO 39
<211> LENGTH: 898
<212> TYPE: DNA
<213> ORGANISM: Artificial Sequence
<220> FEATURE:
<223> OTHER INFORMATION: Sequence of the 5'-Region used for knock out of PpURA5:

<400> SEQUENCE: 39

```
atcggccttt gttgatgcaa gttttacgtg gatcatggac taaggagttt tatttggacc     60
aagttcatcg tcctagacat tacgaaaagg gttctgctcc tcttttgga aacttttgg     120 aacctctgag tatgacagct tggtggattg tacccatggt atggcttcct gtgaatttct    180
```

```
atttttcta cattggattc accaatcaaa acaaattagt cgccatggct ttttggcttt      240
tgggtctatt tgtttggacc ttcttggaat atgctttgca tagattttg ttccacttgg      300 actactatct tccagagaat caaattgcat ttaccattca tttcttattg catgggatac     360
accactattt accaatggat aaatacagat tggtgatgcc acctacactt ttcattgtac     420
tttgctaccc aatcaagacg ctcgtctttt ctgttctacc atattacatg gcttgttctg     480
gatttgcagg tggattcctg ggctatatca tgtatgatgt cactcattac gttctgcatc     540
actccaagct gcctcgttat ttccaagagt tgaagaaata tcatttggaa catcactaca     600
agaattacga gttaggcttt ggtgtcactt ccaaattctg ggacaaagtc tttgggactt     660
atctgggtcc agacgatgtg tatcaaaaga caaattagag tatttataaa gttatgtaag     720
caaatagggg ctaataggga agaaaaaatt ttggttcttt atcagagctg gctcgcgcgc     780 agtgttttc gtgctccttt gtaatagtca tttttgacta ctgttcagat tgaaatcaca     840
ttgaagatgt cactcgaggg gtaccaaaaa aggttttttgg atgctgcagt ggcttcgc      898

<210> SEQ ID NO 40
<211> LENGTH: 1060
<212> TYPE: DNA
<213> ORGANISM: Artificial Sequence
<220> FEATURE:
<223> OTHER INFORMATION: Sequence of the 3'-Region used for knock out of
      PpURA5:

<400> SEQUENCE: 40
ggtcttttca acaaagctcc attagtgagt cagctggctg aatcttatgc acaggccatc      60
attaacagca acctggagat agacgttgta tttggaccag cttataaagg tattcctttg     120
gctgctatta ccgtgttgaa gttgtacgag ctcggcggca aaaaatacga aaatgtcgga     180
tatgcgttca atagaaaaga aaagaaagac cacggagaag gtggaagcat cgttggagaa     240
agtctaaaga ataaaagagt actgattatc gatgatgtga tgactgcagg tactgctatc     300
aacgaagcat ttgctataat tggagctgaa ggtgggagag ttgaaggtag tattattgcc     360
ctagatagaa tggagactac aggagatgac tcaaatacca gtgctaccca ggctgttagt     420
cagagatatg gtacccctgt cttgagtata gtgacattgg accatattgt ggcccatttg     480
ggcgaaactt tcacagcaga cgagaaatct caaatggaaa cgtatagaaa aaagtatttg     540
cccaaataag tatgaatctg cttcgaatga atgaattaat ccaattatct tctcaccatt     600
attttcttct gttccggagc tttgggcacg gcggcgggtg gtgcgggctc aggttccctt     660
tcataaacag atttagtact tggatgctta atagtgaatg gcgaatgcaa aggaacaatt     720
tcgttcatct ttaacccttt cactcggggt acacgttctg gaatgtaccc gccctgttgc     780
aactcaggtg gaccgggcaa ttcttgaact ttctgtaacg ttgttggatg ttcaaccaga     840
aattgtccta ccaactgtat tagttttcct ttggtcttat attgttcatc gagatacttc     900
ccactctcct tgatagccac tctcactctt cctggattac caaaatcttg aggatgagtc     960
ttttcaggct ccaggatgca aggtatatcc aagtacctgc aagcatctaa tattgtcttt    1020 gccaggggt tctccacacc atactccttt tggcgcatgc                           1060

<210> SEQ ID NO 41
<211> LENGTH: 957
<212> TYPE: DNA
<213> ORGANISM: Artificial Sequence
<220> FEATURE:
<223> OTHER INFORMATION: Sequence of the PpURA5 auxotrophic marker
```

<400> SEQUENCE: 41

```
tctagaggga cttatctggg tccagacgat gtgtatcaaa agacaaatta gagtatttat    60
aaagttatgt aagcaaatag gggctaatag ggaaagaaaa attttggttc tttatcagag   120
ctggctcgcg cgcagtgttt ttcgtgctcc tttgtaatag tcattttga ctactgttca    180
gattgaaatc acattgaaga tgtcactgga ggggtaccaa aaaaggtttt tggatgctgc   240
agtggcttcg caggccttga agtttggaac tttcaccttg aaaagtggaa gacagtctcc   300
atacttcttt aacatgggtc ttttcaacaa agctccatta gtgagtcagc tggctgaatc   360
ttatgctcag gccatcatta acagcaacct ggagatagac gttgtatttg gaccagctta   420
taaaggtatt cctttggctg ctattaccgt gttgaagttg tacgagctgg gcggcaaaaa   480
atacgaaaat gtcggatatg cgttcaatag aaaagaaaag aaagaccacg agaaggtgg    540
aagcatcgtt ggagaaagtc taaagaataa aagagtactg attatcgatg atgtgatgac   600
tgcaggtact gctatcaacg aagcatttgc tataattgga gctgaaggtg ggagagttga   660
aggttgtatt attgccctag atagaatgga gactacagga gatgactcaa ataccagtgc   720
tacccaggct gttagtcaga gatatggtac ccctgtcttg agtatagtga cattggacca   780
tattgtggcc catttgggcg aaactttcac agcagacgag aaatctcaaa tggaaacgta   840
tagaaaaaag tatttgccca aataagtatg aatctgcttc gaatgaatga attaatccaa   900
ttatcttctc accattattt tcttctgttt cggagctttg ggcacggcgg cggatcc      957
```

<210> SEQ ID NO 42
<211> LENGTH: 709
<212> TYPE: DNA
<213> ORGANISM: Artificial Sequence
<220> FEATURE:
<223> OTHER INFORMATION: Sequence of the part of the Ec lacZ gene that was used to construct the PpURA5 blaster (recyclable auxotrophic marker)

<400> SEQUENCE: 42

```
cctgcactgg atggtggcgc tggatggtaa gccgctggca agcggtgaag tgcctctgga    60
tgtcgctcca caaggtaaac agttgattga actgcctgaa ctaccgcagc cggagagcgc   120
cgggcaactc tggctcacag tacgcgtagt gcaaccgaac gcgaccgcat ggtcagaagc   180
cgggcacatc agcgcctggc agcagtggcg tctggcggaa aacctcagtg tgacgctccc   240
cgccgcgtcc cacgccatcc cgcatctgac caccagcgaa atggattttt gcatcgagct   300
gggtaataag cgttggcaat taaccgcca gtcaggcttt cttcacaga tgtggattgg    360
cgataaaaaa caactgctga cgccgctgcg cgatcagttc acccgtgcac cgctggataa   420
cgacattggc gtaagtgaag cgacccgcat tgaccctaac gcctgggtcg aacgctggaa   480
gcggcgggc cattaccagg ccgaagcagc gttgttgcag tgcacggcag atacacttgc   540
tgatgcggtg ctgattacga ccgctcacgc gtggcagcat cagggggaaaa ccttatttat   600
cagccggaaa acctaccgga ttgatggtag tggtcaaatg gcgattaccg ttgatgttga   660
agtggcgagc gatacaccgc atccggcgcg gattggcctg aactgccag               709
```

<210> SEQ ID NO 43
<211> LENGTH: 2875
<212> TYPE: DNA
<213> ORGANISM: Artificial Sequence
<220> FEATURE:
<223> OTHER INFORMATION: Sequence of the 5'-Region used for knock out of PpOCH1

<400> SEQUENCE: 43

-continued

```
aaaaccttttt ttcctattca aacacaaggc attgcttcaa cacgtgtgcg tatccttaac    60
acagatactc catacttcta ataatgtgat agacgaatac aaagatgttc actctgtgtt   120
gtgtctacaa gcatttctta ttctgattgg ggatattcta gttacagcac taaacaactg   180
gcgatacaaa cttaaattaa ataatccgaa tctagaaaat gaacttttgg atggtccgcc   240
tgttggttgg ataaatcaat accgattaaa tggattctat tccaatgaga gagtaatcca   300
agacactctg atgtcaataa tcatttgctt gcaacaacaa acccgtcatc taatcaaagg   360
gtttgatgag gcttaccttc aattgcagat aaactcattg ctgtccactg ctgtattatg   420
tgagaatatg ggtgatgaat ctggtcttct ccactcagct aacatggctg tttgggcaaa   480
ggtggtacaa ttatacggag atcaggcaat agtgaaattg ttgaatatgg ctactggacg   540
atgcttcaag gatgtacgtc tagtaggagc cgtgggaaga ttgctggcag aaccagttgg   600
cacgtcgcaa caatccccaa gaaatgaaat aagtgaaaac gtaacgtcaa agacagcaat   660
ggagtcaata ttgataacac cactggcaga gcggttcgta cgtcgttttg gagccgatat   720
gaggctcagc gtgctaacag cacgattgac aagaagactc tcgagtgaca gtaggttgag   780
taaagtattc gcttagattc ccaaccttcg ttttattctt tcgtagacaa agaagctgca   840
tgcgaacata gggacaactt ttataaatcc aattgtcaaa ccaacgtaaa accctctggc   900
accattttca acatatattt gtgaagcagt acgcaatatc gataaatact caccgttgtt   960
tgtaacagcc ccaacttgca tacgccttct aatgacctca aatggataag ccgcagcttg  1020
tgctaacata ccagcagcac cgcccgcggt cagctgcgcc cacacatata aaggcaatct  1080
acgatcatgg gaggaattag ttttgaccgt caggtcttca agagttttga actcttcttc  1140
ttgaactgtg taaccttta aatgacggga tctaaatacg tcatggatga gatcatgtgt  1200
gtaaaaactg actccagcat atggaatcat tccaaagatt gtaggagcga acccacgata  1260
aaagtttccc aaccttgcca aagtgtctaa tgctgtgact tgaaatctgg gttcctcgtt  1320
gaagaccctg cgtactatgc ccaaaaactt tcctccacga gccctattaa cttctctatg  1380
agtttcaaat gccaaacgga cacggattag gtccaatggg taagtgaaaa acacagagca  1440
aaccccagct aatgagccgg ccagtaaccg tcttggagct gtttcataag agtcattagg  1500
gatcaataac gttctaatct gttcataaca tacaaatttt atggctgcat agggaaaaat  1560
tctcaacagg gtagccgaat gaccctgata tagacctgcg acaccatcat acccatagat  1620
ctgcctgaca gccttaaaga gcccgctaaa agacccggaa aaccgagaga actctggatt  1680
agcagtctga aaaagaatct tcactctgtc tagtggagca attaatgtct tagcggcact  1740
tcctgctact ccgccagcta ctcctgaata gatcacatac tgcaaagact gcttgtcgat  1800
gaccttgggg ttatttagct tcaagggcaa ttttgggac atttggaca caggagactc  1860
agaaacagac acagagcgtt ctgagtcctg gtgctcctga cgtaggccta gaacaggaat  1920
tattggcttt atttgtttgt ccatttcata ggcttggggt aatagataga tgacagagaa  1980
atagagaaga cctaatattt tttgttcatg gcaaatcgcg ggttcgcggt cgggtcacac  2040
acggagaagt aatgagaaga gctggtaatc tggggtaaaa gggttcaaaa gaaggtcgcc  2100
tggtagggat gcaatacaag gttgtcttgg agtttacatt gaccagatga tttggctttt  2160
tctctgttca attcacattt ttcagcgaga atcggattga cggagaaatg gcggggtgtg  2220
gggtggatag atggcagaaa tgctcgcaat caccgcgaaa gaaagacttt atggaataga  2280
actactgggt ggtgtaagga ttacatagct agtccaatgg agtccgttgg aaaggtaaga  2340
agaagctaaa accggctaag taactaggga agaatgatca gactttgatt tgatgaggtc  2400
```

```
tgaaaatact ctgctgcttt ttcagttgct ttttccctgc aacctatcat tttccttttc     2460
ataagcctgc cttttctgtt ttcacttata tgagttccgc cgagacttcc ccaaattctc     2520
tcctggaaca ttctctatcg ctctccttcc aagttgcgcc ccctggcact gcctagtaat     2580
attaccacgc gacttatatt cagttccaca atttccagtg ttcgtagcaa atatcatcag     2640
ccatggcgaa ggcagatggc agtttgctct actataatcc tcacaatcca cccagaaggt     2700
attacttcta catggctata ttcgccgttt ctgtcatttg cgttttgtac ggaccctcac     2760
aacaattatc atctccaaaa atagactatg atccattgac gctccgatca cttgatttga     2820
agactttgga agctccttca cagttgagtc caggcaccgt agaagataat cttcg         2875
```

<210> SEQ ID NO 44
<211> LENGTH: 997
<212> TYPE: DNA
<213> ORGANISM: Artificial Sequence
<220> FEATURE:
<223> OTHER INFORMATION: Sequence of the 3'-Region used for knock out of
      PpOCH1

<400> SEQUENCE: 44

```
aaagctagag taaaatagat atagcgagat tagagaatga ataccttctt ctaagcgatc       60
gtccgtcatc atagaatatc atggactgta tagttttttt tttgtacata taatgattaa      120
acggtcatcc aacatctcgt tgacagatct ctcagtacgc gaaatccctg actatcaaag      180
caagaaccga tgaagaaaaa aacaacagta acccaaacac cacaacaaac actttatctt      240
ctccccccca acaccaatca tcaaagagat gtcggaacca acaccaaga agcaaaaact       300 aaccccatat aaaaacatcc tggtagataa tgctggtaac ccgctctcct tccatattct      360
gggctacttc acgaagtctg accggtctca gttgatcaac atgatcctcg aaatgggtgg      420
caagatcgtt ccagacctgc ctcctctggt agatggagtg ttgttttga cagggatta       480 caagtctatt gatgaagata ccctaaagca actgggggac gttccaatat acagagactc      540
cttcatctac cagtgttttg tgcacaagac atctcttccc attgacactt tccgaattga      600
caagaacgtc gacttggctc aagatttgat caatagggcc cttcaagagt ctgtggatca      660
tgtcacttct gccagcacag ctgcagctgc tgctgttgtt gtcgctacca acggcctgtc      720
ttctaaacca gacgctcgta ctagcaaaat acagttcact cccgaagaag atcgttttat      780
tcttgacttt gttaggagaa atcctaaacg aagaaacaca catcaactgt acactgagct      840
cgctcagcac atgaaaaacc atacgaatca ttctatccgc cacagatttc gtcgtaatct      900
ttccgctcaa cttgattggg tttatgatat cgatccattg accaaccaac ctcgaaaaga      960
tgaaaacggg aactacatca aggtacaagg ccttcca                              997
```

<210> SEQ ID NO 45
<211> LENGTH: 2159
<212> TYPE: DNA
<213> ORGANISM: Kluyveromyces lactis

<400> SEQUENCE: 45

```
aaacgtaacg cctggcactc tatttctca aacttctggg acggaagagc taaatattgt        60
gttgcttgaa caacccaaa aaaacaaaaa aatgaacaaa ctaaaactac acctaaataa       120 acgtgtgta aaacgtagta ccatattact agaaaagatc acaagtgtat cacacatgtg       180
catctcatat tacatctttt atccaatcca ttctctctat cccgtctgtt cctgtcagat      240 tcttttttcca taaaagaag aagaccccga atctcaccgg tacaatgcaa aactgctgaa      300
```

```
aaaaaaagaa agttcactgg atacgggaac agtgccagta ggcttcacca catggacaaa    360
acaattgacg ataaaataag caggtgagct tcttttttcaa gtcacgatcc ctttatgtct    420
cagaaacaat atatacaagc taaacccttt tgaaccagtt ctctcttcat agttatgttc    480
acataaattg cgggaacaag actccgctgg ctgtcaggta cacgttgtaa cgttttcgtc    540
cgcccaatta ttagcacaac attggcaaaa agaaaactg ctcgttttct ctacaggtaa     600
attacaattt ttttcagtaa ttttcgctga aaaatttaaa gggcaggaaa aaaagacgat    660
ctcgactttg catagatgca agaactgtgg tcaaacttg aaatagtaat tttgctgtgc     720
gtgaactaat aaatatatat atatatatat atatatattt gtgtattttg tatatgtaat    780
tgtgcacgtc ttggctattg gatataagat tttcgcgggt tgatgacata gagcgtgtac    840
tactgtaata gttgtatatt caaaagctgc tgcgtggaga aagactaaaa tagataaaaa    900
gcacacattt tgacttcggt accgtcaact tagtgggaca gtcttttata tttggtgtaa    960
gctcatttct ggtactattc gaaacagaac agtgttttct gtattaccgt ccaatcgttt    1020
gtcatgagtt ttgtattgat tttgtcgtta gtgttcggag gatgttgttc caatgtgatt    1080
agtttcgagc acatggtgca aggcagcaat ataaatttgg gaaatattgt tacattcact    1140
caattcgtgt ctgtgacgct aattcagttg cccaatgctt tggacttctc tcactttccg    1200
tttaggttgc gacctagaca cattcctctt aagatccata tgttagctgt gttttttgttc    1260 tttaccagtt cagtcgccaa taacagtgtg tttaaatttg acatttccgt tccgattcat    1320
attatcatta gattttcagg taccactttg acgatgataa taggttgggc tgtttgtaat    1380
aagaggtact ccaaacttca ggtgcaatct gccatcatta tgacgcttgg tgcgattgtc    1440
gcatcattat accgtgacaa agaattttca atggacagtt taaagttgaa tacggattca    1500
gtgggtatga cccaaaaatc tatgtttggt atctttgttg tgctagtggc cactgccttg    1560
atgtcattgt tgtcgttgct caacgaatgg acgtataaca agtacgggaa acattggaaa    1620
gaaactttgt tctattcgca tttcttggct ctaccgttgt ttatgttggg gtacacaagg    1680
ctcagagacg aattcagaga cctcttaatt tcctcagact caatggatat tcctattgtt    1740
aaattaccaa ttgctacgaa acttttcatg ctaatagcaa ataacgtgac ccagttcatt    1800
tgtatcaaag gtgttaacat gctagctagt aacacggatg ctttgacact ttctgtcgtg    1860
cttctagtgc gtaaatttgt tagtcttttta ctcagtgtct acatctacaa gaacgtccta    1920
tccgtgactg catacctagg gaccatcacc gtgttcctgg gagctggttt gtattcatat    1980
ggttcggtca aaactgcact gcctcgctga acaatccac gtctgtatga tactcgtttc     2040 agaattttttt tgattttctg ccggatatgg tttctcatct ttacaatcgc attcttaatt    2100
ataccagaac gtaattcaat gatcccagtg actcgtaact cttatatgtc aatttaagc    2159
```

<210> SEQ ID NO 46
<211> LENGTH: 870
<212> TYPE: DNA
<213> ORGANISM: Artificial Sequence
<220> FEATURE:
<223> OTHER INFORMATION: Sequence of the 5'-Region used for knock out of PpBMT2

<400> SEQUENCE: 46

```
ggccgagcgg gcctagattt tcactacaaa tttcaaaact acgcggattt attgtctcag     60
agagcaattt ggcatttctg agcgtagcag gaggcttcat aagattgtat aggaccgtac    120
caacaaattg ccgaggcaca acacggtatg ctgtgcactt atgtggctac ttccctacaa    180
cggaatgaaa ccttcctctt tccgcttaaa cgagaaagtg tgtcgcaatt gaatgcaggt    240
```

```
gcctgtgcgc cttggtgtat tgttttttgag ggcccaattt atcaggcgcc ttttttcttg      300
gttgttttcc cttagcctca agcaaggttg gtctatttca tctccgcttc tataccgtgc      360
ctgatactgt tggatgagaa cacgactcaa cttcctgctg ctctgtattg ccagtgtttt      420
gtctgtgatt tggatcggag tcctccttac ttggaatgat aataatcttg gcggaatctc      480
cctaaacgga ggcaaggatt ctgcctatga tgatctgcta tcattgggaa gcttcaacga      540
catggaggtc gactcctatg tcaccaacat ctacgacaat gctccagtgc taggatgtac      600
ggatttgtct tatcatggat tgttgaaagt caccccaaag catgacttag cttgcgattt      660
ggagttcata agagctcaga ttttggacat tgacgtttac tccgccataa aagacttaga      720
agataaagcc ttgactgtaa aacaaaaggt tgaaaaacac tggtttacgt tttatggtag      780
ttcagtcttt ctgcccgaac acgatgtgca ttacctggtt agacgagtca tcttttcggc      840
tgaaggaaag gcgaactctc cagtaacatc                                       870
```

<210> SEQ ID NO 47
<211> LENGTH: 1733
<212> TYPE: DNA
<213> ORGANISM: Artificial Sequence
<220> FEATURE:
<223> OTHER INFORMATION: Sequence of the 3'-Region used for knock out of
      PpBMT2

<400> SEQUENCE: 47

```
ccatatgatg ggtgtttgct cactcgtatg gatcaaaatt ccatggtttc ttctgtacaa        60
cttgtacact tatttggact tttctaacgg ttttttctggt gatttgagaa gtccttattt      120
tggtgttcgc agcttatccg tgattgaacc atcagaaata ctgcagctcg ttatctagtt      180
tcagaatgtg ttgtagaata caatcaattc tgagtctagt ttgggtgggt cttggcgacg      240
ggaccgttat atgcatctat gcagtgttaa ggtacataga atgaaaatgt aggggttaat      300
cgaaagcatc gttaatttca gtagaacgta gttctattcc ctacccaaat aatttgccaa      360
gaatgcttcg tatccacata cgcagtggac gtagcaaatt tcactttgga ctgtgacctc      420
aagtcgttat cttctacttg gacattgatg gtcattacgt aatccacaaa gaattggata      480
gcctctcgtt ttatctagtg cacagcctaa tagcacttaa gtaagagcaa tggacaaatt      540
tgcatagaca ttgagctaga tacgtaactc agatcttgtt cactcatggt gtactcgaag      600
tactgctgga accgttacct cttatcattt cgctactggc tcgtgaaact actggatgaa      660 aaaaaaaaa gagctgaaag cgagatcatc ccatttgtc atcatacaaa ttcacgcttg       720
cagttttgct tcgttaacaa gacaagatgt ctttatcaaa gacccgtttt ttcttcttga      780
agaatacttc cctgttgagc acatgcaaac catatttatc tcagatttca ctcaacttgg      840
gtgcttccaa gagaagtaaa attcttccca ctgcatcaac ttccaagaaa cccgtagacc      900
agtttctctt cagccaaaag aagttgctcg ccgatcaccg cggtaacaga ggagtcagaa      960
ggtttcacac ccttccatcc cgatttcaaa gtcaaagtgc tgcgttgaac caaggttttc     1020
aggttgccaa agcccagtct gcaaaaacta gttccaaatg gccattaat tcccataaaa      1080 gtgttggcta cgtatgtatc ggtacctcca ttctggtatt tgctattgtt gtcgttggtg     1140
ggttgactag actgaccgaa tccggtcttt ccataacgga gtggaaacct atcactggtt     1200
cggttccccc actgactgag gaagactgga agttggaatt tgaaaaatac aaacaaagcc     1260
ctgagtttca ggaactaaat tctcacataa cattggaaga gttcaagttt atattttcca     1320
tggaatgggg acatagattg ttgggaaggg tcatcggcct gtcgtttgtt cttcccacgt     1380
```

-continued

```
tttacttcat tgcccgtcga aagtgttcca aagatgttgc attgaaactg cttgcaatat    1440
gctctatgat aggattccaa ggtttcatcg gctggtggat ggtgtattcc ggattggaca    1500
aacagcaatt ggctgaacgt aactccaaac caactgtgtc tccatatcgc ttaactaccc    1560
atcttggaac tgcatttgtt atttactgtt acatgattta cacagggctt caagttttga    1620
agaactataa gatcatgaaa cagcctgaag cgtatgttca aattttcaag caaattgcgt    1680
ctccaaaatt gaaaactttc aagagactct cttcagttct attaggcctg gtg           1733
```

<210> SEQ ID NO 48
<211> LENGTH: 981
<212> TYPE: DNA
<213> ORGANISM: Artificial Sequence
<220> FEATURE:
<223> OTHER INFORMATION: DNA encodes MmSLC35A3 UDP-GlcNAc transporter

<400> SEQUENCE: 48

```
atgtctgcca acctaaaata tctttccttg ggaattttgg tgtttcagac taccagtctg     60
gttctaacga tgcggtattc taggacttta aaagaggagg ggcctcgtta tctgtcttct    120
acagcagtgg ttgtggctga attttttgaag ataatggcct gcatcttttt agtctacaaa   180
gacagtaagt gtagtgtgag agcactgaat agagtactgc atgatgaaat tcttaataag    240
cccatggaaa ccctgaagct cgctatcccg tcagggatat atactcttca gaacaactta    300
ctctatgtgg cactgtcaaa cctagatgca gccacttacc aggttacata tcagttgaaa    360
atacttacaa cagcattatt ttctgtgtct atgcttggta aaaaattagg tgtgtaccag    420
tggctctccc tagtaattct gatggcagga gttgcttttg tacagtggcc ttcagattct    480
caagagctga actctaagga cctttcaaca ggctcacagt ttgtaggcct catggcagtt    540
ctcacagcct gtttttcaag tggctttgct ggagtttatt ttgagaaaat cttaaaagaa    600
acaaaacagt cagtatggat aaggaacatt caacttggtt tctttggaag tatatttgga    660
ttaatgggtg tatacgttta tgatggagaa ttggtctcaa agaatggatt ttttcaggga    720
tataatcaac tgacgtggat agttgttgct ctgcaggcac ttggaggcct tgtaatagct    780
gctgtcatca aatatgcaga taacatttta aaaggatttg cgacctcctt atccataata    840
ttgtcaacaa taatatctta tttttggttg caagattttg tgccaaccag tgtcttttc    900 cttggagcca tccttgtaat agcagctact ttcttgtatg ttacgatcc caaacctgca    960 ggaaatccca ctaaagcata g                                              981
```

<210> SEQ ID NO 49
<211> LENGTH: 1128
<212> TYPE: DNA
<213> ORGANISM: Artificial Sequence
<220> FEATURE:
<223> OTHER INFORMATION: Sequence of the 5'-Region used for knock out of
    PpMNN4L1

<400> SEQUENCE: 49

```
gatctggcca ttgtgaaact tgacactaaa gacaaaactc ttagagtttc caatcactta     60
ggagacgatg tttcctacaa cgagtacgat ccctcattga tcatgagcaa tttgtatgtg    120
aaaaaagtca tcgaccttga caccttggat aaaagggctg gaggaggtgg aaccacctgt    180
gcaggcggtc tgaaagtgtt caagtacgga tctactacca aatatacatc tggtaacctg    240
aacggcgtca ggttagtata ctggaacgaa ggaaagttgc aaagctccaa atttgtggtt    300
cgatcctcta attactctca aaagcttgga ggaaacagca acgccgaatc aattgacaac    360
aatggtgtgg gttttgcctc agctggagac tcaggcgcat ggattctttc caagctacaa    420
```

```
gatgttaggg agtaccagtc attcactgaa aagctaggtg aagctacgat gagcattttc    480
gatttccacg gtcttaaaca ggagacttct actacagggc ttggggtagt tggtatgatt    540
cattcttacg acggtgagtt caaacagttt ggtttgttca ctccaatgac atctattcta    600
caaagacttc aacgagtgac caatgtagaa tggtgtgtag cgggttgcga agatggggat    660
gtggacactg aaggagaaca cgaattgagt gatttggaac aactgcatat gcatagtgat    720
tccgactagt caggcaagag agagccctca aatttacctc tctgcccctc ctcactcctt    780
ttggtacgca taattgcagt ataaagaact tgctgccagc cagtaatctt atttcatacg    840
cagttctata tagcacataa tcttgcttgt atgtatgaaa tttaccgcgt tttagttgaa    900
attgtttatg ttgtgtgcct tgcatgaaat ctctcgttag ccctatcctt acatttaact    960
ggtctcaaaa cctctaccaa ttccattgct gtacaacaat atgaggcggc attactgtag   1020
ggttggaaaa aaattgtcat tccagctaga gatcacacga cttcatcacg cttattgctc   1080
ctcattgcta aatcatttac tcttgacttc gacccagaaa agttcgcc                1128
```

<210> SEQ ID NO 50
<211> LENGTH: 1231
<212> TYPE: DNA
<213> ORGANISM: Artificial Sequence
<220> FEATURE:
<223> OTHER INFORMATION: Sequence of the 3'-Region used for knock out of
      PpMNN4L1

<400> SEQUENCE: 50

```
gcatgtcaaa cttgaacaca acgactagat agttgttttt tctatataaa acgaaacgtt     60
atcatcttta ataatcattg aggtttaccc ttatagttcc gtattttcgt ttccaaactt    120
agtaatcttt tggaaatatc atcaaagctg gtgccaatct tcttgtttga agtttcaaac    180
tgctccacca agctacttag agactgttct aggtctgaag caacttcgaa cacagagaca    240
gctgccgccg attgttcttt tttgtgtttt tcttctggaa gaggggcatc atcttgtatg    300
tccaatgccc gtatcctttc tgagttgtcc gacacattgt ccttcgaaga gtttcctgac    360
attgggcttc ttctatccgt gtattaattt tgggttaagt tcctcgtttg catagcagtg    420
gatacctcga tttttttggc tcctatttac ctgacataat attctactat aatccaactt    480
ggacgcgtca tctatgataa ctaggctctc ctttgttcaa aggggacgtc ttcataatcc    540
actggcacga agtaagtctg caacgaggcg cttttgcaa cagaacgata gtgtcgtttc    600
gtacttggac tatgctaaac aaaaggatct gtcaaacatt tcaaccgtgt tcaaggcac    660 tctttacgaa ttatcgacca agaccttcct agacgaacat ttcaacatat ccaggctact    720
gcttcaaggt ggtgcaaatg ataaaggtat agatattaga tgtgtttggg acctaaaaca    780
gttcttgcct gaagattccc ttgagcaaca ggcttcaata gccaagttag agaagcagta    840
ccaaatcggt aacaaaggg ggaagcatat aaaacctttta ctattgcgac aaaatccatc    900
cttgaaagta aagctgtttg ttcaatgtaa agcatacgaa acgaaggagg tagatcctaa    960
gatggttaga gaacttaacg ggacatactc cagctgcatc ccatattacg atcgctggaa   1020 gactttttc atgtacgtat cgcccaccaa cctttcaaag caagctaggt atgattttga   1080
cagttctcac aatccattgg ttttcatgca acttgaaaaa acccaactca aacttcatgg   1140
ggatccatac aatgtaaatc attacgagag ggcgaggttg aaaagtttcc attgcaatca   1200
cgtcgcatca tggctactga aaggccttaa c                                  1231
```

<210> SEQ ID NO 51

```
<211> LENGTH: 937
<212> TYPE: DNA
<213> ORGANISM: Artificial Sequence
<220> FEATURE:
<223> OTHER INFORMATION: Sequence of the 5'-Region used for knock out of
      PpPNO1 and PpMNN4

<400> SEQUENCE: 51
tcattctata tgttcaagaa aagggtagtg aaaggaaaga aaaggcatat aggcgaggga      60
gagttagcta gcatacaaga taatgaagga tcaatagcgg tagttaaagt gcacaagaaa     120
agagcacctg ttgaggctga tgataaagct ccaattacat tgccacagag aaacacagta    180
acagaaatag gagggggatgc accacgagaa gagcattcag tgaacaactt tgccaaattc    240
ataaccccaa gcgctaataa gccaatgtca aagtcggcta ctaacattaa tagtacaaca    300
actatcgatt ttcaaccaga tgtttgcaag gactacaaac agacaggtta ctgcggatat    360
ggtgacactt gtaagttttt gcacctgagg gatgatttca acagggatg gaaattagat     420 agggagtggg aaaatgtcca aaagaagaag cataatactc tcaaagggt taaggagatc     480 caaatgttta tgaagatga gctcaaagat atcccgttta aatgcattat atgcaaagga     540
gattacaaat caccegtgaa aacttcttgc aatcattatt tttgcgaaca atgtttcctg    600
caacggtcaa gaagaaaacc aaattgtatt atatgtggca gagacacttt aggagttgct    660
ttaccagcaa agaagttgtc ccaatttctg gctaagatac ataataatga aagtaataaa    720
gtttagtaat tgcattgcgt tgactattga ttgcattgat gtcgtgtgat actttcaccg    780
aaaaaaaaca cgaagcgcaa taggagcggt tgcatattag tccccaaagc tatttaattg    840
tgcctgaaac tgtttttttaa gctcatcaag cataattgta tgcattgcga cgtaaccaac    900
gtttaggcgc agtttaatca tagcccactg ctaagcc                             937

<210> SEQ ID NO 52
<211> LENGTH: 1906
<212> TYPE: DNA
<213> ORGANISM: Artificial Sequence
<220> FEATURE:
<223> OTHER INFORMATION: Sequence of the 3'-Region used for knock out of
      PpPNO1 and PpMNN4

<400> SEQUENCE: 52
cggaggaatg caaataataa tctccttaat tacccactga taagctcaag agacgcggtt     60
tgaaaacgat ataatgaatc atttggattt tataataaac cctgacagtt tttccactgt    120
attgttttaa cactcattgg aagctgtatt gattctaaga agctagaaat caatacggcc    180
atacaaaaga tgacattgaa taagcaccgg cttttttgat tagcatatac cttaaagcat    240
gcattcatgg ctacatagtt gttaaagggc ttcttccatt atcagtataa tgaattacat    300
aatcatgcac ttatatttgc ccatctctgt tctctcactc ttgcctgggt atattctatg    360
aaattgcgta tagcgtgtct ccagttgaac cccaagcttg gcgagtttga agagaatgct    420
aaccttgcgt attccttgct tcaggaaaca ttcaaggaga acaggtcaa gaagccaaac     480 attttgatcc ttcccgagtt agcattgact ggctacaatt tcaaagcca gcagcggata    540 gagcctttttt tggaggaaac aaccaaggga gctagtaccc aatgggctca aaaagtatcc    600
aagacgtggg attgctttac tttaatagga tacccagaaa aaagtttaga gagccctccc    660
cgtatttaca acagtgcggt acttgtatcg cctcaggaa aagtaatgaa caactacaga   720
aagtccttct tgtatgaagc tgatgaacat tggggatgtt cggaatcttc tgatgggttt    780
caaacagtag atttattaat tgaaggaaag actgtaaaga catcatttgg aatttgcatg    840
```

-continued

```
gatttgaatc cttataaatt tgaagctcca ttcacagact tcgagttcag tggccattgc    900
ttgaaaaccg gtacaagact cattttgtgc ccaatggcct ggttgtcccc tctatcgcct    960
tccattaaaa aggatcttag tgatatagag aaaagcagac ttcaaaagtt ctaccttgaa   1020
aaaatagata ccccggaatt tgacgttaat tacgaattga aaaagatgaa agtattgccc   1080
acccgtatga atgaaacgtt ggaaacaatt gactttgagc cttcaaaacc ggactactct   1140
aatataaatt attggatact aaggttttttt cccttctga ctcatgtcta taacgagat    1200 gtgctcaaag agaatgcagt tgcagtctta tgcaaccgag ttggcattga gagtgatgtc   1260
ttgtacggag gatcaaccac gattctaaac ttcaatggta agttagcatc gacacaagag   1320
gagctggagt tgtacgggca gactaatagt ctcaaccccca gtgtggaagt attggggggcc 1380 cttggcatgg gtcaacaggg aattctagta cgagacattg aattaacata atatacaata   1440
tacaataaac acaaataaag aatacaagcc tgacaaaaat tcacaaatta ttgcctagac   1500
ttgtcgttat cagcagcgac cttttttccaa tgctcaattt cacgatatgc cttttctagc   1560
tctgctttaa gcttctcatt ggaattggct aactcgttga ctgcttggtc agtgatgagt   1620
ttctccaagg tccatttctc gatgttgttg ttttcgtttt cctttaatct cttgatataa   1680
tcaacagcct tctttaatat ctgagccttg ttcgagtccc ctgttggcaa cagagcggcc   1740 agttcctttta ttccgtggtt tatattttct cttctacgcc tttctacttc tttgtgattc   1800
tctttacgca tcttatgcca ttcttcagaa ccagtggctg gcttaaccga atagccagag   1860
cctgaagaag ccgcactaga agaagcagtg gcattgttga ctatgg                  1906
```

<210> SEQ ID NO 53
<211> LENGTH: 1224
<212> TYPE: DNA
<213> ORGANISM: Artificial Sequence
<220> FEATURE:
<223> OTHER INFORMATION: DNA encodes human GnTI
       catalytic domain (NA) Codon-optimized

<400> SEQUENCE: 53

```
tcagtcagtg ctcttgatgg tgacccagca agtttgacca gagaagtgat tagattggcc     60
caagacgcag aggtggagtt ggagagacaa cgtggactgc tgcagcaaat cggagatgca    120
ttgtctagtc aaagaggtag ggtgcctacc gcagctcctc cagcacagcc tagagtgcat    180 gtgaccccctg caccagctgt gattcctatc ttggtcatcg cctgtgacag atctactgtt    240
agaagatgtc tggacaagct gttgcattac agaccatctg ctgagttgtt ccctatcatc     300
gttagtcaag actgtggtca cgaggagact gcccaagcca tcgcctccta cggatctgct    360
gtcactcaca tcagacagcc tgacctgtca tctattgctg tgccaccaga ccacagaaag    420
ttccaaggtt actacaagat cgctagacac tacagatggg cattgggtca agtcttcaga    480
cagtttagat tccctgctgc tgtggtggtg gaggatgact tggaggtggc tcctgacttc    540
tttgagtact ttagagcaac ctatccattg ctgaaggcag accatccct gtggtgtgtc     600 tctgcctgga atgacaacgg taaggagcaa atggtggacg cttctaggcc tgagctgttg    660
tacagaaccg acttctttcc tggtctggga tggttgctgt tggctgagtt gtgggctgag    720
ttggagccta gtggccaaa ggcattctgg gacgactgga tgagaagacc tgagcaaaga    780
cagggtagag cctgtatcag acctgagatc tcaagaacca tgaccttttgg tagaaaggga    840 gtgtctcacg tcaattcett tgaccaacac ttgaagttta tcaagctgaa ccagcaattt    900
gtgcacttca cccaactgga cctgtcttac ttgcagagag aggcctatga cagagatttc    960
ctagctagag tctacggagc tcctcaactg caagtggaga aagtgaggac caatgacaga    1020
```

-continued

```
aaggagttgg gagaggtgag agtgcagtac actggtaggg actccttaa ggctttcgct    1080 aaggctctgg gtgtcatgga tgaccttaag tctggagttc ctagagctgg ttacagaggt   1140
attgtcacct ttcaattcag aggtagaaga gtccacttgg ctcctccacc tacttgggag   1200
ggttatgatc cttcttggaa ttag                                           1224
```

<210> SEQ ID NO 54
<211> LENGTH: 99
<212> TYPE: DNA
<213> ORGANISM: Artificial Sequence
<220> FEATURE:
<223> OTHER INFORMATION: DNA encodes Pp SEC12 (10)

<400> SEQUENCE: 54

```
atgcccagaa aaatatttaa ctacttcatt ttgactgtat tcatggcaat tcttgctatt    60
gttttacaat ggtctataga gaatggacat gggcgcgcc                           99
```

<210> SEQ ID NO 55
<211> LENGTH: 435
<212> TYPE: DNA
<213> ORGANISM: Artificial Sequence
<220> FEATURE:
<223> OTHER INFORMATION: Sequence of the PpSEC4 promoter

<400> SEQUENCE: 55

```
gaagtaaagt tggcgaaact ttgggaacct ttggttaaaa ctttgtaatt tttgtcgcta    60
cccattaggc agaatctgca tcttgggagg gggatgtggt ggcgttctga gatgtacgcg   120
aagaatgaag agccagtggt aacaacaggc ctagagagat acgggcataa tgggtataac   180
ctacaagtta agaatgtagc agccctggaa accagattga aacgaaaaac gaaatcattt   240
aaactgtagg atgttttggc tcattgtctg gaaggctggc tgtttattgc cctgttcttt   300
gcatgggaat aagctattat atccctcaca taatcccaga aaatagattg aagcaacgcg   360
aaatccttac gtatcgaagt agccttctta cacattcacg ttgtacggat aagaaaacta   420
ctcaaacgaa caatc                                                    435
```

<210> SEQ ID NO 56
<211> LENGTH: 404
<212> TYPE: DNA
<213> ORGANISM: Artificial Sequence
<220> FEATURE:
<223> OTHER INFORMATION: Sequence of the PpOCH1 terminator

<400> SEQUENCE: 56

```
aatagatata gcgagattag agaatgaata ccttcttcta agcgatcgtc cgtcatcata    60
gaatatcatg gactgtatag ttttttttt gtacatataa tgattaaacg gtcatccaac   120
atctcgttga cagatctctc agtacgcgaa atccctgact atcaaagcaa gaaccgatga   180
agaaaaaaac aacagtaacc caaacaccac aacaaacact ttatcttctc cccccaaca    240 ccaatcatca aagagatgtc ggaacacaaa caccaagaag caaaaactaa ccccatataa   300
aaacatcctg gtagataatg ctggtaaccc gctctccttc catattctgg gctacttcac   360
gaagtctgac cggtctcagt tgatcaacat gatcctcgaa atgg                    404
```

<210> SEQ ID NO 57
<211> LENGTH: 1407
<212> TYPE: DNA
<213> ORGANISM: Artificial Sequence
<220> FEATURE:
<223> OTHER INFORMATION: DNA encodes Mm ManI catalytic domain (FB)

<400> SEQUENCE: 57

```
gagcccgctg acgccaccat ccgtgagaag agggcaaaga tcaaagagat gatgacccat      60
gcttggaata attataaacg ctatgcgtgg ggcttgaacg aactgaaacc tatatcaaaa     120
gaaggccatt caagcagttt gtttggcaac atcaaaggag ctacaatagt agatgccctg     180
gataccctt tcattatggg catgaagact gaatttcaag aagctaaatc gtggattaaa     240
aaatatttag attttaatgt gaatgctgaa gtttctgttt ttgaagtcaa catacgcttc     300
gtcggtggac tgctgtcagc ctactatttg tccggagagg agatatttcg aaagaaagca     360
gtggaacttg gggtaaaatt gctacctgca tttcatactc cctctggaat accttgggca     420
ttgctgaata tgaaaagtgg gatcgggcgg aactggccct gggcctctgg aggcagcagt     480
atcctggccg aatttggaac tctgcattta gagtttatgc acttgtccca cttatcagga     540
gacccagtct ttgccgaaaa ggttatgaaa attcgaacag tgttgaacaa actggacaaa     600
ccagaaggcc tttatcctaa ctatctgaac cccagtagtg gacagtgggg tcaacatcat     660
gtgtcggttg gaggacttgg agacagcttt tatgaatatt tgcttaaggc gtggttaatg     720
tctgacaaga cagatctcga agccaagaag atgtattttg atgctgttca ggccatcgag     780
actcacttga tccgcaagtc aagtggggga ctaacgtaca tcgcagagtg aaggggggc     840
ctcctggaac acaagatggg ccacctgacg tgctttgcag gaggcatgtt tgcacttggg     900
gcagatggag ctccggaagc ccgggcccaa cactaccttg aactcggagc tgaaattgcc     960
cgcacttgtc atgaatctta taatcgtaca tatgtgaagt tgggaccgga agcgtttcga    1020
tttgatggcg gtgtggaagc tattgccacg aggcaaaatg aaaagtatta catcttacgg    1080
cccgaggtca tcgagacata catgtacatg tggcgactga ctcacgaccc caagtacagg    1140
acctgggcct gggaagccgt ggaggctcta gaaagtcact gcagagtgaa cggaggctac    1200
tcaggcttac gggatgttta cattgcccgt gagagttatg acgatgtcca gcaaagtttc    1260
ttcctggcag agacactgaa gtatttgtac ttgatatttt ccgatgatga ccttcttcca    1320
ctagaacact ggatcttcaa caccgaggct catcctttcc ctatactccg tgaacagaag    1380
aaggaaattg atggcaaaga gaaatga                                         1407
```

<210> SEQ ID NO 58
<211> LENGTH: 318
<212> TYPE: DNA
<213> ORGANISM: Artificial Sequence
<220> FEATURE:
<223> OTHER INFORMATION: DNA encodes ScSEC12 (8)

<400> SEQUENCE: 58

```
atgaacacta tccacataat aaaattaccg cttaactacg ccaactacac ctcaatgaaa      60
caaaaaatct ctaaattttt caccaacttc atccttattg tgctgctttc ttacatttta     120
cagttctcct ataagcacaa tttgcattcc atgcttttca attacgcgaa ggacaatttt     180
ctaacgaaaa gagacaccat ctcttcgccc tacgtagttg atgaagactt acatcaaaca     240
actttgtttg gcaaccacgg tacaaaaaca tctgtaccta gcgtagattc cataaaagtg     300
catggcgtgg ggcgcgcc                                                    318
```

<210> SEQ ID NO 59
<211> LENGTH: 1250
<212> TYPE: DNA
<213> ORGANISM: Artificial Sequence
<220> FEATURE:
<223> OTHER INFORMATION: Sequence of the 5'-region that was used to knock into the PpADE1 locus

<400> SEQUENCE: 59

```
gagtcggcca agagatgata actgttacta agcttctccg taattagtgg tattttgtaa      60
cttttaccaa taatcgttta tgaatacgga tattttcga ccttatccag tgccaaatca      120
cgtaacttaa tcatggttta aatactccac ttgaacgatt cattattcag aaaaaagtca     180
ggttggcaga aacacttggg cgctttgaag agtataagag tattaagcat taaacatctg     240
aactttcacc gccccaatat actactctag gaaactcgaa aaattccttt ccatgtgtca     300
tcgcttccaa cacactttgc tgtatccttc caagtatgtc cattgtgaac actgatctgg     360
acggaatcct acctttaatc gccaaaggaa aggttagaga catttatgca gtcgatgaga     420
acaacttgct gttcgtcgca actgaccgta tctccgctta cgatgtgatt atgacaaacg     480
gtattcctga taagggaaag attttgactc agctctcagt tttctggttt gattttttgg     540
caccctacat aaagaatcat ttggttgctt ctaatgacaa ggaagtcttt gctttactac     600
catcaaaact gtctgaagaa aaatacaaat ctcaattaga gggacgatcc ttgatagtaa     660
aaaagcacag actgatacct ttggaagcca ttgtcagagg ttacatcact ggaagtgcat     720
ggaaagagta caagaactca aaaactgtcc atggagtcaa ggttgaaaac gagaaccttc     780
aagagagcga cgccttttcca actccgattt tcacaccttc aacgaaagct gaacagggtg    840
aacacgatga aaacatctct attgaacaag ctgctgagat tgtaggtaaa gacatttgtg    900
agaaggtcgc tgtcaaggcg gtcgagttgt attctgctgc aaaaaacctc gccctttga     960
aggggatcat tattgctgat acgaaattcg aatttggact ggacgaaaac aatgaattgg   1020
tactagtaga tgaagtttta actccagatt cttctagatt ttggaatcaa aagacttacc   1080
aagtgggtaa atcgcaagag agttacgata agcagtttct cagagattgg ttgacggcca   1140
acggattgaa tggcaaagag ggcgtagcca tggatgcaga aattgctatc aagagtaaag   1200
aaaagtatat tgaagcttat gaagcaatta ctggcaagaa atgggcttga              1250
```

<210> SEQ ID NO 60
<211> LENGTH: 882
<212> TYPE: DNA
<213> ORGANISM: Artificial Sequence
<220> FEATURE:
<223> OTHER INFORMATION: Sequence of the 3'-region that was used to knock into the PpADE1 locus

<400> SEQUENCE: 60

```
atgattagta ccctcctcgc cttttttcaga catctgaaat ttcccttatt cttccaattc      60
catataaaat cctatttagg taattagtaa acaatgatca taaagtgaaa tcattcaagt     120
aaccattccg tttatcgttg atttaaaatc aataacgaat gaatgtcggt ctgagtagtc     180
aatttgttgc cttggagctc attggcaggg ggtcttttgg ctcagtatgg aaggttgaaa     240
ggaaaacaga tggaaagtgg ttcgtcagaa aagaggtatc ctacatgaag atgaatgcca     300
aagagatatc tcaagtgata gctgagttca gaattcttag tgagttaagc catcccaaca     360
ttgtgaagta ccttcatcac gaacatattt ctgagaataa aactgtcaat ttatacatgg     420
aatactgtga tggtggagat ctctccaagc tgattcgaac acatagaagg aacaaagagt     480
acatttcaga agaaaaaata tggagtattt ttacgcaggt tttattagca ttgtatcgtt     540
gtcattatgg aactgatttc acggcttcaa aggagtttga atcgctcaat aaaggtaata     600
gacgaaccca gaatccttcg tgggtagact cgacaagagt tattattcac agggatataa     660
aacccgacaa catctttctg atgaacaatt caaaccttgt caaactggga gattttggat     720
```

| | |
|---|---|
| tagcaaaaat tctggaccaa gaaaacgatt ttgccaaaac atacgtcggt acgccgtatt | 780 |
| acatgtctcc tgaagtgctg ttggaccaac cctactcacc attatgtgat atatggtctc | 840 |
| ttgggtgcgt catgtatgag ctatgtgcat tgaggcctcc tt | 882 |

<210> SEQ ID NO 61
<211> LENGTH: 2100
<212> TYPE: DNA
<213> ORGANISM: Artificial Sequence
<220> FEATURE:
<223> OTHER INFORMATION: DNA encodes ScGAL10

<400> SEQUENCE: 61

| | |
|---|---|
| atgacagctc agttacaaag tgaaagtact tctaaaattg ttttggttac aggtggtgct | 60 |
| ggatacattg gttcacacac tgtggtagag ctaattgaga atggatatga ctgtgttgtt | 120 |
| gctgataacc tgtcgaattc aacttatgat tctgtagcca ggttagaggt cttgaccaag | 180 |
| catcacattc ccttctatga ggttgatttg tgtgaccgaa aggtctgga aaaggttttc | 240 |
| aaagaatata aaattgattc ggtaattcac tttgctggtt taaaggctgt aggtgaatct | 300 |
| acacaaatcc cgctgagata ctatcacaat aacattttgg gaactgtcgt tttattagag | 360 |
| ttaatgcaac aatacaacgt ttccaaattt gttttttcat cttctgctac tgtctatggt | 420 |
| gatgctacga gattcccaaa tatgattcct atcccagaag aatgtcccct agggcctact | 480 |
| aatccgtatg gtcatacgaa atacgccatt gagaatatct tgaatgatct ttacaatagc | 540 |
| gacaaaaaaa gttggaagtt tgctatcttg cgttatttta acccaattgg cgcacatccc | 600 |
| tctggattaa tcggagaaga tccgctaggt ataccaaaca atttgttgcc atatatggct | 660 |
| caagtagctg ttggtaggcg cgagaagctt tacatcttcg agacgatta tgattccaga | 720 |
| gatggtaccc cgatcaggga ttatatccac gtagttgatc tagcaaaagg tcatattgca | 780 |
| gccctgcaat acctagaggc ctacaatgaa aatgaaggtt tgtgtcgtga gtggaacttg | 840 |
| ggttccggta aaggttctac agtttttgaa gtttatcatg cattctgcaa agcttctggt | 900 |
| attgatcttc catacaaagt tacgggcaga agagcaggtg atgttttgaa cttgacggct | 960 |
| aaaccagata gggccaaacg cgaactgaaa tggcagaccg agttgcaggt tgaagactcc | 1020 |
| tgcaaggatt tatggaaatg gactactgag aatccttttg gttaccagtt aaggggtgtc | 1080 |
| gaggccagat tttccgctga agatatgcgt tatgacgcaa gatttgtgac tattggtgcc | 1140 |
| ggcaccagat ttcaagccac gtttgccaat ttgggcgcca gcattgttga cctgaaagtg | 1200 |
| aacggacaat cagttgttct tggctatgaa aatgaggaag ggtatttgaa tcctgatagt | 1260 |
| gcttatatag cgccacgat cggcaggtat gctaatcgta tttcgaaggg taagtttagt | 1320 |
| ttatgcaaca aagactatca gttaaccgtt aataacggcg ttaatgcgaa tcatagtagt | 1380 |
| atcggttctt tccacagaaa aagattttg ggacccatca ttcaaaatcc ttcaaaggat | 1440 |
| gttttttaccg ccgagtacat gctgatagat aatgagaagg acaccgaatt tccaggtgat | 1500 |
| ctattggtaa ccatacagta tactgtgaac gttgcccaaa aagtttgga atggtatat | 1560 |
| aaaggtaaat tgactgctgg tgaagcgacg ccaataaatt taacaaatca tagttatttc | 1620 |
| aatctgaaca agccatatgg agacactatt gagggtacgg agattatggt gcgttcaaaa | 1680 |
| aaatctgttt atgtcgacaa aaacatgatt cctacgggta atatcgtcga tagagaaatt | 1740 |
| gctacctta actctacaaa gccaacggtc ttaggcccca aaaatcccca gtttgattgt | 1800 |
| tgttttgtgg tggatgaaaa tgctaagcca agtcaaatca atactctaaa caatgaattg | 1860 |
| acgcttattg tcaaggcttt tcatcccgat tccaatatta cattagaagt tttaagtaca | 1920 |

```
gagccaactt atcaatttta taccggtgat ttcttgtctg ctggttacga agcaagacaa   1980
ggttttgcaa ttgagcctgg tagatacatt gatgctatca atcaagagaa ctggaaagat   2040
tgtgtaacct gaaaaacgg tgaaacttac gggtccaaga ttgtctacag attttcctga    2100

<210> SEQ ID NO 62
<211> LENGTH: 512
<212> TYPE: DNA
<213> ORGANISM: Artificial Sequence
<220> FEATURE:
<223> OTHER INFORMATION: Sequence of the PpPMA1 terminator

<400> SEQUENCE: 62
taagcttcac gatttgtgtt ccagtttatc cccccttat ataccgttaa ccctttccct     60
gttgagctga ctgttgttgt attaccgcaa ttttccaag tttgccatgc ttttcgtgtt    120
atttgaccga tgtcttttt cccaaatcaa actatatttg ttaccattta aaccaagtta    180
tcttttgtat taagagtcta agtttgttcc caggcttcat gtgagagtga taaccatcca   240
gactatgatt cttgttttt attgggttg tttgtgtgat acatctgagt tgtgattcgt     300
aaagtatgtc agtctatcta gattttaat agttaattgg taatcaatga cttgtttgtt   360
ttaactttta aattgtgggt cgtatccacg cgtttagtat agctgttcat ggctgttaga   420
ggagggcgat gtttatatac agaggacaag aatgaggagg cggcgtgtat ttttaaaatg   480
gagacgcgac tcctgtacac cttatcggtt gg                                 512

<210> SEQ ID NO 63
<211> LENGTH: 1068
<212> TYPE: DNA
<213> ORGANISM: Artificial Sequence
<220> FEATURE:
<223> OTHER INFORMATION: hGalT codon optimized (XB)

<400> SEQUENCE: 63
ggtagagatt tgtctagatt gccacagttg gttggtgttt ccactccatt gcaaggaggt    60
tctaactctg ctgctgctat tggtcaatct tccggtgagt tgagaactgg tggagctaga   120
ccacctccac cattgggagc ttcctctcaa ccaagaccag gtggtgattc ttctccagtt   180
gttgactctg gtccaggtcc agcttctaac ttgacttccg ttccagttcc acacactact   240
gctttgtcct tgccagcttg tccagaagaa tccccattgt tggttggtcc aatgttgatc   300
gagttcaaca tgccagttga cttggagttg gttgctaagc agaacccaaa cgttaagatg   360
ggtggtagat acgctccaag agactgtgtt tccccacaca agttgctat catcatccca    420 ttcagaaaca gacaggagca cttgaagtac tggttgtact acttgcaccc agttttgcaa   480
agacagcagt tggactacgg tatctacgtt atcaaccagg ctggtgacac tatttcaac   540 agagctaagt tgttgaatgt tggttccag gaggctttga aggattacga ctacacttgt   600
ttcgttttct ccgacgttga cttgattcca atgaacgacc acaacgctta cagatgttc    660 tcccagccaa gacacattc tgttgctatg gacaagttcg gtttctcctt gccatacgtt   720
caatacttcg gtggtgtttc cgctttgtcc aagcagcagt tcttgactat caacggtttc   780
ccaaacaatt actggggatg gggtggtgaa gatgacgaca tctttaacag attggttttc   840
agaggaatgt ccatctctag accaaacgct gttgttggta gatgtagaat gatcagacac    900
tccagagaca agaagaacga gccaaaccca caaagatcg acagaatcgc tcacactaag    960
gaaactatgt tgtccgacgg attgaactcc ttgacttacc aggttttgga cgttcagaga   1020
tacccattgt acactcagat cactgttgac atcggtactc catcctag                1068
```

<210> SEQ ID NO 64
<211> LENGTH: 183
<212> TYPE: DNA
<213> ORGANISM: Artificial Sequence
<220> FEATURE:
<223> OTHER INFORMATION: DNA encodes ScMnt1 (Kre2) (33)

<400> SEQUENCE: 64

```
atggccctct ttctcagtaa gagactgttg agatttaccg tcattgcagg tgcggttatt      60
gttctcctcc taacattgaa ttccaacagt agaactcagc aatatattcc gagttccatc     120
tccgctgcat ttgattttac ctcaggatct atatccctg aacaacaagt catcgggcgc     180
gcc                                                                   183
```

<210> SEQ ID NO 65
<211> LENGTH: 1074
<212> TYPE: DNA
<213> ORGANISM: Artificial Sequence
<220> FEATURE:
<223> OTHER INFORMATION: DNA encodes DmUGT

<400> SEQUENCE: 65

```
atgaatagca tacacatgaa cgccaatacg ctgaagtaca tcagcctgct gacgctgacc      60
ctgcagaatg ccatcctggg cctcagcatg cgctacgccc gcacccggcc aggcgacatc     120
ttcctcagct ccacggccgt actcatggca gagttcgcca aactgatcac gtgcctgttc     180
ctggtcttca cgaggaggg caaggatgcc cagaagtttg tacgctcgct gcacaagacc     240
atcattgcga atcccatgga cacgctgaag gtgtgcgtcc cctcgctggt ctatatcgtt     300
caaaacaatc tgctgtacgt ctctgcctcc catttggatg cggccaccta ccaggtgacg     360
taccagctga agattctcac cacggccatg ttcgcggttg tcattctgcg ccgcaagctg     420
ctgaacacgc agtggggtgc gctgctgctc ctggtgatgg catcgtcct ggtgcagttg     480
gcccaaacgg agggtccgac gagtggctca gccggtggtg ccgcagctgc agccacggcc     540
gcctcctctg gcggtgctcc cgagcagaac aggatgctcg gactgtgggc cgcactgggc     600
gcctgcttcc tctccggatt cgcgggcatc tactttgaga agatcctcaa gggtgccgag     660
atctccgtgt ggatgcggaa tgtgcagttg agtctgctca gcattccctt cggcctgctc     720
acctgtttcg ttaacgacgg cagtaggatc ttcgaccagg gattcttcaa gggctacgat     780
ctgtttgtct ggtacctggt cctgctgcag gccggcggtg gattgatcgt tgccgtggtg     840
gtcaagtacg cggataacat tctcaagggc ttcgccacct cgctggccat catcatctcg     900
tgcgtggcct ccatatacat cttcgacttc aatctcacgc tgcagttcag cttcggagct     960
ggcctggtca tcgcctccat atttctctac ggctacgatc cggccaggtc ggcgccgaag    1020
ccaactatgc atggtcctgg cggcgatgag gagaagctgc tgccgcgcgt ctag          1074
```

<210> SEQ ID NO 66
<211> LENGTH: 798
<212> TYPE: DNA
<213> ORGANISM: Artificial Sequence
<220> FEATURE:
<223> OTHER INFORMATION: Sequence of the PpOCH1 promoter

<400> SEQUENCE: 66

```
tggacacagg agactcagaa acagacacag agcgttctga gtcctggtgc tcctgacgta      60
ggcctagaac aggaattatt ggctttattt gtttgtccat ttcataggct tggggtaata     120
gatagatgac agagaaatag agaagaccta atattttttg ttcatggcaa atcgcgggtt     180
```

```
cgcggtcggg tcacacacgg agaagtaatg agaagagctg gtaatctggg gtaaagggt      240 tcaaaagaag gtcgcctggt agggatgcaa tacaaggttg tcttggagtt tacattgacc     300
agatgatttg gcttttctc tgttcaattc acatttttca gcgagaatcg gattgacgga     360
gaaatggcgg ggtgtggggt ggatagatgg cagaaatgct cgcaatcacc gcgaaagaaa     420
gactttatgg aatagaacta ctgggtggtg taaggattac atagctagtc caatggagtc     480
cgttggaaag gtaagaagaa gctaaaaccg gctaagtaac tagggaagaa tgatcagact     540
ttgatttgat gaggtctgaa aatactctgc tgcttttca gttgcttttt ccctgcaacc      600
tatcattttc cttttcataa gcctgccttt tctgttttca cttatgag ttccgccgag       660 acttccccaa attctctcct ggaacattct ctatcgctct ccttccaagt tgcgccccct    720
ggcactgcct agtaatatta ccacgcgact tatattcagt tccacaattt ccagtgttcg    780
tagcaaatat catcagcc                                                  798

<210> SEQ ID NO 67
<211> LENGTH: 302
<212> TYPE: DNA
<213> ORGANISM: Artificial Sequence
<220> FEATURE:
<223> OTHER INFORMATION: Sequence of the PpALG12 terminator

<400> SEQUENCE: 67
aatatatacc tcatttgttc aatttggtgt aaagagtgtg gcggatagac ttcttgtaaa     60
tcaggaaagc tacaattcca attgctgcaa aaataccaa tgcccataaa ccagtatgag     120
cggtgccttc gacggattgc ttactttccg acccttgtc gtttgattct tctgcctttg    180
gtgagtcagt ttgtttcgac tttatatctg actcatcaac ttcctttacg gttgcgtttt   240
taatcataat tttagccgtt ggcttattat cccttgagtt ggtaggagtt ttgatgatgc    300
tg                                                                  302

<210> SEQ ID NO 68
<211> LENGTH: 461
<212> TYPE: DNA
<213> ORGANISM: Artificial Sequence
<220> FEATURE:
<223> OTHER INFORMATION: Sequence of the 5'-Region used for knock out of
      PpHIS1

<400> SEQUENCE: 68
taactggccc tttgacgttt ctgacaatag ttctagagga gtcgtccaaa aactcaactc     60
tgacttgggt gacaccacca cgggatccgg ttcttccgag gaccttgatg accttggcta    120
atgtaactgg agttttagta tccatttaa gatgtgtgtt tctgtaggtt ctgggttgga     180 aaaaatttt agacaccaga agagaggagt gaactggttt gcgtgggttt agactgtgta    240
aggcactact ctgtcgaagt tttagatagg ggttacccgc tccgatgcat gggaagcgat    300
tagcccggct gttgcccgtt tggtttttga agggtaattt tcaatatctc tgtttgagtc    360
atcaatttca tattcaaaga ttcaaaaaca aaatctggtc caaggagcgc atttaggatt    420
atggagttgg cgaatcactt gaacgataga ctattatttg c                       461

<210> SEQ ID NO 69
<211> LENGTH: 1841
<212> TYPE: DNA
<213> ORGANISM: Artificial Sequence
<220> FEATURE:
<223> OTHER INFORMATION: Sequence of the 3'-Region used for knock out of
      PpHIS1
```

<400> SEQUENCE: 69

```
gtgacattct tgtctttgag atcagtaatt gtagagcata gatagaataa tattcaagac      60
caacggcttc tcttcggaag ctccaagtag cttatagtga tgagtaccgg catatattta     120
taggcttaaa atttcgaggg ttcactatat tcgtttagtg ggaagagttc ctttcactct     180
tgttatctat attgtcagcg tggactgttt ataactgtac caacttagtt tctttcaact     240
ccaggttaag agacataaat gtcctttgat gctgacaata atcagtggaa ttcaaggaag     300
gacaatcccg acctcaatct gttcattaat gaagagttcg aatcgtcctt aaatcaagcg     360
ctagactcaa ttgtcaatga gaacccttc tttgaccaag aaactataaa tagatcgaat      420
gacaaagttg gaaatgagtc cattagctta catgatattg agcaggcaga ccaaaataaa     480
ccgtcctttg agagcgatat tgatggttcg gcgccgttga taagagacga caaattgcca     540
aagaaacaaa gctgggggct gagcaatttt ttttcaagaa gaaatagcat atgtttacca     600
ctacatgaaa atgattcaag tgttgttaag accgaaagat ctattgcagt gggaacaccc     660
catcttcaat actgcttcaa tggaatctcc aatgccaagt acaatgcatt tacctttttc     720
ccagtcatcc tatacgagca attcaaattt tttttcaatt tatactttac tttagtggct     780
ctctctcaag cgataccgca acttcgcatt ggatatcttt cttcgtatgt cgtcccactt     840
ttgtttgtac tcatagtgac catgtcaaaa gaggcgatgg atgatattca acgccgaaga     900
agggatagag aacagaacaa tgaaccatat gaggttctgt ccagcccatc accagttttg     960
tccaaaaact taaatgtgg tcacttggtt cgattgcata agggaatgag agtgcccgca     1020
gatatggttc ttgtccagtc aagcgaatcc accggagagt catttatcaa gacagatcag     1080
ctggatggtg agactgattg gaagcttcgg attgtttctc cagttacaca atcgttacca     1140
atgactgaac ttcaaaatgt cgccatcact gcaagcgcac cctcaaaatc aattcactcc     1200
tttcttggaa gattgaccta caatgggcaa tcatatggtc ttacgataga caacacaatg     1260
tggtgtaata ctgtattagc ttctggttca gcaattggtt gtataattta cacaggtaaa     1320
gatactcgac aatcgatgaa cacaactcag cccaaactga aacgggctt gttagaactg      1380
gaaatcaata gtttgtccaa gatcttatgt gtttgtgtgt ttgcattatc tgtcatctta     1440
gtgctattcc aaggaatagc tgatgattgg tacgtcgata tcatgcggtt tctcattcta     1500
ttctccacta ttatcccagt gtctctgaga gttaaccttg atcttggaaa gtcagtccat     1560
gctcatcaaa tagaaactga tagctcaata cctgaaaccg ttgttagaac tagtacaata     1620
ccggaagacc tgggaagaat tgaataccta ttaagtgaca aaactggaac tcttactcaa     1680
aatgatatgg aaatgaaaaa actacaccta ggaacagtct cttatgctgg tgataccatg     1740
gatattattt ctgatcatgt taaaggtctt aataacgcta aacatcgag gaaagatctt      1800
ggtatgagaa taagagattt ggttacaact ctggccatct g                         1841
```

<210> SEQ ID NO 70
<211> LENGTH: 3105
<212> TYPE: DNA
<213> ORGANISM: Artificial Sequence
<220> FEATURE:
<223> OTHER INFORMATION: DNA encodes Drosophila melanogaster ManII codon-optimized (KD)

<400> SEQUENCE: 70

```
agagacgatc caattagacc tccattgaag gttgctagat ccccaagacc aggtcaatgt      60
caagatgttg ttcaggacgt cccaaacgtt gatgtccaga tgttggagtt gtacgataga     120
```

```
atgtccttca aggacattga tggtggtgtt tggaagcagg gttggaacat taagtacgat      180
ccattgaagt acaacgctca tcacaagttg aaggtcttcg ttgtcccaca ctcccacaac      240
gatcctggtt ggattcagac cttcgaggaa tactaccagc acgacaccaa gcacatcttg      300
tccaacgctt tgagacattt gcacgacaac ccagagatga agttcatctg ggctgaaatc      360
tcctacttcg ctagattcta ccacgatttg ggtgagaaca agaagttgca gatgaagtcc      420
atcgtcaaga acgtcagtt ggaattcgtc actggtggat gggtcatgcc agacgaggct       480
aactcccact ggagaaacgt tttgttgcag ttgaccgaag gtcaaacttg gttgaagcaa      540
ttcatgaacg tcactccaac tgcttcctgg gctatcgatc cattcggaca ctctccaact      600
atgccataca ttttgcagaa gtctggtttc aagaatatgt tgatccagag aacccactac      660
tccgttaaga aggagttggc tcaacagaga cagttggagt tcttgtggag acagatctgg      720
gacaacaaag gtgacactgc tttgttcacc cacatgatgc cattctactc ttacgacatt      780
cctcatacct gtggtccaga tccaaaggtt tgttgtcagt tcgatttcaa agaatgggt      840 tccttcggtt tgtcttgtcc atggaaggtt ccacctagaa ctatctctga tcaaaatgtt      900
gctgctagat ccgatttgtt ggttgatcag tggaagaaga aggctgagtt gtacagaacc      960
aacgtcttgt tgattccatt gggtgacgac ttcagattca agcagaacac cgagtgggat     1020
gttcagagag tcaactacga aagattgttc gaacacatca actctcaggc tcacttcaat     1080
gtccaggctc agttcggtac tttgcaggaa tacttcgatg ctgttcacca ggctgaaaga     1140
gctggacaag ctgagttccc aaccttgtct ggtgacttct tcacttacgc tgatagatct     1200
gataactact ggtctggtta ctacacttcc agaccatacc ataagagaat ggacagagtc     1260
ttgatgcact acgttagagc tgctgaaatg ttgtccgctt ggcactcctg ggacggtatg     1320
gctagaatcg aggaaagatt ggagcaggct agaagagagt tgtccttgtt ccagcaccac     1380
gacggtatta ctggtactgc taaaactcac gttgtcgtcg actacgagca agaatgcag      1440 gaagctttga agcttgtca atggtcatg caacagtctg tctacagatt gttgactaag       1500
ccatccatct actctccaga cttctccttc tcctacttca cttttggacga ctccagatgg    1560 ccaggttctg gtgttgagga ctctagaact accatcatct gggtgagga tatcttgcca      1620 tccaagcatg ttgtcatgca aacaccttg ccacactgga gagcagtt ggttgacttc        1680 tacgtctcct ctccattcgt ttctgttacc gacttggcta acaatccagt tgaggctcag    1740
gtttctccag tttggtcttg gcaccacgac actttgacta agactatcca cccacaaggt    1800
tccaccacca agtacagaat catcttcaag gctagagttc caccaatggg tttggctacc    1860
tacgttttga ccatctccga ttccaagcca gagcacacct cctacgcttc caatttgttg    1920
cttagaaaga acccaacttc cttgccattg ggtcaatacc cagaggatgt caagttcggt    1980
gatccaagag agatctcctt gagagttggt aacggtccaa ccttggcttt ctctgagcag    2040
ggtttgttga gtccattca gttgactcag gattctccac atgttccagt tcacttcaag     2100
ttcttgaagt acggtgttag atctcatggt gatagatctg gtgcttactt gttcttgcca    2160
aatggtccag cttctccagt cgagttgggt cagccagttg tcttggtcac taagggtaaa    2220
ttggagtctt ccgtttctgt tggtttgcca tctgtcgttc accagaccat catgagaggt    2280
ggtgctccag agattagaaa tttggtcgat attggttctt tggacaacac tgagatcgtc    2340
atgagattgg agactcatat cgactctggt gatatcttct acactgattt gaatggattg    2400
caattcatca gaggagaag attggacaag ttgccattgc aggctaacta ctacccaatt     2460
ccatctggta tgttcattga ggatgctaat accagattga ctttgttgac cggtcaacca    2520
```

```
ttgggtggat cttctttggc ttctggtgag ttggagatta tgcaagatag aagattggct    2580
tctgatgatg aaagaggttt gggtcagggt gttttggaca acaagccagt tttgcatatt    2640
tacagattgg tcttggagaa ggttaacaac tgtgtcagac catctaagtt gcatccagct    2700
ggttacttga cttctgctgc tcacaaagct tctcagtctt tgttggatcc attggacaag    2760
ttcatcttcg ctgaaaatga gtggatcggt gctcagggtc aattcggtgg tgatcatcca    2820
tctgctagag aggatttgga tgtctctgtc atgagaagat tgaccaagtc ttctgctaaa    2880
acccagagag ttggttacgt tttgcacaga accaatttga tgcaatgtgg tactccagag    2940
gagcatactc agaagttgga tgtctgtcac ttgttgccaa atgttgctag atgtgagaga    3000
actaccttga ctttcttgca gaatttggag cacttggatg gtatggttgc tccagaagtt    3060
tgtccaatgg aaaccgctgc ttacgtctct tctcactctt cttga                   3105

<210> SEQ ID NO 71
<211> LENGTH: 108
<212> TYPE: DNA
<213> ORGANISM: Artificial Sequence
<220> FEATURE:
<223> OTHER INFORMATION: DNA encodes Mnn2 leader (53)

<400> SEQUENCE: 71
atgctgctta ccaaaaggtt ttcaaagctg ttcaagctga cgttcatagt tttgatattg      60
tgcgggctgt tcgtcattac aaacaaatac atggatgaga acacgtcg                 108

<210> SEQ ID NO 72
<211> LENGTH: 1729
<212> TYPE: DNA
<213> ORGANISM: Artificial Sequence
<220> FEATURE:
<223> OTHER INFORMATION: Sequence of the PpHIS1 auxotrophic marker

<400> SEQUENCE: 72
caagttgcgt ccggtatacg taacgtctca cgatgatcaa agataatact taatcttcat      60
ggtctactga ataactcatt taaacaattg actaattgta cattatattg aacttatgca    120
tcctattaac gtaatcttct ggcttctctc tcagactcca tcagacacag aatatcgttc    180
tctctaactg gtcctttgac gtttctgaca atagttctag aggagtcgtc caaaaactca    240
actctgactt gggtgacacc accacgggat ccggttcttc cgaggacctt gatgaccttg    300
gctaatgtaa ctggagtttt agtatccatt ttaagatgtg tgtttctgta ggttctgggt    360
tggaaaaaaa ttttagacac cagaagagag gagtgaactg gtttgcgtgg gtttagactg    420
tgtaaggcac tactctgtcg aagttttaga taggggttac ccgctccgat gcatgggaag    480
cgattagccc ggctgttgcc cgtttggttt ttgaagggta atttttcaata tctctgtttg    540 agtcatcaat ttcatattca aagattcaaa acaaaatct ggtccaagga gcgcatttag    600
gattatggag ttggcgaatc acttgaacga tagactatta tttgctgttc ctaaagaggg    660
cagattgtat gagaaatgcg ttgaattact taggggatca gatattcagt ttcgaagatc    720
cagtagattg gatatagctt tgtgcactaa cctgccctg gcattggttt tccttccagc    780
tgctgacatt cccacgtttg taggagaggg taaatgtgat ttgggtataa ctggtattga    840
ccaggttcag gaaagtgacg tagatgtcat acctttatta gacttgaatt tcggtaagtg    900
caagttgcag attcaagttc ccgagaatgg tgacttgaaa gaacctaaac agctaattgg    960
taaagaaatt gtttcctcct ttactagctt aaccaccagg tactttgaac aactggaagg   1020
agttaagcct ggtgagccac taaagacaaa aatcaaatat gttggagggt ctgttgaggc   1080
```

-continued

```
ctcttgtgcc ctaggagttg ccgatgctat tgtggatctt gttgagagtg gagaaaccat    1140
gaaagcggca gggctgatcg atattgaaac tgttctttct acttccgctt acctgatctc    1200
ttcgaagcat cctcaacacc cagaactgat ggatactatc aaggagagaa ttgaaggtgt    1260
actgactgct cagaagtatg tcttgtgtaa ttacaacgca cctagaggta accttcctca    1320
gctgctaaaa ctgactccag gcaagagagc tgctaccgtt tctccattag atgaagaaga    1380
ttgggtggga gtgtcctcga tggtagagaa gaaagatgtt ggaagaatca tggacgaatt    1440
aaagaaacaa ggtgccagtg acattcttgt ctttgagatc agtaattgta gagcatagat    1500
agaataatat tcaagaccaa cggcttctct tcggaagctc caagtagctt atagtgatga    1560
gtaccggcat atatttatag gcttaaaatt tcgaggttc actatattcg tttagtggga    1620
agagttcctt tcactcttgt tatctatatt gtcagcgtgg actgtttata actgtaccaa    1680
cttagtttct ttcaactcca ggttaagaga cataaatgtc ctttgatgc                1729
```

<210> SEQ ID NO 73
<211> LENGTH: 1068
<212> TYPE: DNA
<213> ORGANISM: Artificial Sequence
<220> FEATURE:
<223> OTHER INFORMATION: DNA encodes Rat GnT II
      (TC) Codon-optimized

<400> SEQUENCE: 73

```
tccttggttt accaattgaa cttcgaccag atgttgagaa acgttgacaa ggacggtact      60
tggtctcctg gtgagttggt tttggttgtt caggttcaca acagaccaga gtacttgaga    120
ttgttgatcg actccttgag aaaggctcaa ggtatcagag aggttttggt tatcttctcc    180
cacgatttct ggtctgctga gatcaactcc ttgatctcct ccgttgactt ctgtccagtt    240
ttgcaggttt tcttcccatt ctccatccaa ttgtacccat ctgagttccc aggttctgat    300
ccaagagact gtccaagaga cttgaagaag aacgctgctt tgaagttggg ttgtatcaac    360
gctgaatacc cagattcttt cggtcactac agagaggcta agttctccca aactaagcat    420
cattggtggt ggaagttgca cttttgtttgg gagagagtta aggttttgca ggactacact    480
ggattgatct tgttcttgga ggaggatcat tacttggctc cagacttcta ccacgttttc    540
aagaagatgt ggaagttgaa gcaacaagag tgtccaggtt gtgacgtttt gtccttggga    600
acttacacta ctatcagatc cttctacggt atcgctgaca aggttgacgt taagacttgg    660
aagtccactg aacacaacat gggattggct ttgactagag atgcttacca gaagttgatc    720
gagtgtactg acactttctg tacttacgac gactacaact gggactggac tttgcagtac    780
ttgactttgg cttgtttgcc aaaagtttgg aaggttttgg ttccacaggc tccaagaatt    840
ttccacgctg gtgactgtgg aatgcaccac aagaaaactt gtagaccatc cactcagtcc    900
gctcaaattg agtccttgtt gaacaacaac aagcagtact tgttcccaga cttttggtt    960 atcggagaga gtttccaat ggctgctatt tccccaccaa gaaagaatgg tggatggggt    1020
gatattagag accacgagtt gtgtaaatcc tacagaagat tgcagtag                 1068
```

<210> SEQ ID NO 74
<211> LENGTH: 300
<212> TYPE: DNA
<213> ORGANISM: Artificial Sequence
<220> FEATURE:
<223> OTHER INFORMATION: DNA encodes Mnn2 leader (54)

<400> SEQUENCE: 74

```
atgctgctta ccaaaaggtt ttcaaagctg ttcaagctga cgttcatagt tttgatattg      60
```

```
tgcgggctgt tcgtcattac aaacaaatac atggatgaga acacgtcggt caaggagtac    120
aaggagtact tagacagata tgtccagagt tactccaata agtattcatc ttcctcagac    180
gccgccagcg ctgacgattc aaccccattg agggacaatg atgaggcagg caatgaaaag    240
ttgaaaagct tctacaacaa cgttttcaac tttctaatgg ttgattcgcc cgggcgcgcc    300
```

<210> SEQ ID NO 75
<211> LENGTH: 1373
<212> TYPE: DNA
<213> ORGANISM: Artificial Sequence
<220> FEATURE:
<223> OTHER INFORMATION: Sequence of the 5'-Region used for knock out of
      PpARG1

<400> SEQUENCE: 75

```
gatctggcct tccctgaatt tttacgtcca gctatacgat ccgttgtgac tgtatttcct     60
gaaatgaagt ttcaacctaa agttttggtt gtacttgctc cacctaccac ggaaactaat    120
atcgaaacca atgaaaaagt agaactggaa tcgtcaatcg aaattcgcaa ccaagtggaa    180
cccaaagact tgaatctttc taaagtctat tctagtgaca ctaatggcaa cagaagattt    240
gagctgactt ttcaaatgaa tctcaataat gcaatatcaa catcagacaa tcaatgggct    300
ttgtctagtg acacaggatc aattatagta gtgtcttctg caggaagaat aacttccccg    360
atcctagaag tcggggcatc cgtctgtgtc ttaagatcgt acaacgaaca ccttttggca    420
ataacttgtg aaggaacatg cttttcatgg aatttaaaga agcaagaatg tgttctaaac    480
agcatttcat tagcacctat agtcaattca cacatgctag ttaagaaagt tggagatgca    540
aggaactatt ctattgtatc tgccgaagga gacaacaatc cgttacccca gattctagac    600
tgcgaacttt ccaaaaatgg cgctccaatt gtggctctta gcacgaaaga catctactct    660
tattcaaaga aaatgaaatg ctggatccat tgattgatt cgaaatactt tgaattgttg    720
ggtgctgaca atgcactgtt tgagtgtgtg aagcgctag aaggtccaat tggaatgcta    780
attcatagat tggtagatga gttcttccat gaaaacactg ccggtaaaaa actcaaactt    840
tacaacaagc gagtactgga ggacctttca aattcacttg aagaactagg tgaaaatgcg    900
tctcaattaa gagagaaact tgacaaactc tatggtgatg aggttgaggc ttcttgacct    960
cttctctcta tctgcgtttc ttttttttt tttttttttt ttttttcag ttgagccaga   1020 ccgcgctaaa cgcataccaa ttgccaaatc aggcaattgt gagacagtgg taaaaaagat   1080
gcctgcaaag ttagattcac acagtaagag agatcctact cataaatgag gcgcttattt   1140
agtagctagt gatagccact gcggttctgc tttatgctat tgttgtatg ccttactatc   1200 tttgtttggc tccttttct tgacgttttc cgttggaggg actccctatt ctgagtcatg   1260
agccgcacag attatcgccc aaaattgaca aaatcttctg gcgaaaaag tataaaagga   1320 gaaaaaagct caccctttc cagcgtagaa agtatatatc agtcattgaa gac          1373
```

<210> SEQ ID NO 76
<211> LENGTH: 1470
<212> TYPE: DNA
<213> ORGANISM: Artificial Sequence
<220> FEATURE:
<223> OTHER INFORMATION: Sequence of the 3'-Region used for knock out of
      PpARG1

<400> SEQUENCE: 76

```
gggactttaa ctcaagtaaa aggatagttg tacaattata tatacgaaga ataaatcatt     60
acaaaaagta ttcgtttctt tgattcttaa caggattcat tttctgggtg tcatcaggta    120
```

```
cagcgctgaa tatcttgaag ttaacatcga gctcatcatc gacgttcatc acactagcca    180
cgtttccgca acggtagcaa taattaggag cggaccacac agtgacgaca tctttctctt    240
tgaaatggta tctgaagcct tccatgacca attgatgggc tctagcgatg agttgcaagt    300
tattaatgtg gttgaactca cgtgctactc gagcaccgaa taaccagcca gctccacgag    360
gagaaacagc ccaactgtcg acttcatctg ggtcagacca aaccaagtca caaatcctc    420 cttcatgagg gacctcttgc gctcggctga gaactctgat ttgatctaac atgcgaatat    480
cgggagagag accaccatgg atacataata ttttaccatc aatgatgcca ctaagggtta    540
aaaagtcgaa cacctggcaa cagtacttcc agacagtggt ggaaccatat ttattgagac    600
attcctcata aaatccataa acctgagtga tctgtctgga ttcatgattt ccccttacca    660
atgtgatatg ttgaggaaac ttaattttta aaatcatgag taacgtgaac gtctccaacg    720
agaaatagcc tctatccaca tagtctccta ggaagatata gttctgtttt attccattag    780
aggaggatcc gggaaaccca ccactaatct tgaaaagttc cagtagatcg tgaaattggc    840
cgtgaatatc tccgcatact gtcactggac tctgcactgg ctgtatattg gattcctcca    900
tcagcaaatc cttcacccgt tcgcaaagat gcttcatatc attttcactt aaagccttgc    960
agcttttgac ttcttcaaac cactgatctg gtcctctttc tggcatgatt aaggtctata   1020
atatttctga gctgagatgt aaaaaaaaat aataaaaatg gggagtgaaa aagtgtgtag   1080
cttttaggag tttgggattg atacccccaaa atgatcttta tgagaattaa aaggtagata   1140
cgcttttaat aagaacacct atctatagta ctttgtggtc ttgagtaatt gagatgttca   1200
gcttctgagg tttgccgtta ttctgggata gtagtgcgcg accaaacaac ccgccaggca   1260
aagtgtgttg tgctcgaaga cgattgccag aagagtaagt ccgtcctgcc tcagatgtta   1320
cacactttct tccctagaca gtcgatgcat catcggattt aaacctgaaa ctttgatgcc   1380
atgatacgcc tagtcacgtc gactgagatt ttagataagc cccgatccct ttagtacatt   1440
cctgttatcc atggatggaa tggcctgata                                    1470
```

<210> SEQ ID NO 77
<211> LENGTH: 1043
<212> TYPE: DNA
<213> ORGANISM: Artificial Sequence
<220> FEATURE:
<223> OTHER INFORMATION: Sequence of the 5'-Region used for knock out of BMT4

<400> SEQUENCE: 77

```
aagcttgttc accgttggga cttttccgtg gacaatgttg actactccag gagggattcc     60
agctttctct actagctcag caataatcaa tgcagcccca ggcgcccgtt ctgatggctt    120
gatgaccgtt gtattgcctg tcactatagc caggggtagg gtccataaag gaatcatagc    180
agggaaatta aaagggcata ttgatgcaat cactcccaat ggctctcttg ccattgaagt    240
ctccatatca gcactaactt ccaagaagga ccccttcaag tctgacgtga tagagcacgc    300
ttgctctgcc acctgtagtc ctctcaaaac gtcaccttgt gcatcagcaa agactttacc    360
ttgctccaat actatgacgg aggcaattct gtcaaaattc tctctcagca attcaaccaa    420
cttgaaagca aattgctgtc tcttgatgat ggagactttt ttccaagatt gaaatgcaat    480
gtgggacgac tcaattgctt cttccagctc ctcttcggtt gattgaggaa cttttgaaac    540
cacaaaattg gtcgttgggt catgtacatc aaaccattct gtagatttag attcgacgaa    600
agcgttgttg atgaaggaaa aggttggata cggtttgtcg gtctctttgg tatggccggt    660
```

```
ggggtatgca attgcagtag aagataattg gacagccatt gttgaaggta gagaaaaggt      720
cagggaactt gggggttatt tataccattt taccccacaa ataacaactg aaaagtaccc      780
attccatagt gagaggtaac cgacggaaaa agacgggccc atgttctggg accaatagaa      840
ctgtgtaatc cattgggact aatcaacaga cgattggcaa tataatgaaa tagttcgttg      900
aaaagccacg tcagctgtct tttcattaac tttggtcgga cacaacattt tctactgttg      960
tatctgtcct actttgctta tcatctgcca cagggcaagt ggatttcctt ctcgcgcggc     1020
tgggtgaaaa cggttaacgt gaa                                              1043

<210> SEQ ID NO 78
<211> LENGTH: 695
<212> TYPE: DNA
<213> ORGANISM: Artificial Sequence
<220> FEATURE:
<223> OTHER INFORMATION: Sequence of the 3'-Region used for knock out of
      BMT4

<400> SEQUENCE: 78
gccttggggg acttcaagtc tttgctagaa actagatgag gtcaggcccct cttatggttg       60 tgtcccaatt gggcaatttc actcacctaa aaagcatgac aattatttag cgaaataggt      120
agtatatttt ccctcatctc ccaagcagtt tcgttttgc atccatatct ctcaaatgag      180
cagctacgac tcattagaac cagagtcaag taggggtgag ctcagtcatc agccttcgtt      240
tctaaaacga ttgagttctt tgttgctac aggaagcgcc ctagggaact ttcgcacttt      300
ggaaatagat tttgatgacc aagagcggga gttgatatta gagaggctgt ccaaagtaca      360
tgggatcagg ccggccaaat tgattggtgt gactaaacca ttgtgtactt ggacactcta      420
ttacaaaagc gaagatgatt tgaagtatta caagtcccga agtgttagag gattctatcg      480
agcccagaat gaaatcatca accgttatca gcagattgat aaactcttgg aaagcggtat      540
cccattttca ttattgaaga actacgataa tgaagatgtg agagacggcg accctctgaa      600
cgtagacgaa gaaacaaatc tacttttggg gtacaataga gaaagtgaat caaggaggt      660 atttgtggcc ataatactca actctatcat taatg                                 695

<210> SEQ ID NO 79
<211> LENGTH: 1103
<212> TYPE: DNA
<213> ORGANISM: Artificial Sequence
<220> FEATURE:
<223> OTHER INFORMATION: Sequence of the 5'-Region used for knock out of
      BMT1

<400> SEQUENCE: 79
catatggtga gagccgttct gcacaactag atgttttcga gcttcgcatt gtttcctgca       60
gctcgactat tgaattaaga tttccggata tctccaatct cacaaaaact tatgttgacc      120
acgtgctttc ctgaggcgag gtgttttata tgcaagctgc caaaaatgga aaacgaatgg      180
ccatttttcg cccaggcaaa ttattcgatt actgctgtca taagacagt gttgcaaggc      240 tcacattttt ttttaggatc cgagataaag tgaatacagg acagcttatc tctatatctt      300
gtaccattcg tgaatcttaa gagttcggtt aggggactc tagttgaggg ttggcactca      360
cgtatggctg ggcgcagaaa taaaattcag gcgcagcagc acttatcgat ggaattcaca      420
gttataaata aaacaaaaa ctcaaaagt ttgggctcca caaataact taatttaaat      480 ttttgtctaa taaatgaatg taattccaag attatgtgat gcaagcacag tatgcttcag      540
ccctatgcag ctactaatgt caatctcgcc tgcgagcggg cctagatttt cactacaaat      600
```

```
ttcaaaacta cgcggattta ttgtctcaga gagcaatttg gcatttctga gcgtagcagg    660
aggcttcata agattgtata ggaccgtacc aacaaattgc cgaggcacaa acggtatgc     720 tgtgcactta tgtggctact ccctacaac ggaatgaaac cttcctcttt ccgcttaaac     780
gagaaagtgt gtcgcaattg aatgcaggtg cctgtgcgcc ttggtgtatt gttttgaggg    840
gcccaattta tcaggcgcct tttttcttgg ttgttttccc ttagcctcaa gcaaggttgg    900
tctatttcat ctccgcttct ataccgtgcc tgatactgtt ggatgagaac acgactcaac    960
ttcctgctgc tctgtattgc cagtgttttg tctgtgattt ggatcggagt cctccttact   1020
tggaatgata ataatcttgg cggaatctcc ctaaacggag gcaaggattc tgcctatgat   1080
gatctgctat cattgggaag ctt                                           1103

<210> SEQ ID NO 80
<211> LENGTH: 692
<212> TYPE: DNA
<213> ORGANISM: Artificial Sequence
<220> FEATURE:
<223> OTHER INFORMATION: Sequence of the 3'-Region used for knock out of
      BMT1

<400> SEQUENCE: 80
gaattcacag ttataaataa aaacaaaaac tcaaaaagtt tgggctccac aaaataactt     60
aatttaaatt tttgtctaat aaatgaatgt aattccaaga ttatgtgatg caagcacagt    120
atgcttcagc cctatgcagc tactaatgtc aatctcgcct gcgagcgggc ctagattttc    180
actacaaatt tcaaaactac gcggatttat tgtctcagag agcaatttgg catttctgag    240
cgtagcagga ggcttcataa gattgtatag gaccgtacca acaaattgcc gaggcacaac    300
acggtatgct gtgcacttat gtggctactt ccctacaacg gaatgaaacc ttcctctttc    360
cgcttaaacg agaaagtgtg tcgcaattga atgcaggtgc ctgtgcgcct tggtgtattg    420 ttttgaggg cccaatttat caggcgcctt ttttcttggt tgttttccct tagcctcaag    480
caaggttggt ctatttcatc tccgcttcta taccgtgcct gatactgttg atgagaaca    540 cgactcaact tcctgctgct ctgtattgcc agtgttttgt ctgtgatttg gatcggagtc    600
ctccttactt ggaatgataa taatcttggc ggaatctccc taaacggagg caaggattct    660
gcctatgatg atctgctatc attgggaagc tt                                 692

<210> SEQ ID NO 81
<211> LENGTH: 546
<212> TYPE: DNA
<213> ORGANISM: Artificial Sequence
<220> FEATURE:
<223> OTHER INFORMATION: Sequence of the 5'-Region used for knock out of
      BMT3

<400> SEQUENCE: 81
gatatctccc tggggacaat atgtgttgca actgttcgtt gttggtgccc cagtccccca     60
accggtacta atcggtctat gttcccgtaa ctcatattcg gttagaacta gaacaataag    120
tgcatcattg ttcaacattg tggttcaatt gtcgaacatt gctggtgctt atatctacag    180
ggaagacgat aagcctttgt acaagagagg taacagacag ttaattggta tttctttggg    240
agtcgttgcc ctctacgttg tctccaagac atactacatt ctgagaaaca gatggaagac    300
tcaaaaatgg gagaagctta gtgaagaaga gaaagttgcc tacttggaca gagctgagaa    360
ggagaacctg ggttctaaga ggctggactt tttgttcgag agttaaactg cataattttt    420
tctaagtaaa tttcatagtt atgaaatttc tgcagcttag tgtttactgc atcgtttact    480
```

```
gcatcaccct gtaaataatg tgagcttttt tccttccatt gcttggtatc ttccttgctg    540
ctgttt                                                              546

<210> SEQ ID NO 82
<211> LENGTH: 378
<212> TYPE: DNA
<213> ORGANISM: Artificial Sequence
<220> FEATURE:
<223> OTHER INFORMATION: Sequence of the 3'-Region used for knock out of
      BMT3

<400> SEQUENCE: 82
acaaaacagt catgtacaga actaacgcct ttaagatgca gaccactgaa aagaattggg     60
tcccattttt cttgaaagac gaccaggaat ctgtccattt tgtttactcg ttcaatcctc    120
tgagagtact caactgcagt cttgataacg gtgcatgtga tgttctattt gagttaccac    180
atgattttgg catgtcttcc gagctacgtg gtgccactcc tatgctcaat cttcctcagg    240
caatcccgat ggcagacgac aaagaaattt gggtttcatt cccaagaacg agaatatcag    300
attgcgggtg ttctgaaaca atgtacaggc caatgttaat gcttttgtt agagaaggaa     360 caaacttttt tgctgagc                                                  378

<210> SEQ ID NO 83
<211> LENGTH: 1494
<212> TYPE: DNA
<213> ORGANISM: Artificial Sequence
<220> FEATURE:
<223> OTHER INFORMATION: DNA encodes Tr ManI catalytic domain

<400> SEQUENCE: 83
cgcgccggat ctcccaaccc tacgagggcg gcagcagtca aggccgcatt ccagacgtcg     60
tggaacgctt accaccattt tgcctttccc catgacgacc tccacccggt cagcaacagc    120
tttgatgatg agagaaacgg ctggggctcg tcggcaatcg atggcttgga cacggctatc    180
ctcatggggg atgccgacat tgtgaacacg atccttcagt atgtaccgca gatcaacttc    240
accacgactg cggttgccaa ccaaggcatc tccgtgttcg agaccaacat tcggtacctc    300
ggtggcctgc tttctgccta tgacctgttg cgaggtcctt tcagctcctt ggcgacaaac    360
cagaccctgg taaacagcct tctgaggcag gctcaaacac tggccaacgg cctcaaggtt    420
gcgttcacca ctcccagcgg tgtcccggac cctaccgtct tcttcaaccc tactgtccgg    480
agaagtggtg catctagcaa caacgtcgct gaaattggaa gcctggtgct cgagtggaca    540
cggttgagcg acctgacggg aaacccgcag tatgcccagc ttgcgcagaa gggcgagtcg    600
tatctcctga atccaaaggg aagcccggag gcatggcctg gcctgattgg aacgtttgtc    660
agcacgagca acggtacctt tcaggatagc agcggcagct ggtccggcct catggacagc    720
ttctacgagt acctgatcaa gatgtacctg tacgacccgg ttgcgtttgc acactacaag    780
gatcgctggg tccttgctgc cgactcgacc attgcgcatc tcgcctctca cccgtcgacg    840
cgcaaggact tgacctttt gtcttcgtac aacggacagt ctacgtcgcc aaactcagga    900
catttggcca gttttgccgg tggcaacttc atcttgggag gcattctcct gaacgagcaa    960
aagtacattg actttggaat caagcttgcc agctcgtact tgccacgta caaccagacg    1020 gcttctggaa tcggccccga aggcttcgcg tgggtggaca cgtgacggg cgccggcggc    1080 tcgccgccct cgtcccagtc cgggttctac tcgtcggcag gattctgggt gacggcaccg    1140
tattacatcc tgcggccgga gacgctggag agcttgtact acgcataccg cgtcacgggc    1200
gactccaagt ggcaggacct ggcgtgggaa gcgttcagtg ccattgagga cgcatgccgc    1260
```

```
gccggcagcg cgtactcgtc catcaacgac gtgacgcagg ccaacggcgg gggtgcctct    1320
gacgatatgg agagcttctg gtttgccgag gcgctcaagt atgcgtacct gatctttgcg    1380
gaggagtcgg atgtgcaggt gcaggccaac ggcgggaaca aatttgtctt taacacggag    1440
gcgcacccct ttagcatccg ttcatcatca cgacggggcg gccaccttgc ttaa          1494
```

<210> SEQ ID NO 84
<211> LENGTH: 1792
<212> TYPE: DNA
<213> ORGANISM: Artificial Sequence
<220> FEATURE:
<223> OTHER INFORMATION: 5'ARG1 and ORF

<400> SEQUENCE: 84

```
taccaattgc caaatcaggc aattgtgaga cagtggtaaa aaagatgcct gcaaagttag      60
attcacacag taagagagat cctactcata aatgaggcgc ttatttagta gctagtgata     120
gccactgcgg ttctgcttta tgctatttgt tgtatgcctt actatctttg tttggctcct     180
ttttcttgac gttttccgtt ggagggactc cctattctga gtcatgagcc gcacagatta     240
tcgcccaaaa ttgacaaaat cttctggcga aaaagtata aaaggagaaa aaagctcacc      300
cttttccagc gtagaaagta tatatcagtc attgaagact attatttaaa taacacaatg     360
tctaaaggaa aagtttgttt ggcctactcc ggtggtttgg atacctccat catcctagct     420
tggttgttgg agcagggata cgaagtcgtt gccttttag ccaacattgg tcaagaggaa      480
gactttgagg ctgctagaga gaaagctctg aagatcggtg ctaccaagtt tatcgtcagt     540
gacgttagga aggaatttgt tgaggaagtt ttgttcccag cagtccaagt taacgctatc     600
tacgagaacg tctacttact gggtacctct ttggccagac cagtcattgc caaggcccaa     660
atagaggttg ctgaacaaga aggttgtttt gctgttgccc acggttgtac cggaaagggt     720
aacgatcagg ttagatttga cttccttt tatgctctga gcctgacgt tgtctgtatc        780 gccccatgga gagacccaga attcttcgaa agattcgctg gtagaaatga cttgctgaat     840
tacgctgctg agaaggatat tccagttgct cagactaaag ccaagccatg gtctactgat     900
gagaacatgg ctcacatctc cttcgaggct ggtattctag aagatccaaa cactactcct     960
ccaaaggaca tgtggaagct cactgttgac ccagaagatg caccagacaa gccagagttc    1020
tttgacgtcc actttgagaa gggtaagcca gttaaattag ttctcgagaa caaaactgag    1080
gtcaccgatc cggttgagat cttttttgact gctaacgcca ttgctagaag aaacggtgtt    1140
ggtagaattg acattgtcga gaacagattc atcggaatca gtccagagg ttgttatgaa      1200 actccaggtt tgactctact gagaaccact cacatcgact tggaaggtct taccgttgac    1260
cgtgaagtta gatcgatcag agacactttt gttacccccaa cctactctaa gttgttatac    1320
aacgggttgt actttacccc agaaggtgag tacgtcagaa ctatgattca gccttctcaa    1380
aacaccgtca acggtgttgt tagagccaag gcctacaaag gtaatgtgta taacctagga    1440
agatactctg aaaccgagaa attgtacgat gctaccgaat cttccatgga tgagttgacc    1500
ggattccacc ctcaagaagc tggaggattt atcacaacac aagccatcag aatcaagaag    1560
tacggagaaa gtgtcagaga aagggaaag ttttgggac tttaactcaa gtaaaggat       1620 agttgtacaa ttatatatac gaagaataaa tcattacaaa aagtattcgt ttctttgatt    1680
cttaacagga ttcatttct gggtgtcatc aggtacagcg ctgaatatct tgaagttaac      1740
atcgagctca tcatcgacgt tcatcacact agccacgttt ccgcaacggt ag             1792
```

<210> SEQ ID NO 85
<211> LENGTH: 414
<212> TYPE: DNA
<213> ORGANISM: Artificial Sequence
<220> FEATURE:
<223> OTHER INFORMATION: PpCITI TT

<400> SEQUENCE: 85

```
ccggccattt aaatatgtga cgactgggtg atccgggtta gtgagttgtt ctcccatctg      60
tatatttttc atttacgatg aatacgaaat gagtattaag aaatcaggcg tagcaatatg     120
ggcagtgttc agtcctgtca tagatggcaa gcactggcac atccttaata ggttagagaa     180
aatcattgaa tcatttgggt ggtgaaaaaa aattgatgta aacaagccac ccacgctggg     240
agtcgaaccc agaatctttt gattagaagt caaacgcgtt aaccattacg ctacgcaggc     300
atgtttcacg tccattttg  attgctttct atcataatct aaagatgtga actcaattag     360
ttgcaatttg accaattctt ccattacaag tcgtgcttcc tccgttgatg caac           414
```

<210> SEQ ID NO 86
<211> LENGTH: 388
<212> TYPE: DNA
<213> ORGANISM: Artificial Sequence
<220> FEATURE:
<223> OTHER INFORMATION: Ashbya gossypii TEF1 promoter

<400> SEQUENCE: 86

```
gatctgttta gcttgcctcg tccccgccgg gtcacccggc cagcgacatg gaggcccaga      60
ataccctcct tgacagtctt gacgtgcgca gctcaggggc atgatgtgac tgtcgcccgt     120
acatttagcc catacatccc catgtataat catttgcatc catacatttt gatggccgca     180
cggcgcgaag caaaaattac ggctcctcgc tgcagacctg cgagcaggga acgctcccc      240 tcacagacgc gttgaattgt ccccacgccg cgcccctgta gagaaatata aaaggttagg     300
atttgccact gaggttcttc tttcatatac ttccttttaa atcttgcta  ggatacagtt     360 ctcacatcac atccgaacat aaacaacc                                         388
```

<210> SEQ ID NO 87
<211> LENGTH: 247
<212> TYPE: DNA
<213> ORGANISM: Artificial Sequence
<220> FEATURE:
<223> OTHER INFORMATION: Ashbya gossypii TEF1 termination sequence

<400> SEQUENCE: 87

```
taatcagtac tgacaataaa aagattcttg ttttcaagaa cttgtcattt gtatagtttt      60
tttatattgt agttgttcta ttttaatcaa atgttagcgt gatttatatt ttttttcgcc     120
tcgacatcat ctgcccagat gcgaagttaa gtgcgcagaa agtaatatca tgcgtcaatc     180
gtatgtgaat gctggtcgct atactgctgt cgattcgata ctaacgccgc catccagtgt     240
cgaaaac                                                                247
```

<210> SEQ ID NO 88
<211> LENGTH: 1037
<212> TYPE: DNA
<213> ORGANISM: Artificial Sequence
<220> FEATURE:
<223> OTHER INFORMATION: Sequence of the PpPMA1 promoter

<400> SEQUENCE: 88

```
aaatgcgtac ctcttctacg agattcaagc gaatgagaat aatgtaatat gcaagatcag      60
aaagaatgaa aggagttgaa aaaaaaaacc gttgcgtttt gaccttgaat ggggtggagg     120
```

```
tttccattca aagtaaagcc tgtgtcttgg tattttcggc ggcacaagaa atcgtaattt      180
tcatcttcta aacgatgaag atcgcagccc aacctgtatg tagttaaccg gtcggaatta      240
taagaaagat tttcgatcaa caaaccctag caaatagaaa gcagggttac aactttaaac      300
cgaagtcaca aacgataaac cactcagctc ccacccaaat tcattcccac tagcagaaag      360
gaattattta atccctcagg aaacctcgat gattctcccg ttcttccatg ggcgggtatc      420
gcaaaatgag gaattttca aatttctcta ttgtcaagac tgtttattat ctaagaaata      480
gcccaatccg aagctcagtt ttgaaaaaat cacttccgcg tttctttttt acagcccgat      540
gaatatccaa atttggaata tggattactc tatcgggact gcagataata tgacaacaac      600
gcagattaca ttttaggtaa ggcataaaca ccagccagaa atgaaacgcc cactagccat      660
ggtcgaatag tccaatgaat tcagatagct atggtctaaa agctgatgtt ttttattggg      720
taatggcgaa gagtccagta cgacttccag cagagctgag atggccattt ttgggggtat      780
tagtaacttt ttgagctctt ttcacttcga tgaagtgtcc cattcgggat ataatcggat      840
cgcgtcgttt tctcgaaaat acagcttagc gtcgtccgct tgttgtaaaa gcagcaccac      900
attcctaatc tcttatataa acaaaacaac ccaaattatc agtgctgttt tcccaccaga      960
tataagtttc ttttctcttc cgcttttga ttttttatct cttccttta aaacttctt      1020 taccttaaag ggcggcc                                                    1037

<210> SEQ ID NO 89
<211> LENGTH: 1231
<212> TYPE: DNA
<213> ORGANISM: Artificial Sequence
<220> FEATURE:
<223> OTHER INFORMATION: Sequence of the 5'-region that was used to
      knock into the PpPRO1 locus

<400> SEQUENCE: 89
gaagggccat cgaattgtca tcgtctcctc aggtgccatc gctgtgggca tgaagagagt       60
caacatgaag cggaaaccaa aaaagttaca gcaagtgcag gcattggctg ctataggaca      120
aggccgtttg ataggacttt gggacgacct tttccgtcag ttgaatcagc ctattgcgca      180
gattttactg actagaacgg atttggtcga ttacacccag tttaagaacg ctgaaaatac      240
attggaacag cttattaaaa tgggtattat tcctattgtc aatgagaatg acaccctatc      300
cattcaagaa atcaaatttg gtgacaatga caccttatcc gccataacag ctggtatgtg      360
tcatgcagac tacctgtttt tggtgactga tgtggactgt ctttacacgg ataaccctcg      420
tacgaatccg gacgctgagc caatcgtgtt agttagaaat atgaggaatc taaacgtcaa      480
taccgaaagt ggaggttccg ccgtaggaac aggaggaatg acaactaaat tgatcgcagc      540
tgatttgggt gtatctgcag gtgttacaac gattatttgc aaaagtgaac atcccgagca      600
gattttggac attgtagagt acagtatccg tgctgataga gtcgaaaatg aggctaaata      660
tctggtcatc aacgaagagg aaactgtgga acaatttcaa gagatcaatc ggtcagaact      720
gagggagttg aacaagctgg acattccttt gcatacacgt ttcgttggcc acagttttaa      780
tgctgttaat aacaaagagt tttggttact ccatggacta aaggccaacg gagccattat      840
cattgatcca ggttgttata aggctatcac tagaaaaaac aaagctggta ttcttccagc      900
tggaattatt tccgtagagg gtaatttcca tgaatacgag tgtgttgatg ttaaggtagg      960
actaagagat ccagatgacc cacattcact agacccaat gaagaacttt acgtcgttgg      1020
ccgtgcccgt tgtaattacc ccagcaatca aatcaacaaa attaagggtc tacaaagctc      1080
```

```
gcagatcgag caggttctag gttacgctga cggtgagtat gttgttcaca gggacaactt    1140
ggctttccca gtatttgccg atccagaact gttggatgtt gttgagagta ccctgtctga    1200
acaggagaga gaatccaaac caaataaata g                                    1231
```

<210> SEQ ID NO 90
<211> LENGTH: 1425
<212> TYPE: DNA
<213> ORGANISM: Artificial Sequence
<220> FEATURE:
<223> OTHER INFORMATION: Sequence of the 3'-region that was used to knock into the PpPRO1 locus

<400> SEQUENCE: 90

```
aatttcacat atgctgcttg attatgtaat tataccttgc gttcgatggc atcgatttcc      60
tcttctgtca atcgcgcatc gcattaaaag tatactttt ttttttttcct atagtactat     120 tcgccttatt ataaactttg ctagtatgag ttctaccccc aagaaagagc ctgatttgac     180
tcctaagaag agtcagcctc caaagaatag tctcggtggg ggtaaaggct ttagtgagga     240
gggtttctcc caaggggact tcagcgctaa gcatatacta atcgtcgcc ctaacaccga      300 aggctcttct gtggcttcga acgtcatcag ttcgtcatca ttgcaaaggt taccatcctc     360
tggatctgga agcgttgctg tgggaagtgt gttgggatct tcgccattaa ctctttctgg     420
agggttccac gggcttgatc caaccaagaa taaaatagac gttccaaagt cgaaacagtc     480
aaggagacaa agtgttcttt ctgacatgat ttccacttct catgcagcta gaaatgatca     540
ctcagagcag cagttacaaa ctggacaaca atcagaacaa aaagaagaag atggtagtcg     600
atcttctttt tctgtttctt ccccgcaag agatatccgg cacccagatg tactgaaaac      660
tgtcgagaaa catcttgcca atgacagcga gatcgactca tctttacaac ttcaaggtgg     720
agatgtcact agaggcattt atcaatgggt aactggagaa agtagtcaaa agataacccc     780
gcctttgaaa cgagcaaata gttttaatga ttttctctct gtgcatggtg acgaggtagg     840
caaggcagat gctgaccacg atcgtgaaag cgtattcgac gaggatgata tctccattga     900
tgatatcaaa gttccgggag ggatgcgtcg aagtttttta ttacaaaagc atagagacca     960
acaactttct ggactgaata aaacggctca ccaaccaaaa caacttacta aacctaattt    1020
cttcacgaac aactttatag agtttttggc attgtatggg cattttgcag gtgaagattt    1080
ggaggaagac gaagatgaag atttagacag tggttccgaa tcagtcgcag tcagtgatag    1140
tgagggagaa ttcagtgagg ctgacaacaa tttgttgtat gatgaagagt ctctcctatt    1200
agcacctagt acctccaact atgcgagatc aagaatagga agtattcgta ctcctactta    1260
tggatctttc agttcaaatg ttggttcttc gtctattcat cagcagttaa tgaaaagtca    1320
aatcccgaag ctgaagaaac gtggacagca caagcataaa acacaatcaa aaatacgctc    1380
gaagaagcaa actaccaccg taaaagcagt gttgctgcta ttaaa                    1425
```

<210> SEQ ID NO 91
<211> LENGTH: 1793
<212> TYPE: DNA
<213> ORGANISM: Artificial Sequence
<220> FEATURE:
<223> OTHER INFORMATION: Sequence of the PpTRP2 gene integration locus

<400> SEQUENCE: 91

```
ggtttctcaa ttactatata ctactaacca tttacctgta gcgtatttct tttccctctt      60
cgcgaaagct caagggcatc ttcttgactc atgaaaaata tctggatttc ttctgacaga     120
tcatcaccct tgagcccaac tctctagcct atgagtgtaa gtgatagtca tcttgcaaca     180
```

```
gattattttg gaacgcaact aacaaagcag atacacccct cagcagaatc ctttctggat    240
attgtgaaga atgatcgcca aagtcacagt cctgagacag ttcctaatct ttaccccatt    300
tacaagttca tccaatcaga cttcttaacg cctcatctgg cttatatcaa gcttaccaac    360
agttcagaaa ctcccagtcc aagtttcttg cttgaaagtg cgaagaatgg tgacaccgtt    420
gacaggtaca cctttatggg acattccccc agaaaaataa tcaagactgg gcctttagag    480
ggtgctgaag ttgacccctt ggtgcttctg gaaaagaaac tgaagggcac cagacaagcg    540
caacttcctg gtattcctcg tctaagtggt ggtgccatag gatacatctc gtacgattgt    600
attaagtact ttgaaccaaa aactgaaaga aaactgaaag atgttttgca acttccggaa    660
gcagctttga tgttgttcga cacgatcgtg gcttttgaca atgtttatca aagattccag    720
gtaattggaa acgtttctct atccgttgat gactcggacg aagctattct tgagaaatat    780
tataagacaa gagaagaagt ggaaaagatc agtaaagtgg tatttgacaa taaaaactgtt    840 ccctactatg aacagaaaga tattattcaa ggccaaacgt tcacctctaa tattggtcag    900
gaagggtatg aaaaccatgt tcgcaagctg aaagaacata ttctgaaagg agacatcttc    960
caagctgttc cctctcaaag ggtagccagg ccgacctcat tgcaccctt caacatctat    1020 cgtcatttga aactgtcaa tccttctcca tacatgttct atattgacta tctagacttc    1080
caagttgttg gtgcttcacc tgaattacta gttaaatccg acaacaacaa caaaatcatc    1140
acacatccta ttgctggaac tcttcccaga ggtaaaacta tcgaagagga cgacaattat    1200
gctaagcaat gaagtcgtc tttgaaagac agggccgagc acgtcatgct ggtagatttg    1260
gccagaaatg atattaaccg tgtgtgtgag cccaccagta ccacggttga tcgtttattg    1320
actgtggaga gatttctca tgtgatgcat cttgtgtcag aagtcagtgg aacattgaga    1380
ccaaacaaga ctcgcttcga tgctttcaga tccattttcc cagcaggaac cgtctccggt    1440
gctccgaagg taagagcaat gcaactcata ggagaattgg aaggagaaaa gagaggtgtt    1500 tatgcgggg ccgtaggaca ctggtcgtac gatggaaaat cgatggacac atgtattgcc    1560
ttaagaacaa tggtcgtcaa ggacggtgtc gcttaccttc aagccggagg tggaattgtc    1620
tacgattctg acccctatga cgagtacatc gaaaccatga acaaaatgag atccaacaat    1680
aacaccatct tggaggctga aaaatctgg accgataggt tggccagaga cgagaatcaa    1740
agtgaatccg aagaaaacga tcaatgaacg gaggacgtaa gtaggaattt atg    1793
```

<210> SEQ ID NO 92
<211> LENGTH: 2172
<212> TYPE: DNA
<213> ORGANISM: Artificial Sequence
<220> FEATURE:
<223> OTHER INFORMATION: Human UDP-GlcNAc 2-epimerase/N-
      acetylmannosamine kinase (HsGNE) codon opitimized

<400> SEQUENCE: 92

```
atggaaaaga acggtaacaa cagaaagttg agagtttgtg ttgctacttg taacagagct     60
gactactcca agttggctcc aatcatgttc ggtatcaaga ctgagccaga gttcttcgag    120
ttggacgttg ttgttttggg ttcccacttg attgatgact acgtaacac ttacagaatg    180 atcgagcagg acgacttcga catcaacact agattgcaca ctattgttag aggagaggac    240
gaagctgcta tggttgaatc tgttggattg gctttggtta agttgccaga cgttttgaac    300
agattgaagc cagacatcat gattgttcac ggtgacagat tcgatgcttt ggcttttggct    360 acttccgctg cttttgataa cattagaatc ttgcacatcg agggtggtga agtttctggt    420
```

-continued

```
actatcgacg actccatcag acacgctatc actaagttgg ctcactacca tgtttgttgt    480
actagatccg ctgagcaaca cttgatttcc atgtgtgagg accacgacag aattttgttg    540
gctggttgtc catcttacga caagttgttg tccgctaaga acaaggacta catgtccatc    600
atcagaatgt ggttgggtga cgacgttaag tctaaggact acatcgttgc tttgcagcac    660
ccagttacta ctgacatcaa gcactccatc aagatgttcg agttgacttt ggacgctttg    720
atctccttca acaagagaac tttggttttg ttcccaaaca ttgacgctgg ttccaaagag    780
atggttagag ttatgagaaa aagggtatc gaacaccacc caaacttcag agctgttaag    840
cacgttccat tcgaccaatt catccagttg gttgctcatg ctggttgtat gatcggtaac    900
tcctcctgtg gtgttagaga agttggtgct ttcggtactc cagttatcaa cttgggtact    960
agacagatcg gtagagagac tggagaaaac gttttgcatg ttagagatgc tgacactcag   1020
gacaagattt tgcaggcttt gcacttgcaa ttcggaaagc agtacccatg ttccaaaatc   1080
tacggtgacg gtaacgctgt tccaagaatc ttgaagtttt tgaagtccat cgacttgcaa   1140
gagccattgc agaagaagtt ctgtttccca ccagttaagg agaacatctc ccaggacatt   1200
gaccacatct tggagacatt gtccgctttg gctgttgatt tgggtggaac taacttgaga   1260
gttgctatcg tttccatgaa gggagagatc gttaagaagt acactcagtt caacccaaag   1320
acttacgagg agagaatcaa cttgatcttg cagatgtgtg ttgaagctgc tgctgaggct   1380
gttaagttga actgtagaat cttgggtgtt ggtatctcta ctggtggtag agttaatcca   1440
agagagggta tcgttttgca ctccactaag ttgattcagg agtggaactc cgttgatttg   1500
agaactccat tgtccgacac attgcacttg ccagtttggg ttgacaacga cggtaattgt   1560
gctgctttgg ctgagagaaa gttcggtcaa ggaaagggat tggagaactt cgttactttg   1620
atcactggta ctggtattgg tggtggtatc attcaccagc acgagttgat tcacggttct   1680
tccttctgtg ctgctgaatt gggacacttg gttgtttctt tggacggtcc agactgttct   1740
tgtggttccc acggttgtat tgaagcttac gcatcaggaa tggcattgca gagagaggct   1800
aagaagttgc acgacgagga cttgttgttg gttgagggaa tgtctgttcc aaaggacgag   1860
gctgttggtg ctttgcattt gatccaggct gctaagttgg gtaatgctaa ggctcagtcc   1920
atcttgagaa ctgctggtac tgcttgggga ttgggtgttg ttaatatctt gcacactatg   1980
aacccatcct tggttatctt gtccggtgtt ttggcttctc actacatcca catcgttaag   2040
gacgttatca gacagcaagc tttgtcctcc gttcaagacg ttgatgttgt tgtttccgac   2100
ttggttgacc cagctttgtt gggtgctgct tccatggttt tggactacac tactagaaga   2160
atctactaat ag                                                       2172
```

<210> SEQ ID NO 93
<211> LENGTH: 1854
<212> TYPE: DNA
<213> ORGANISM: Artificial Sequence
<220> FEATURE:
<223> OTHER INFORMATION: Sequence of the PpARG1 auxotrophic marker:

<400> SEQUENCE: 93

```
cagttgagcc agaccgcgct aaacgcatac caattgccaa atcaggcaat tgtgagacag     60
tggtaaaaaa gatgcctgca aagttagatt cacacagtaa gagagatcct actcataaat    120
gaggcgctta tttagtagct agtgatagcc actgcggttc tgctttatgc tatttgttgt    180
atgccttact atctttgttt ggctcctttt tcttgacgtt ttccgttgga gggactccct    240
attctgagtc atgagccgca cagattatcg cccaaaattg acaaaatctt ctggcgaaaa    300
```

```
aagtatataaa ggagaaaaaa gctcacccct ttccagcgta gaaagtatat atcagtcatt    360
gaagactatt atttaaataa cacaatgtct aaaggaaaag tttgtttggc ctactccggt    420 ggttttggata cctccatcat cctagcttgg ttgttggagc agggatacga agtcgttgcc    480
tttttagcca acattggtca agaggaagac tttgaggctg ctagagagaa agctctgaag    540
atcggtgcta ccaagtttat cgtcagtgac gttaggaagg aatttgttga ggaagttttg    600
ttcccagcag tccaagttaa cgctatctac gagaacgtct acttactggg tacctctttg    660
gccagaccag tcattgccaa ggcccaaata gaggttgctg aacaagaagg ttgttttgct    720
gttgcccacg ttgtaccgg aaagggtaac gatcaggtta gatttgagct ttccttttat    780
gctctgaagc ctgacgttgt ctgtatcgcc ccatggagag acccagaatt cttcgaaaga    840
ttcgctggta gaaatgactt gctgaattac gctgctgaga aggatattcc agttgctcag    900
actaaagcca agccatggtc tactgatgag aacatggctc acatctcctt cgaggctggt    960
attctagaag atccaaacac tactcctcca aaggacatgt ggaagctcac tgttgaccca   1020
gaagatgcac cagacaagcc agagttcttt gacgtccact ttgagaaggg taagccagtt   1080
aaattagttc tcgagaacaa aactgaggtc accgatccgg ttgagatctt tttgactgct   1140
aacgccattg ctagaagaaa cggtgttggt agaattgaca ttgtcgagaa cagattcatc   1200
ggaatcaagt ccagaggttg ttatgaaact ccaggtttga ctctactgag aaccactcac   1260
atcgacttgg aaggtcttac cgttgaccgt gaagttagat cgatcagaga cacttttgtt   1320
accccaacct actctaagtt gttatacaac ggggttgtact ttaccccaga aggtgagtac   1380
gtcagaacta tgattcagcc ttctcaaaac accgtcaacg tgttgttag agccaaggcc   1440 tacaaaggta atgtgtataa cctaggaaga tactctgaaa ccgagaaatt gtacgatgct   1500
accgaatctt ccatggatga gttgaccgga ttccaccctc aagaagctgg aggatttatc   1560
acaacacaag ccatcagaat caagaagtac ggagaaagtg tcagagagaa gggaaagttt   1620
ttgggacttt aactcaagta aaaggatagt tgtacaatta tatatacgaa gaataaatca   1680
ttacaaaaag tattcgtttc tttgattctt aacaggattc attttctggg tgtcatcagg   1740
tacagcgctg aatatcttga agttaacatc gagctcatca tcgacgttca tcacactagc   1800 cacgttttccg caacggtagc aataattagg agcggaccac acagtgacga catc        1854
```

<210> SEQ ID NO 94
<211> LENGTH: 1308
<212> TYPE: DNA
<213> ORGANISM: Artificial Sequence
<220> FEATURE:
<223> OTHER INFORMATION: Encodes human CMP-sialic acid synthase (HsCSS)
      codon optimized

<400> SEQUENCE: 94

```
atggactctg ttgaaaaggg tgctgctact tctgtttcca acccaagagg tagaccatcc     60
agaggtagac ctcctaagtt gcagagaaac tccagaggtg gtcaaggtag aggtgttgaa    120
aagccaccac acttggctgc tttgatcttg gctagaggag gttctaaggg tatcccattg    180
aagaacatca gcacttggc tggtgttcca ttgattggat gggttttgag agctgctttg    240
gactctggtg ctttccaatc tgtttgggtt tccactgacc acgacgagat tgagaacgtt    300
gctaagcaat tcggtgctca ggttcacaga agatcctctg aggttttcaa ggactcttct    360
acttccttgg acgctatcat cgagttcttg aactaccaca acgaggttga catcgttggt    420
aacatccaag ctacttcccc atgtttgcac ccaactgact tgcaaaaagt tgctgagatg    480
atcagagaag agggttacga ctccgttttc tccgttgtta gaaggcacca gttcagatgg    540
```

```
tccgagattc agaagggtgt tagagaggtt acagagccat tgaacttgaa cccagctaaa    600
agaccaagaa ggcaggattg ggacggtgaa ttgtacgaaa acggttcctt ctacttcgct    660
aagagacact tgatcgagat gggatacttg caaggtggaa agatggctta ctacgagatg    720
agagctgaac actccgttga catcgacgtt gatatcgact ggccaattgc tgagcagaga    780
gttttgagat acggttactt cggaaaggag aagttgaagg atcaagtt gttggtttgt      840 aacatcgacg gttgtttgac taacggtcac atctacgttt ctggtgacca aaggagatt    900 atctcctacg acgttaagga cgctattggt atctccttgt tgaagaagtc cggtatcgaa    960
gttagattga tctccgagag agcttgttcc aagcaaacat tgtcctcttt gaagttggac    1020
tgtaagatgg aggtttccgt ttctgacaag ttggctgttg ttgacgaatg gagaaaggag    1080
atgggtttgt gttggaagga agttgcttac ttgggtaacg aagtttctga cgaggagtgt    1140
ttgaagagag ttggttttgtc tggtgctcca gctgatgctt gttccactgc tcaaaaggct    1200
gttggttaca tctgtaagtg taacggtggt agaggtgcta ttagagagtt cgctgagcac    1260
atctgtttgt tgatggagaa agttaataac tcctgtcaga gtagtag                  1308
```

<210> SEQ ID NO 95
<211> LENGTH: 1080
<212> TYPE: DNA
<213> ORGANISM: Artificial Sequence
<220> FEATURE:
<223> OTHER INFORMATION: Encodes human N-acetylneuraminate-9-phosphate synthase (HsSPS) codon optimized

<400> SEQUENCE: 95

```
atgccattgg aattggagtt gtgtcctggt agatgggttg gtggtcaaca cccatgtttc    60
atcatcgctg agatcggtca aaaccaccaa ggagacttgg acgttgctaa gagaatgatc    120
agaatggcta aggaatgtgg tgctgactgt gctaagttcc agaagtccga gttggagttc    180
aagttcaaca gaaaggcttt ggaaagacca tacacttcca agcactcttg gggaaagact    240
tacggagaac acaagagaca cttggagttc tctcacgacc aatacagaga gttgcagaga    300
tacgctgagg aagttggtat cttcttcact gcttctggaa tggacgaaat ggctgttgag    360
ttcttgcacg agttgaacgt tccattcttc aaagttggtt ccggtgacac taacaacttc    420
ccatacttgg aaaagactgc taagaaaggt agaccaatgg ttatctcctc tggaatgcag    480
tctatggaca ctatgaagca ggtttaccag atcgttaagc cattgaaccc aaacttttgt    540
ttcttgcagt gtacttccgc ttacccattg caaccagagg acgttaattt gagagttatc    600
tccgagtacc agaagttgtt cccagacatc ccaattggtt actctggtca cgagactggt    660
attgctattt ccgttgctgc tgttgctttg ggtgctaagg ttttggagag acacatcact    720
ttggacaaga cttggaaggg ttctgatcac tctgcttctt tggaacctgg tgagttggct    780
gaacttgtta gatcagttag attggttgag agactttggg ttccccaac taagcaattg    840 ttgccatgtg agatggcttg taacgagaag ttgggaaagt ccgttgttgc taaggttaag    900
atcccagagg gtactatctt gactatggac atgttgactg ttaaagttgg agagccaaag    960
ggttacccac cagaggacat ctttaacttg gttggtaaaa aggttttggt tactgttgag    1020
gaggacgaca ctattatgga ggagttggtt gacaaccacg gaaagaagat caagtcctag    1080
```

<210> SEQ ID NO 96
<211> LENGTH: 1092
<212> TYPE: DNA
<213> ORGANISM: Artificial Sequence
<220> FEATURE:

<223> OTHER INFORMATION: Encodes mouse alpha-2,6-sialyl transferase
catalytic domain (MmmST6) (codon optimized)

<400> SEQUENCE: 96

| | | | | | |
|---|---|---|---|---|---|
| gtttttcaaa | tgccaaagtc | ccaggagaaa | gttgctgttg | gtccagctcc | acaagctgtt | 60 |
| ttctccaact | ccaagcaaga | tccaaaggag | ggtgttcaaa | tcttgtccta | cccaagagtt | 120 |
| actgctaagg | ttaagccaca | accatccttg | caagtttggg | acaaggactc | cacttactcc | 180 |
| aagttgaacc | caagattgtt | gaagatttgg | agaaactact | tgaacatgaa | caagtacaag | 240 |
| gtttcctaca | agggtccagg | tccaggtgtt | aagttctccg | ttgaggcttt | gagatgtcac | 300 |
| ttgagagacc | acgttaacgt | tccatgatc | gaggctactg | acttcccatt | caacactact | 360 |
| gaatgggagg | gatacttgcc | aaaggagaac | ttcagaacta | aggctggtcc | atggcataag | 420 |
| tgtgctgttg | tttcttctgc | tggttccttg | aagaactccc | agtggggtag | agaaattgac | 480 |
| aaccacgacg | ctgttttgag | attcaacggt | gctccaactg | acaacttcca | gcaggatgtt | 540 |
| ggtactaaga | ctactatcag | attggttaac | tcccaattgg | ttactactga | aagagattc | 600 |
| ttgaaggact | ccttgtacac | tgagggaatc | ttgattttgt | gggacccatc | tgtttaccac | 660 |
| gctgacattc | acaatggta | tcagaagcca | gactacaact | tcttcgagac | ttacaagtcc | 720 |
| tacagaagat | tgcacccatc | ccagccattc | tacatcttga | agccacaaat | gccatgggaa | 780 |
| ttgtgggaca | tcatccagga | aatttcccca | gacttgatcc | aaccaaaccc | accatcttct | 840 |
| ggaatgttgg | gtatcatcat | catgatgact | ttgtgtgacc | aggttgacat | ctacgagttc | 900 |
| ttgccatcca | agagaaagac | tgatgtttgt | tactaccacc | agaagttctt | cgactccgct | 960 |
| tgtactatgg | gagcttacca | cccattgttg | ttcgagaaga | acatggttaa | gcacttgaac | 1020 |
| gaaggtactg | acgaggacat | ctacttgttc | ggaaaggcta | ctttgtccgg | tttcagaaac | 1080 |
| aacagatgtt | ag | | | | | 1092 |

<210> SEQ ID NO 97
<211> LENGTH: 2172
<212> TYPE: DNA
<213> ORGANISM: Artificial Sequence
<220> FEATURE:
<223> OTHER INFORMATION: Encodes human UDP-GlcNAc
2-epimerase/N-acetylmannosamine kinase (HsGNE)
(codon optimized)

<400> SEQUENCE: 97

| | | | | | |
|---|---|---|---|---|---|
| atggaaaaga | acggtaacaa | cagaaagttg | agagtttgtg | ttgctacttg | taacagagct | 60 |
| gactactcca | agttggctcc | aatcatgttc | ggtatcaaga | ctgagccaga | gttcttcgag | 120 |
| ttggacgttg | ttgttttggg | ttcccacttg | attgatgact | acggtaacac | ttacagaatg | 180 |
| atcgagcagg | acgacttcga | catcaacact | agattgcaca | ctattgttag | aggagaggac | 240 |
| gaagctgcta | tggttgaatc | tgttggattg | gcttttggtta | agttgccaga | cgttttgaac | 300 |
| agattgaagc | cagacatcat | gattgttcac | ggtgacagat | tcgatgcttt | ggctttggct | 360 |
| acttccgctg | ctttgatgaa | cattagaatc | ttgcacatcg | agggtggtga | agtttctggt | 420 |
| actatcgacg | actccatcag | acacgctatc | actaagttgg | ctcactacca | tgttgttgt | 480 |
| actagatccg | ctgagcaaca | cttgattcc | atgtgtgagg | accacgacag | aattttgttg | 540 |
| gctggttgtc | catcttacga | caagttgttg | tccgctaaga | acaaggacta | catgtccatc | 600 |
| atcagaatgt | ggttgggtga | cgacgttaag | tctaaggact | acatcgttgc | tttgcagcac | 660 |
| ccagttacta | ctgacatcaa | gcactccatc | aagatgttcg | agttgacttt | ggacgctttg | 720 |
| atctccttca | acaagagaac | tttggttttg | ttcccaaaca | ttgacgctgg | ttccaaagag | 780 |

```
atggttagag ttatgagaaa gaagggtatc gaacaccacc caaacttcag agctgttaag      840
cacgttccat tcgaccaatt catccagttg gttgctcatg ctggttgtat gatcggtaac      900
tcctcctgtg gtgttagaga agttggtgct tcggtactc cagttatcaa cttgggtact       960
agacagatcg gtagagagac tggagaaaac gttttgcatg ttagagatgc tgacactcag     1020
gacaagattt tgcaggcttt gcacttgcaa ttcggaaagc agtacccatg ttccaaaatc     1080
tacggtgacg gtaacgctgt tccaagaatc ttgaagtttt tgaagtccat cgacttgcaa     1140
gagccattgc agaagaagtt ctgtttccca ccagttaagg agaacatctc ccaggacatt     1200
gaccacatct tggagacatt gtccgctttg gctgttgatt tgggtggaac taacttgaga     1260
gttgctatcg tttccatgaa gggagagatc gttaagaagt acactcagtt caacccaaag     1320
acttacgagg agagaatcaa cttgatcttg cagatgtgtg ttgaagctgc tgctgaggct     1380
gttaagttga actgtagaat cttgggtgtt ggtatctcta ctggtggtag agttaatcca     1440
agagagggta tcgttttgca ctccactaag ttgattcagg agtggaactc cgttgatttg     1500
agaactccat tgtccgacac attgcacttg ccagtttggg ttgacaacga cggtaattgt     1560
gctgctttgg ctgagagaaa gttcggtcaa ggaaagggat tggagaactt cgttactttg     1620
atcactggta ctggtattgg tggtggtatc attcaccagc acgagttgat tcacggttct     1680
tccttctgtg ctgctgaatt gggacacttg gttgttcttt tggacggtcc agactgttct     1740
tgtggttccc acgttgtat tgaagcttac gcatcaggaa tggcattgca gagagaggct     1800
aagaagttgc acgacgagga cttgttgttg gttgagggaa tgtctgttcc aaaggacgag     1860
gctgttggtg ctttgcattt gatccaggct gctaagttgg gtaatgctaa ggctcagtcc     1920
atcttgagaa ctgctggtac tgctttggga ttgggtgttg ttaatatctt gcacactatg     1980
aacccatcct tggttatctt gtccggtgtt ttggcttctc actacatcca catcgttaag     2040
gacgttatca gacagcaagc tttgtcctcc gttcaagacg ttgatgttgt tgtttccgac     2100
ttggttgacc cagctttgtt gggtgctgct tccatggttt tggactacac tactagaaga     2160
atctactaat ag                                                          2172

<210> SEQ ID NO 98
<211> LENGTH: 1302
<212> TYPE: DNA
<213> ORGANISM: Artificial Sequence
<220> FEATURE:
<223> OTHER INFORMATION: Pichia pastoris TRP2: 5' and ORF

<400> SEQUENCE: 98
actgggcctt tagagggtgc tgaagttgac cccttggtgc ttctggaaaa agaactgaag       60
ggcaccagac aagcgcaact tcctggtatt cctcgtctaa gtggtggtgc cataggatac      120
atctcgtacg attgtattaa gtactttgaa ccaaaaactg aaagaaaact gaaagatgtt      180
ttgcaacttc cggaagcagc tttgatgttg ttcgacacga tcgtggcttt tgacaatgtt      240
tatcaaagat tccaggtaat tggaaacgtt tctctatccg ttgatgactc ggacgaagct      300
attcttgaga aatattataa gacaagagaa gaagtggaaa agatcagtaa agtggtattt      360
gacaataaaa ctgttcccta ctatgaacag aaagatatta ttcaaggcca aacgttcacc      420
tctaatattg gtcaggaagg gtatgaaaac catgttcgca agctgaaaga acatattctg      480
aaaggagaca tcttccaagc tgttccctct caaagggtag ccaggccgac ctcattgcac      540
cctttcaaca tctatcgtca tttgagaact gtcaatcctt ctccatacat gttctatatt      600
gactatctag acttccaagt tgttggtgct tcacctgaat tactagttaa atccgacaac      660
```

```
aacaacaaaa tcatcacaca tcctattgct ggaactcttc ccagaggtaa aactatcgaa      720
gaggacgaca attatgctaa gcaattgaag tcgtctttga aagacagggc cgagcacgtc      780
atgctggtag atttggccag aaatgatatt aaccgtgtgt gtgagcccac cagtaccacg      840
gttgatcgtt tattgactgt ggagagattt tctcatgtga tgcatcttgt gtcagaagtc      900
agtggaacat tgagaccaaa caagactcgc ttcgatgctt tcagatccat tttcccagca      960
ggtaccgtct ccggtgctcc gaaggtaaga gcaatgcaac tcataggaga attggaagga     1020
gaaaagagag gtgtttatgc gggggccgta ggacactggt cgtacgatgg aaaatcgatg     1080
gacacatgta ttgccttaag aacaatggtc gtcaaggacg gtgtcgctta ccttcaagcc     1140
ggaggtggaa ttgtctacga ttctgacccc tatgacgagt acatcgaaac catgaacaaa     1200
atgagatcca acaataacac catccttgga gctgagaaaa tctggaccga taggttggcc     1260
agagacgaga atcaaagtga atccgaagaa aacgatcaat ga                        1302
```

<210> SEQ ID NO 99
<211> LENGTH: 1085
<212> TYPE: DNA
<213> ORGANISM: Artificial Sequence
<220> FEATURE:
<223> OTHER INFORMATION: Pichia pastoris TRP2 3' region

<400> SEQUENCE: 99

```
acggaggacg taagtaggaa tttatgtaat catgccaata catctttaga tttcttcctc       60 ttcttttttaa cgaaagacct ccagttttgc actctcgact ctctagtatc ttcccatttc     120
tgttgctgca acctcttgcc ttctgtttcc ttcaattgtt cttctttctt ctgttgcact      180
tggccttctt cctccatctt tcgtttttttt tcaagccttt tcagcagttc ttcttccaag     240
agcagttctt tgattttctc tctccaatcc accaaaaaac tggatgaatt caaccgggca     300
tcatcaatgt tccactttct ttctcttatc aataatctac gtgcttcggc atacgaggaa      360
tccagttgct ccctaatcga gtcatccaca aggttagcat gggccttttt cagggtgtca      420
aaagcatctg gagctcgttt attcggagtc ttgtctggat ggatcagcaa agactttttg      480
cggaaagtct ttcttatatc ttccggagaa caacctggtt tcaaatccaa gatggcatag      540
ctgtccaatt tgaaagtgga aagaatcctg ccaatttcct tctctcgtgt cagctcgttc      600
tcctcctttt gcaacaggtc cacttcatct ggcattttttc tttatgttaa ctttaattat     660
tattaattat aaagttgatt atcgttatca aaataatcat attcgagaaa taatccgtcc      720
atgcaatata taaataagaa ttcataataa tgtaatgata acagtacctc tgatgacctt      780
tgatgaaccg caattttctt tccaatgaca agacatccct ataatacaat tatacagttt      840
atatatcaca aataatcacc ttttttataag aaaaccgtcc tctccgtaac agaacttatt    900
atccgcacgt tatggttaac acactactaa taccgatata gtgtatgaag tcgctacgag      960
atagccatcc aggaaactta ccaattcatc agcactttca tgatccgatt gttggcttta     1020
ttctttgcga gacagatact tgccaatgaa ataactgatc ccacagatga gaatccggtg     1080
ctcgt                                                                  1085
```

<210> SEQ ID NO 100
<211> LENGTH: 747
<212> TYPE: DNA
<213> ORGANISM: Artificial Sequence
<220> FEATURE:
<223> OTHER INFORMATION: 5'-Region of STE13

<400> SEQUENCE: 100

```
ttgggggcct ccaggacttg ctgaaatttg ctgactcatc ttcgccatcc aaggataatg    60
agttagctaa tgtgacagtt aatgagtcgt cttgactaac ggggaacatt tcattattta   120
tatccagagt caatttgata gcagagtttg tggttgaaat acctatgatt cgggagactt   180
tgttgtaacg accattatcc acagtttgga ccgtgaaaat gtcatcgaag agagcagacg   240
acatattatc tattgtggta agtgatagtt ggaagtccga ctaaggcatg aaaatgagaa   300
gactgaaaat ttaaagtttt tgaaaacact aatcgggtaa taacttggaa attacgttta   360
cgtgccttta gctcttgtcc ttacccctga taatctatcc atttcccgag agacaatgac   420
atctcggaca gctgagaacc cgttcgatat agagcttcaa gagaatctaa gtccacgttc   480
ttccaattcg tccatattgg aaaacattaa tgagtatgct agaagacatc gcaatgattc   540
gctttcccaa gaatgtgata tgaagatgaa gaacgaaaat ctcaattata ctgataactt   600
ggccaagttt tcaaagtctg gagtatcaag aaagagctgt atgctaatat ttggtatttg   660
ctttgttatc tggctgtttc tctttgcctt gtatgcgagg gacaatcgat tttccaattt   720
gaacgagtac gttccagatt caaacag                                       747
```

<210> SEQ ID NO 101
<211> LENGTH: 924
<212> TYPE: DNA
<213> ORGANISM: Artificial Sequence
<220> FEATURE:
<223> OTHER INFORMATION: 3'-Region of STE13

<400> SEQUENCE: 101

```
ctactgggaa ccacgagaca tcactgcagt agtttccaag tggatttcag atcactcatt    60
tgtgaatcct gacaaaactg cgatatgggg gtggtcttac ggtgggttca ctacgcttaa   120
gacattggaa tatgattctg gagaggtttt caaatatggt atggctgttg ctccagtaac   180
taattggctt ttgtatgact ccatctacac tgaaagatac atgaaccttc caaaggacaa   240
tgttgaaggc tacagtgaac acagcgtcat taagaaggtt tccaattta agaatgtaaa   300 ccgattcttg gtttgtcacg ggactactga tgataacgtg catttcaga acacactaac   360 cttactggac cagttcaata ttaatggtgt tgtgaattac gatcttcagg tgtatcccga   420
cagtgaacat agcattgccc atcacaacgc aaataaagtg atctacgaga ggttattcaa   480
gtggttagag cgggcattta acgatagatt tttgtaacat tccgtacttc atgccatact   540
atatatcctg caaggtttcc ctttcagaca caataattgc tttgcaattt tacataccac   600
caattggcaa aaataatctc ttcagtaagt tgaatgcttt tcaagccagc accgtgagaa   660
attgctacag cgcgcattct aacatcactt taaaattccc tcgccggtgc tcactggagt   720
ttccaaccct tagcttatca aaatcgggtg ataactctga gttttttttt tcacttctat   780
tcctaaacct tcgcccaatg ctaccacctc caatcaacat cccgaaatgg atagaagaga   840
atggacatct cttgcaacct ccggttaata attactgtct ccacagagga ggatttacgg   900
taatgattgt aggtgggcct aatg                                          924
```

<210> SEQ ID NO 102
<211> LENGTH: 980
<212> TYPE: DNA
<213> ORGANISM: Artificial Sequence
<220> FEATURE:
<223> OTHER INFORMATION: 5'-Region of DAP2

<400> SEQUENCE: 102

```
cacctgggcc tgttgctgct ggtactgctg ttggaactgt tggtattgtt gctgatctaa    60
```

```
ggccgcctgt tccacaccgt gtgtatcgaa tgcttgggca aaatcatcgc ctgccggagg      120
ccccactacc gcttgttcct cctgctcttg tttgttttgc tcattgatga tatcggcgtc      180
aatgaattga tcctcaatcg tgtggtggtg gtgtcgtgat tcctcttctt tcttgagtgc      240
cttatccata ttcctatctt agtgtaccaa taattttgtt aaacacacgc tgttgtttat      300
gaaaagtcgt caaaaggtta aaaattctac ttggtgtgtg tcagagaaag tagtgcagac      360
ccccagtttg ttgactagtt gagaaggcgg ctcactattg cgcgaatagc atgagaaatt      420
tgcaaacatc tggcaaagtg gtcaatacct gccaacctgc caatcttcgc gacggaggct      480
gttaagcggg ttgggttccc aaagtgaatg gatattacgg gcaggaaaaa cagccccttc      540
cacactagtc tttgctactg acatcttccc tctcatgtat cccgaacaca agtatcggga      600
gtatcaacgg agggtgccct tatggcagta ctccctgttg gtgattgtac tgctatacgg      660
gtctcatttg cttatcagca ccatcaactt gatacactat aaccacaaaa attatcatgc      720
acacccagtc aatagtggta tcgttcttaa tgagtttgct gatgacgatt cattctcttt      780
gaatggcact ctgaacttgg agaactggag aaatggtacc ttttccccta aatttcattc      840
cattcagtgg accgaaatag gtcaggaaga tgaccaggga tattcattc tctcttccaa       900 ttcctcttac atagtaaagt ctttatccga cccagacttt gaatctgttc tattcaacga      960
gtctacaatc acttacaacg                                                  980

<210> SEQ ID NO 103
<211> LENGTH: 1117
<212> TYPE: DNA
<213> ORGANISM: Artificial Sequence
<220> FEATURE:
<223> OTHER INFORMATION: 3'-Region of DAP2

<400> SEQUENCE: 103
ggcagcaaag ccttacgttg atgagaatag actggccatt tggggttggt cttatggagg       60
ttacatgacg ctaaaggttt tagaacagga taaaggtgaa acattcaaat atggaatgtc      120
tgttgcccct gtgacgaatt ggaaattcta tgattctatc tacacagaaa gatacatgca      180
cactcctcag gacaatccaa actattataa ttcgtcaatc catgagattg ataatttgaa      240
gggagtgaag aggttcttgc taatgcacgg aactggtgac gacaatgttc acttccaaaa      300
tacactcaaa gttctagatt tatttgattt acatggtctt gaaaactatg atatccacgt      360
gttccctgat agtgatcaca gtattagata tcacaacggt aatgttatag tgtatgataa      420
gctattccat tggattaggc gtgcattcaa ggctggcaaa taaataggtg caaaaatatt      480
attagacttt ttttttcgtt cgcaagttat tactgtgtac ataccgatc caatccgtat      540 tgtaattcat gttctagatc caaaatttgg gactctaatt catgaggtct aggaagatga      600
tcatctctat agttttcagc gggggctcg atttgcggtt ggtcaaagct aacatcaaaa      660
tgtttgtcag gttcagtgaa tggtaactgc tgctcttgaa ttggtcgtct gacaaattct      720
ctaagtgata gcacttcatc tacaatcatt tgcttcatcg tttctatatc gtccacgacc      780
tcaaacgaga atcgaatttt ggaagaacag acgggctcat cgttaggatc atgccaaacc      840
ttgagatatg gatgctctaa agcctcagta actgtaattc tgtgagtggg atctaccgtg      900
agcattcgat ccagtaagtc tatcgcttca gggttggcac cggaaataa ctggctgaat      960 gggatcttgg gcatgaatgg cagggagcga acataatcct gggcacgctc tgatctgata     1020
gactgaagtg tctcttccga aacagtaccc agcgtactca aaatcaagtt caattgatcc     1080
acatagtctc ttcctctaaa aatgggtcgg ccaccta                              1117
```

<210> SEQ ID NO 104
<211> LENGTH: 1666
<212> TYPE: DNA
<213> ORGANISM: Artificial Sequence
<220> FEATURE:
<223> OTHER INFORMATION: HYGR resistance cassette

<400> SEQUENCE: 104

```
gatctgttta gcttgcctcg tccccgccgg gtcacccggc cagcgacatg gaggcccaga      60
atacccctcct tgacagtctt gacgtgcgca gctcagggc atgatgtgac tgtcgcccgt     120
acatttagcc catacatccc catgtataat catttgcatc catacatttt gatggccgca     180
cggcgcgaag caaaaattac ggctcctcgc tgcggacctg cgagcaggga acgctcccc     240
tcacagacgc gttgaattgt ccccacgccg cgcccctgta gagaaatata aaaggttagg     300
atttgccact gaggttcttc tttcatatac ttccttttaa aatcttgcta ggatacagtt     360
ctcacatcac atccgaacat aaacaaccat gggtaaaaag cctgaactca ccgcgacgtc     420
tgtcgagaag tttctgatcg aaaagttcga cagcgtctcc gacctgatgc agctctcgga     480
gggcgaagaa tctcgtgctt tcagcttcga gtaggaggg cgtggatatg tcctgcgggt     540
aaatagctgc gccgatggtt tctacaaaga tcgttatgtt tatcggcact ttgcatcggc     600
cgcgctcccg attccggaag tgcttgacat tgggaattc agcgagagcc tgacctattg     660
catctcccgc cgtgcacagg gtgtcacgtt gcaagacctg cctgaaaccg aactgcccgc     720
tgttctgcag ccggtcgcgg aggccatgga tgcgatcgct gcggccgatc ttagccagac     780
gagcgggttc ggcccattcg gaccgcaagg aatcggtcaa tacactacat ggcgtgattt     840
catatgcgcg attgctgatc cccatgtgta tcactggcaa actgtgatgg acgacaccgt     900
cagtgcgtcc gtcgcgcagg ctctcgatga gctgatgctt tgggccgagg actgccccga     960
agtccggcac ctcgtgcacg cggatttcgg ctccaacaat gtcctgacgg acaatggccg    1020
cataacagcg gtcattgact ggagcgaggc gatgttcggg gattcccaat acgaggtcgc    1080
caacatcttc ttctggaggc cgtggttggc ttgtatggag cagcagacgc gctacttcga    1140
gcggaggcat ccggagcttg caggatcgcc gcggctccgg gcgtatatgc tccgcattgg    1200
tcttgaccaa ctctatcaga gcttggttga cggcaatttc gatgatgcag cttgggcgca    1260
gggtcgatgc gacgcaatcg tccgatccgg agccgggact gtcgggcgta cacaaatcgc    1320
ccgcagaagc gcggccgtct ggaccgatgg ctgtgtagaa gtactcgccg atagtggaaa    1380
ccgacgcccc agcactcgtc cgagggcaaa ggaataatca gtactgacaa taaaaagatt    1440
cttgttttca agaacttgtc atttgtatag ttttttttata ttgtagttgt tctattttaa    1500
tcaaatgtta gcgtgattta tatttttttt cgcctcgaca tcatctgccc agatgcgaag    1560
ttaagtgcgc agaaagtaat atcatgcgtc aatcgtatgt gaatgctggt cgctatactg    1620
ctgtcgattc gatactaacg ccgccatcca gtgtcgaaaa cgagct                  1666
```

<210> SEQ ID NO 105
<211> LENGTH: 365
<212> TYPE: DNA
<213> ORGANISM: Artificial Sequence
<220> FEATURE:
<223> OTHER INFORMATION: Sequence of Pichia pastoris TRP5 5' integration
      fragment

<400> SEQUENCE: 105

```
acgacggcca aattcatgat acacactctg tttcagctgg tttggactac cctggagttg      60
```

```
gtcctgaatt ggctgcctgg aaagcaaatg gtagagccca attttccgct gtaactgatg    120
cccaagcatt agagggattc aaaatcctgt ctcaattgga agggatcatt ccagcactag    180
agtctagtca tgcaatctac ggcgcattgc aaattgcaaa gactatgtct tcggaccagt    240
ccttagttat taatgtatct ggaagggtg ataaggacgt ccagagtgta gctgagattt    300
tacctaaatt gggacctcaa attggatggg atttgcgttt cagcgaagac attactaaag    360
agtga                                                                365
```

<210> SEQ ID NO 106
<211> LENGTH: 613
<212> TYPE: DNA
<213> ORGANISM: Artificial Sequence
<220> FEATURE:
<223> OTHER INFORMATION: Sequence of Pichia pastoris TRP5 3' integration fragment

<400> SEQUENCE: 106

```
tcgatagcac aatattcaac ttgactgggt gttaagaact aagagctctg ggaaactttg     60
tatttattac taccaacaca gtcaaattat tggatgtgtt ttttttttcca gtacatttca   120 ctgagcagtt tgttatactc ggtctttaat ctccatatac atgcagattg taatacagat   180
ctgaacagtt tgattctgat tgatcttgcc accaatattc tattttttgta tcaagtaaca   240 gagtcaatga tcattggtaa cgtaacggtt ttcgtgtata gtagtagag cccatcttgt     300 aacctcattt cctcccatat taaagtatca gtgattcgct ggaacgatta actaagaaaa    360
aaaaaatatc tgcacatact catcagtctg taaatctaag tcaaaactgc tgtatccaat    420
agaaatcggg atatacctgg atgttttttc cacataaaca aacgggagtt cagcttactt    480
atggtgttga tgcaattcag tatgatccta ccaataaaac gaaactttgg gattttggct    540
gtttgaggga tcaaaagctg caccttaca agattgacgg atcgaccatt agaccaaagc     600
aaatggccac caa                                                        613
```

<210> SEQ ID NO 107
<211> LENGTH: 384
<212> TYPE: DNA
<213> ORGANISM: Artificial Sequence
<220> FEATURE:
<223> OTHER INFORMATION: Encodes human GM-CSF

<400> SEQUENCE: 107

```
ccagctagat ctccatctcc atccactcaa ccatgggaac acgttaacgc tatccaagag     60
gctttgagat tgttgaactt gtccagagac actgctgctg aaatgaacga gactgttgag    120
gttatctccg agatgttcga cttgcaagag ccaacttgtt tgcagactag attggagttg    180
tacaagcagg gattgagagg atccttgact aagttgaagg gaccattgac tatgatggct    240
tcccactaca gcaacactg tccaccaact ccagaaacat cctgtgctac tcagatcatc    300
actttcgagt ccttcaaaga gaacttgaag gacttcttgt tggttatccc attcgactgt    360
tgggaaccag ttcaagaata ataa                                            384
```

<210> SEQ ID NO 108
<211> LENGTH: 126
<212> TYPE: PRT
<213> ORGANISM: Homo sapiens

<400> SEQUENCE: 108

Pro Ala Arg Ser Pro Ser Pro Ser Thr Gln Pro Trp Glu His Val Asn
1               5                   10                  15

```
Ala Ile Gln Glu Ala Leu Arg Leu Leu Asn Leu Ser Arg Asp Thr Ala
            20                  25                  30

Ala Glu Met Asn Glu Thr Val Glu Val Ile Ser Glu Met Phe Asp Leu
        35                  40                  45

Gln Glu Pro Thr Cys Leu Gln Thr Arg Leu Glu Leu Tyr Lys Gln Gly
    50                  55                  60

Leu Arg Gly Ser Leu Thr Lys Leu Lys Gly Pro Leu Thr Met Met Ala
65                  70                  75                  80

Ser His Tyr Lys Gln His Cys Pro Pro Thr Pro Glu Thr Ser Cys Ala
                85                  90                  95

Thr Gln Ile Ile Thr Phe Glu Ser Phe Lys Glu Asn Leu Lys Asp Phe
            100                 105                 110

Leu Leu Val Ile Pro Phe Asp Cys Trp Glu Pro Val Gln Glu
        115                 120                 125

<210> SEQ ID NO 109
<211> LENGTH: 1275
<212> TYPE: DNA
<213> ORGANISM: Artificial Sequence
<220> FEATURE:
<223> OTHER INFORMATION: Encodes CWP1-GMCSF fusion protein

<400> SEQUENCE: 109
atgttcaacc tgaaaactat tctcatctca acacttgcat cgatcgctgt tgccgaccaa      60
accttcggtg tccttctaat ccggagtgga tccccatatc actattcgac tctcactaat     120
agagacgaaa agattgttgc tggaggtggc aacaaaaaag tgaccctcac agatgaggga     180
gctctgaagt atgatggtgg taaatggata ggtcttgatg atgatggcta tgcggtacag     240
accgacaaac cagttacagg ttggagcact aacggtggat acctctattt tgaccaaggc     300
ttaattgttt gcacggagga ctatatcgga tatgtgaaga aacatggtga atgcaaaggt     360
gacagctatg gtatggcttg gaaggtactc ccagccgacg atgacaagga tgatgacaag     420
gatgatgata aagatgatga caaggattat gacgatgaca atgaccacgg tgatggtgat     480
tactattgct cgatcacagg aacctatgcc atcaaatcca aaggcagtaa gcatcaatac     540
gaggccatca aaaaagttga tgcacatcct catgtcttct ctgtaggagg agatcaggga     600
aacgatctga ttgtgacttt ccaaaaggat tgttcgctgg tagatcaaga taacagaggc     660
gtatatgttg accctaattc tggagaagtc ggaaacgttg acccttgggg agaactcacg     720
ccatctgtta aatgggatat tgacgacgga tacctgatct ttaatggtga gtccaatttc     780
aggtcatgtc catctggtaa tggatattca ttgtctatca aggattgtgt tgggggaact     840
gacattggcc ttaaagtatg ggagaaaggt ggaggttctt tggttaagag ggctccagct     900
agatctccat ctccatccac tcaaccatgg gaacacgtta acgctatcca agaggctttg     960
agattgttga acttgtccag agacactgct gctgaaatga acgagactgt tgaggttatc    1020
tccgagatgt tcgacttgca agagccaact tgtttgcaga ctagattgga gttgtacaag    1080
cagggattga gaggatcctt gactaagttg aagggaccat tgactatgat ggcttcccac    1140
tacaagcaac actgtccacc aactccagaa acatcctgtg ctactcagat catcactttc    1200
gagtccttca aagagaactt gaaggacttc ttgttggtta tcccattcga ctgttgggaa    1260
ccagttcaag aataa                                                      1275

<210> SEQ ID NO 110
<211> LENGTH: 424
<212> TYPE: PRT
<213> ORGANISM: Artificial Sequence
```

-continued

<220> FEATURE:
<223> OTHER INFORMATION: CWP1-GMCSF fusion protein

<400> SEQUENCE: 110

```
Met Phe Asn Leu Lys Thr Ile Leu Ile Ser Thr Leu Ala Ser Ile Ala
1               5                   10                  15

Val Ala Asp Gln Thr Phe Gly Val Leu Leu Ile Arg Ser Gly Ser Pro
            20                  25                  30

Tyr His Tyr Ser Thr Leu Thr Asn Arg Asp Glu Lys Ile Val Ala Gly
        35                  40                  45

Gly Gly Asn Lys Lys Val Thr Leu Thr Asp Glu Gly Ala Leu Lys Tyr
    50                  55                  60

Asp Gly Gly Lys Trp Ile Gly Leu Asp Asp Asp Gly Tyr Ala Val Gln
65                  70                  75                  80

Thr Asp Lys Pro Val Thr Gly Trp Ser Thr Asn Gly Gly Tyr Leu Tyr
                85                  90                  95

Phe Asp Gln Gly Leu Ile Val Cys Thr Glu Asp Tyr Ile Gly Tyr Val
            100                 105                 110

Lys Lys His Gly Glu Cys Lys Gly Asp Ser Tyr Gly Met Ala Trp Lys
        115                 120                 125

Val Leu Pro Ala Asp Asp Asp Lys Asp Asp Asp Lys Asp Asp Asp Lys
    130                 135                 140

Asp Asp Asp Lys Asp Tyr Asp Asp Asp Asn Asp His Gly Asp Gly Asp
145                 150                 155                 160

Tyr Tyr Cys Ser Ile Thr Gly Thr Tyr Ala Ile Lys Ser Lys Gly Ser
                165                 170                 175

Lys His Gln Tyr Glu Ala Ile Lys Lys Val Asp Ala His Pro His Val
            180                 185                 190

Phe Ser Val Gly Gly Asp Gln Gly Asn Asp Leu Ile Val Thr Phe Gln
        195                 200                 205

Lys Asp Cys Ser Leu Val Asp Gln Asp Asn Arg Gly Val Tyr Val Asp
    210                 215                 220

Pro Asn Ser Gly Glu Val Gly Asn Val Asp Pro Trp Gly Glu Leu Thr
225                 230                 235                 240

Pro Ser Val Lys Trp Asp Ile Asp Asp Gly Tyr Leu Ile Phe Asn Gly
                245                 250                 255

Glu Ser Asn Phe Arg Ser Cys Pro Ser Gly Asn Gly Tyr Ser Leu Ser
            260                 265                 270

Ile Lys Asp Cys Val Gly Gly Thr Asp Ile Gly Leu Lys Val Trp Glu
        275                 280                 285

Lys Gly Gly Gly Ser Leu Val Lys Arg Ala Pro Ala Arg Ser Pro Ser
    290                 295                 300

Pro Ser Thr Gln Pro Trp Glu His Val Asn Ala Ile Gln Glu Ala Leu
305                 310                 315                 320

Arg Leu Leu Asn Leu Ser Arg Asp Thr Ala Ala Glu Met Asn Glu Thr
                325                 330                 335

Val Glu Val Ile Ser Glu Met Phe Asp Leu Gln Glu Pro Thr Cys Leu
            340                 345                 350

Gln Thr Arg Leu Glu Leu Tyr Lys Gln Gly Leu Arg Gly Ser Leu Thr
        355                 360                 365

Lys Leu Lys Gly Pro Leu Thr Met Met Ala Ser His Tyr Lys Gln His
    370                 375                 380

Cys Pro Pro Thr Pro Glu Thr Ser Cys Ala Thr Gln Ile Ile Thr Phe
385                 390                 395                 400
```

-continued

```
Glu Ser Phe Lys Glu Asn Leu Lys Asp Phe Leu Leu Val Ile Pro Phe
            405                 410                 415

Asp Cys Trp Glu Pro Val Gln Glu
            420

<210> SEQ ID NO 111
<211> LENGTH: 8
<212> TYPE: PRT
<213> ORGANISM: Artificial Sequence
<220> FEATURE:
<223> OTHER INFORMATION: KEX2 linker

<400> SEQUENCE: 111

Gly Gly Gly Ser Leu Val Lys Arg
1               5
```